(12) United States Patent
Davis

(10) Patent No.: US 9,861,451 B1
(45) Date of Patent: Jan. 9, 2018

(54) COMBINATION ORTHODONTIC AND PERIODONTAL; ORTHODONTIC AND IMPLANT; AND ORTHODONTIC AND TEMPEROMANDIBULAR JOINT DYSFUNCTION AND ORTHODONTIC ORTHOGNATHIC TREATMENT

(71) Applicant: Elliot Davis, New York, NY (US)

(72) Inventor: Elliot Davis, New York, NY (US)

( * ) Notice: Subject to any disclaimer, the term of this patent is extended or adjusted under 35 U.S.C. 154(b) by 658 days.

(21) Appl. No.: 14/229,186

(22) Filed: Mar. 28, 2014

Related U.S. Application Data

(60) Provisional application No. 61/853,430, filed on Apr. 4, 2013.

(51) Int. Cl.
*A61C 7/08* (2006.01)

(52) U.S. Cl.
CPC .................................. *A61C 7/08* (2013.01)

(58) Field of Classification Search
CPC ........ A61C 7/08; A61C 19/063; A63B 71/085
See application file for complete search history.

(56) References Cited

U.S. PATENT DOCUMENTS

| | | | | |
|---|---|---|---|---|
| 6,682,346 B2 * | 1/2004 | Chishti | ..................... | A61C 7/00 433/24 |
| 7,320,592 B2 * | 1/2008 | Chishti | ..................... | A61C 7/00 433/213 |
| 7,326,051 B2 * | 2/2008 | Miller | ...................... | A61C 7/00 433/24 |
| 7,905,725 B2 * | 3/2011 | Chishti | ..................... | A61C 7/00 433/24 |
| 8,062,031 B2 * | 11/2011 | Inman | ...................... | A61C 7/10 433/18 |
| 2007/0026358 A1 * | 2/2007 | Schultz | .................... | A61C 7/00 433/24 |
| 2007/0087300 A1 * | 4/2007 | Willison | .................. | A61C 7/12 433/6 |
| 2007/0207434 A1 * | 9/2007 | Kuo | ...................... | A61C 19/063 433/6 |
| 2008/0050692 A1 * | 2/2008 | Hilliard | ................... | A61C 7/08 433/24 |
| 2008/0206701 A1 * | 8/2008 | Miller | ...................... | A61C 7/08 433/24 |
| 2008/0299507 A1 * | 12/2008 | Li | ........................... | A61C 7/08 433/6 |

(Continued)

FOREIGN PATENT DOCUMENTS

| | | |
|---|---|---|
| WO | WO 2008/010057 | 1/2008 |
| WO | WO 2011/155990 | 12/2011 |
| WO | WO 2011/156207 | 12/2011 |

OTHER PUBLICATIONS

Simon J. Littlewood et al., "Orthodontic retention: A systematic review", *Journal of Orthodontics*, vol. 33, pp. 205-212 (2006).

(Continued)

*Primary Examiner* — Nicholas Lucchesi
(74) *Attorney, Agent, or Firm* — Ostrolenk Faber LLP

(57) ABSTRACT

Disclosed is a non-invasive method of realignment of mal-occluded teeth of a patient suffering from a periodontal and/or an orthognathic condition that includes application of flexible aligners to induce the movement of the maloccluded teeth toward a realigned position along an ideal arch.

7 Claims, 114 Drawing Sheets
(101 of 114 Drawing Sheet(s) Filed in Color)

flexible aligner in a deformed state

(56) References Cited

U.S. PATENT DOCUMENTS

| | | | |
|---|---|---|---|
| 2009/0191502 A1* | 7/2009 | Cao | A61C 7/08 433/24 |
| 2009/0191503 A1* | 7/2009 | Matov | A61C 7/00 433/24 |
| 2010/0068671 A1* | 3/2010 | Kakavand | A61C 7/08 433/6 |
| 2011/0247214 A1* | 10/2011 | Huge | A61C 7/002 29/896.11 |
| 2012/0244488 A1* | 9/2012 | Chishti | A61C 7/00 433/24 |
| 2012/0270173 A1* | 10/2012 | Pumphrey | A61C 7/08 433/6 |
| 2012/0288818 A1* | 11/2012 | Vendittelli | A61C 7/00 433/24 |
| 2012/0322018 A1* | 12/2012 | Lowe | A61C 7/00 433/6 |
| 2013/0095446 A1* | 4/2013 | Andreiko | A61C 7/08 433/6 |
| 2013/0122448 A1* | 5/2013 | Kitching | A61C 7/002 433/24 |
| 2013/0302742 A1* | 11/2013 | Li | A61C 7/08 433/6 |
| 2013/0302743 A1* | 11/2013 | Chishti | A61C 7/00 433/6 |
| 2013/0323665 A1* | 12/2013 | Dinh | A61C 7/08 433/6 |
| 2014/0023980 A1* | 1/2014 | Kitching | A61C 7/00 433/6 |
| 2014/0193766 A1* | 7/2014 | Miller | A61C 7/00 433/6 |
| 2014/0315153 A1* | 10/2014 | Kitching | A61C 7/002 433/213 |
| 2015/0238280 A1* | 8/2015 | Wu | A61C 7/002 433/6 |
| 2016/0106521 A1* | 4/2016 | Tanugula | A61C 7/08 433/6 |

OTHER PUBLICATIONS

Anne-Marie Bollen et al., "The Effects of Orthodontic Therapy on Periodontal Health: A Systematic Review of Controlled Evidence", *The Journal of the American Dental Association (JADA)*, 139(4):413-422 (2008).

Anne-Marie Bollen, "Effects of Malocclusions and Orthodontics on Periodontal Health: Evidence from a Systematic Review", *Journal of Dental Education*, 72(8):912-918.

Dr. M. Kaan et al., "Retention and relapse: Review of the literature", *Fogorv Sz.*, 104(4):139-146, Dec. 2011 (with an English language Abstract).

R.A. Riedel, "A post-retention assessment of relapse, recidivism, adjustment, change, and stability", *International Conference Orthodontics: Evaluation and Future: Proceedings of the International Conference on the occasion of the 25th anniversary of the Orthodontic Department of the University of Nijmegen*, The Netherlands, pp. 281-306, Oct. 1987.

G. Tsomos et al., "Objective assessment of patient compliance with removable orthodontic appliances, A cross-sectional cohort study", *Angle Orthodontist*, 84(1):56-61, 2014.

A. Bartsch et al., "Correlates of objective patient compliance with removable appliance wear", *American Journal of Orthodontics and Dentofacial Orthopedics*, 378-386, Oct. 1993.

L. Bondemark et al., "Long-term Stability of Orthodontic Treatment and Patient Satisfaction, A Systematic Review", *Angle Orthodontist*, 77(1):181-191, 2007.

B. Zachrisson et al., "Periodontal Condition in Orthodontically Treated and Untreated Individuals", *Angle Orthodontist*, 43(4):402-411, 1973.

N. Gkantidis et al., "The orthodontic-perodontic interrelationship in integrated treatment challenges: a systematic review", *Journal of Oral Rehabilitation*, 37:377-390, 2010.

A.M. Renkema et al., "Development of labial gingival recessions in orthodontically treated patients", *Am J Orthod Dentofacial Orthop*, 143:206-212, 2013.

A. Bollen et al., "The Effects of Orthodontic Therapy on Periodontal Health: A Systematic Review of Controlled Evidence"m *JADA*, 139:413-417, Apr. 2008.

"Why Straighten Teeth", *American Association of Orthodontists*, http://www.braces.org/beautifulsmile/straighten/, (Accessed Nov. 27, 2016).

S. Slutzkey et al., "Gingival recession in young adults: Occurrence, severity, and relationship to past orthodontic treatment and oral piercing", *American Journal of Orthodontics and Dentofacial Orthopedics*, 134(5): 652-656, Nov. 2008.

Clearcorrect.com, Case Parameters, https://support.clearcorrect.com/hc/en-us/articles/206676997-Case-Parameters (accessed Nov. 28, 2016).

Clearcorrect.com, Case Parameters, https://support.clearcorrect.com/hc/en-us/articles/216127717-Complex-Cases-Contraindications (accessed Nov. 28, 2016).

Clearcorrect.com. Case Parameters, https://support.clearcorrect.com/hc/en-us/articles/206556268-Periodontal-Disease (accessed Nov. 28, 2016).

"The American Board of Orthodontics, Grading System for Dental Casts and Panoramic Radiographs", *The American Board of Orthodontics*, pp. 1-22, 1999-2012.

R. M. Little, "Stability and Relapse of Mandibular Anterior Alignment: University of Washington Studies", *Seminars in Orthodontics*, 5(3):191-204, Sep. 1999.

R.M. Little, "Stability and Relapse of Dental Arch Alignment", *British Journal of Orthodontics*, 17:235-241, 1990.

P.L. Block, "Restorative margins and periodontal health: A new look at an old perspective", *The Journal of Prosthetic Dentistry*, 57(6):683-689, Jun. 1987.

A. Bouri Jr. et al., "Width of Keratinized Gingiva and the Health Status of the Supporting Tissues Around Dental Implants", *The International Journal of Oral & Maxillofacial Implants*, 23(2):323-326, 2008.

S. Friedman et al., "The Success of Endodontic Therapy—Healing and Functionality", *CDA Journal*, 32(6):40-503, Jun. 2004.

G. Armitage, "Periodontal Diagnoses and classification of periodontal diseases", *Periodontology 2000*, 34:9-21, 2004.

A. Geiger et al., "Relationship of Occlusion and Periodontal Disease", *J Periodontol.*, pp. 283-290, May 1980.

T.M. Tirk, "Limitations in Orthodontic Treatment", *Department of Orthodontics, Eastman Dental Dispensary*, Read before the 1964 meeting of the University of Illinois Orthodontic Alumni Association, 35(3):165-177, Jul. 1965.

M.C. Pratt et al., "Evaluation of retention protocols among members of the American Association of Orthodontists in the United States", *Am J Orthod Dentofacial Orthop*, 140:520-526, 2011.

M. Valiathan et al., "Results of a survey-based study to identify common retention practices in the United States", *Am J Orthod Dentofacial Orthop*, 137:170-177, 2010.

P. Singh et al., "Orthodontic retention pasterns in the United Kingdom", *Journal of Orthodontics*, 36:115-121, 2009.

P.M. Wong et al., "A comprehensive survey of retention procedures in Australia and New Zealand", *Australian Orthodontic Journal*, 20(2):99-106, Nov. 2004.

A.M. Renkema et al., "A survey on orthodontic retention procedures in the Netherlands", *European Journal of Orthodontics*, 31:432-437, Jun. 2009.

C.S. Lai et al., "Orthodontic retention procedures in Switzerland", *Swiss Dental Journal*, 124:655-661, Jun. 2014.

S.J. Littlewood et al., Retention procedures for stabilising tooth position after treatment with orthodontic braces (Review), *Cochrane Database Syst Rev.*, Jan. 2006.

* cited by examiner

Fig. 1A: flexible aligner at rest
Fig. 1B: flexible aligner in a deformed state
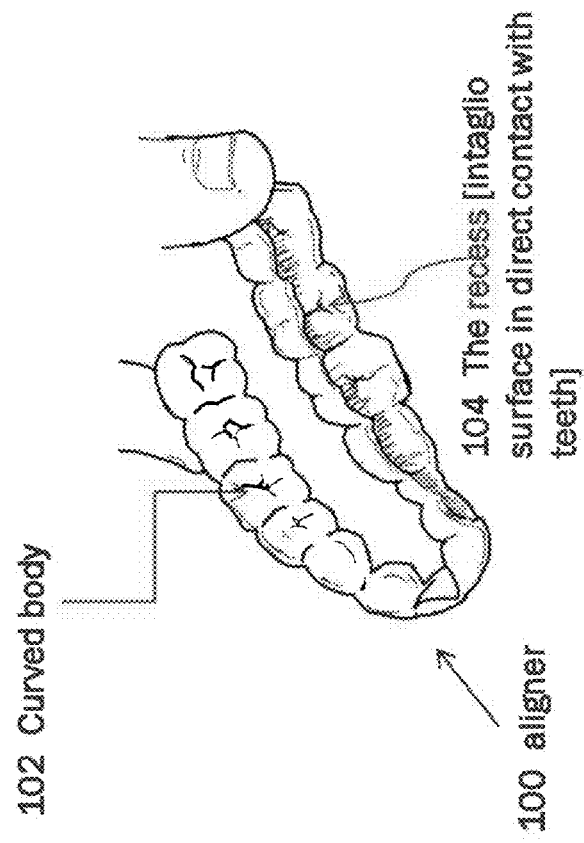
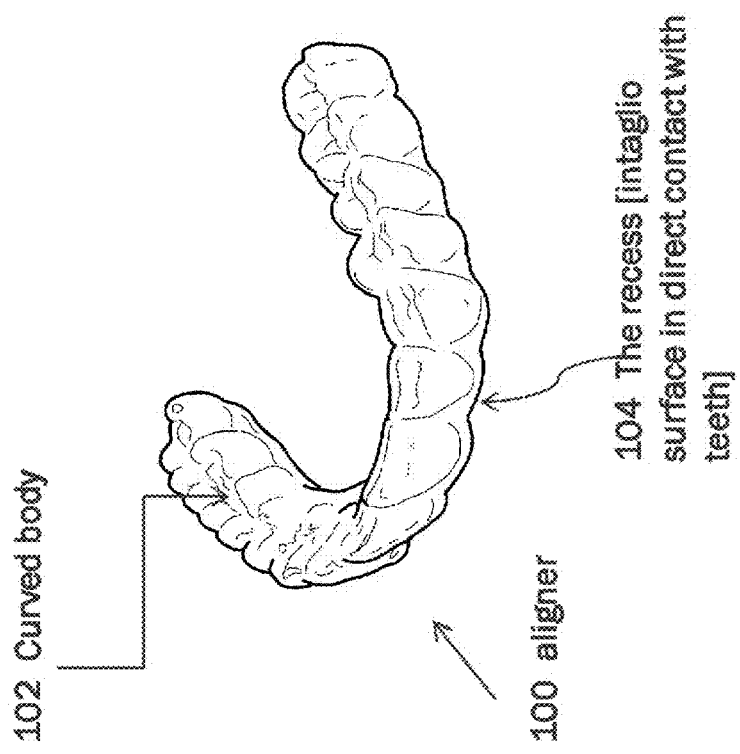
102 Curved body
104 The recess [intaglio surface in direct contact with teeth]
100 aligner

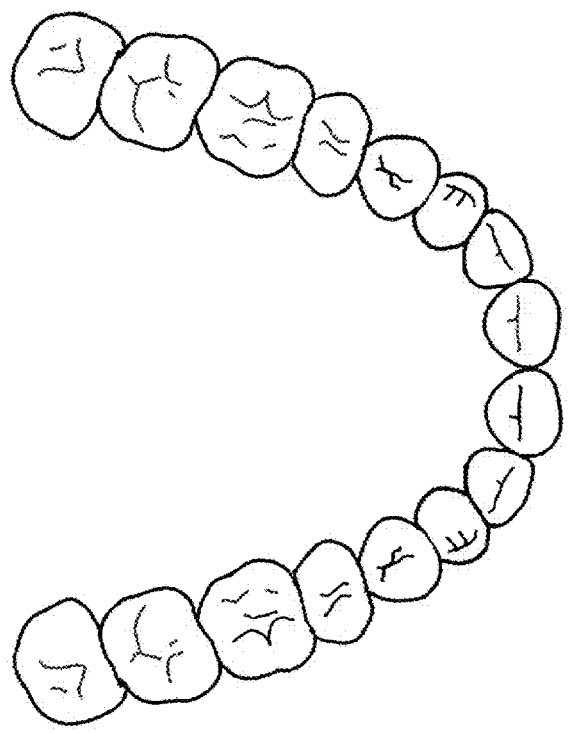
Fig. 1C: misaligned and maloccluded teeth within an irregular arch form
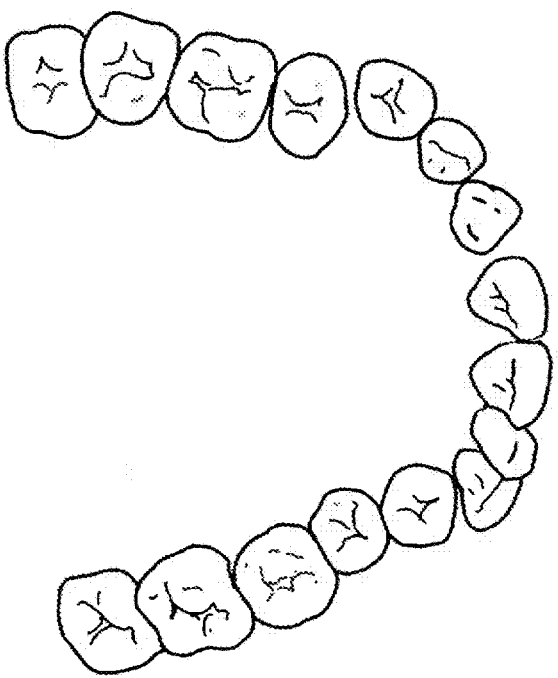
Fig. 1D: properly aligned and occluded teeth within an ideal arch form

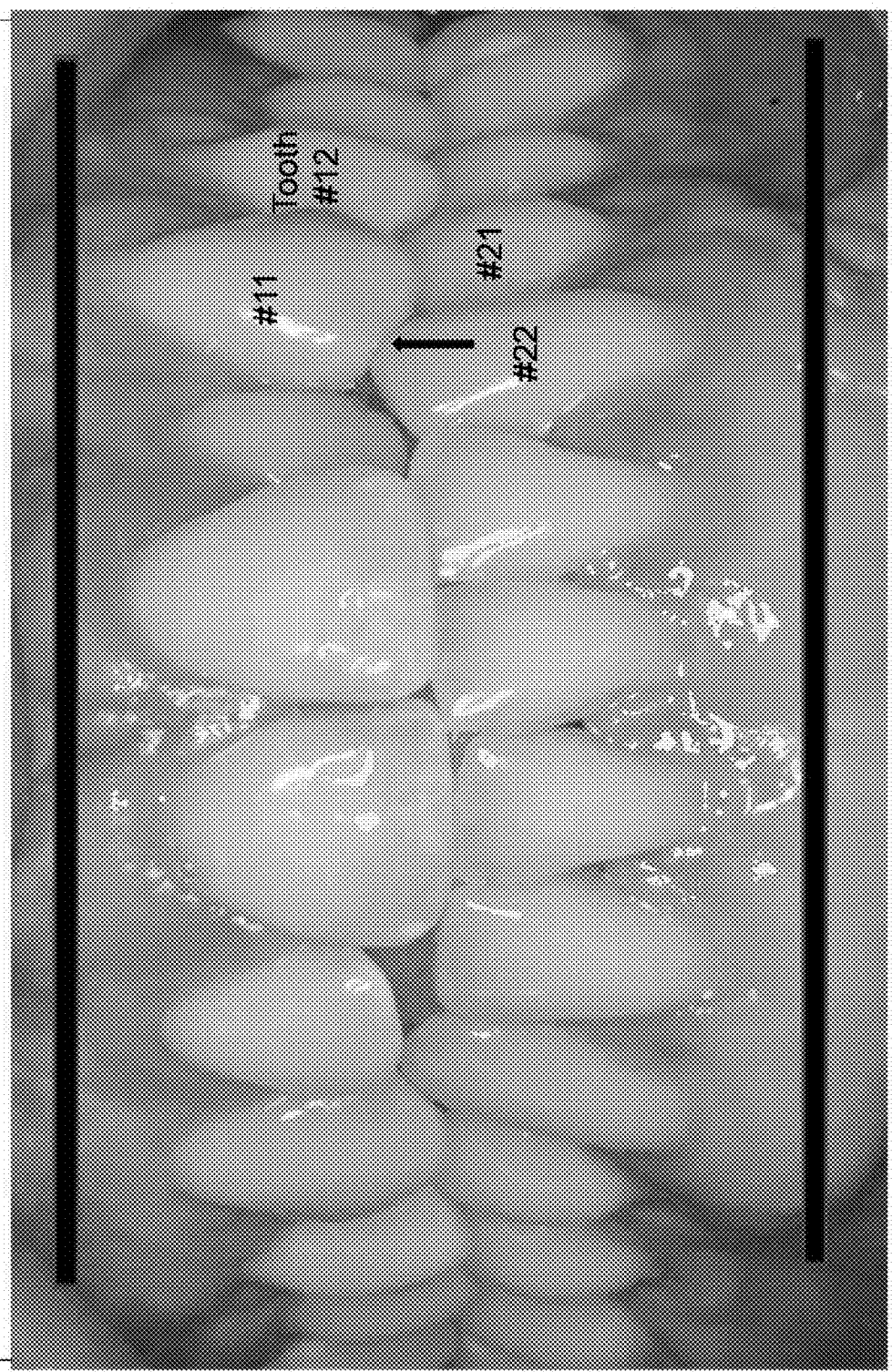
Fig. 2A: anterior view prior to the initiation of treatment

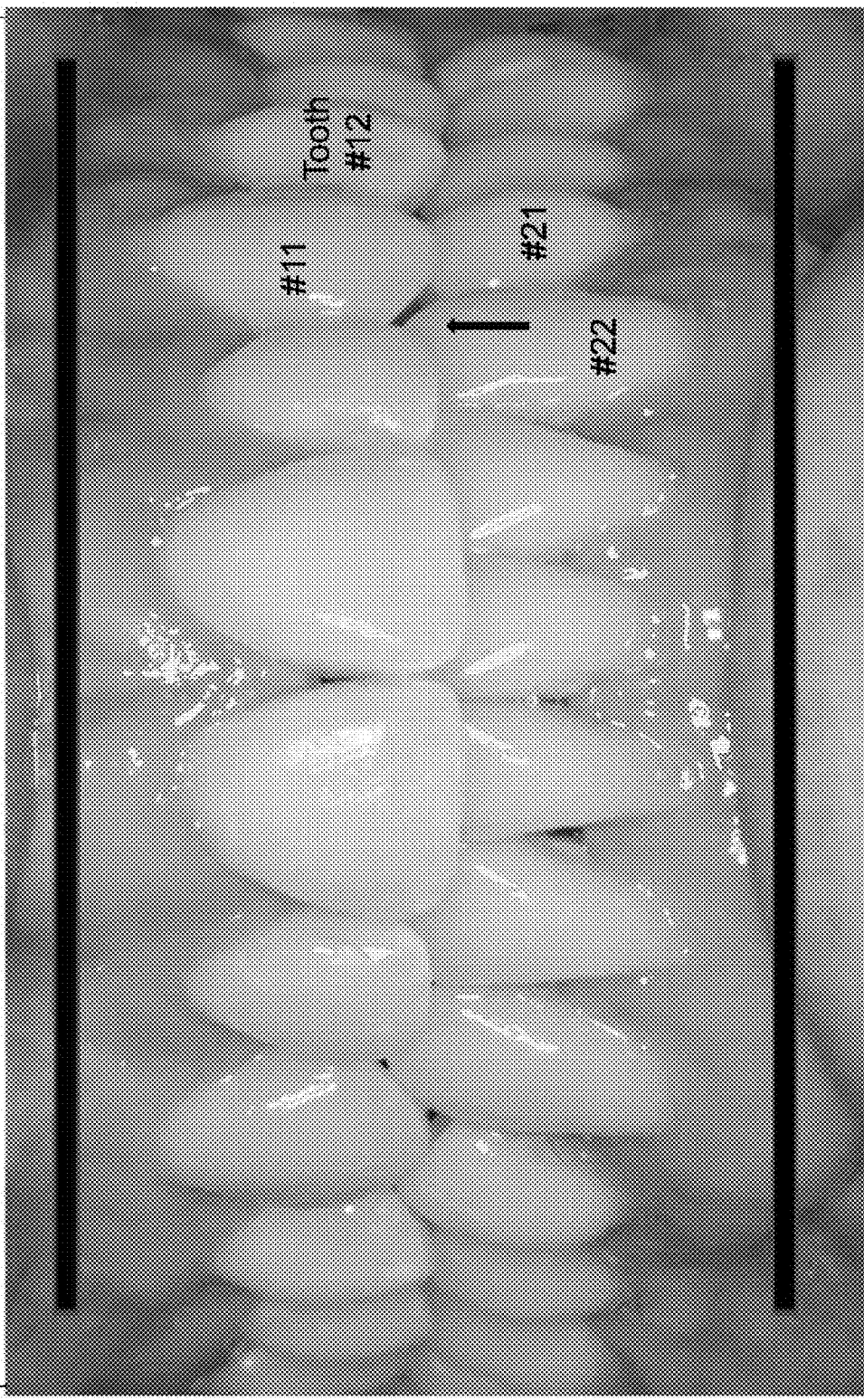
Fig. 2B: anterior view after 7 months of active aligner therapy
Gingival Health Level I achieved

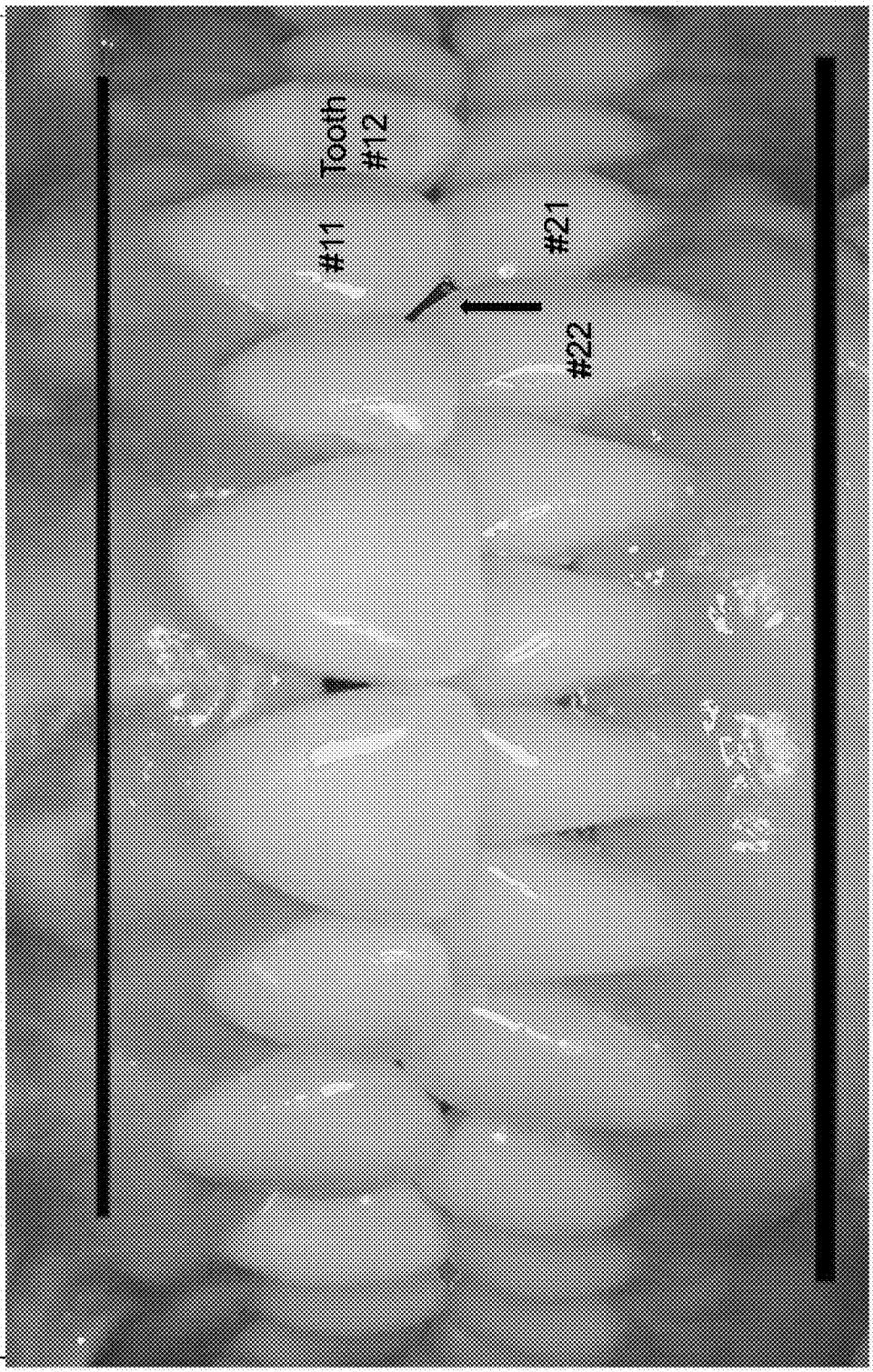

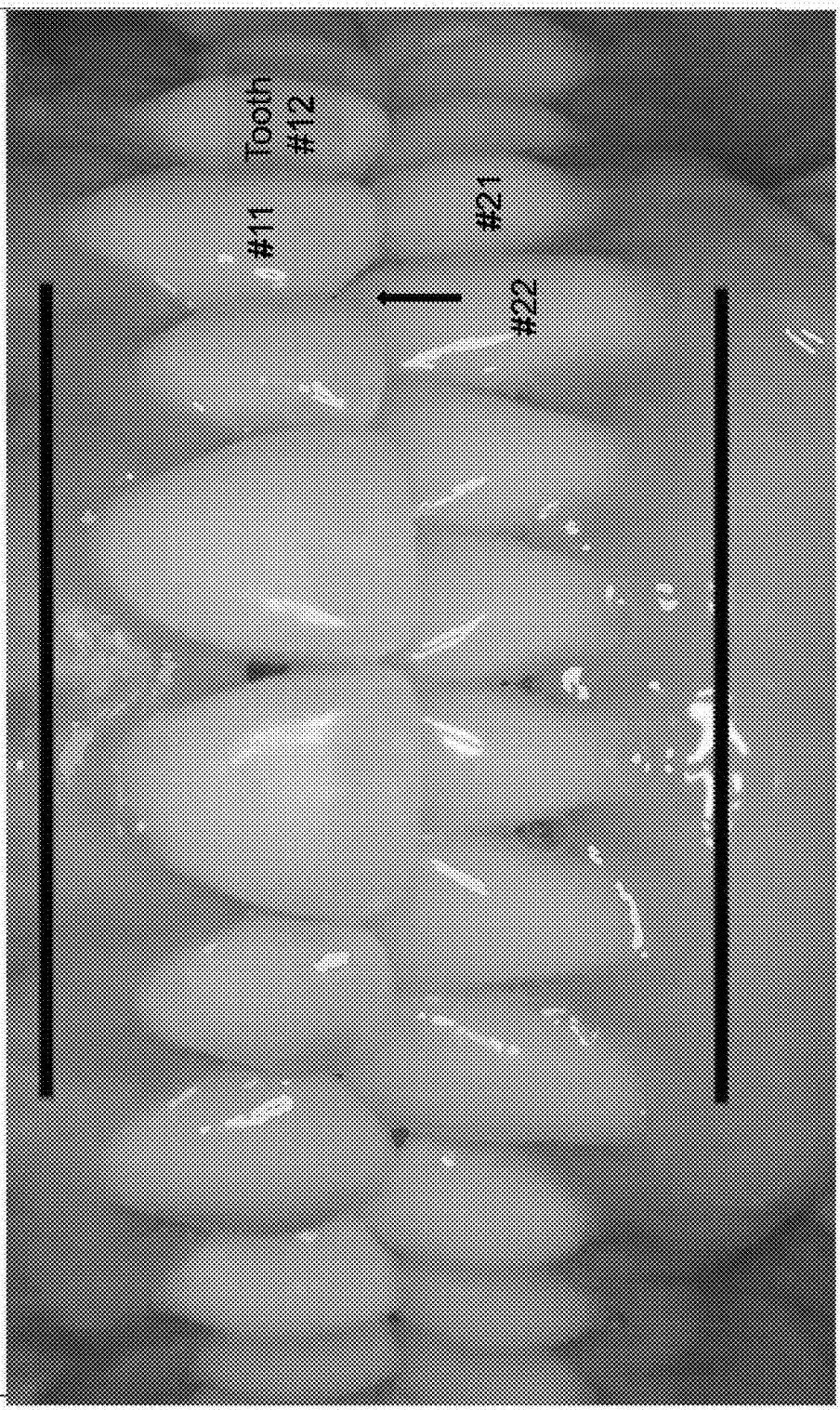
Fig. 2D: anterior view after 6 months of PT retainer usage
total therapy time = 19 months (7m aligners + 6m FT + 6m PT retainers)
Gingival Health Level III achieved

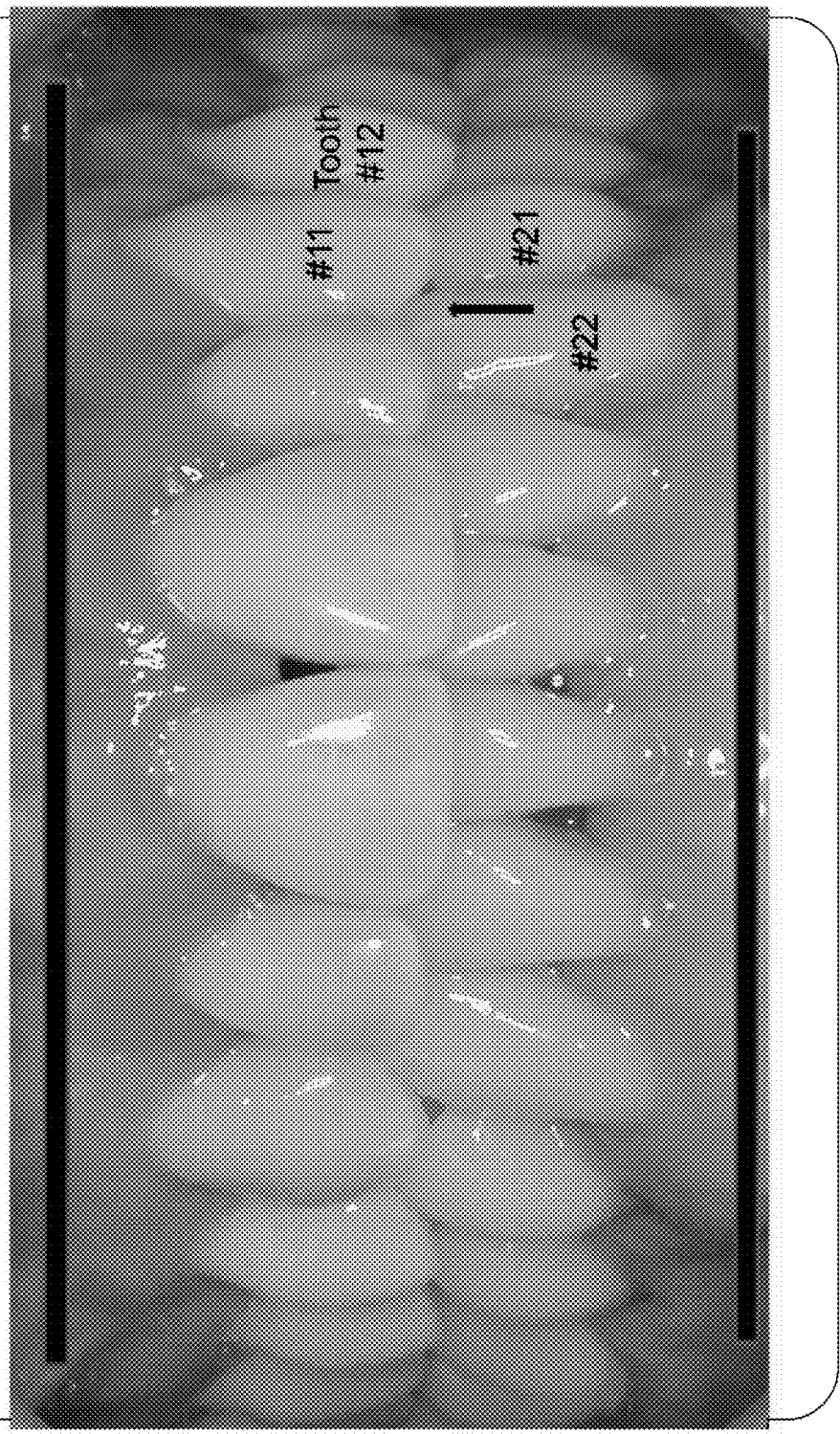
Fig. 2E: anterior view 3 years post-aligner therapy
Gingival Health Level III maintained

Fig. 2F: Levels of Gingival Health

| Month | Active Aligners Usage | Full Time Retainer Wear | Part Time Retainer Wear | Level of Gingival Health Achieved |
|---|---|---|---|---|
| 0 (Start) | | | | |
| 7 | Months 1-7 | | | Level I |
| 13 | M 1-7 | Months 8-13 | | Level II |
| 19 | M 1-7 | M 8-13 | Months 14-19 | Level III |
| 29 | M 1-7 | M 8-13 | M 14-29 | Level III |
| 44 | M 1-7 | M 8-13 | M 14-19 | Level III |

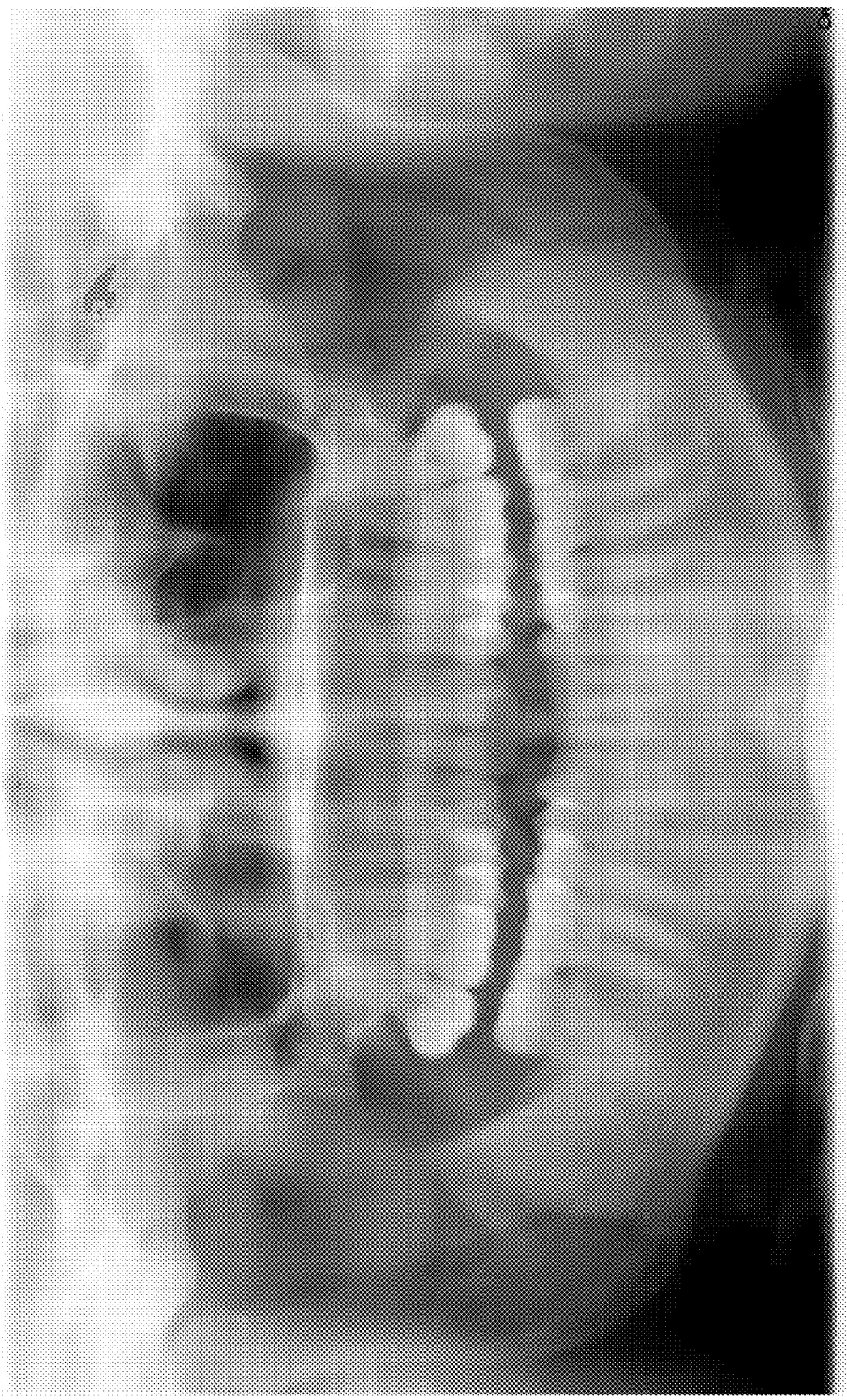
Fig. 2G: panoramic x-ray

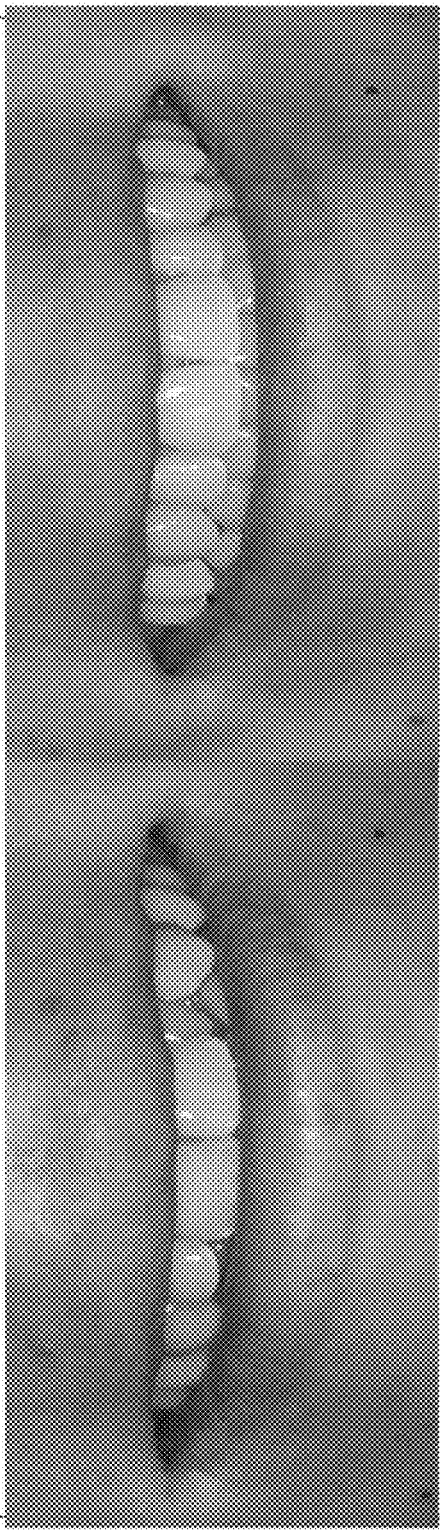
Fig. 2H: start
Fig. 2I: 7M active therapy concluded

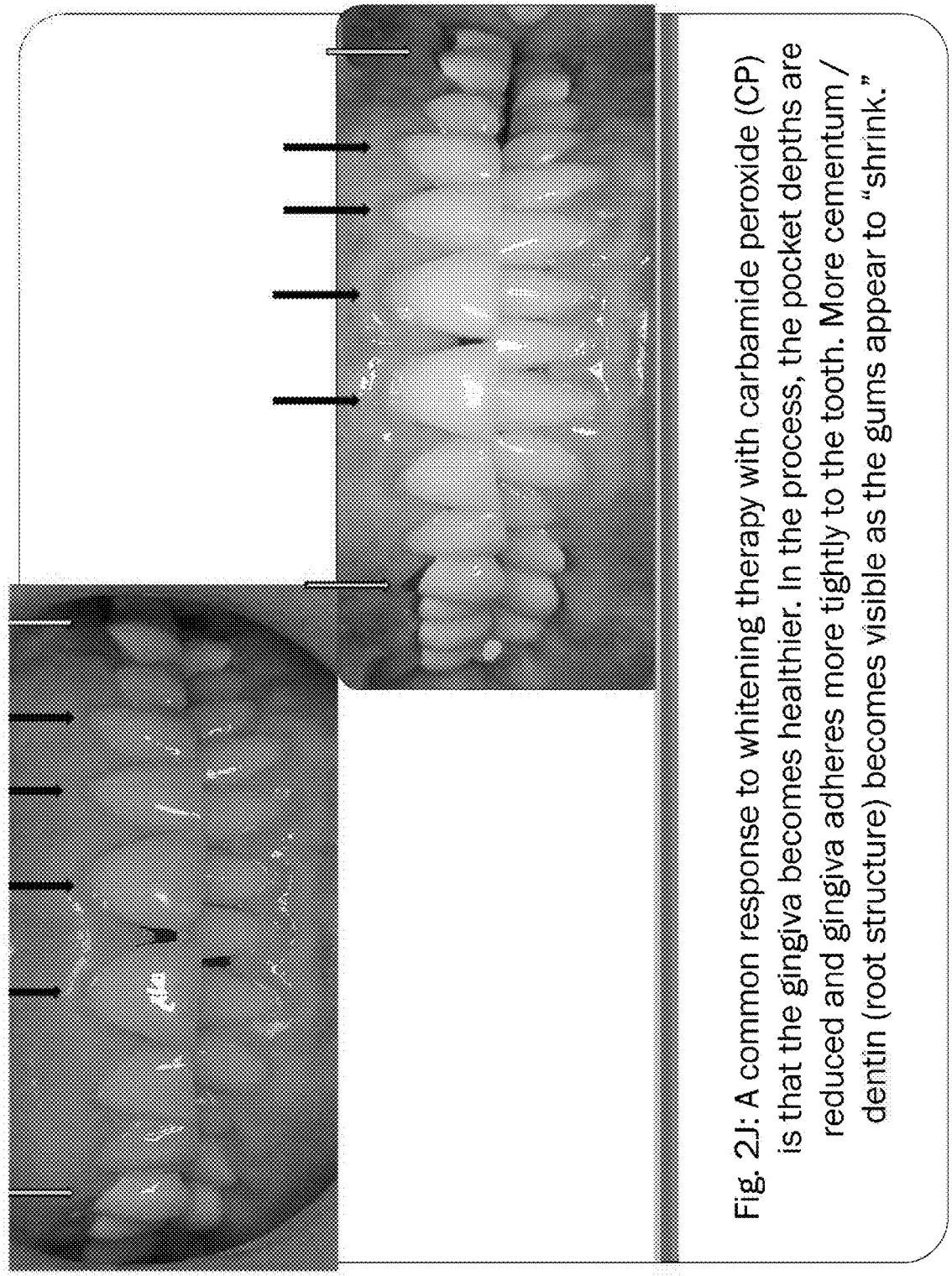
Fig. 2J: A common response to whitening therapy with carbamide peroxide (CP) is that the gingiva becomes healthier. In the process, the pocket depths are reduced and gingiva adheres more tightly to the tooth. More cementum / dentin (root structure) becomes visible as the gums appear to "shrink."

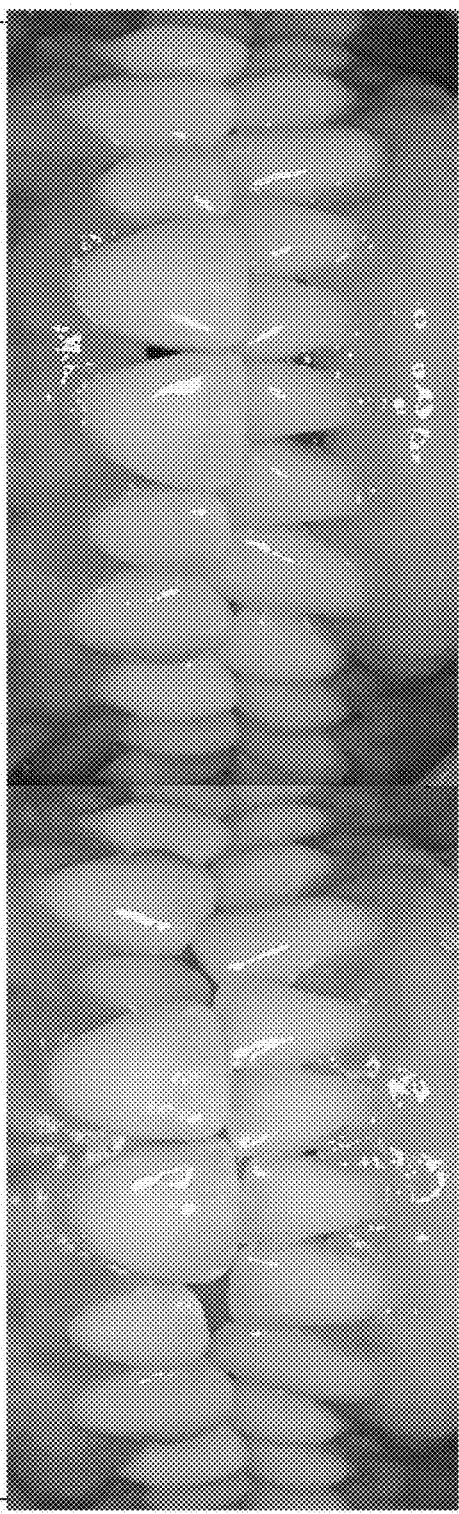
Fig. 2K: While CP was utilized as a component of the therapy, the gingiva yielded an unexpected result. Less additional root structure became exposed than would have been expected based upon findings in published dental literature.
Fig. 2A (start)
Fig. 2E (3.67 years later)

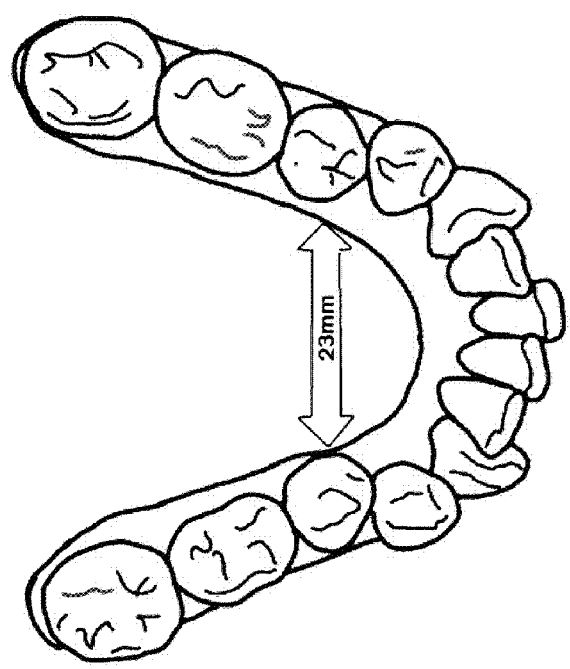

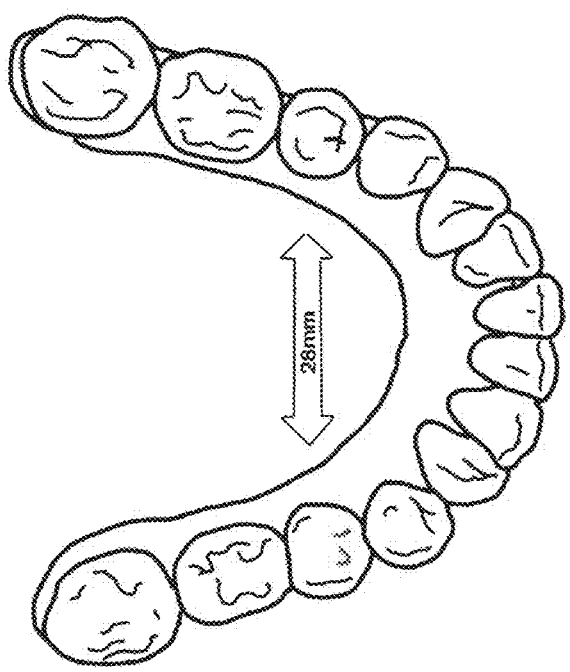
Fig. 3B: mandibular arch (intermediate progress)

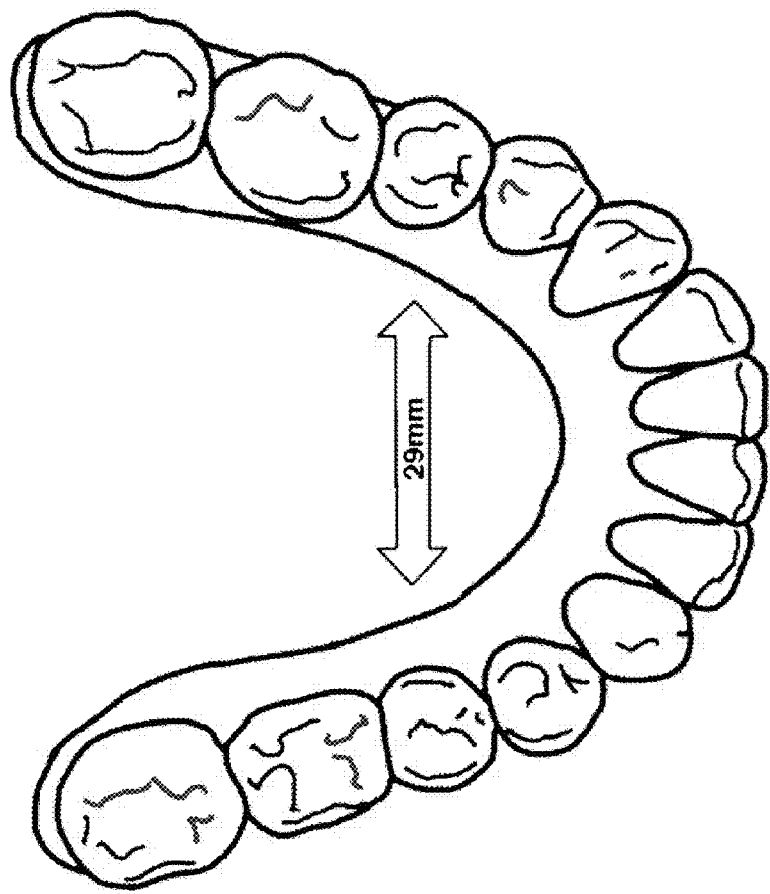
Fig. 3C: mandibular arch (projected finish)

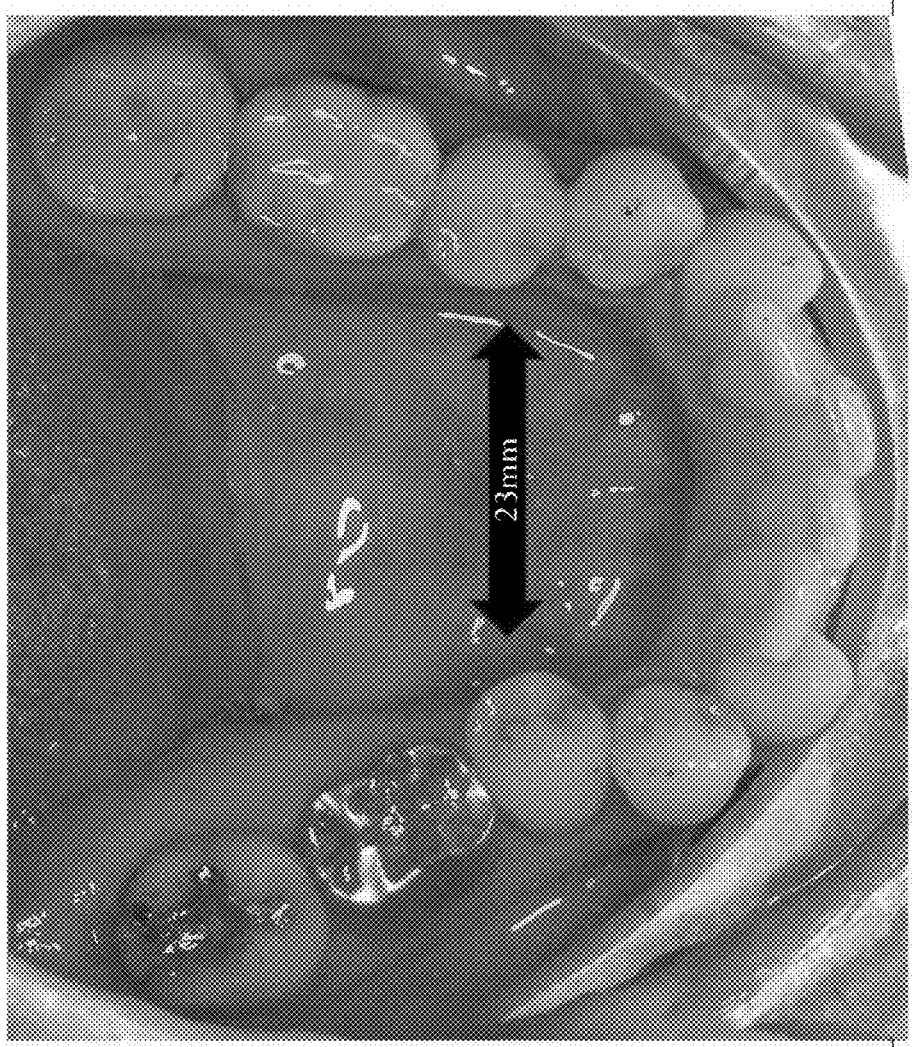
Fig. 3D: mandibular arch (start)

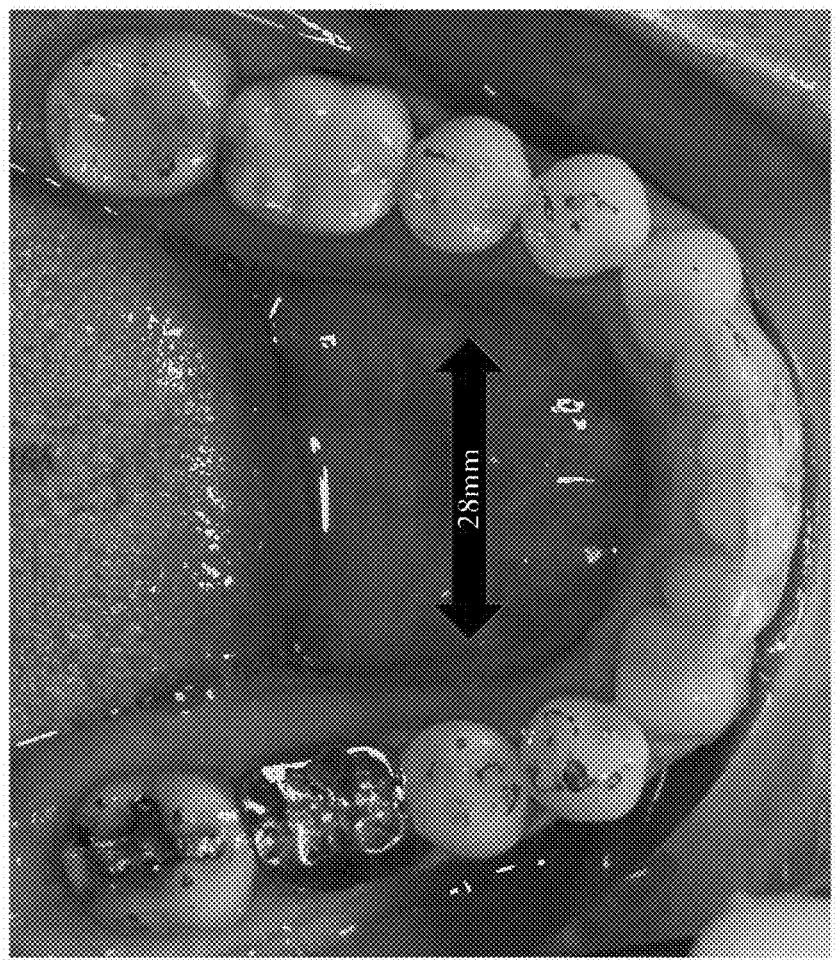
Fig. 3E: mandibular arch (intermediate view)

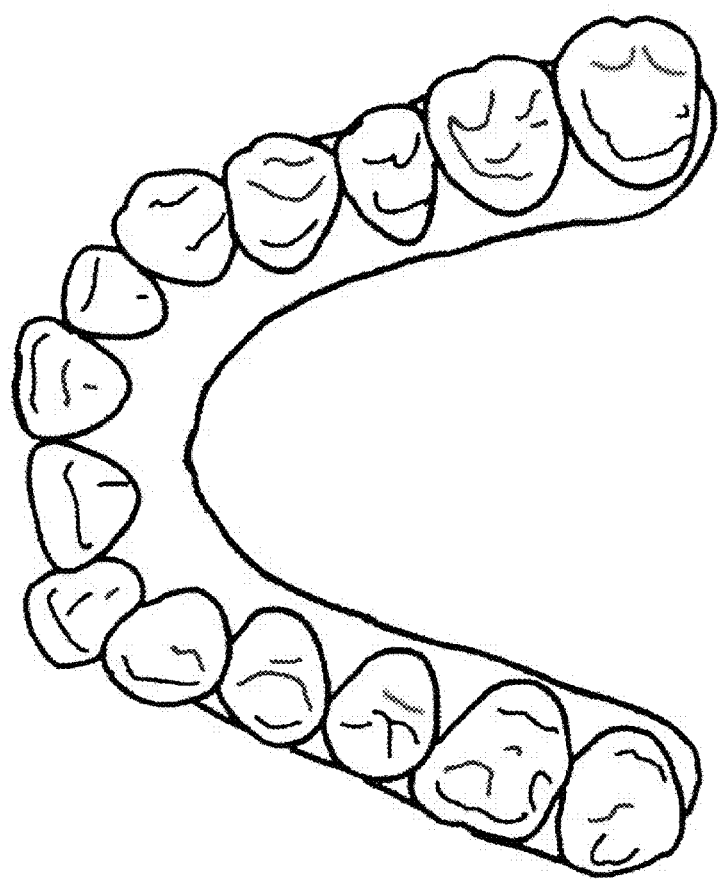
Fig. 3F: maxillary arch (start)

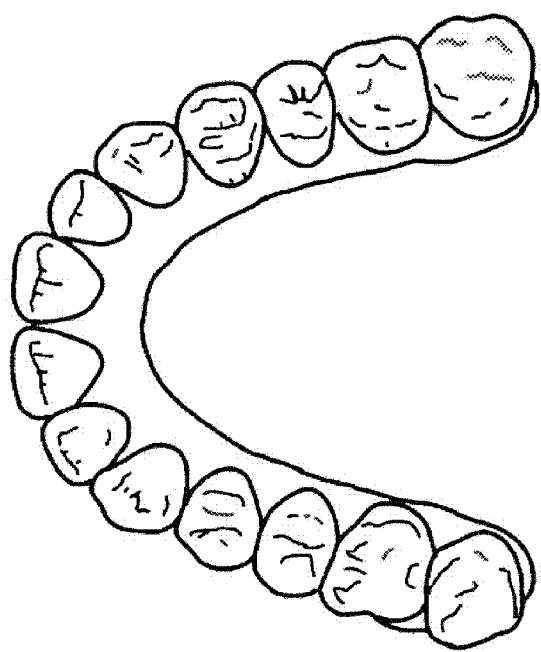
Fig. 3G: maxillary arch (midway)

Fig. 3H: maxillary arch (start)

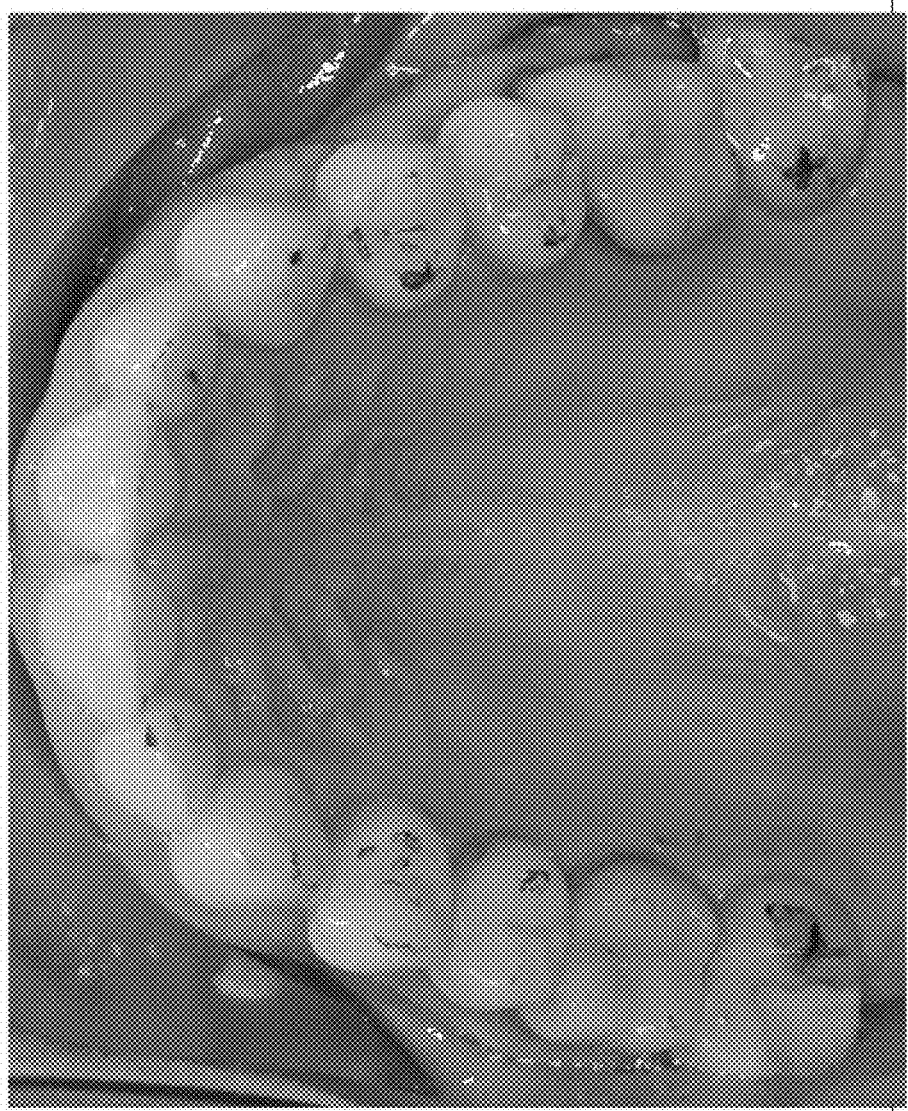
Fig. 3l: maxillary arch (midway)

Fig. 3J: smile (start)

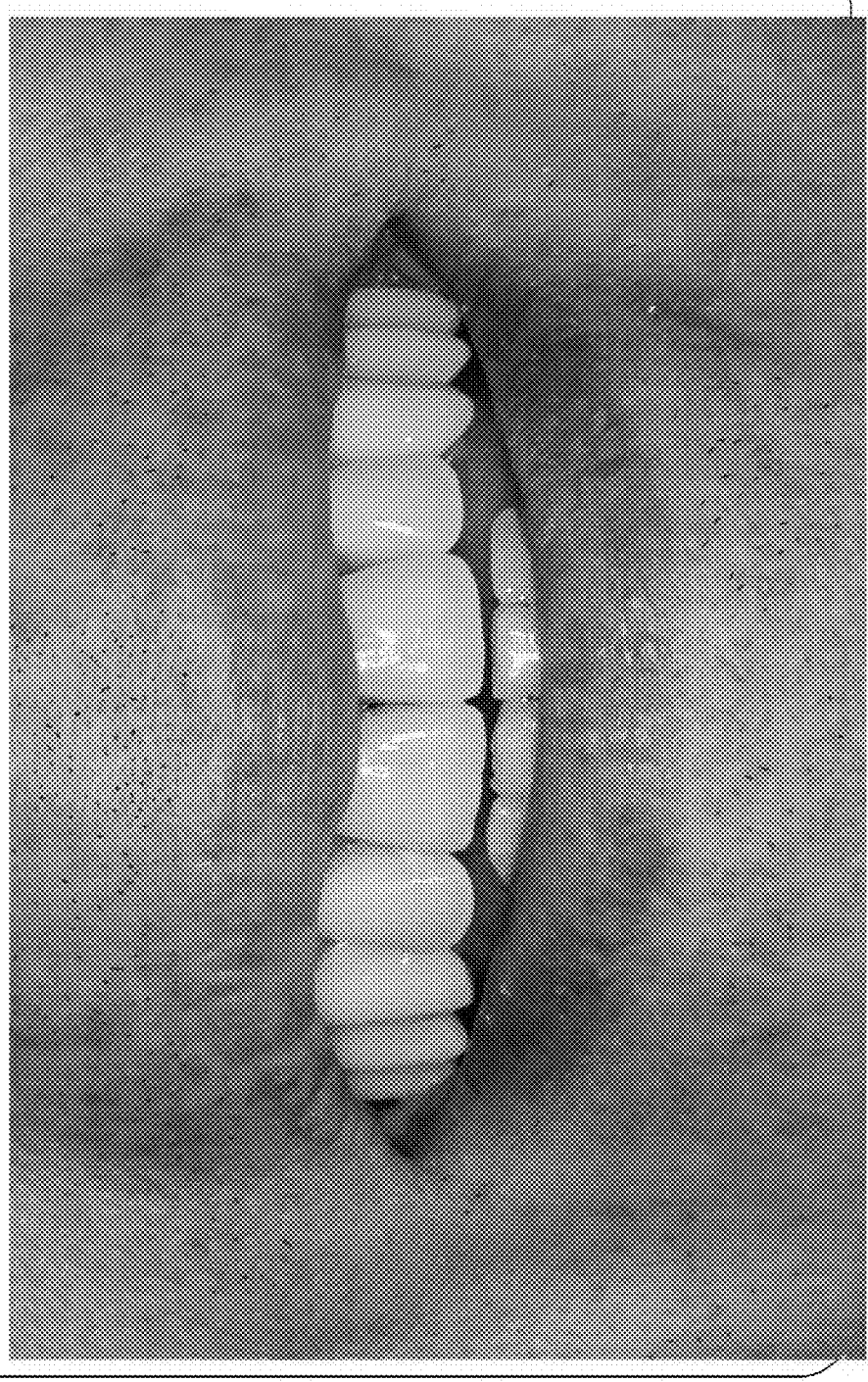
Fig. 3K: smile (midway)

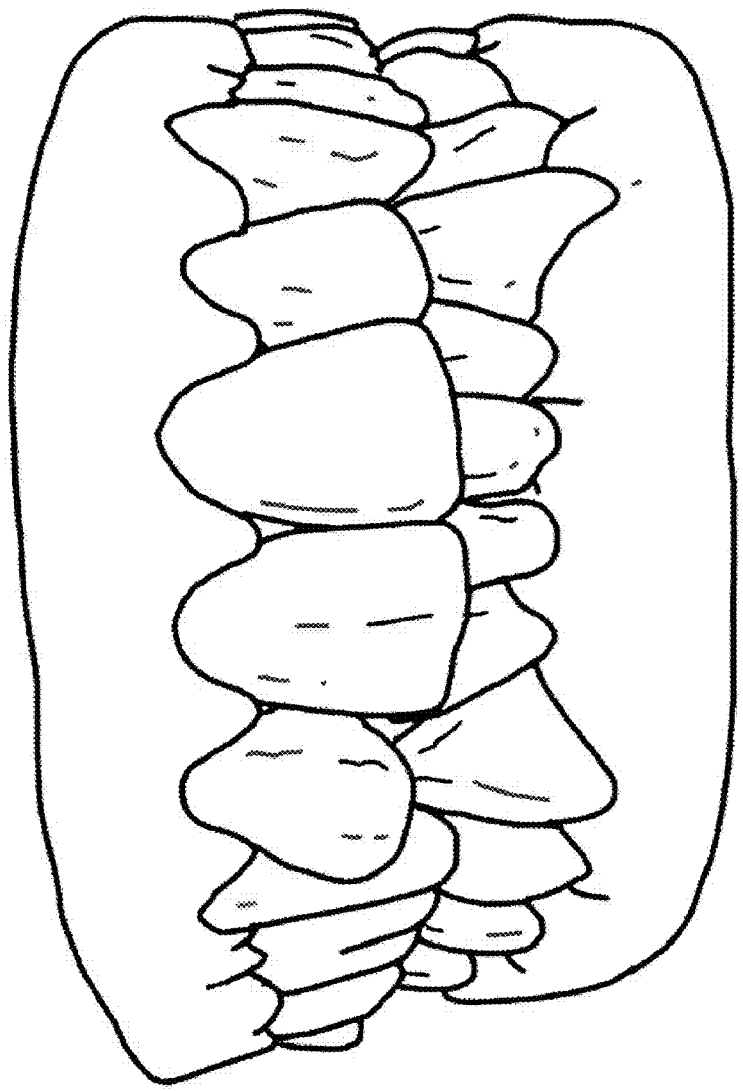
Fig. 3L: anterior (start)

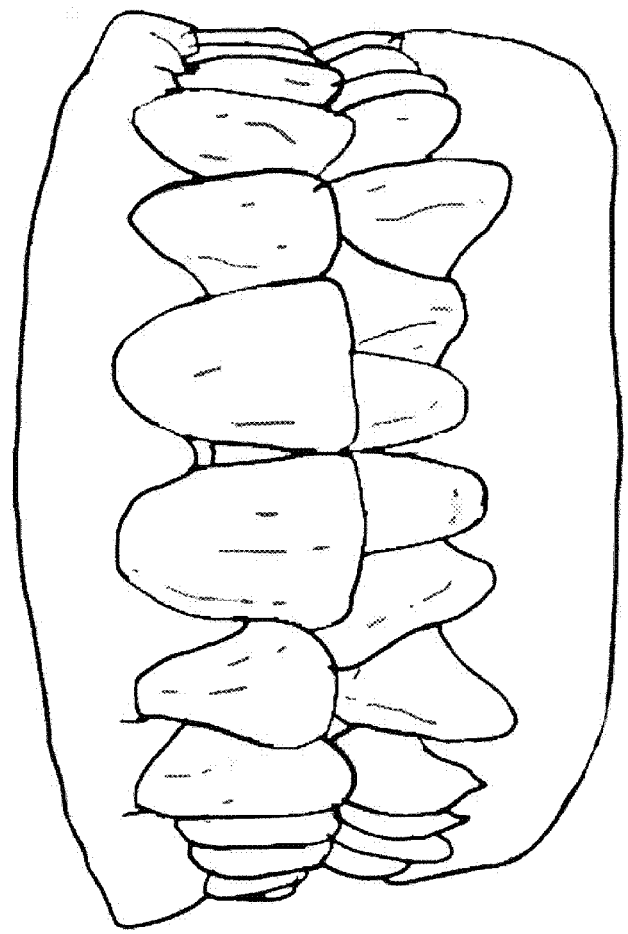
Fig. 3M: anterior (partway)

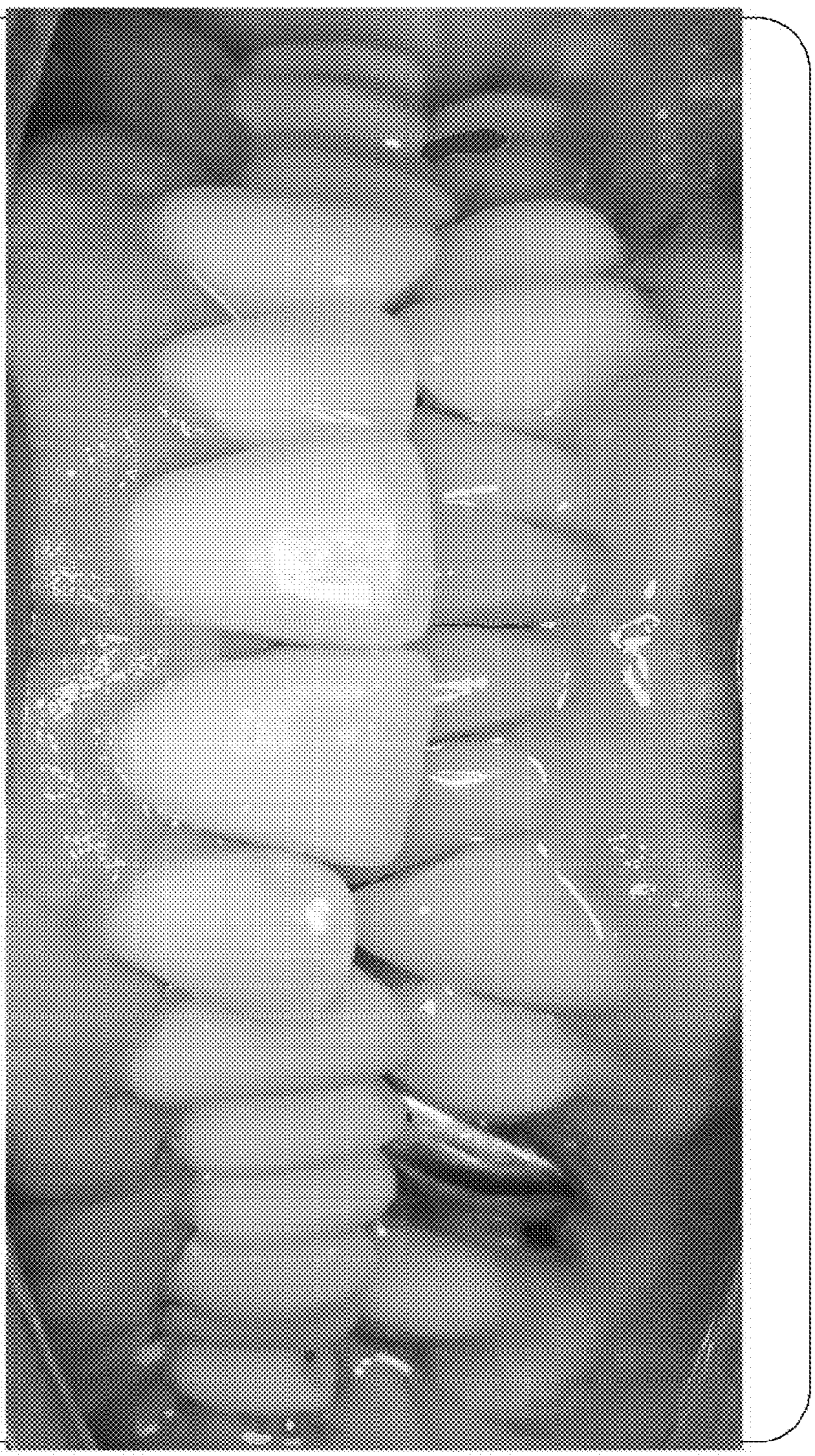
Fig. 3N: anterior (start)

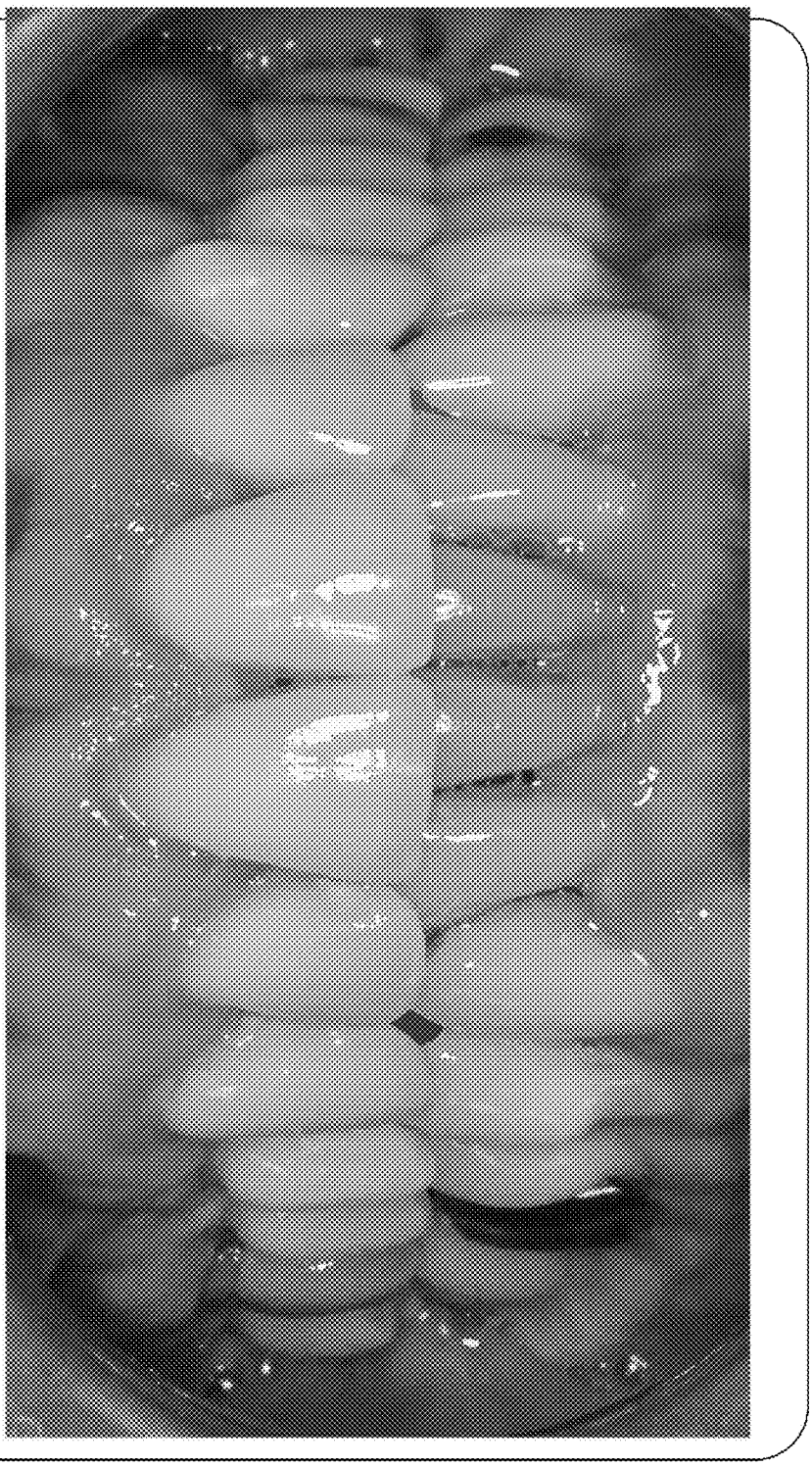
Fig. 30: anterior (partway)

Fig. 3P: Levels of Gingival Health

| Month | Active Aligners Usage | Full Time Retainer Wear | Part Time Retainer Wear | Level of Gingival Health Achieved |
|---|---|---|---|---|
| 0 (Start) | | | | |
| 13 | ongoing | | | Level I |
| 24 | ongoing | | | Level I |

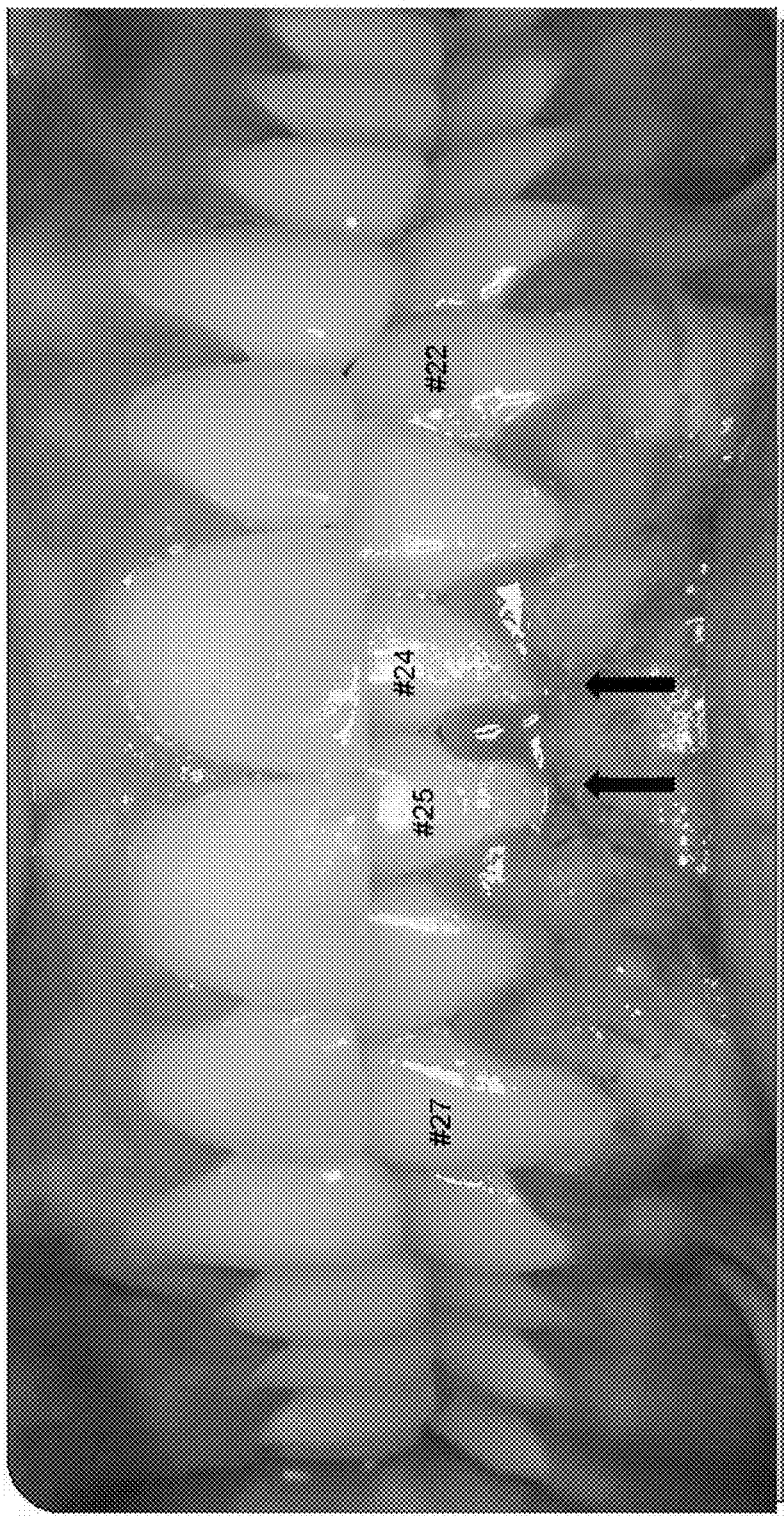
Fig. 4A: The 3rd patient has chronic malocclusion. Key indicators include: exposed cementum in 3 of the 4 posterior regions (UL, UR, LR) and hyperemic gingiva in the mandibular anterior. The patient declined periodontally purposed orthodontic and arch reformulation therapy.

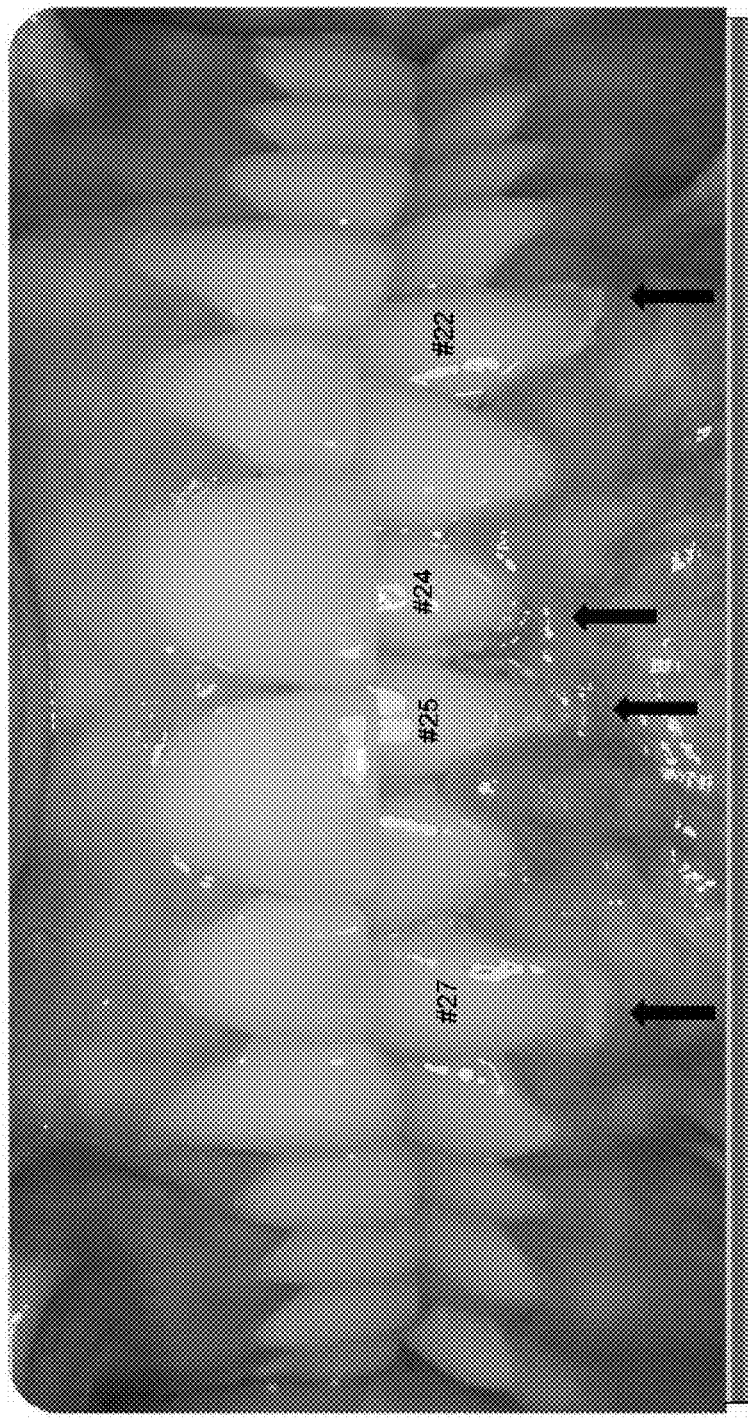

Fig. 4B: 13 months later

The oral condition has declined. The new diagnosis is moderate periodontitis secondary to an acute episode of chronic malocclusion. The mandibular anterior region shows quantitative and qualitative signs of alveolar bone loss. Treatment considerations: periodontal grafting surgery and/or periodontally purposed orthodontic and arch reformulation therapy.

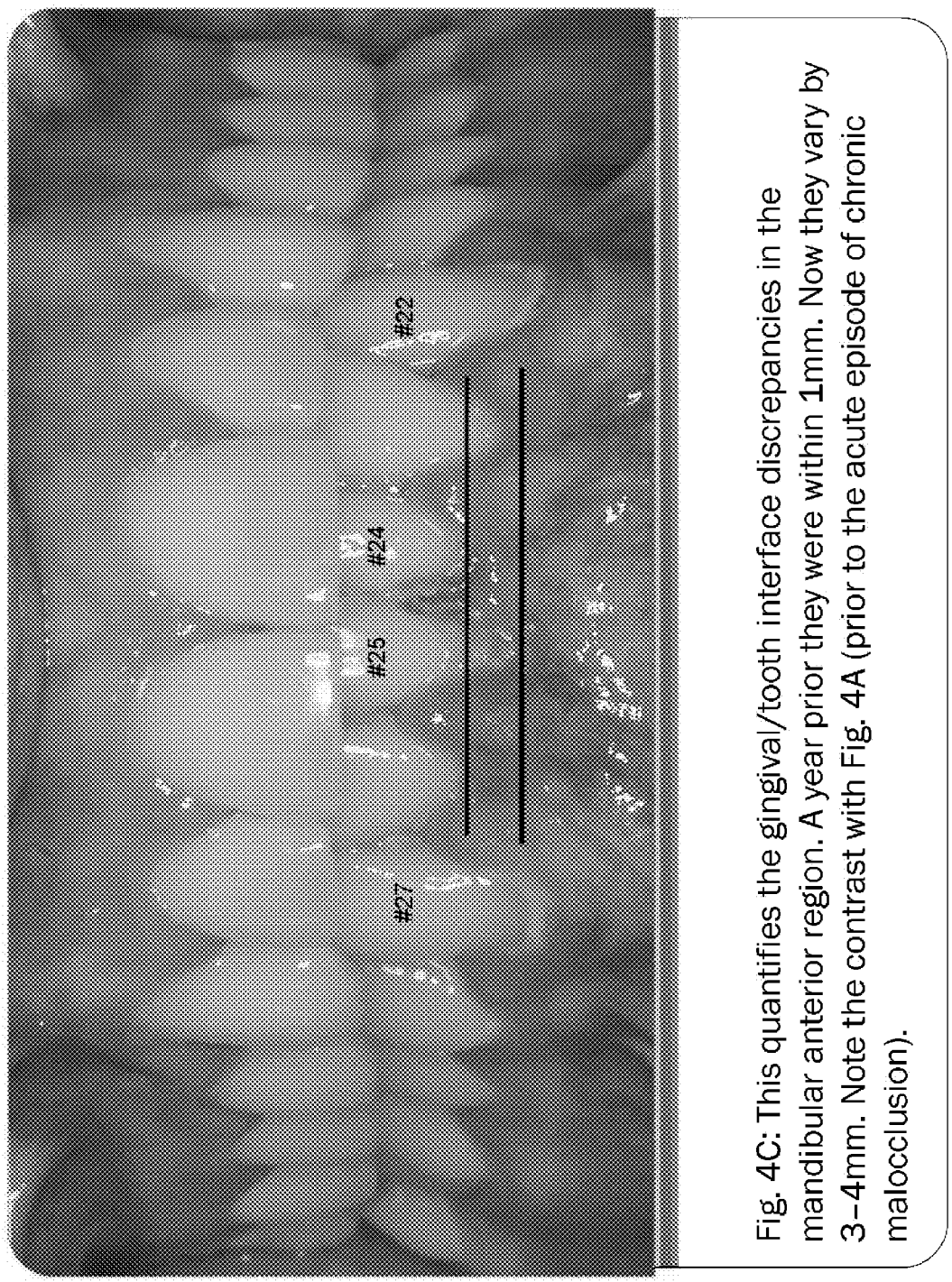
Fig. 4C: This quantifies the gingival/tooth interface discrepancies in the mandibular anterior region. A year prior they were within 1mm. Now they vary by 3-4mm. Note the contrast with Fig. 4A (prior to the acute episode of chronic malocclusion).

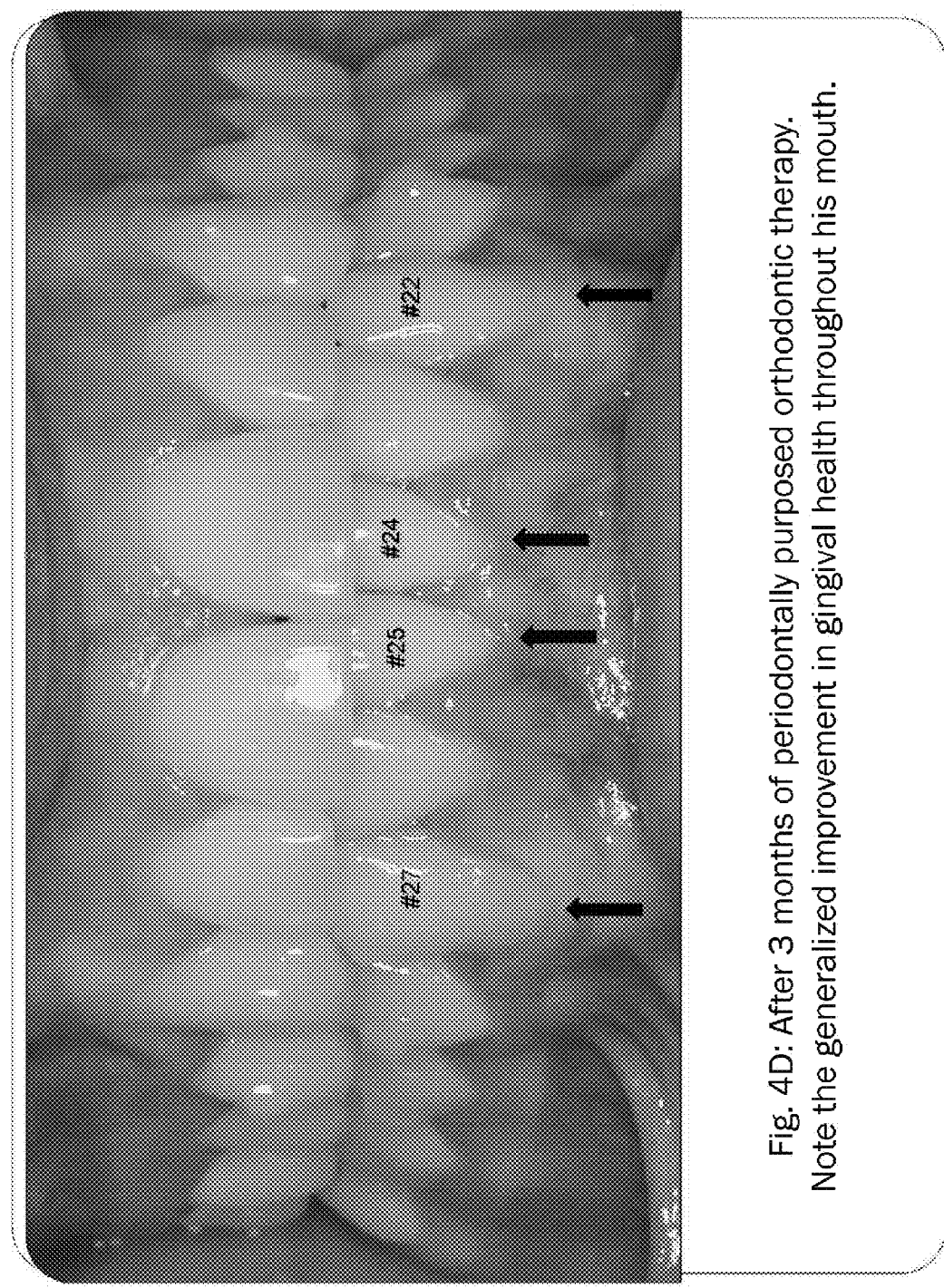
Fig. 4D: After 3 months of periodontally purposed orthodontic therapy. Note the generalized improvement in gingival health throughout his mouth.

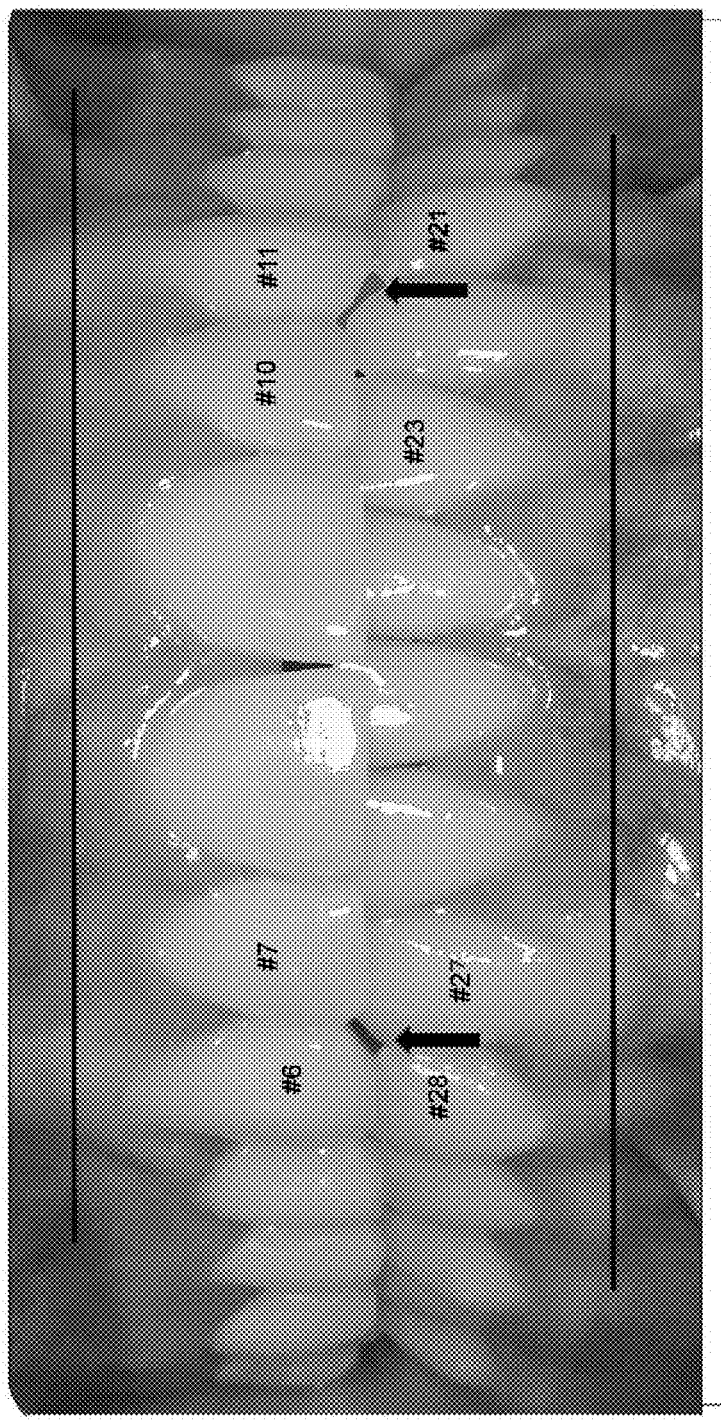
Fig. 4E: 10 months of active therapy
The maturation of the gingiva throughout his mouth at the conclusion of the Active Phase of periodontally purposed orthodontic and arch reformulation therapy is evident. The number of areas possessing inflamed gingiva have been reduced.

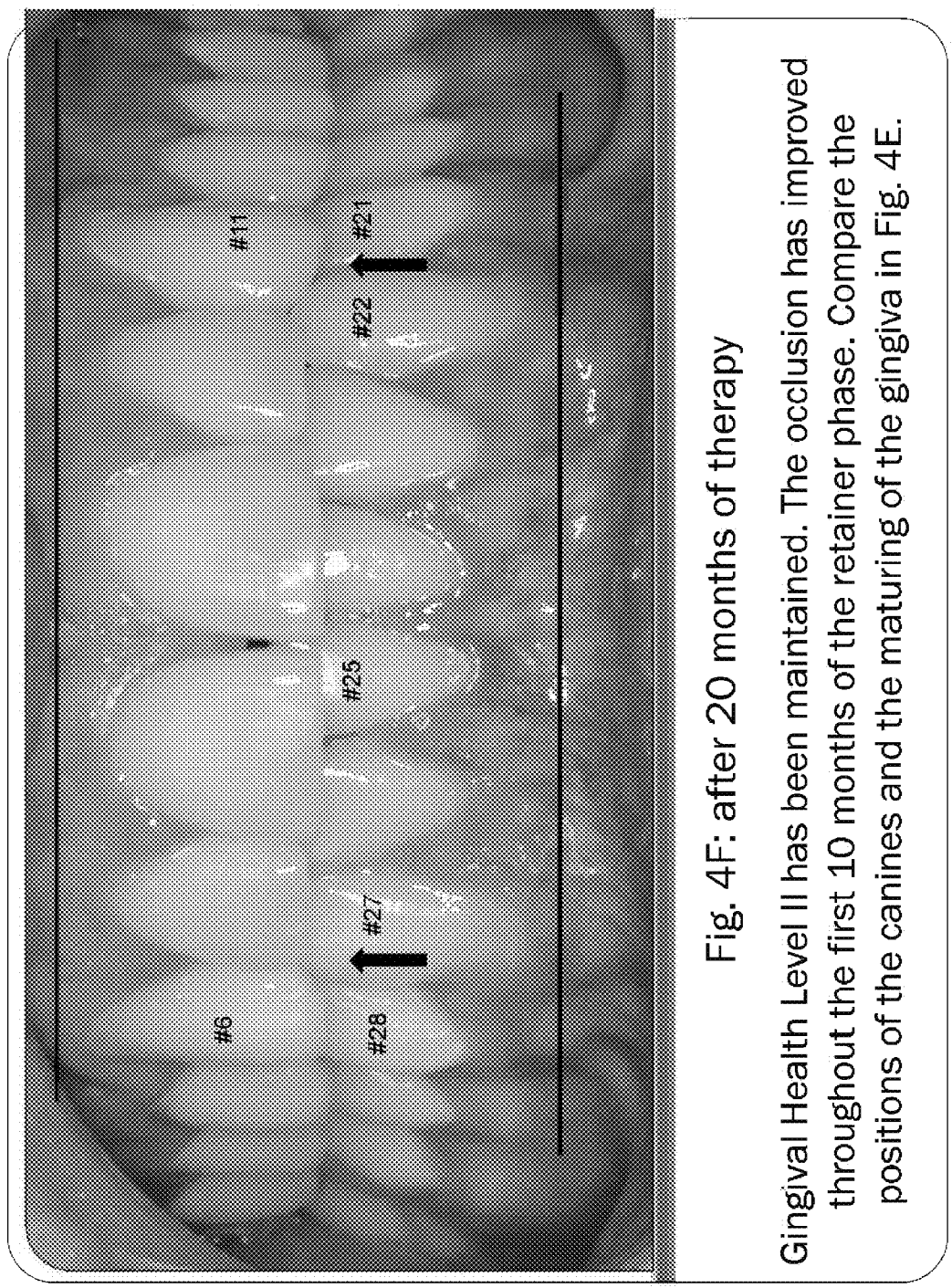
Fig. 4F: after 20 months of therapy
Gingival Health Level II has been maintained. The occlusion has improved throughout the first 10 months of the retainer phase. Compare the positions of the canines and the maturing of the gingiva in Fig. 4E.

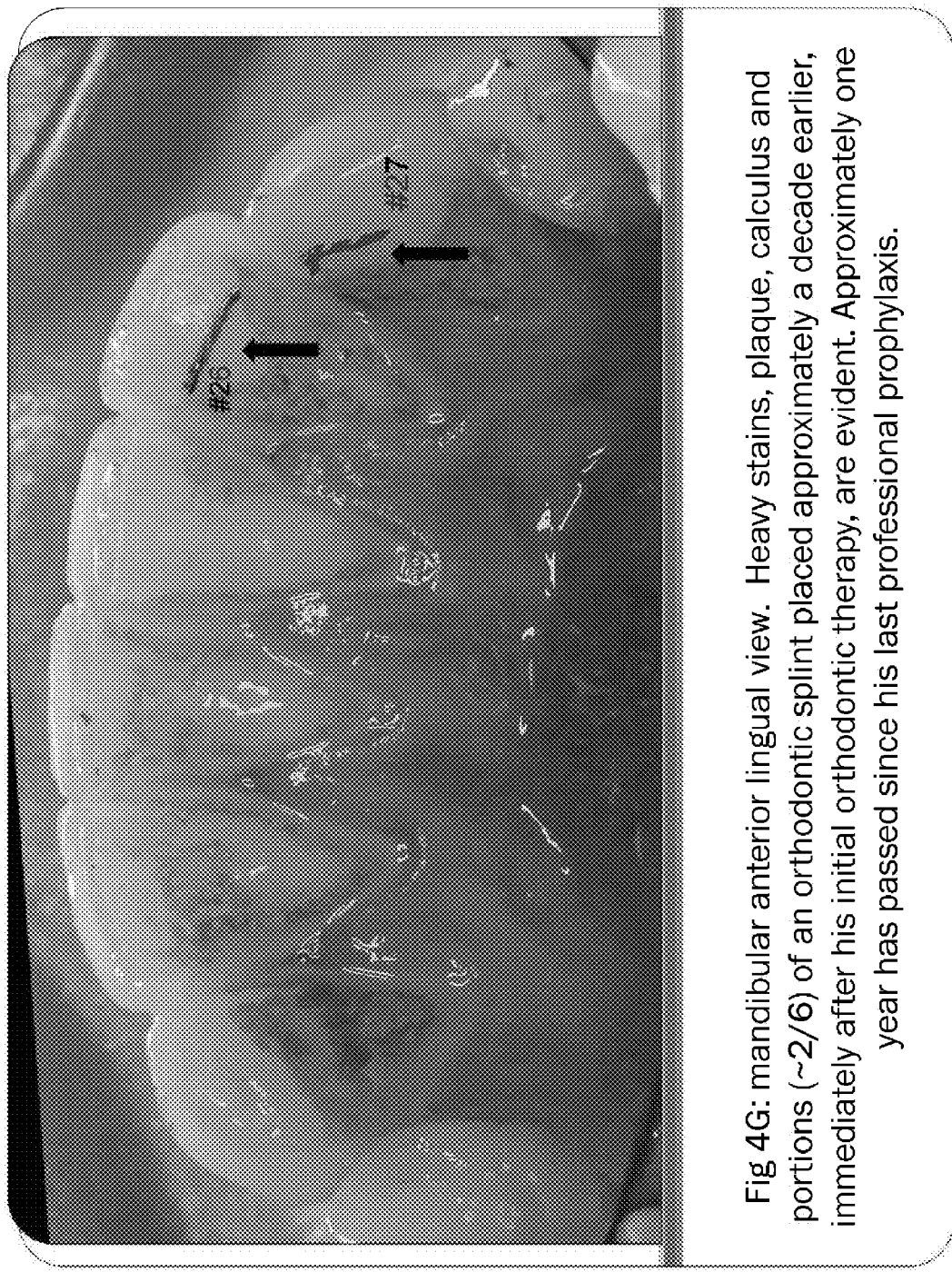
Fig 4G: mandibular anterior lingual view. Heavy stains, plaque, calculus and portions (~2/6) of an orthodontic splint placed approximately a decade earlier, immediately after his initial orthodontic therapy, are evident. Approximately one year has passed since his last professional prophylaxis.

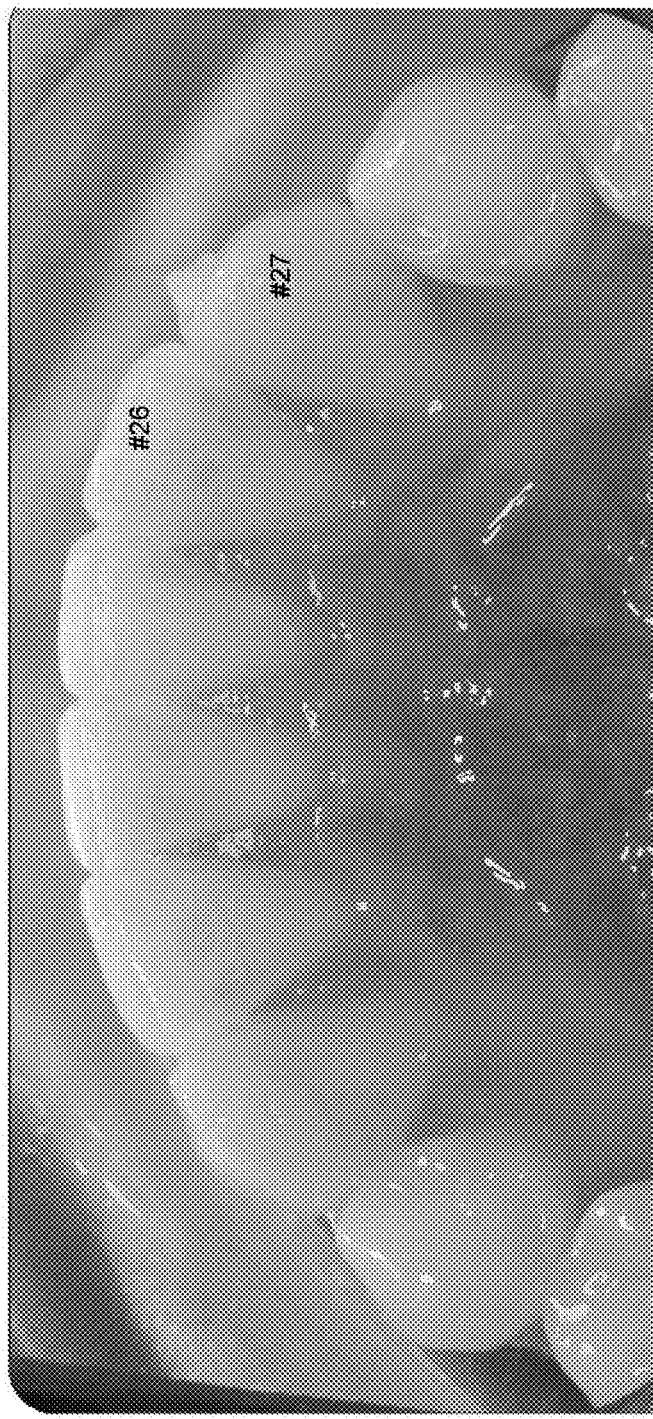
Fig 4H: mandibular anterior lingual view: 7 months into the periodontally purposed therapy and 4.5 months since his last oral prophylaxis. Note the reduced amount of residue, plaque and stain accumulation and the improved health of the gingival tissue (Fig. 4H/4G), a positive response to and confirmation of the success of the arch reformulation therapy.

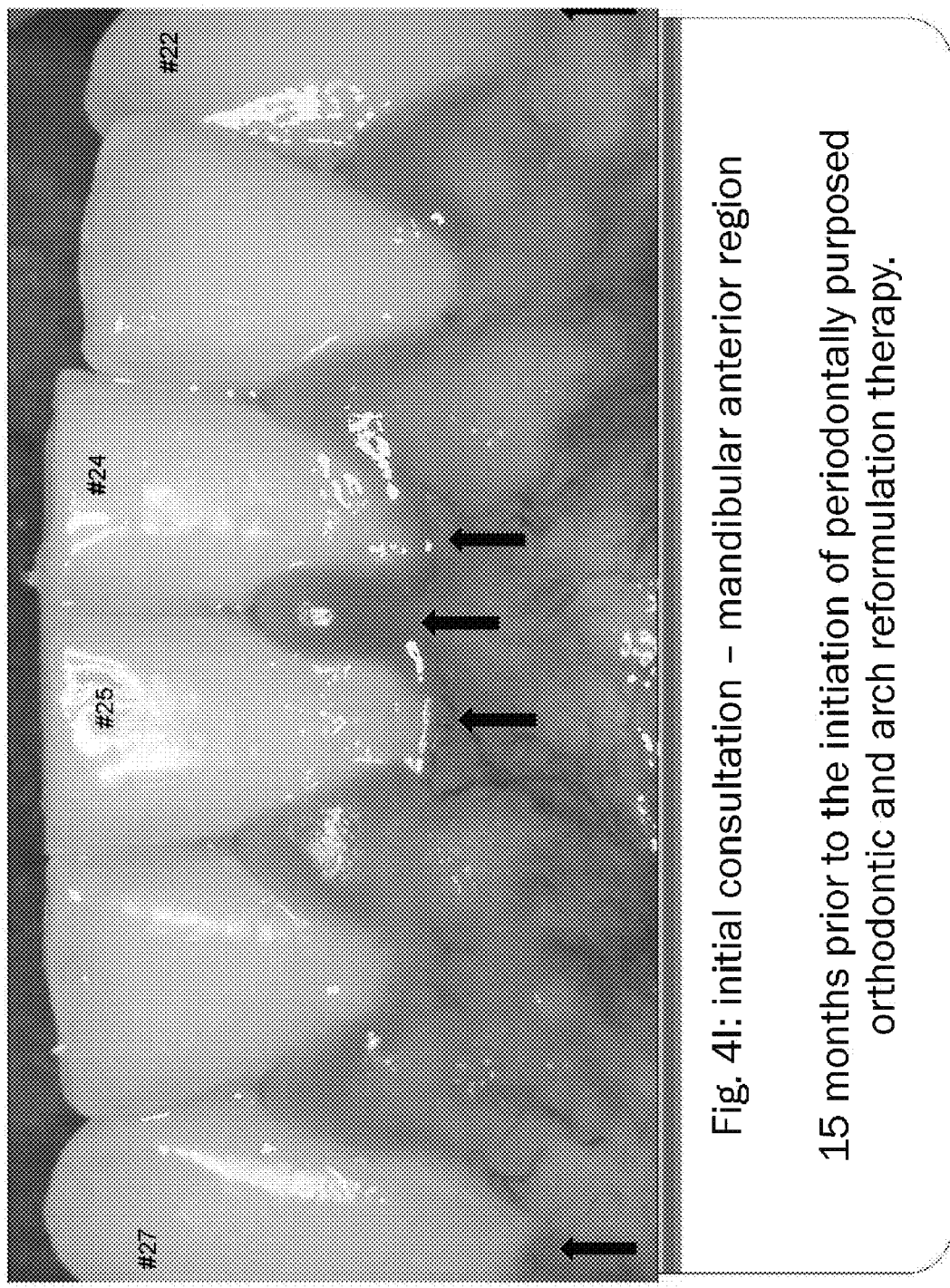
Fig. 4I: initial consultation – mandibular anterior region
15 months prior to the initiation of periodontally purposed orthodontic and arch reformulation therapy.

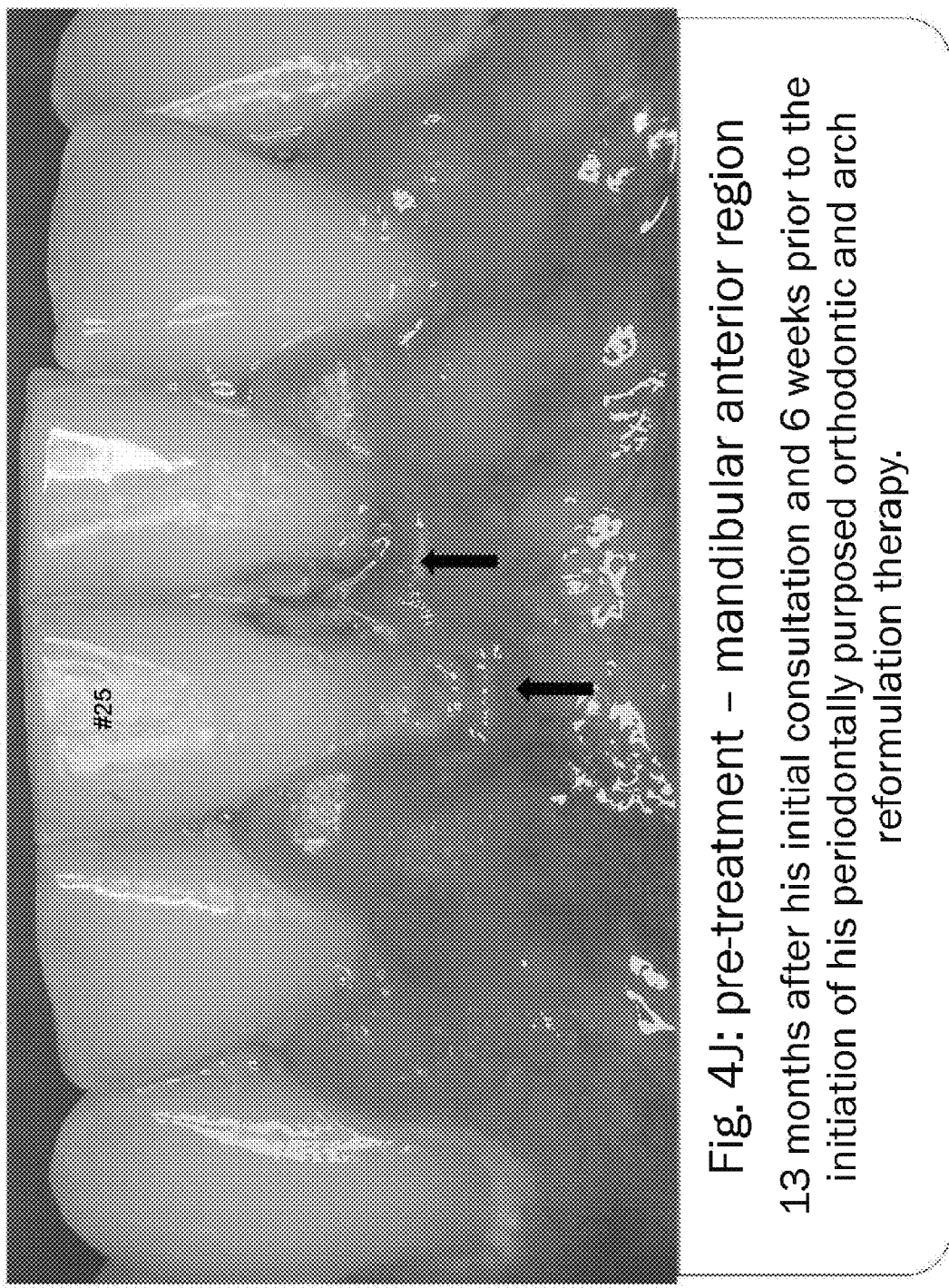
Fig. 4J: pre-treatment – mandibular anterior region
13 months after his initial consultation and 6 weeks prior to the initiation of his periodontally purposed orthodontic and arch reformulation therapy.

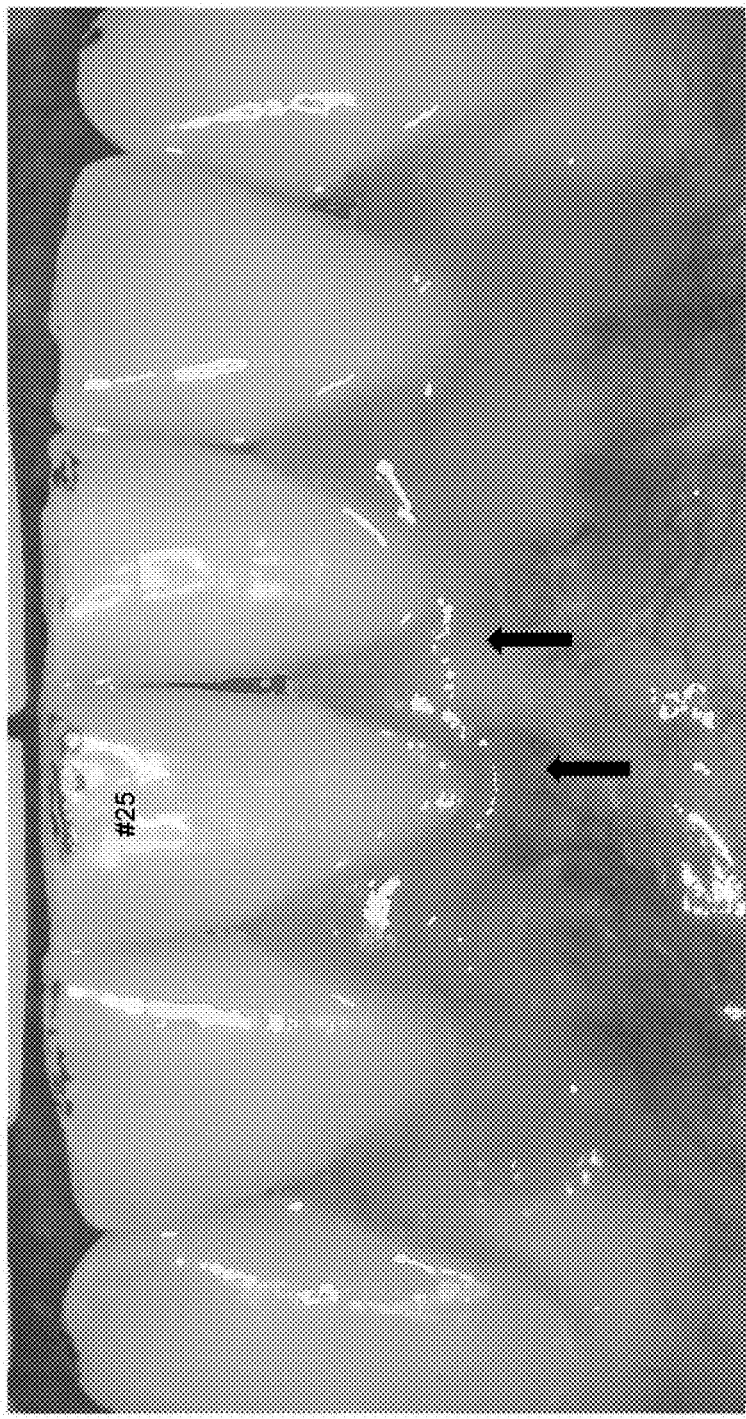
Fig. 4K: 3 months into treatment
The repositioning of the teeth has lead to an improved arch form, better occlusal force distribution and the deposition of new alveolar bone and gingival tissues. Traditional periodontal gingival grafting procedures are not intended to induced bone growth. Gingival Health Level I has been achieved.

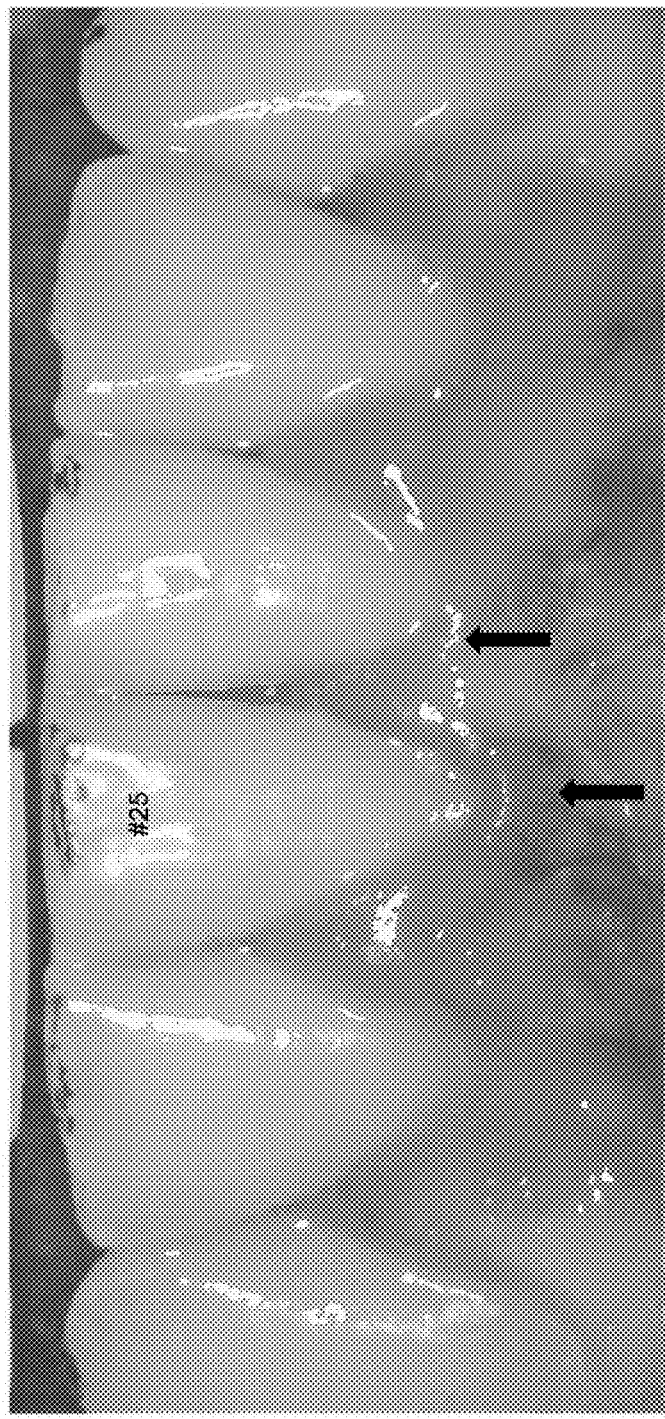
Fig. 4L: 5 months into treatment
Healing of the periodontium is continuing to progress nicely.

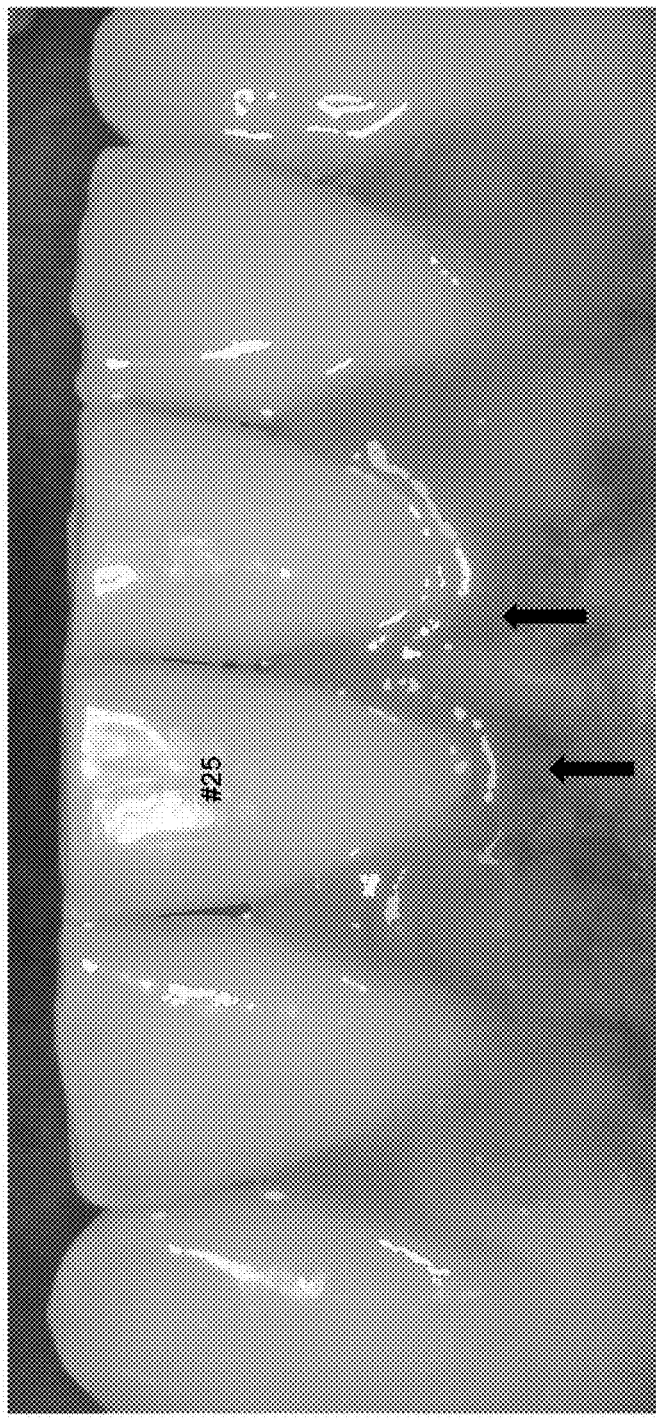
Fig. 4M: 10 months of treatment
The ongoing and desired maturation confirms the improvement of the health of the gingival tissues. Gingival Health Level II has been achieved. 7.5 months have progressed since his most recent prophylaxis.

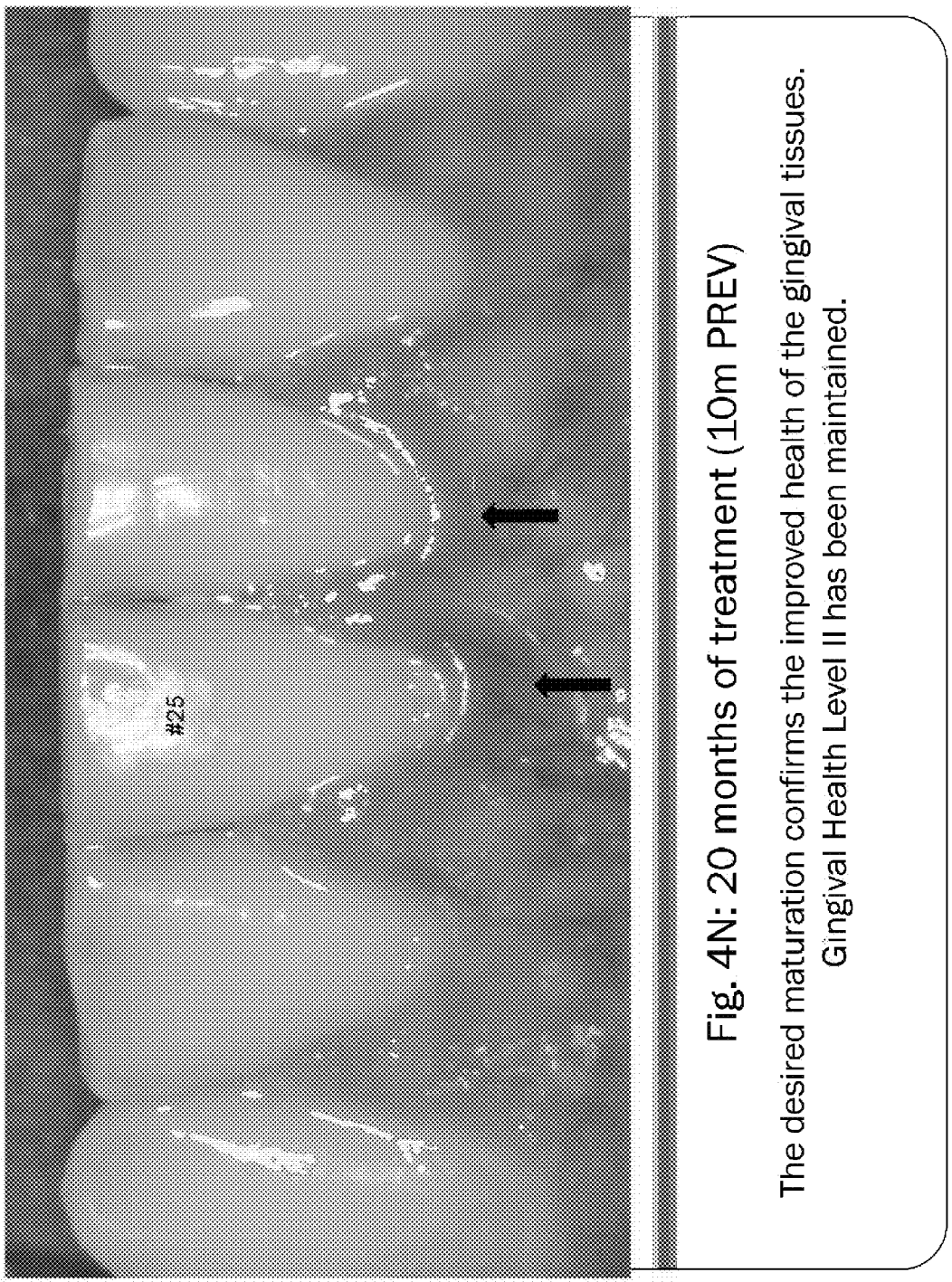
Fig. 4N: 20 months of treatment (10m PREV)
The desired maturation confirms the improved health of the gingival tissues. Gingival Health Level II has been maintained.

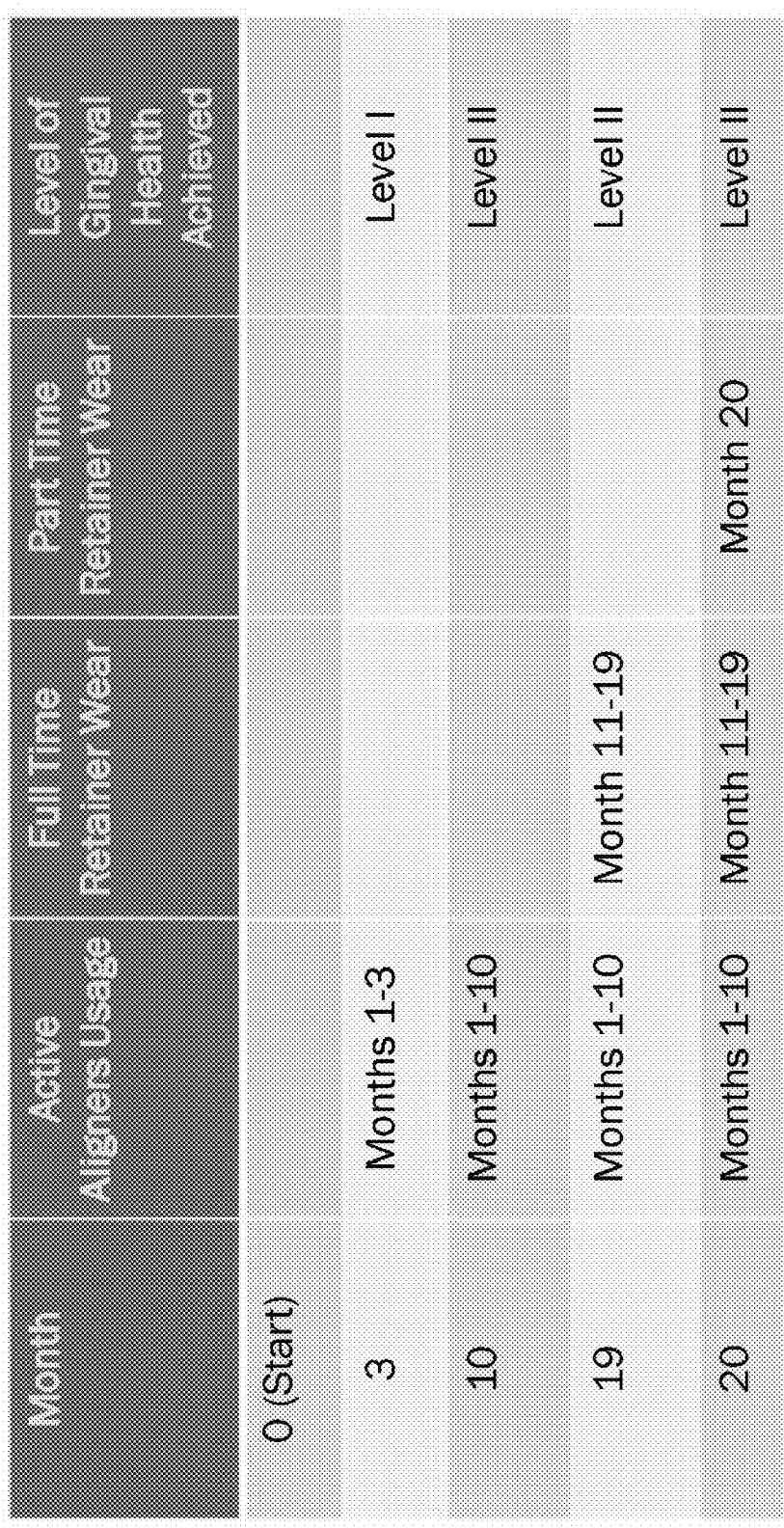

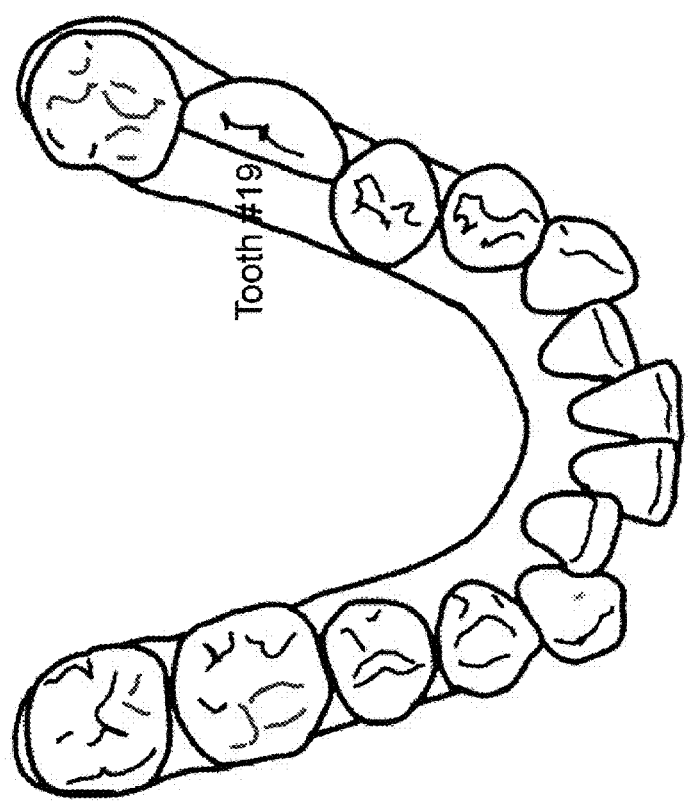
Fig 5A: mandibular arch (start)

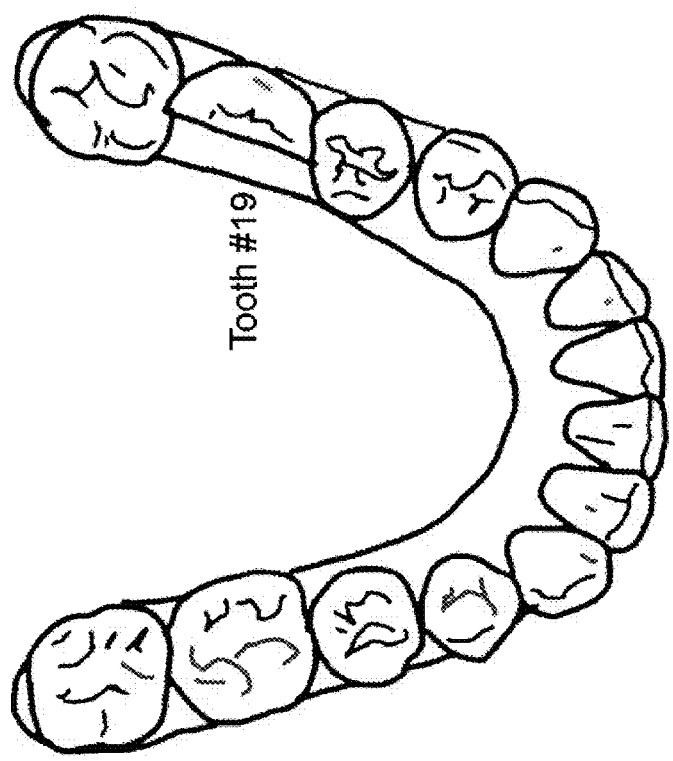
Fig. 5B: mandibular arch (projected finish)

Fig. 5C: mandibular arch (start)

Fig. 5D: active therapy at 5 months

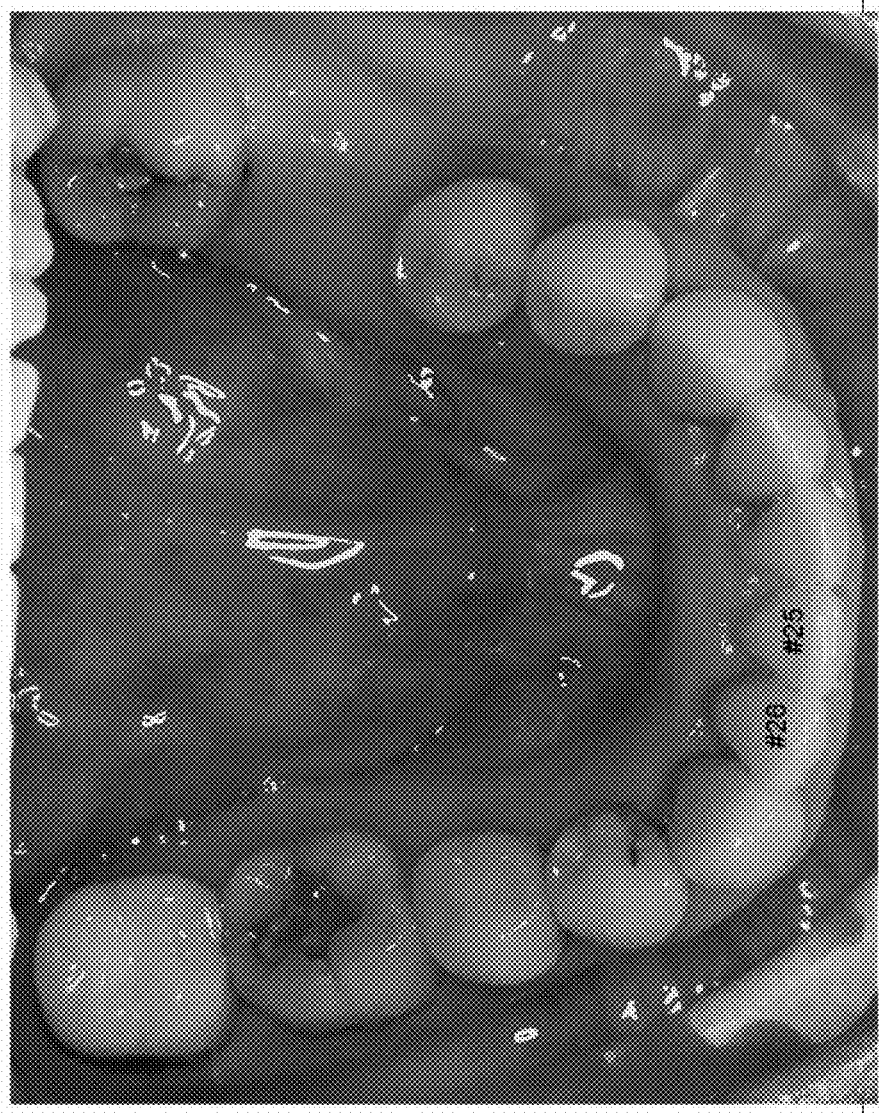
Fig. 5E: month 9 – end of active therapy

Fig. 5F: 18 months PREV (PT retainer 12m)

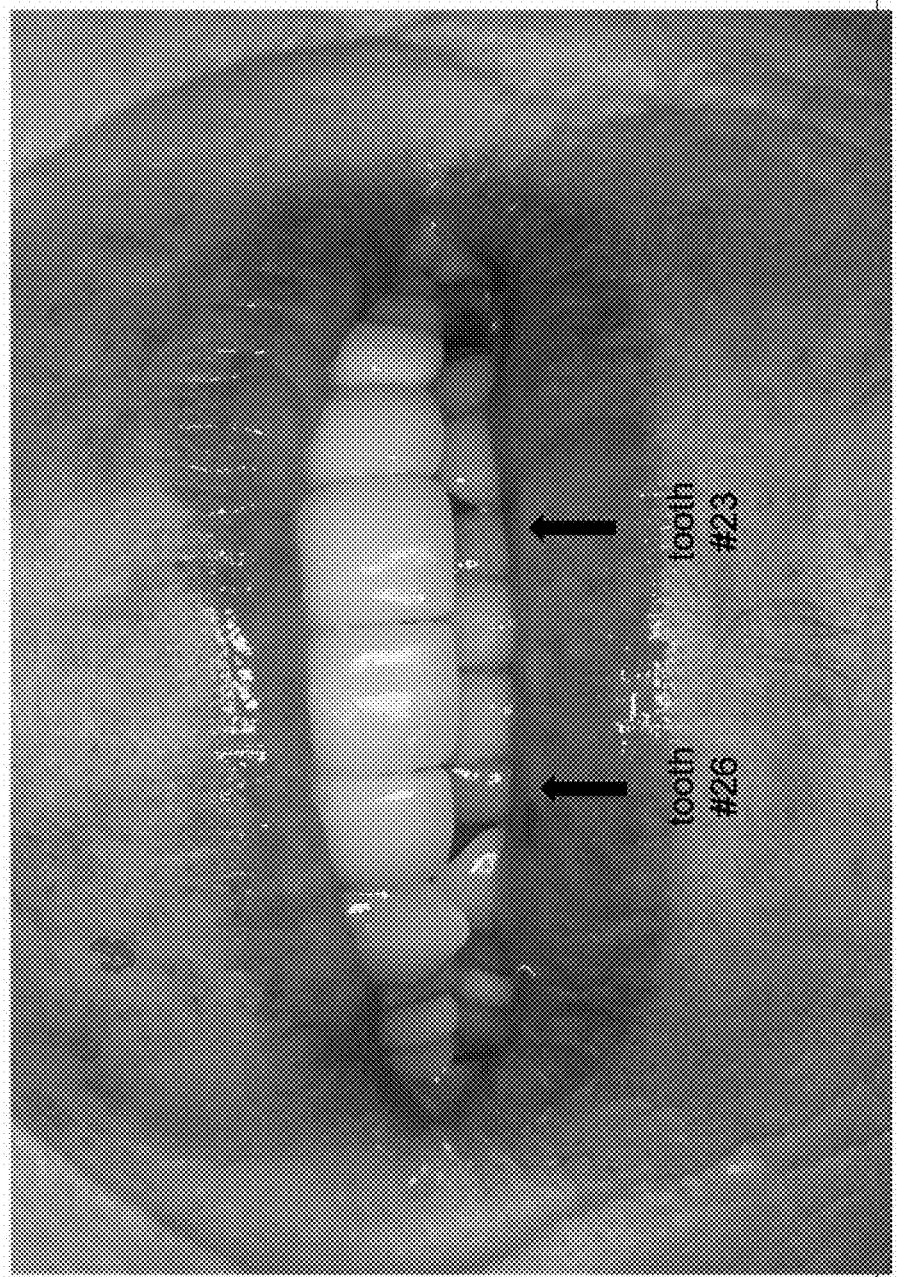

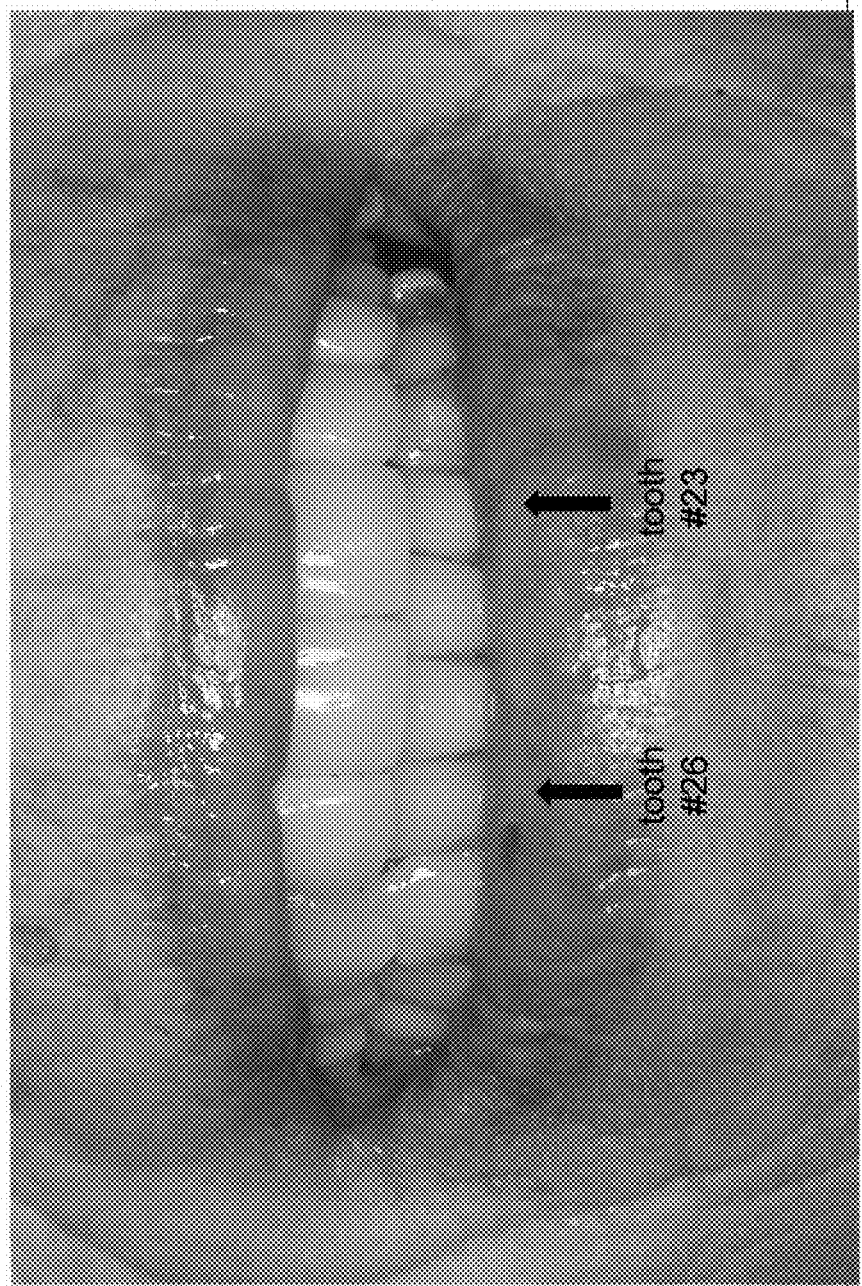
Fig. 5H: smile – month 9 active therapy complete

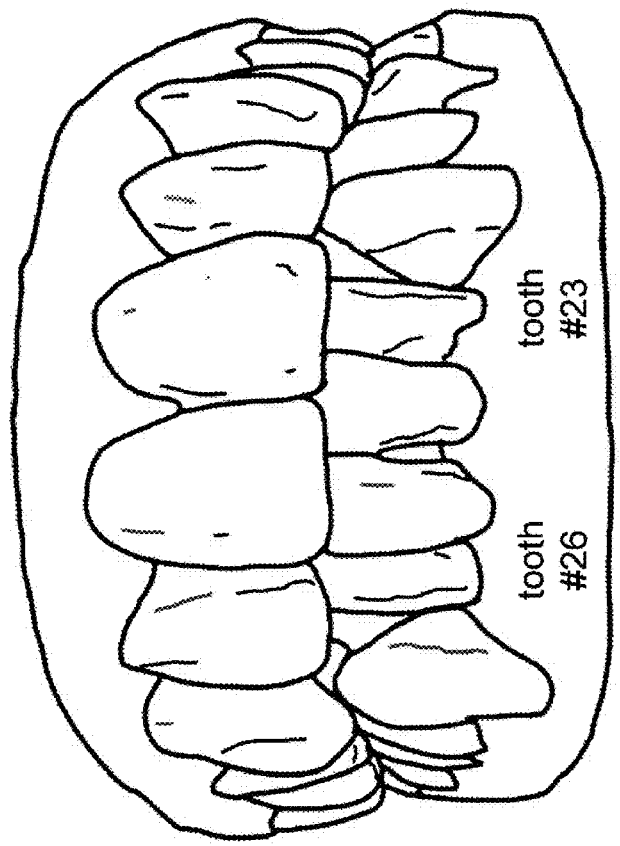

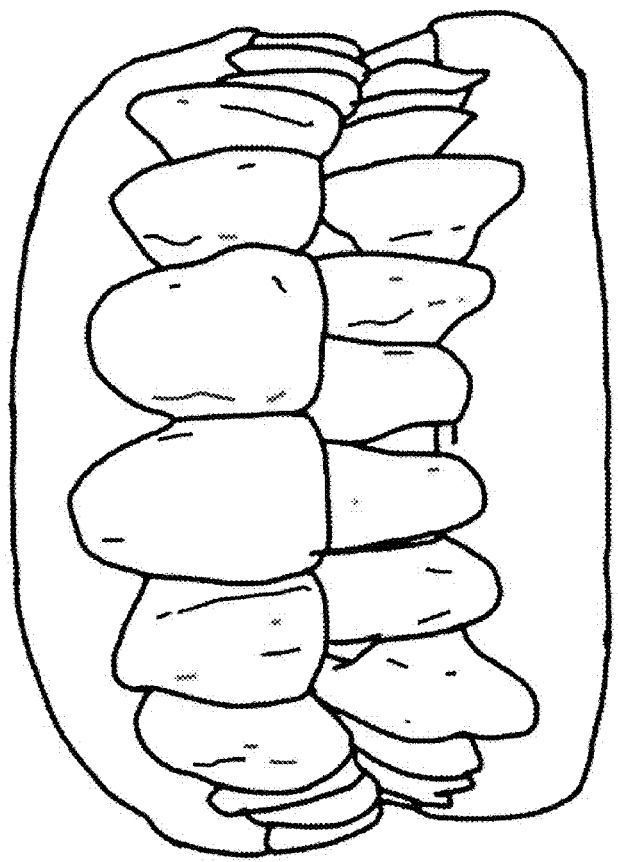
Fig. 5J: anterior (projected finish)

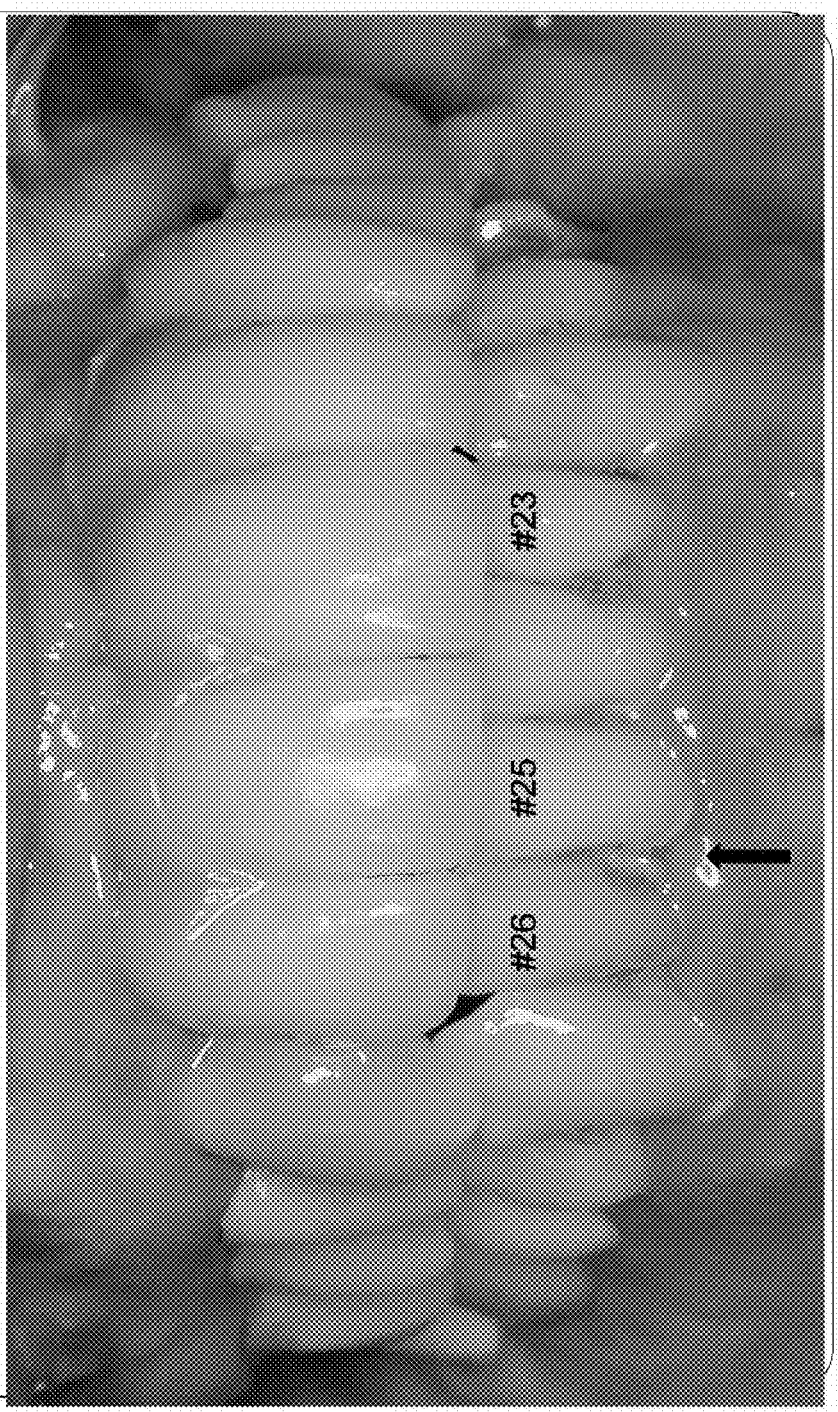

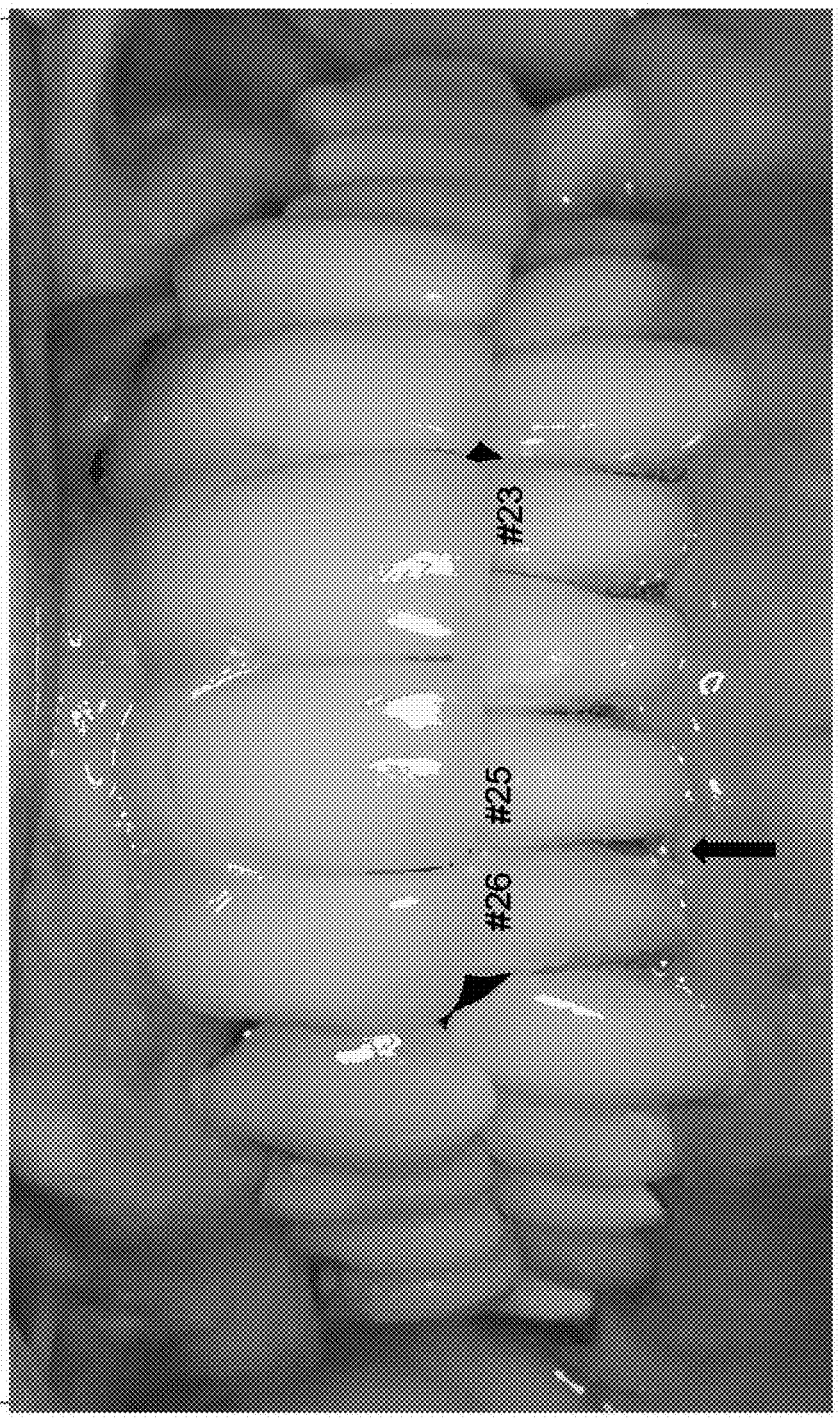
Fig. 5M: anterior
24m PREV: [6m FT + 18m PT] retainers

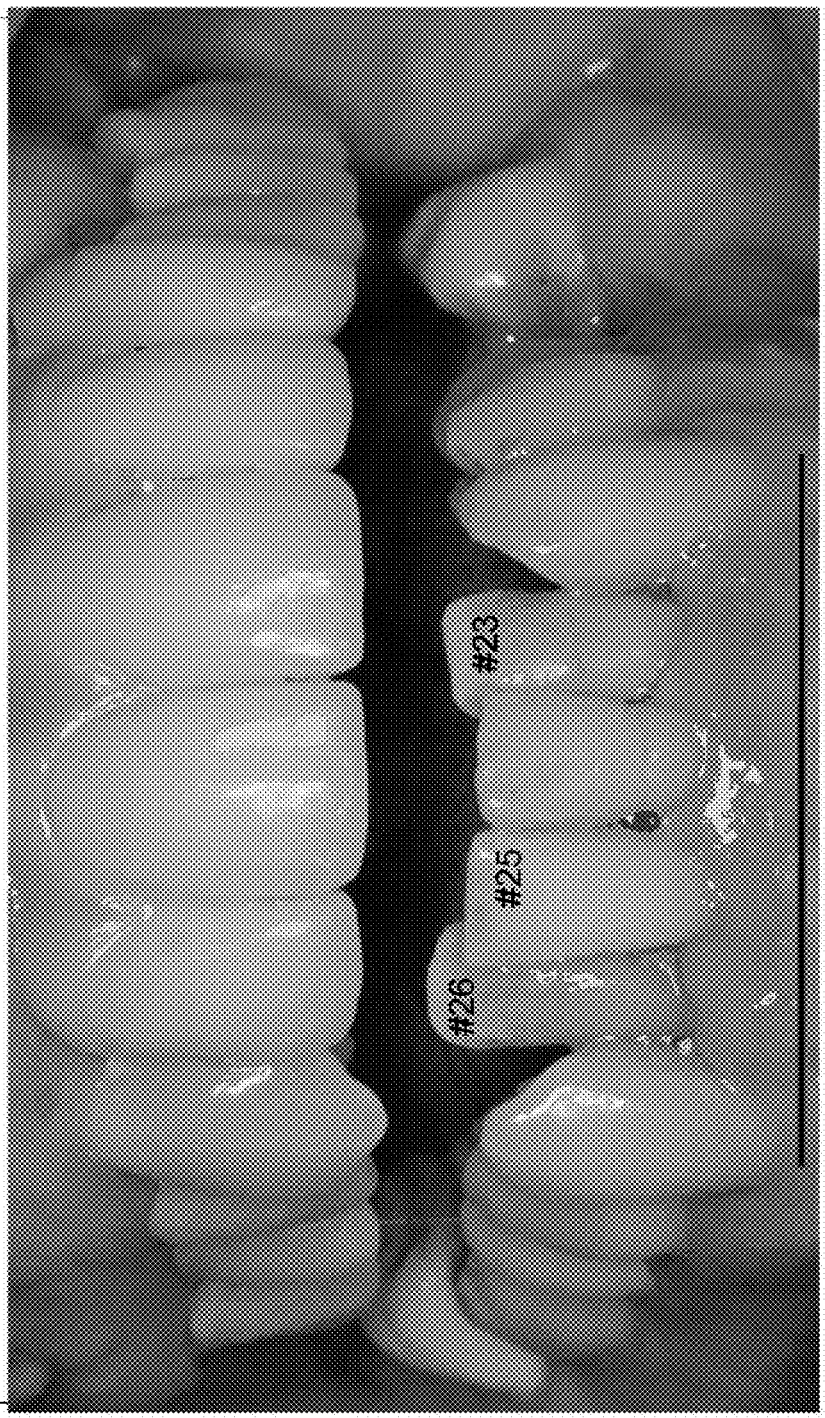

Fig. 50: anterior open month 9 – end of active therapy

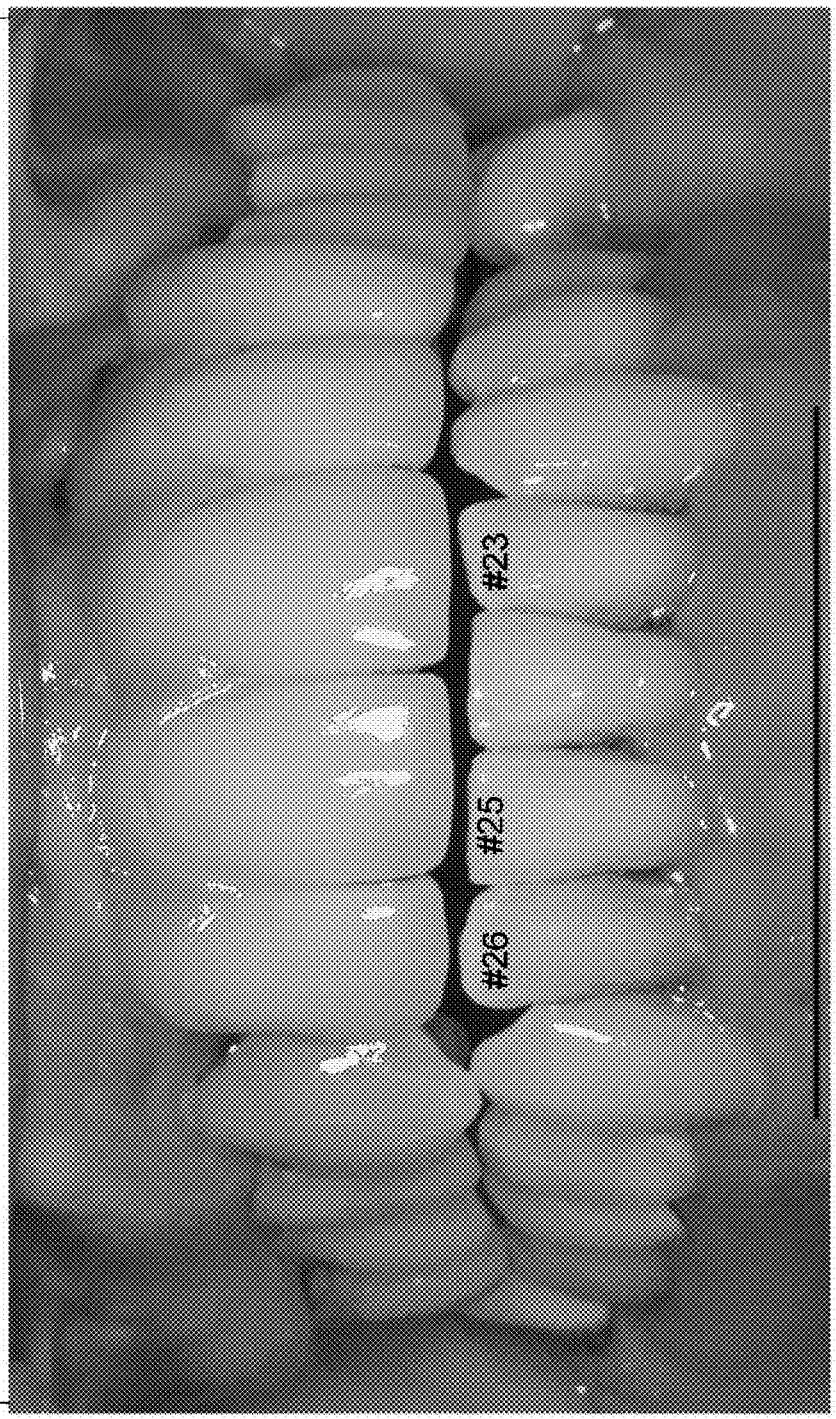

Fig. 5Q: Levels of Gingival Health

| Month | Active Aligners Usage | Full Time Retainer Wear | Part Time Retainer Wear | Level of Gingival Health Achieved |
|---|---|---|---|---|
| 0 (Start) | | | | |
| 9 | Months 1-9 | | | Level I |
| 15 | Months 1-9 | Months 10-15 | | Level I |
| 27 | Months 1-9 | Months 10-15 | Months 16-30 | Level I |

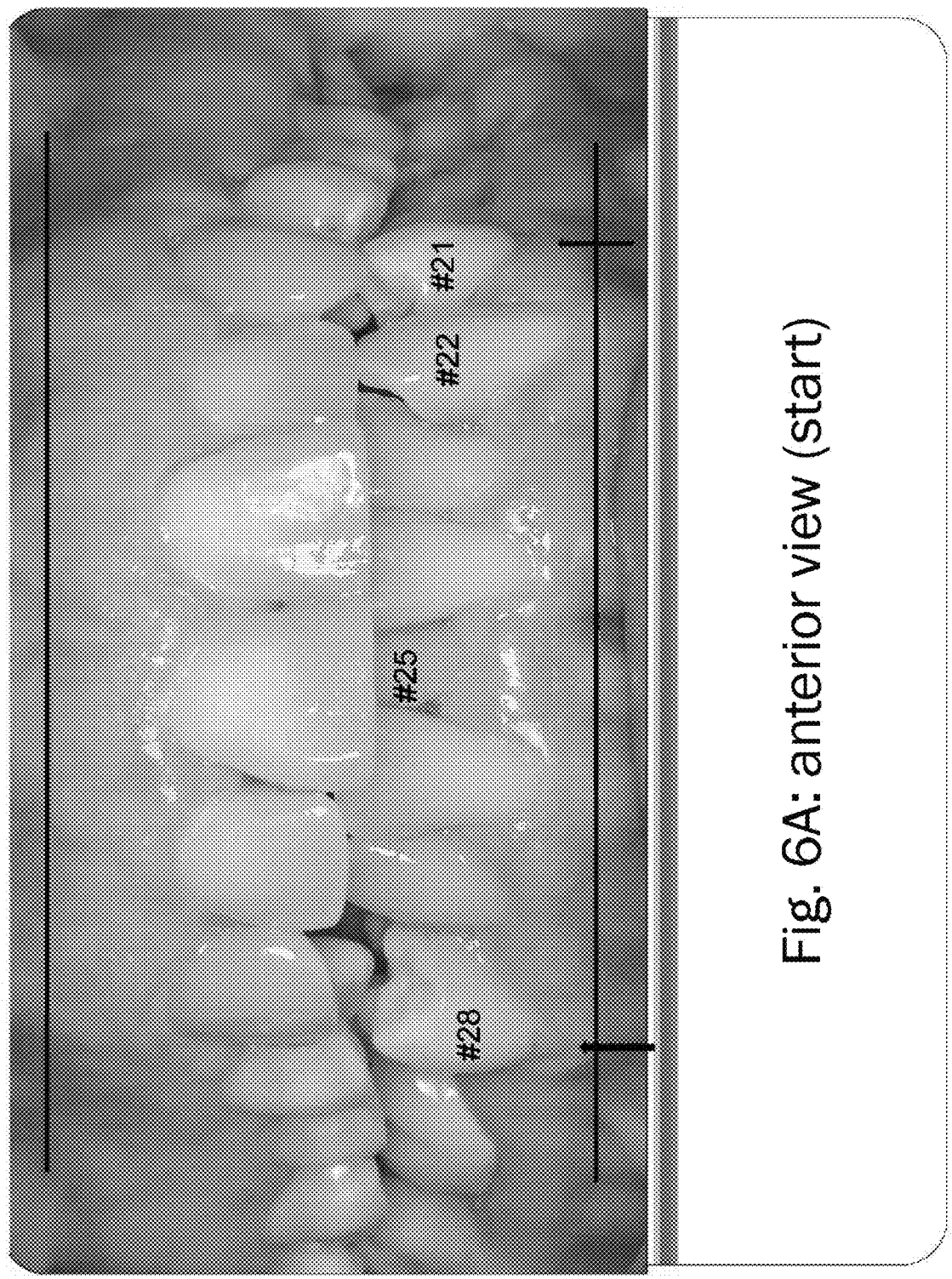

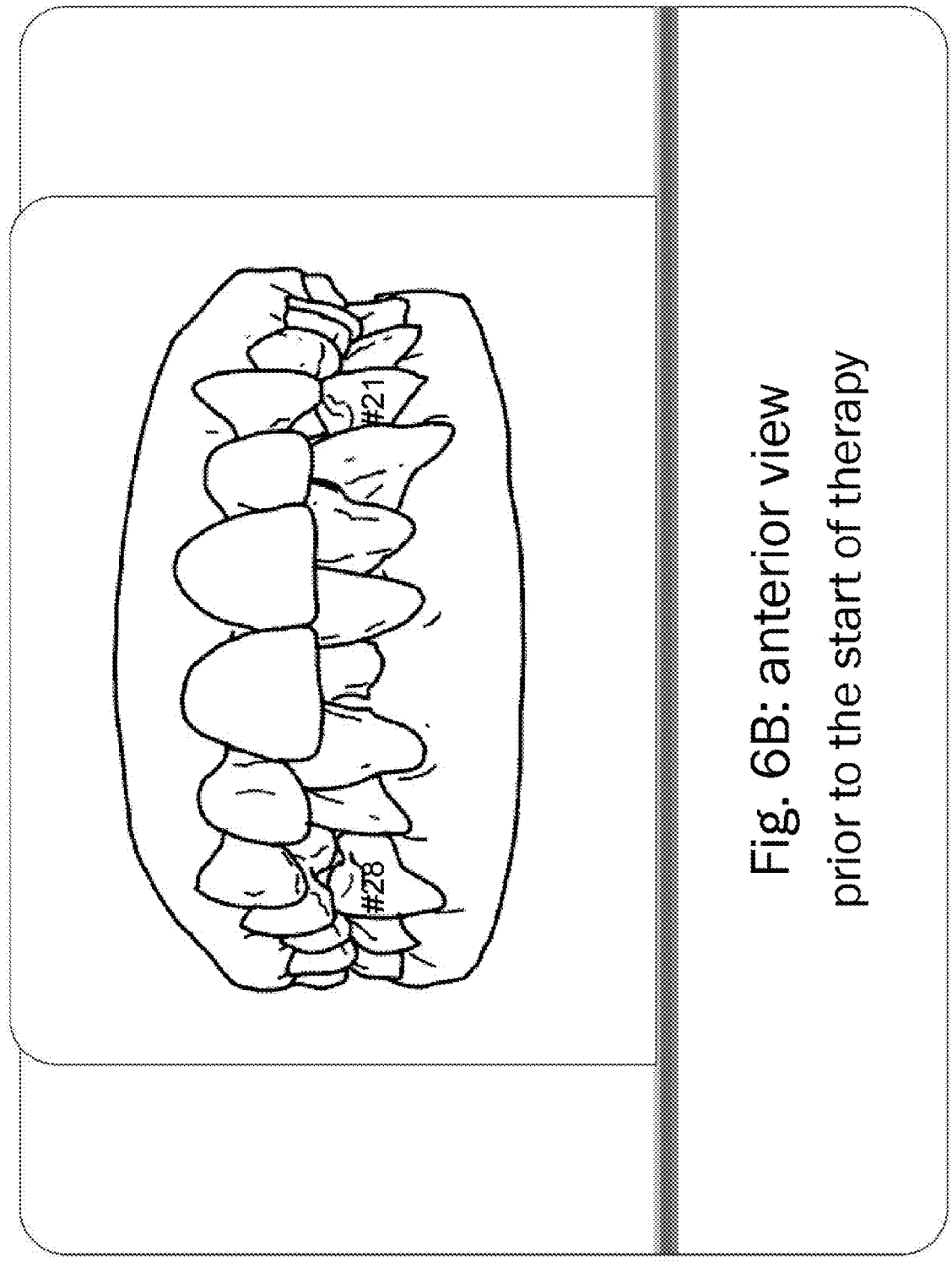
Fig. 6B: anterior view
prior to the start of therapy

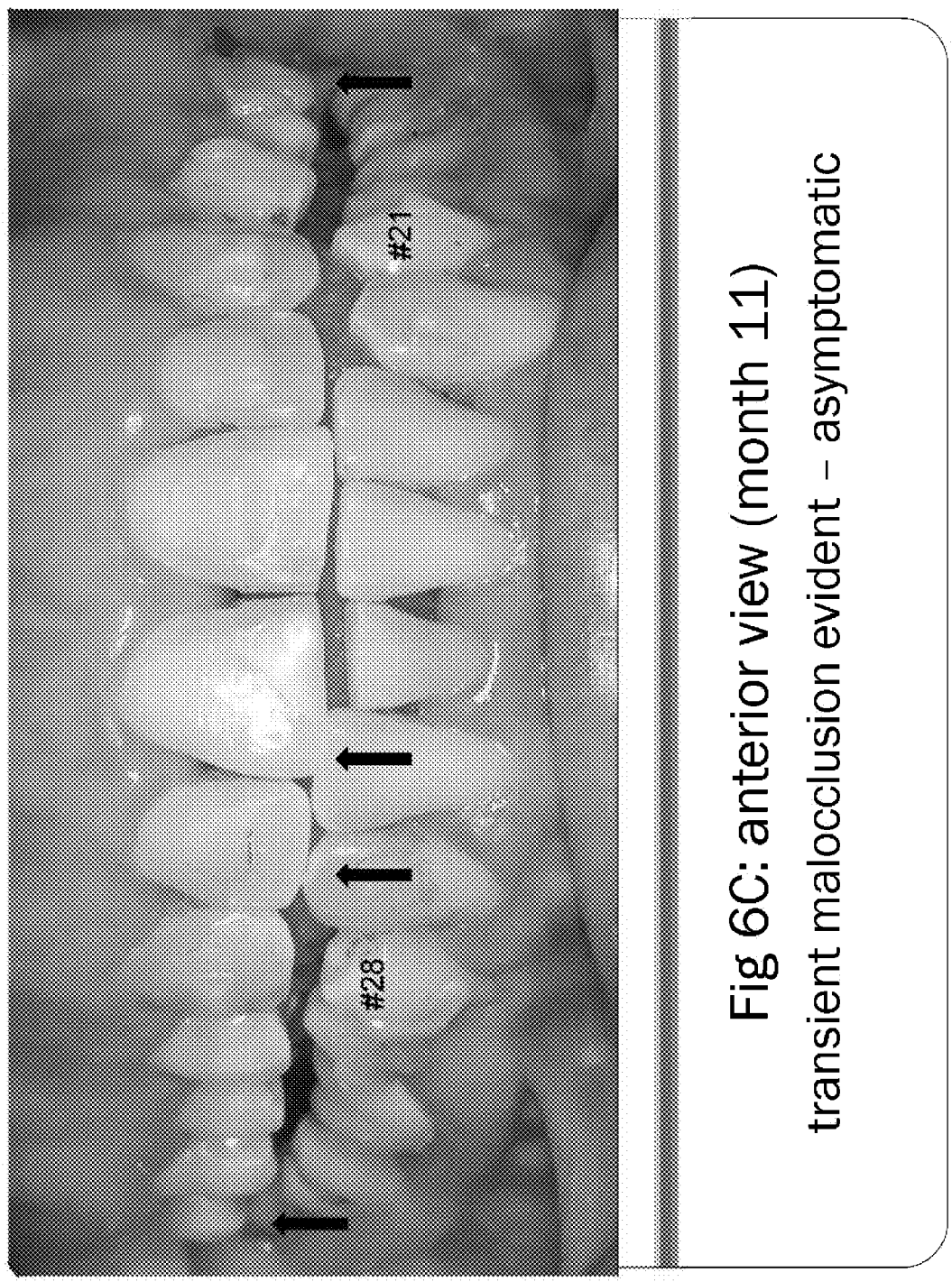
Fig 6C: anterior view (month 11) transient malocclusion evident – asymptomatic

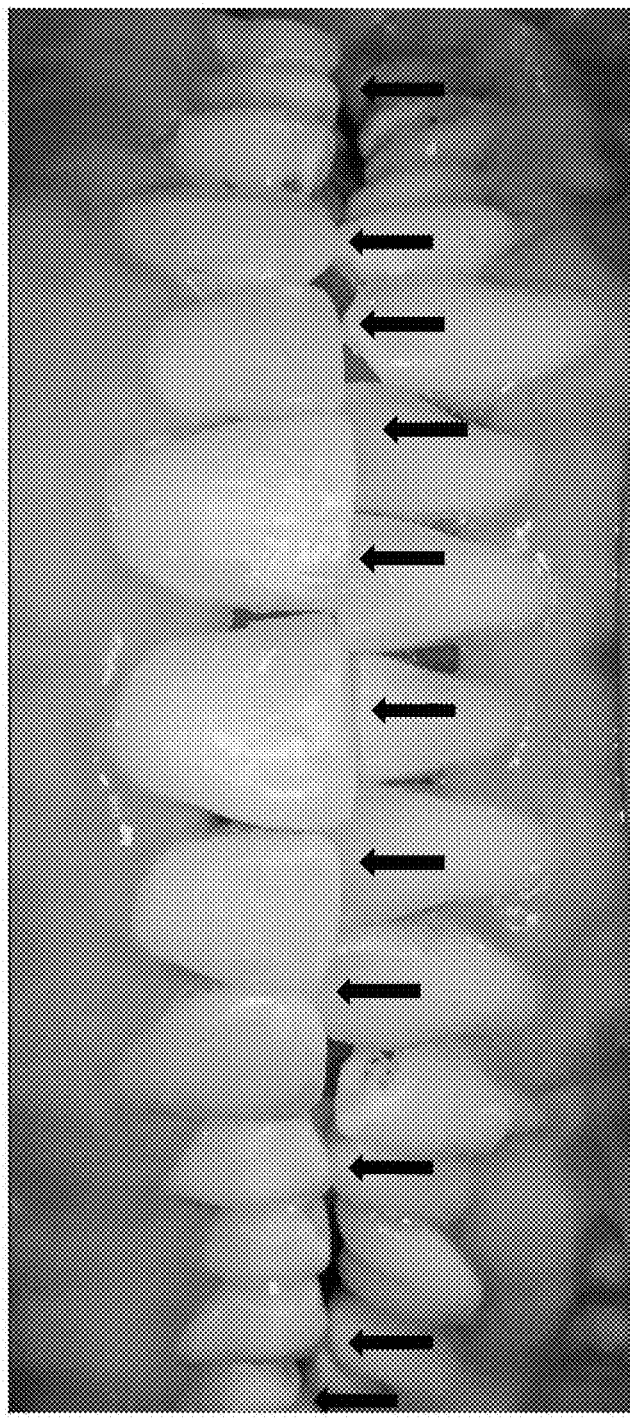
Fig. 6D: anterior (month 12) transient malocclusion diminished – asymptomatic – more teeth are in contact

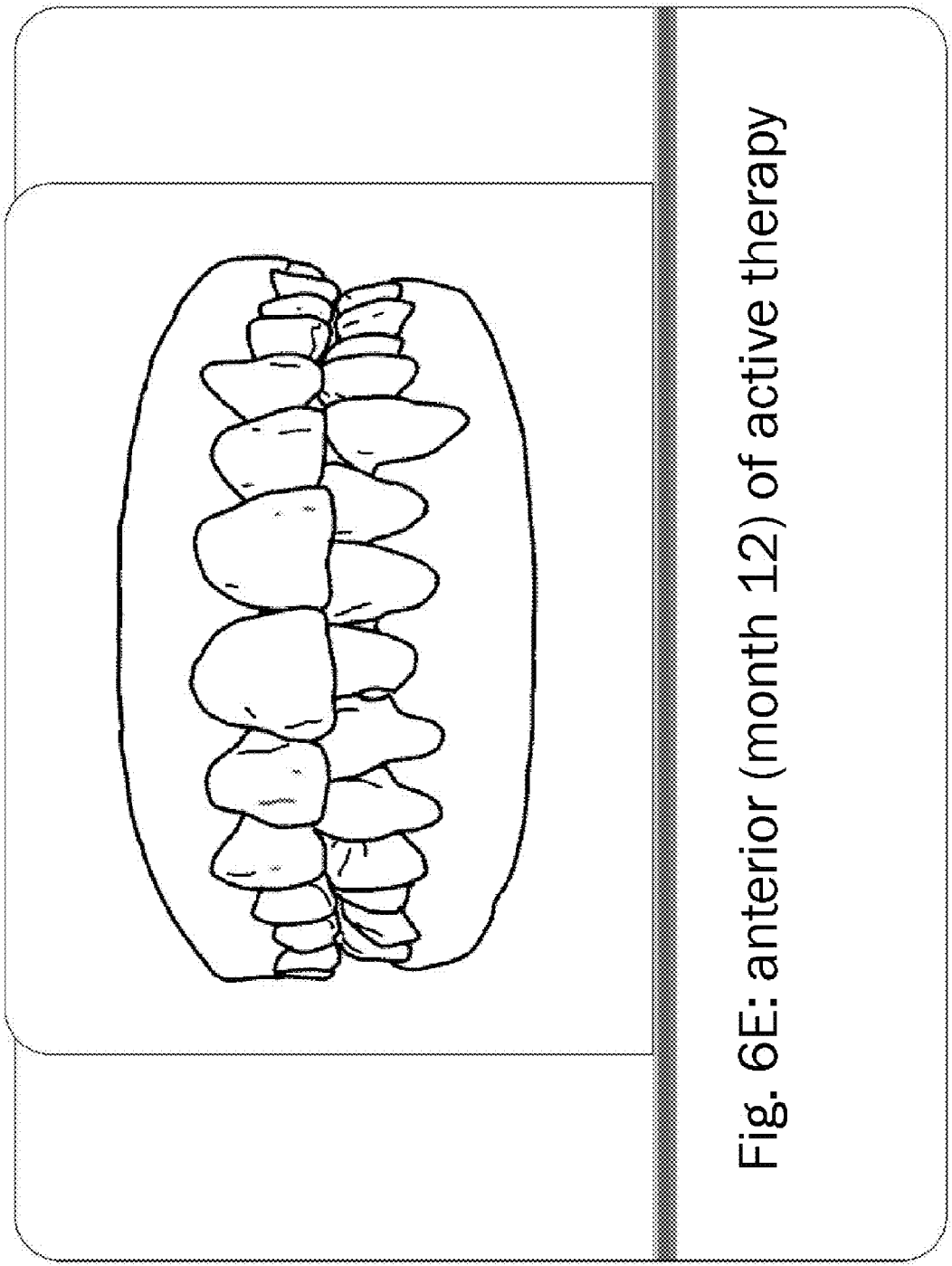
Fig. 6E: anterior (month 12) of active therapy

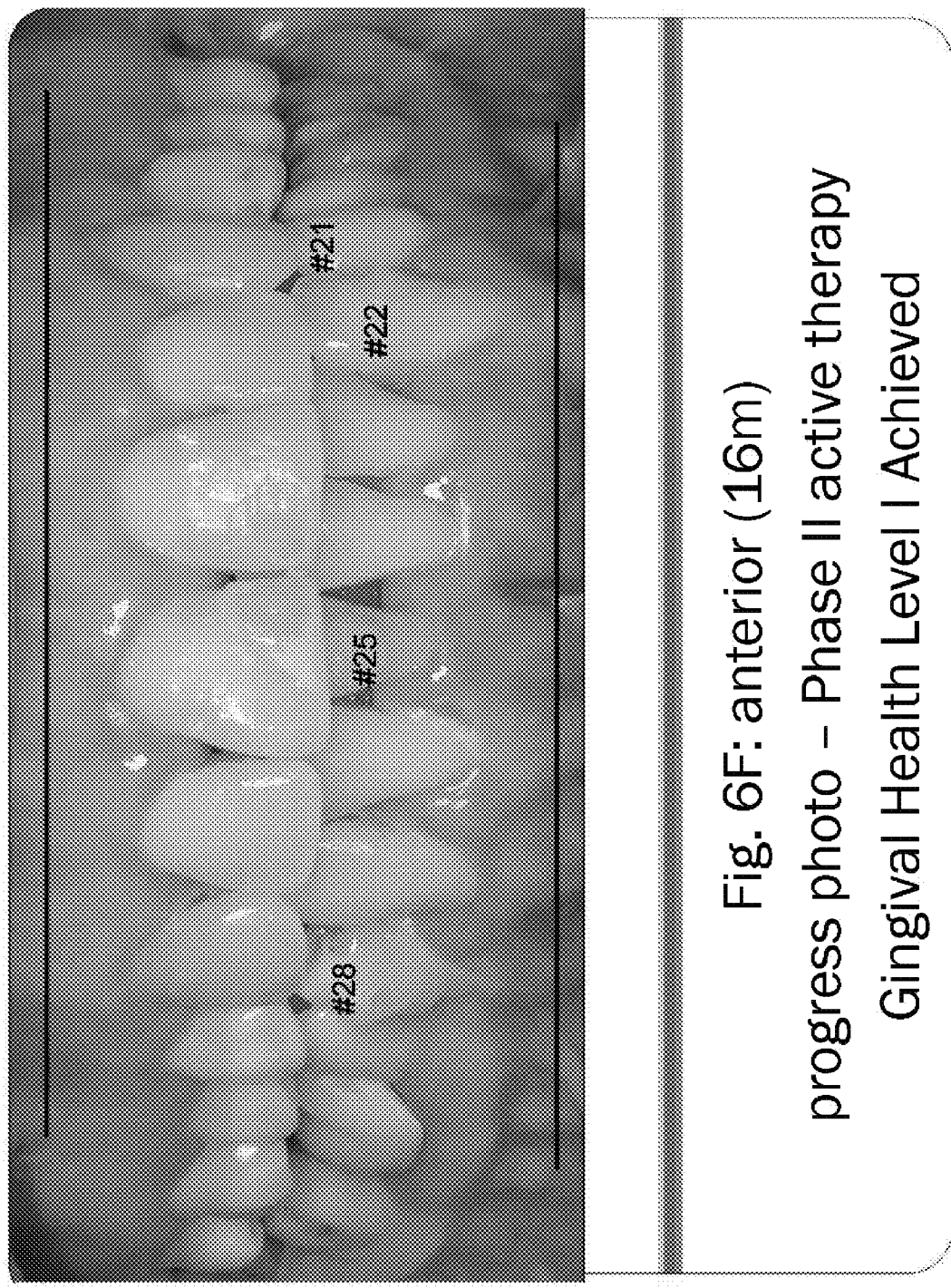
Fig. 6F: anterior (16m) progress photo – Phase II active therapy Gingival Health Level I Achieved

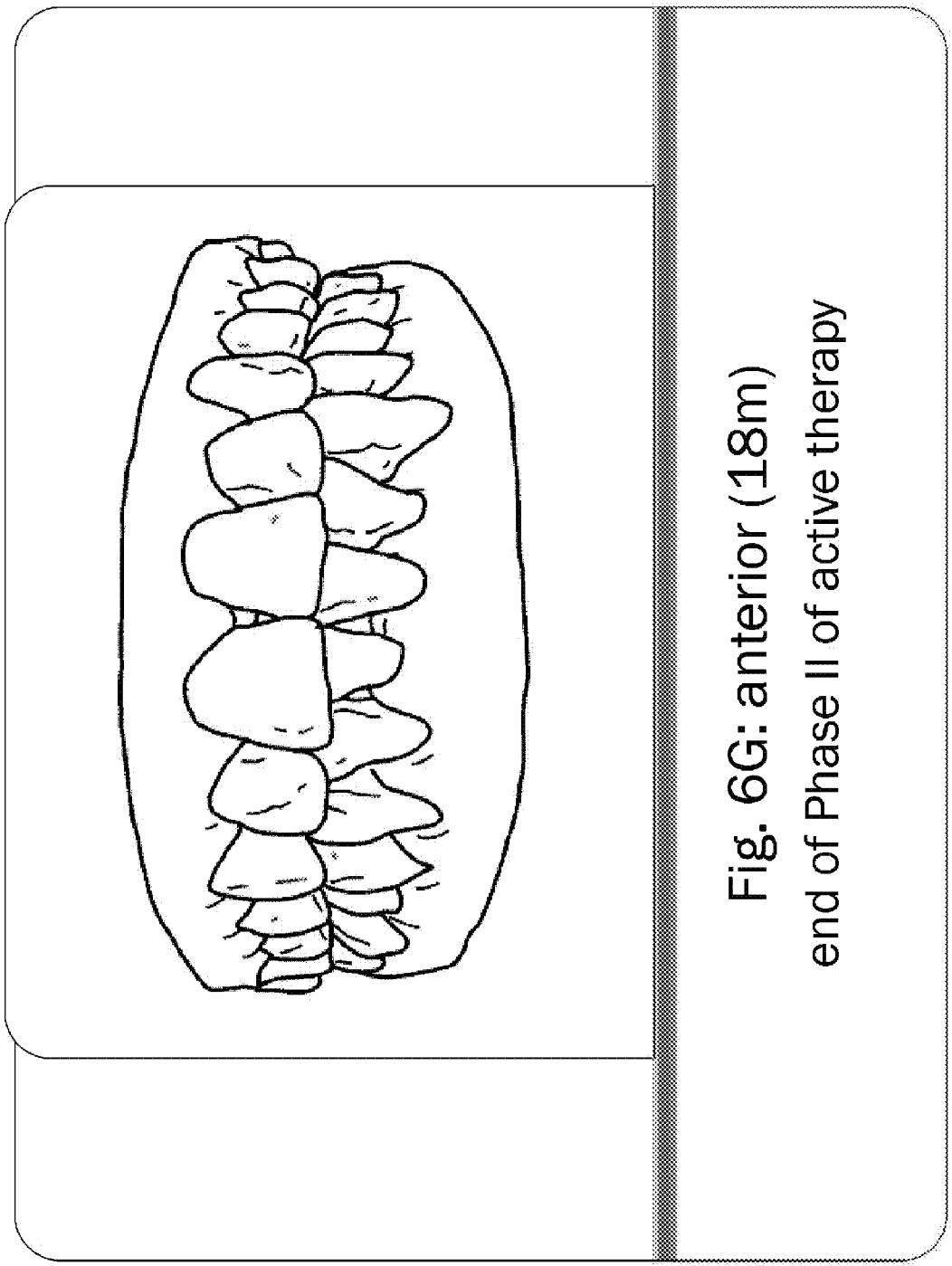
Fig. 6G: anterior (18m)
end of Phase II of active therapy

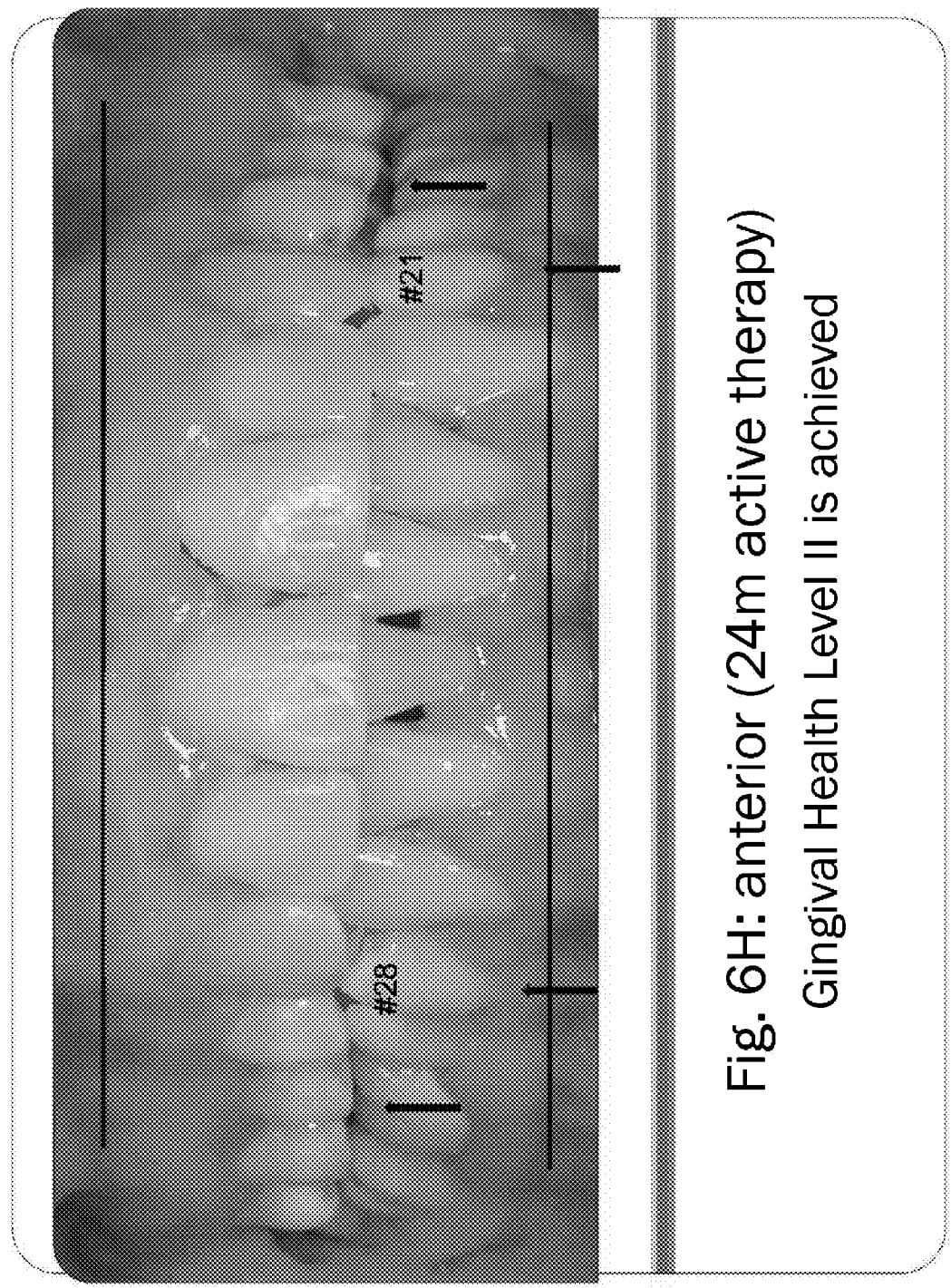
Fig. 6H: anterior (24m active therapy)
Gingival Health Level II is achieved

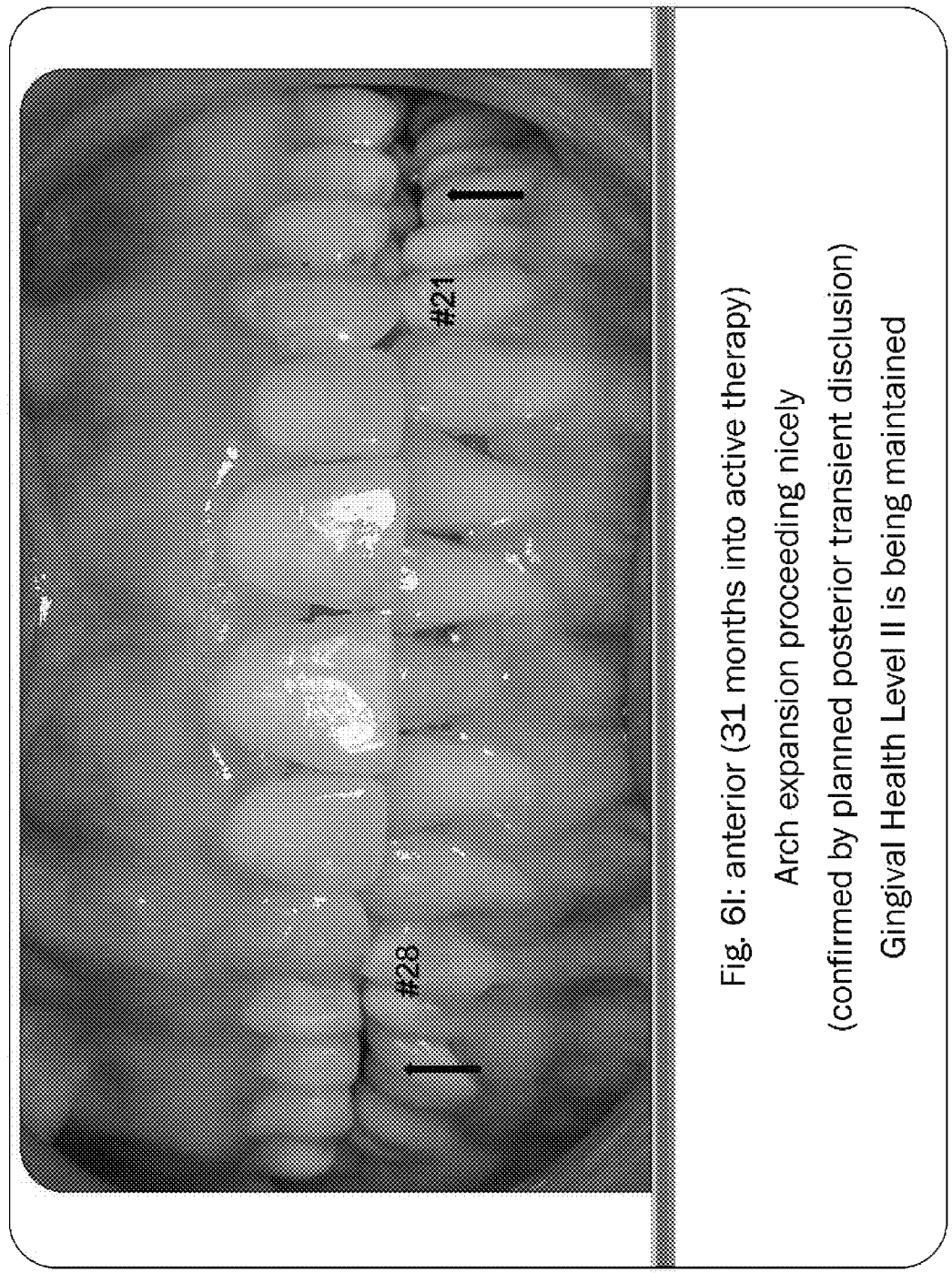
Fig. 6l: anterior (31 months into active therapy)
Arch expansion proceeding nicely
(confirmed by planned posterior transient disclusion)
Gingival Health Level II is being maintained

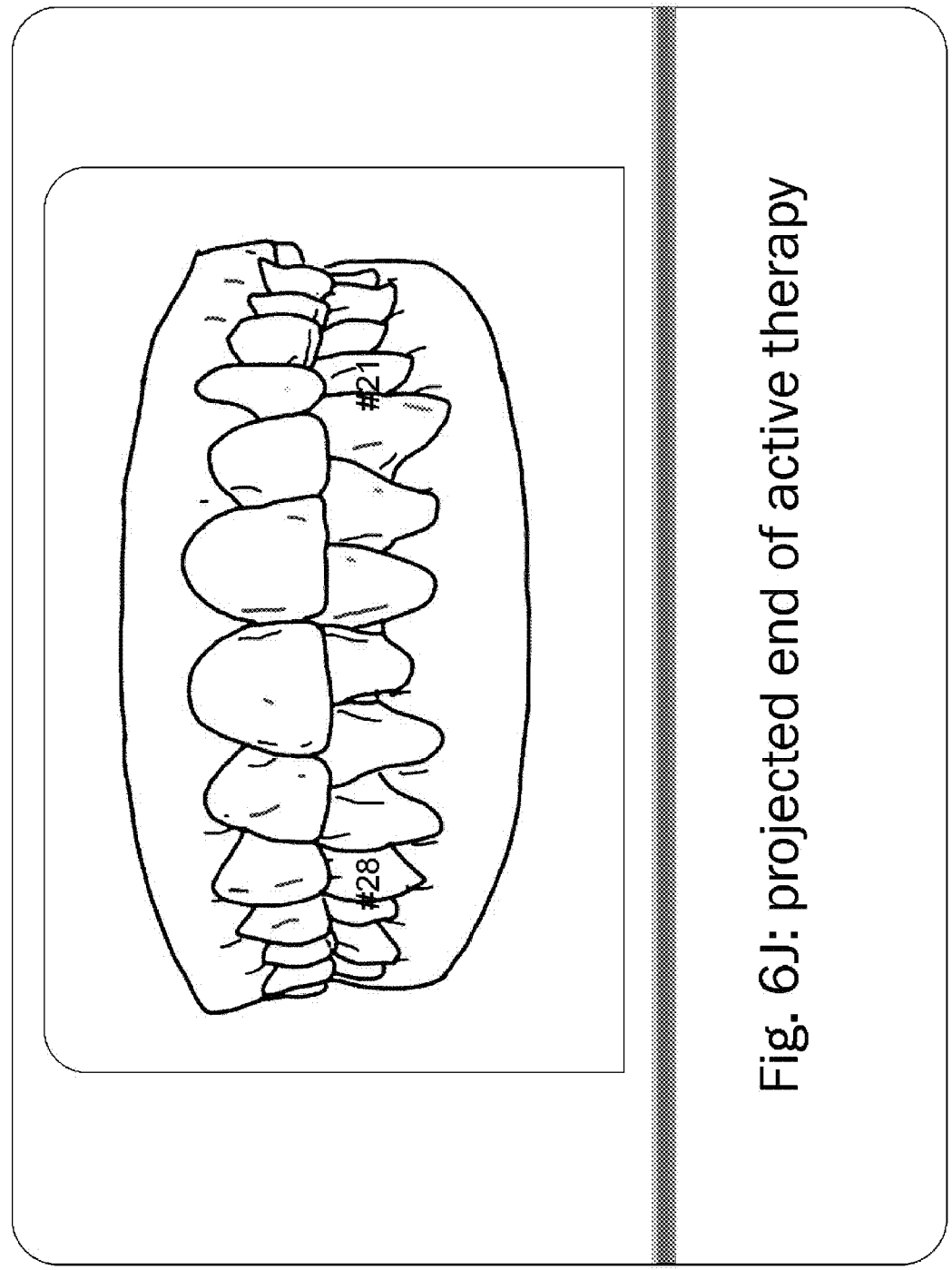
Fig. 6J: projected end of active therapy

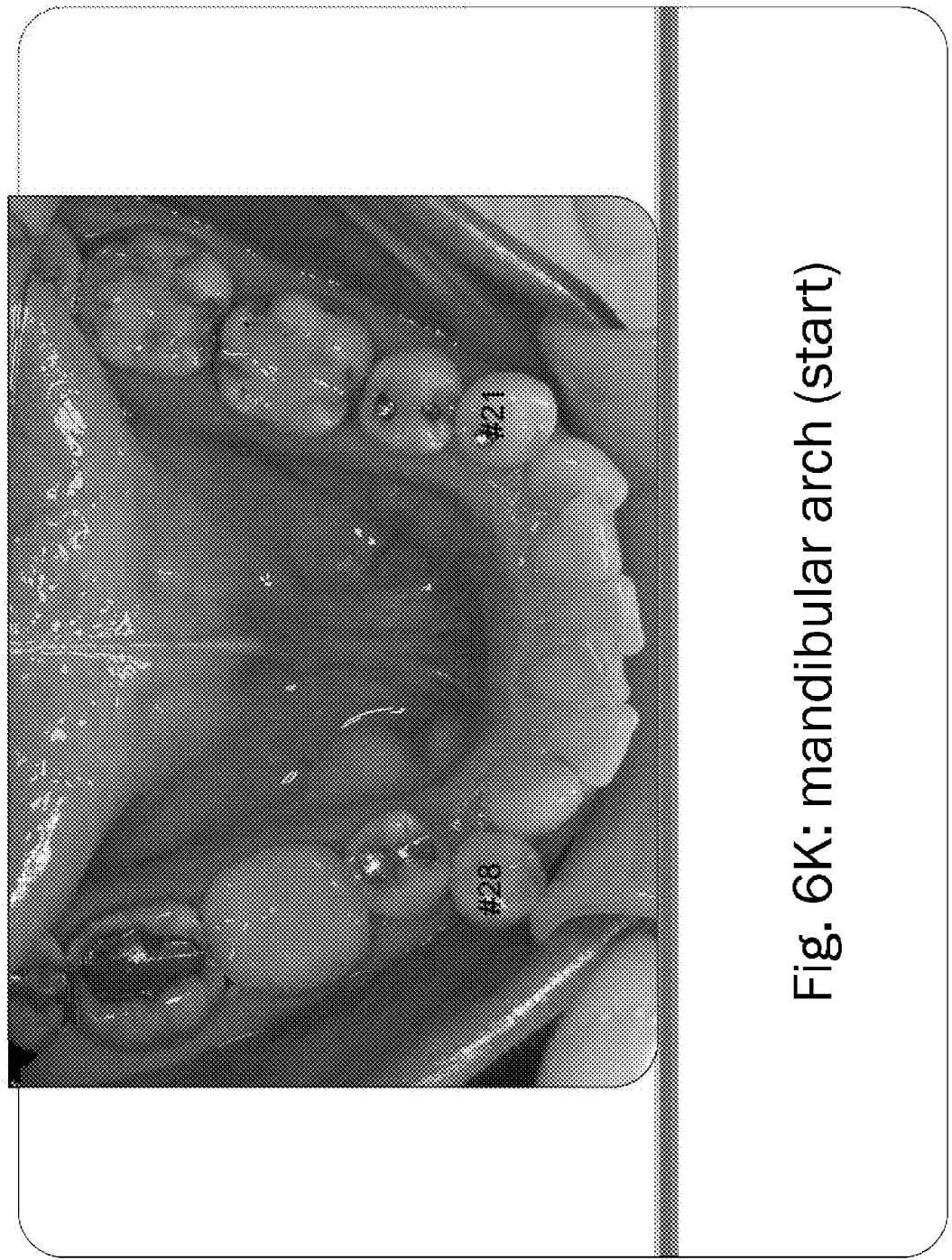
Fig. 6K: mandibular arch (start)

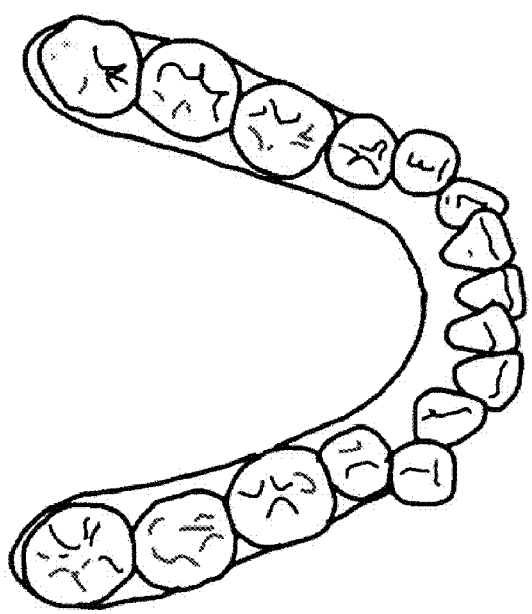
Fig. 6L: mandibular arch (start)

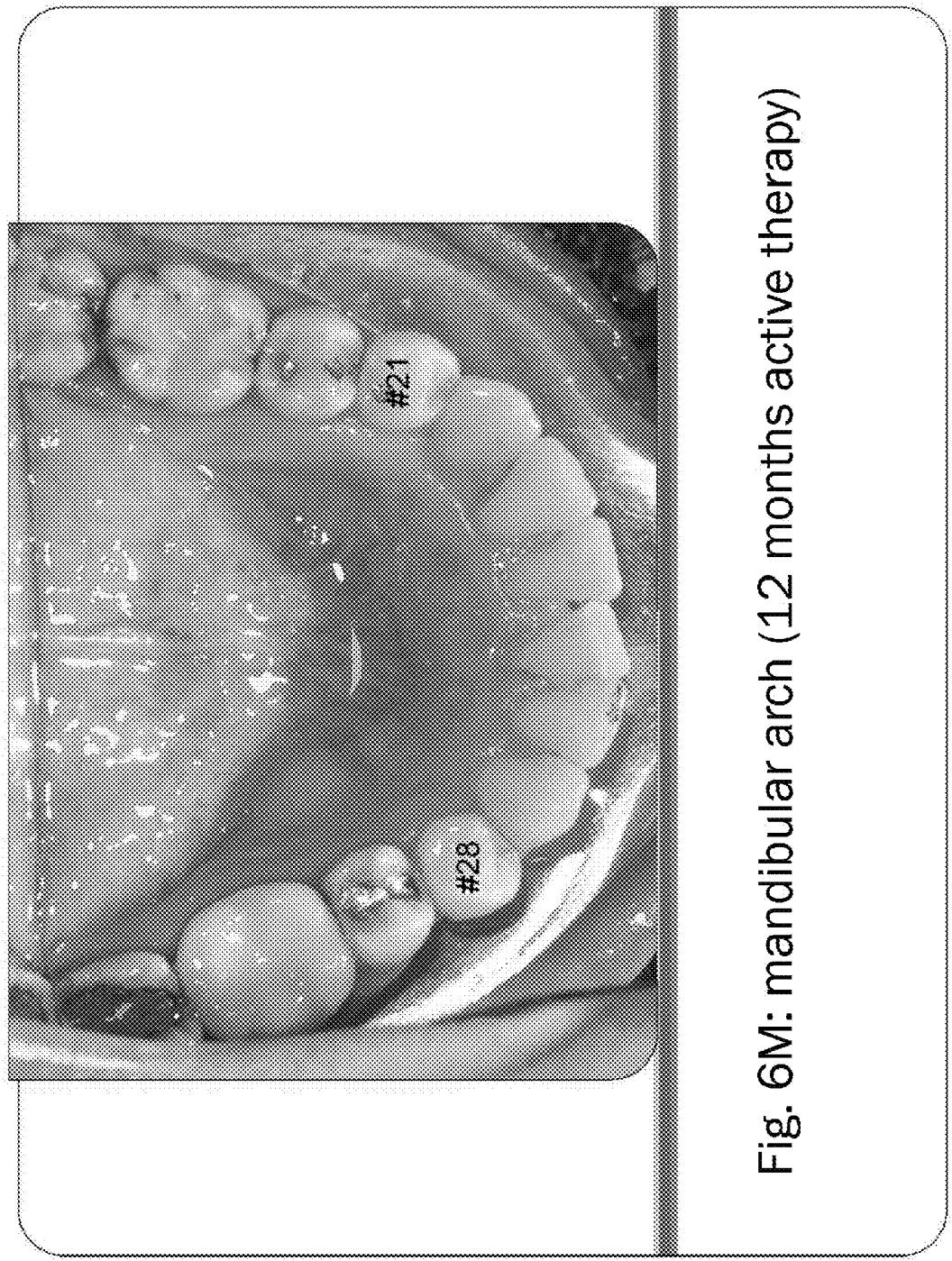
Fig. 6M: mandibular arch (12 months active therapy)

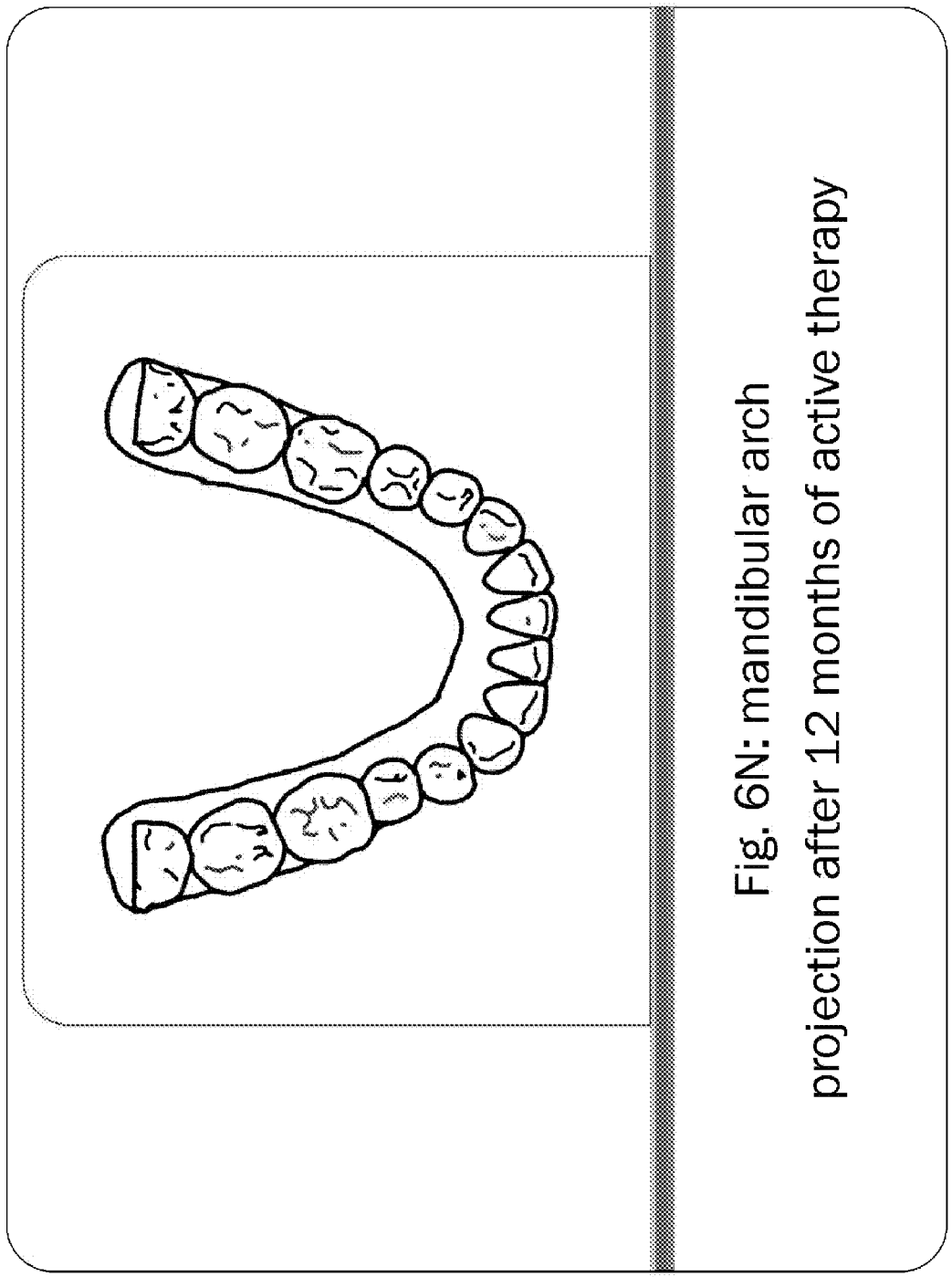
Fig. 6N: mandibular arch projection after 12 months of active therapy

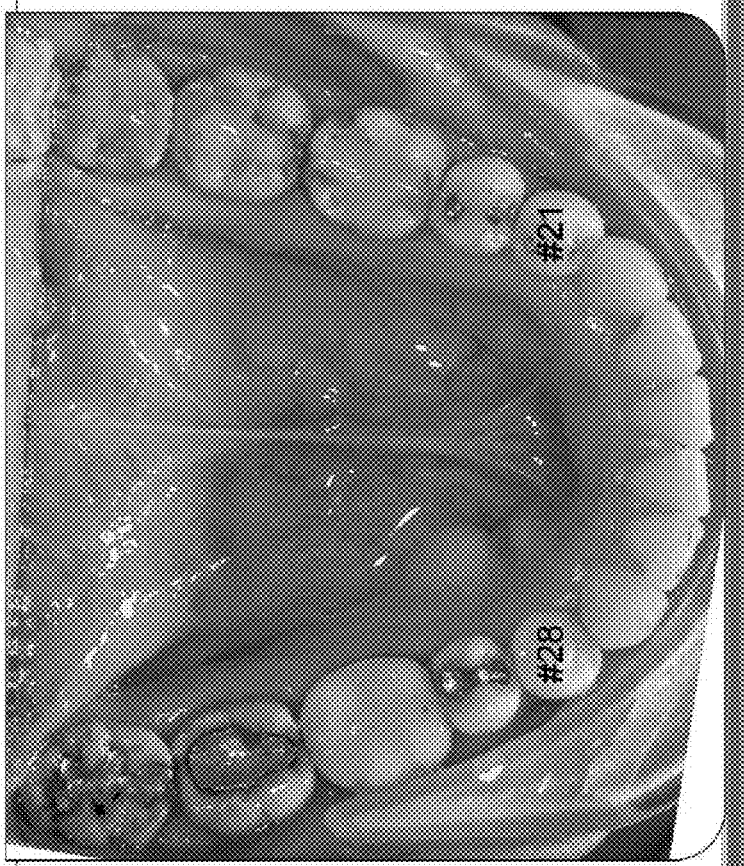
Fig. 60: mandibular arch (month 18)
Gingival Health Level I is being maintained. The quantitative magnitude of her arch reformulation (the antero/postero dimension of the mandible), is an increase of 4mm.

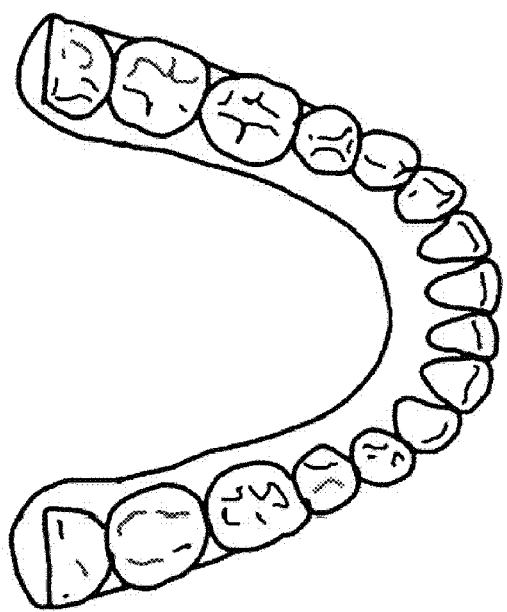
Fig. 6P: mandibular arch
(projection – 18 months of active therapy)

Fig. 6Q: Levels of Gingival Health

| Month | Active Aligners Usage | Full Time Retainer Wear | Part Time Retainer Wear | Level of Gingival Health Achieved |
|---|---|---|---|---|
| 0 (Start) | | | | |
| 18 | Months 1-18 | | | Level I |
| 24 | Months 1-24 | | | Level I |
| 31 | Months 1-31 (ongoing) | | | Level II |

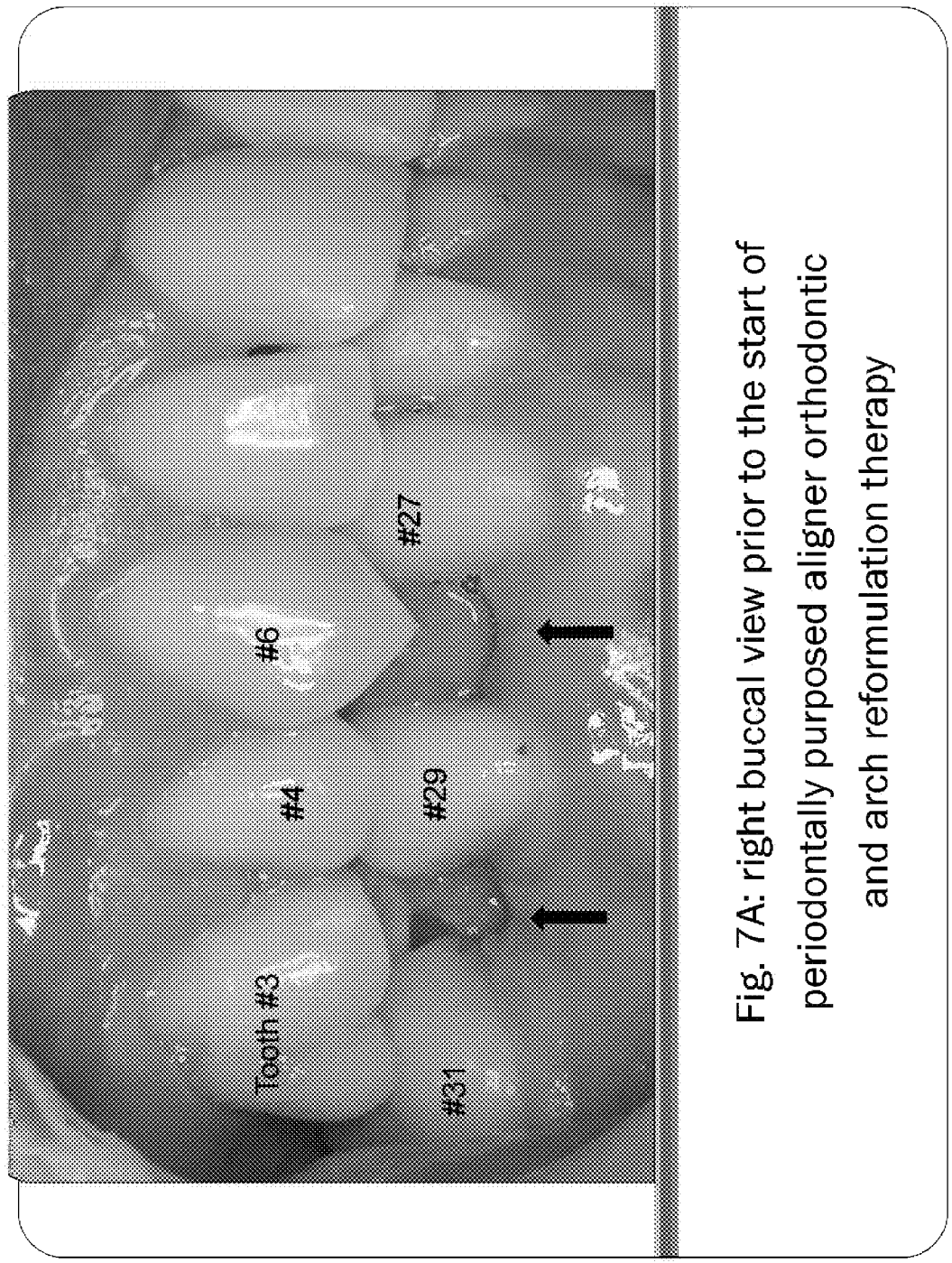
Fig. 7A: right buccal view prior to the start of periodontally purposed aligner orthodontic and arch reformulation therapy

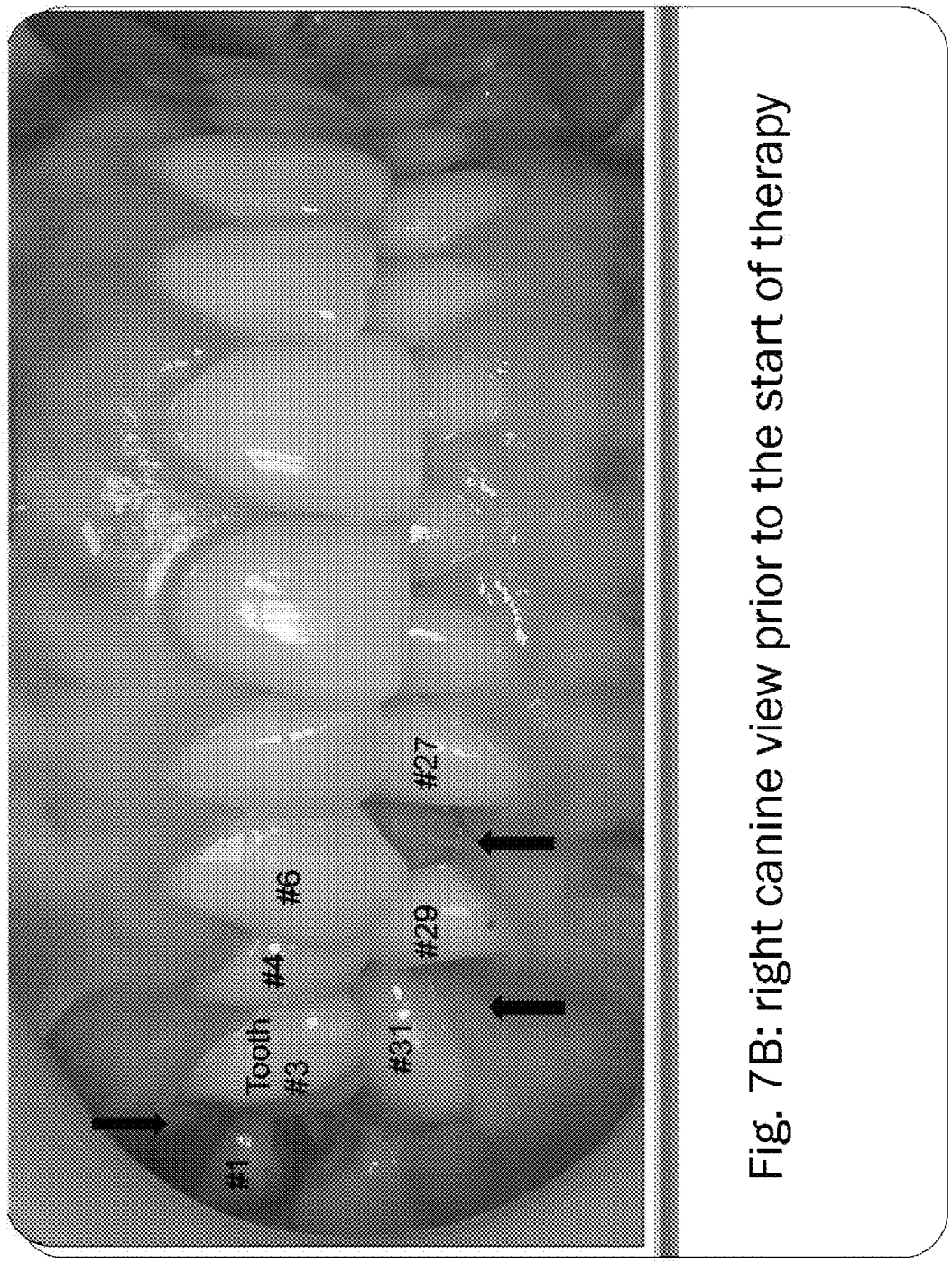
Fig. 7B: right canine view prior to the start of therapy

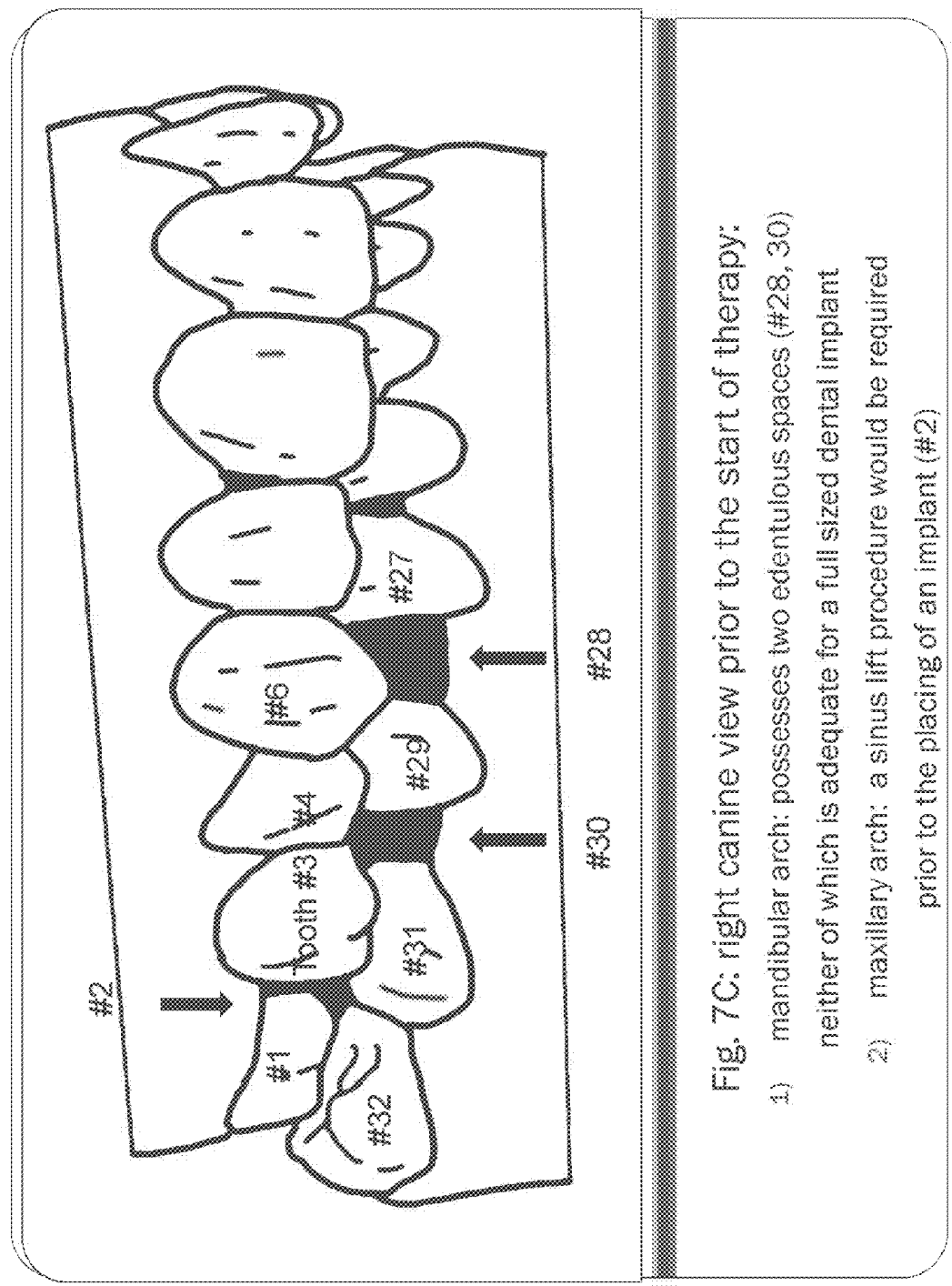

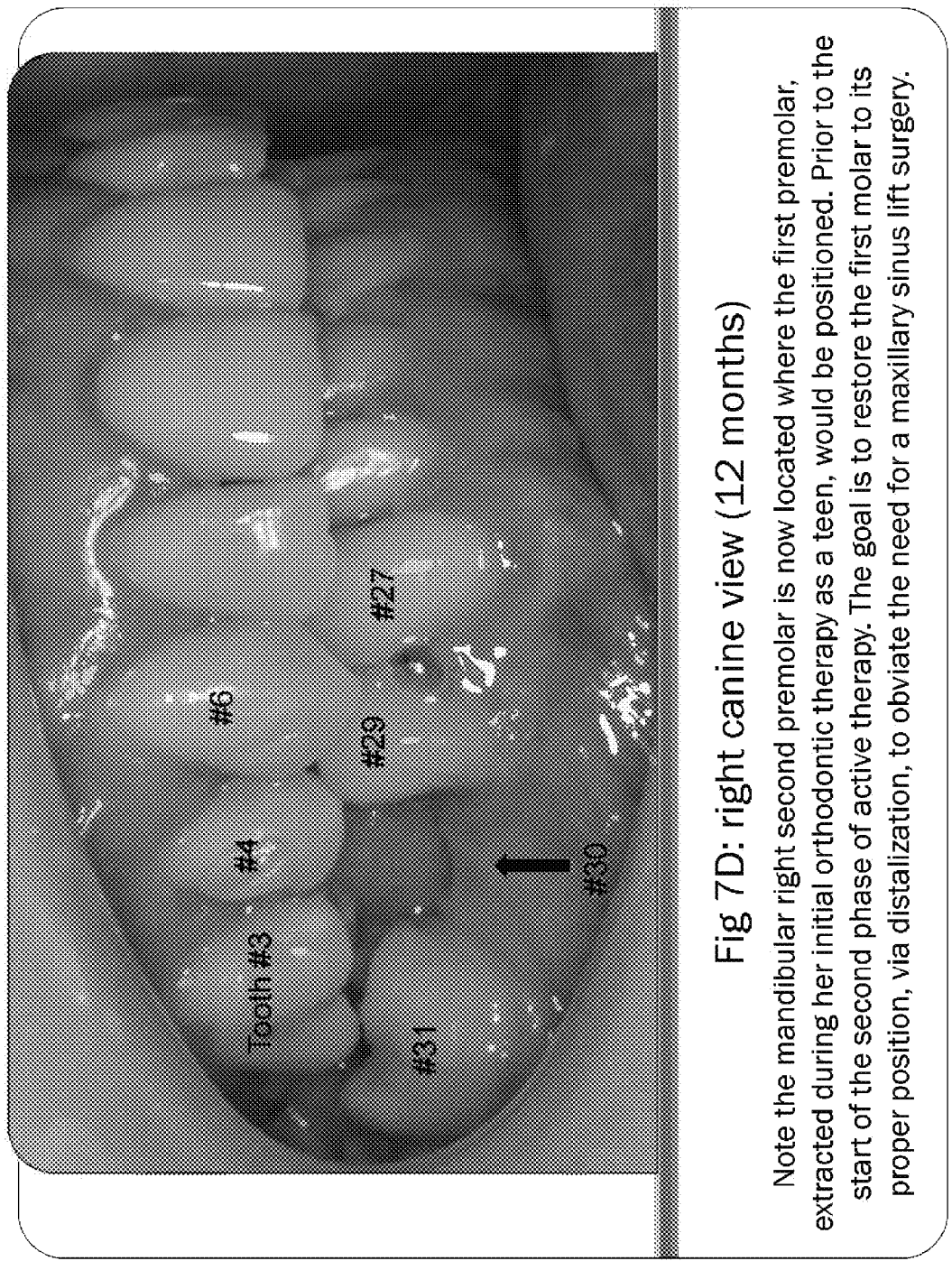

Fig 7D: right canine view (12 months)

Note the mandibular right second premolar is now located where the first premolar, extracted during her initial orthodontic therapy as a teen, would be positioned. Prior to the start of the second phase of active therapy. The goal is to restore the first molar to its proper position, via distalization, to obviate the need for a maxillary sinus lift surgery.

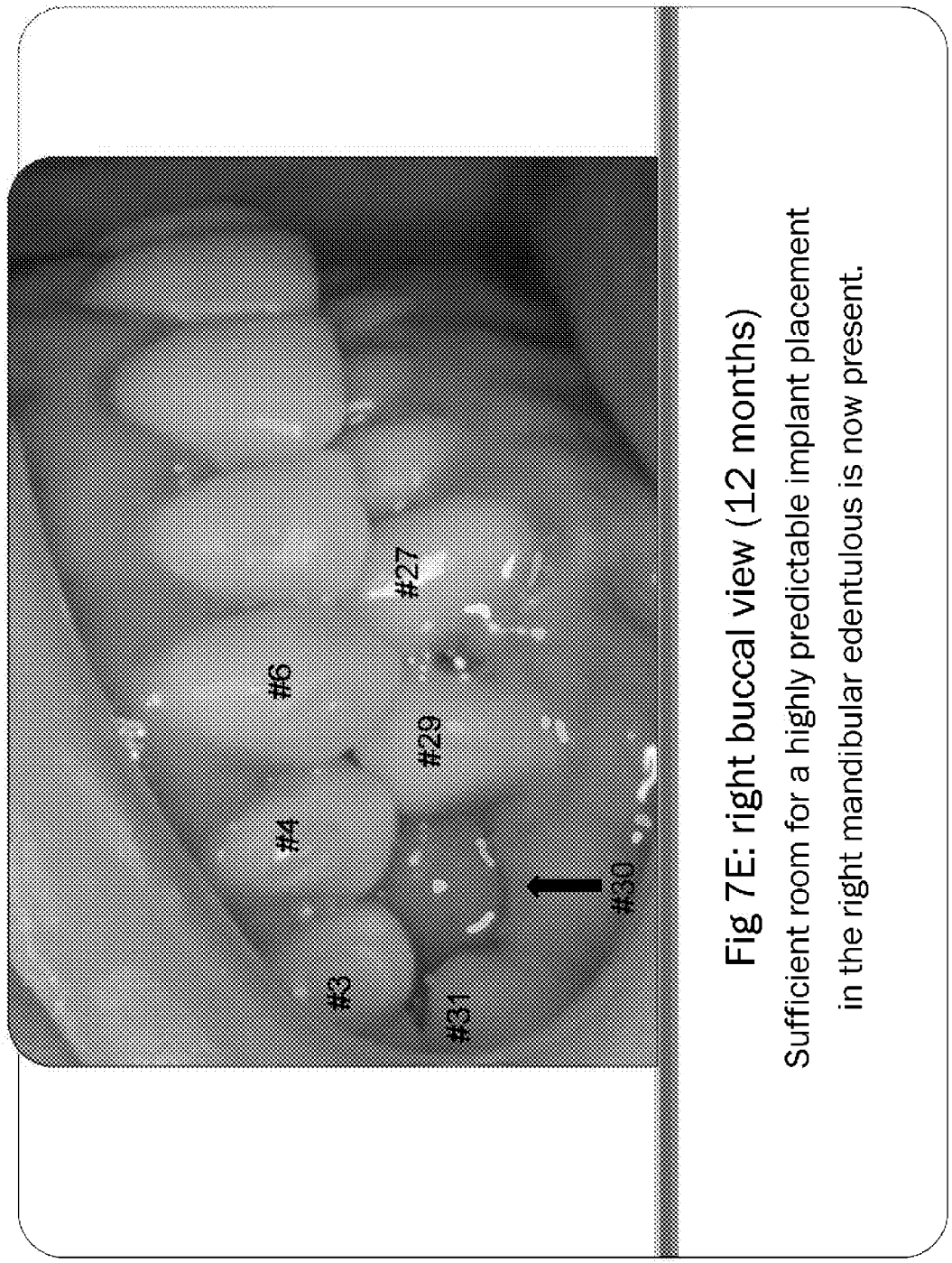
Fig 7E: right buccal view (12 months)
Sufficient room for a highly predictable implant placement in the right mandibular edentulous is now present.

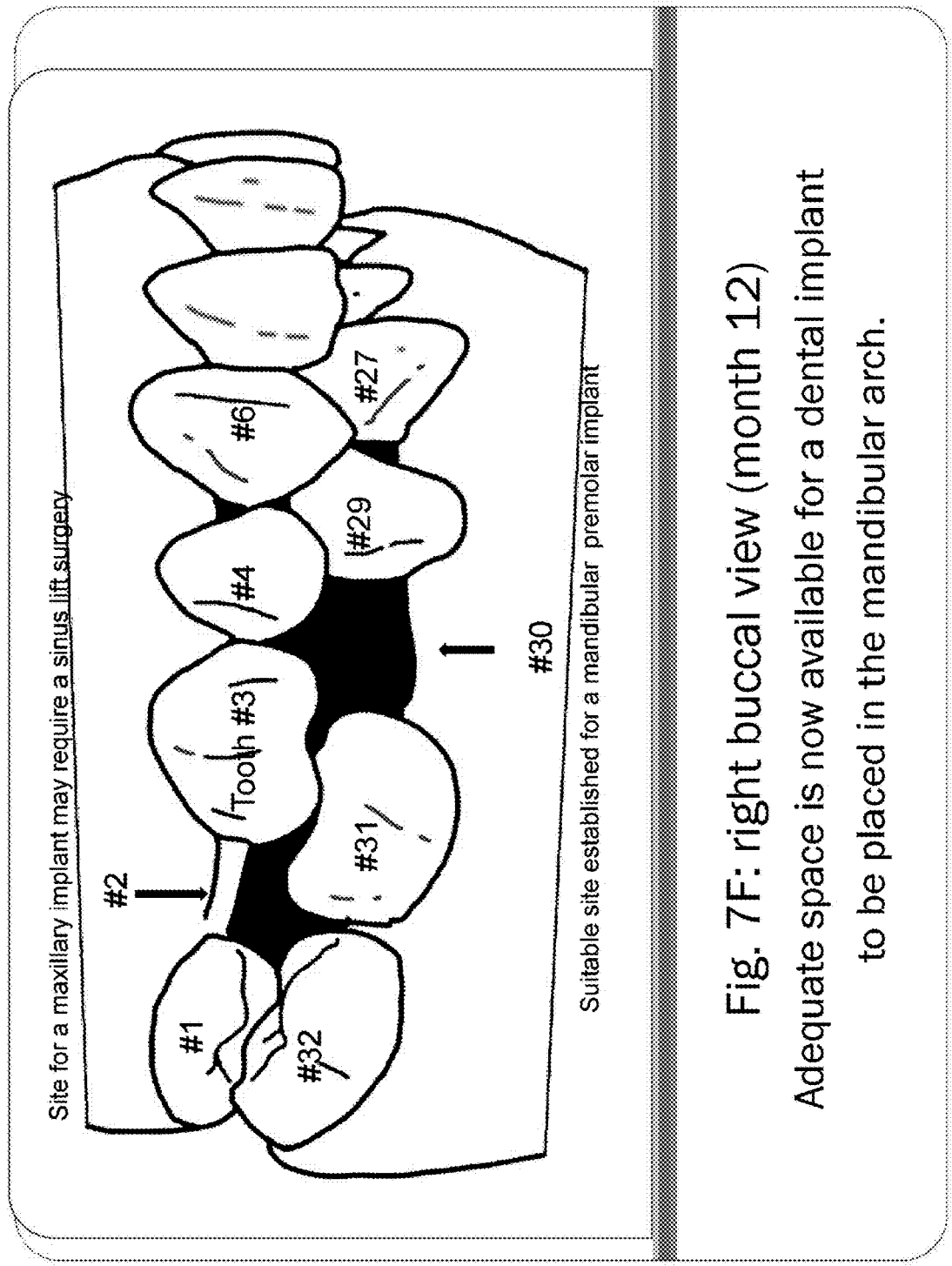
Fig. 7F: right buccal view (month 12)
Adequate space is now available for a dental implant to be placed in the mandibular arch.

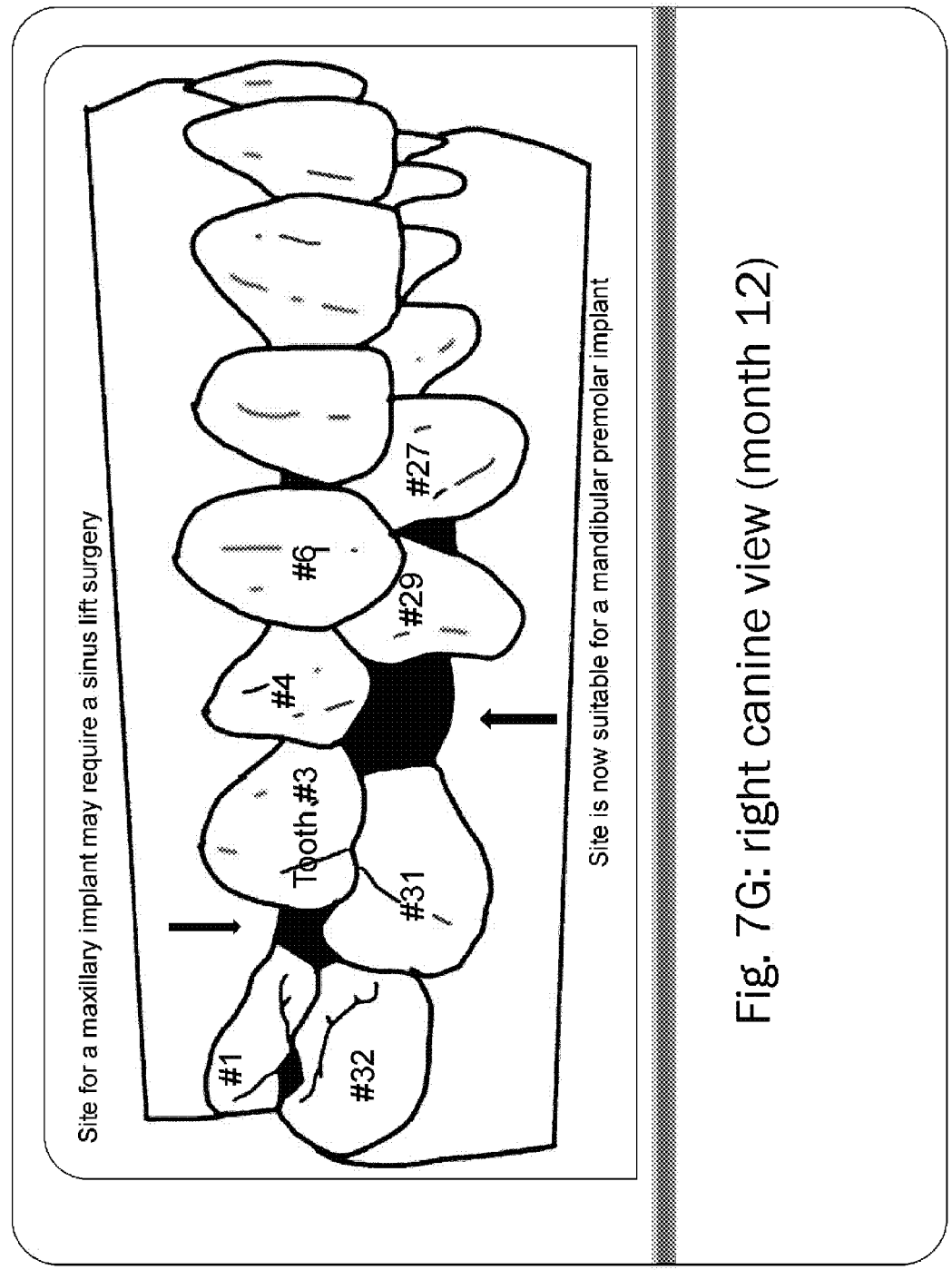
Fig. 7G: right canine view (month 12)

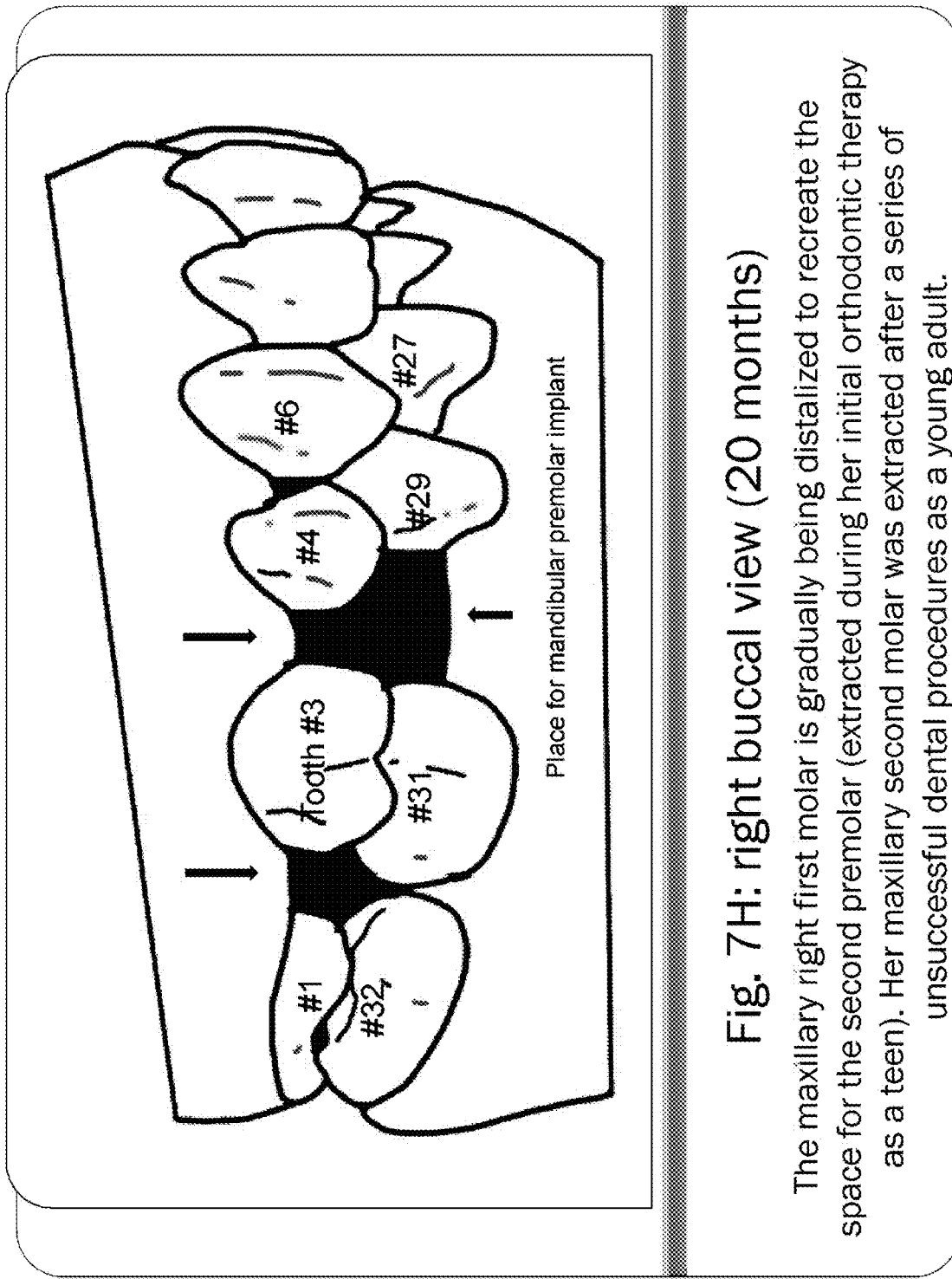
Fig. 7H: right buccal view (20 months)
The maxillary right first molar is gradually being distalized to recreate the space for the second premolar (extracted during her initial orthodontic therapy as a teen). Her maxillary second molar was extracted after a series of unsuccessful dental procedures as a young adult.

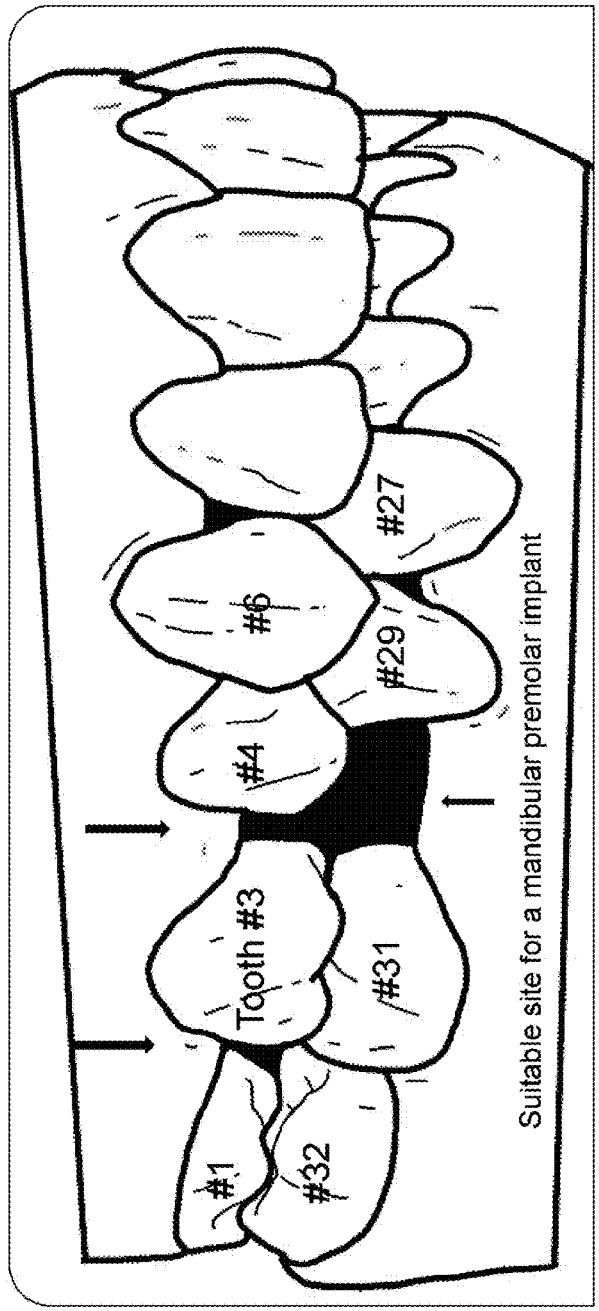
Fig. 7I: right canine view (20 months)
The maxillary right first molar is gradually being distalized to recreate the space for the second premolar, which was extracted during her initial orthodontic therapy as a teen. Her maxillary second molar was extracted after a series of dental procedures were unsuccessful as an adult in her 20s.

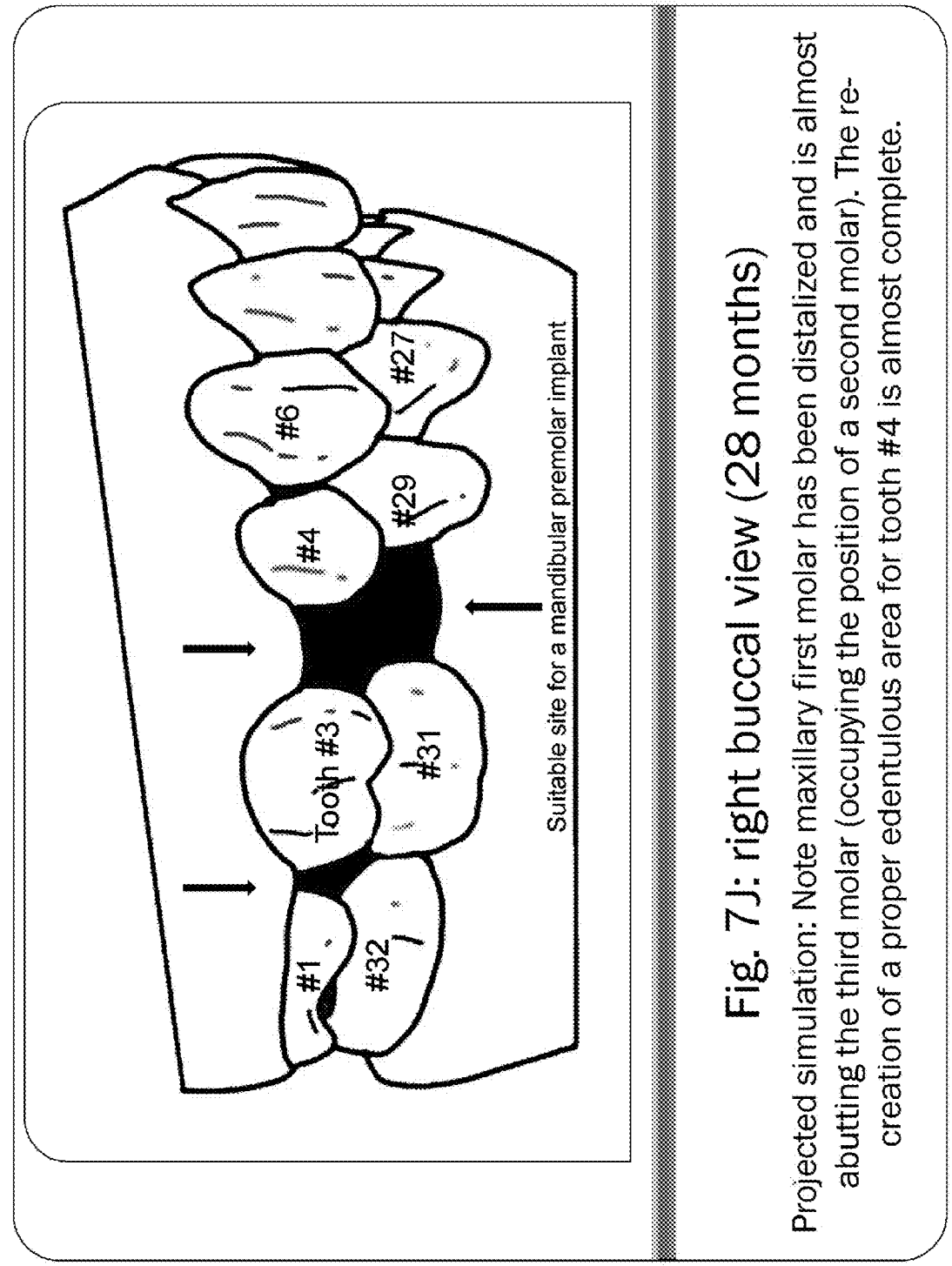
Fig. 7J: right buccal view (28 months)
Projected simulation: Note maxillary first molar has been distalized and is almost abutting the third molar (occupying the position of a second molar). The re-creation of a proper edentulous area for tooth #4 is almost complete.

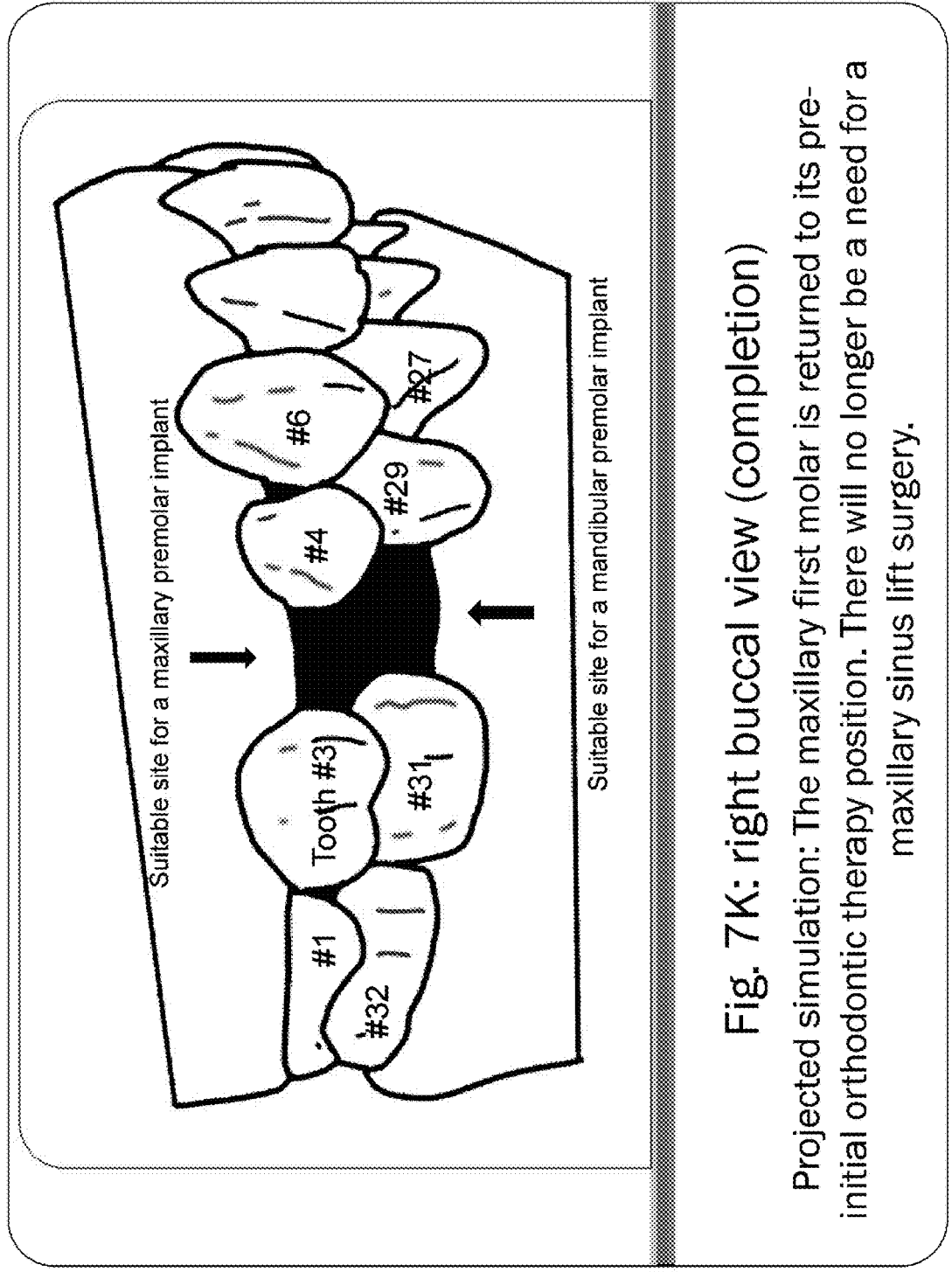
Fig. 7K: right buccal view (completion)
Projected simulation: The maxillary first molar is returned to its pre-initial orthodontic therapy position. There will no longer be a need for a maxillary sinus lift surgery.

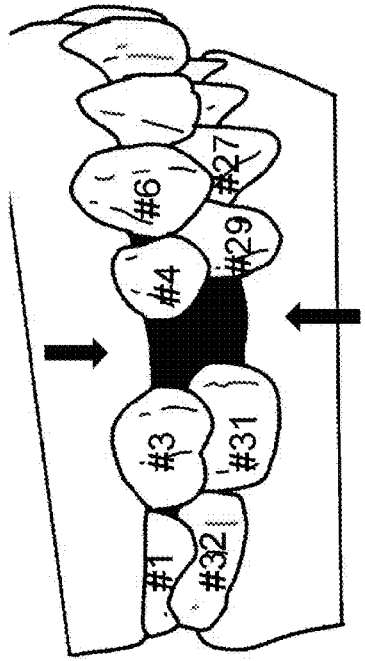
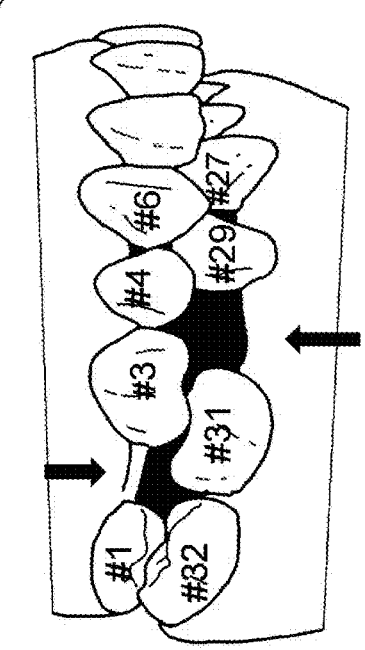
Fig. 7L: 12 months / end of therapy (32 months – est.)
Note: Because the first molar has been repositioned into its proper position, there is no longer a need for a sinus lift pre-implant surgical procedure.

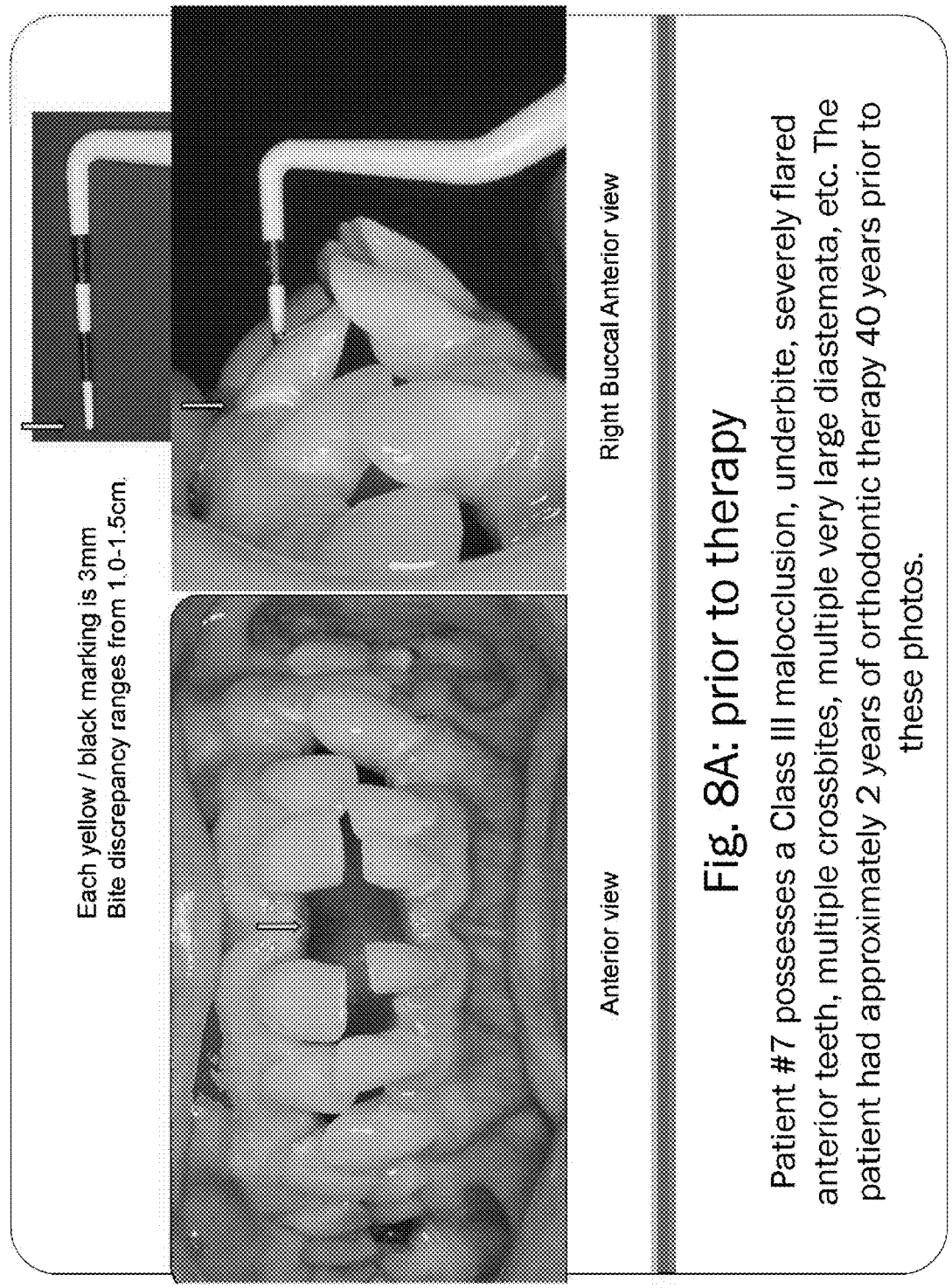

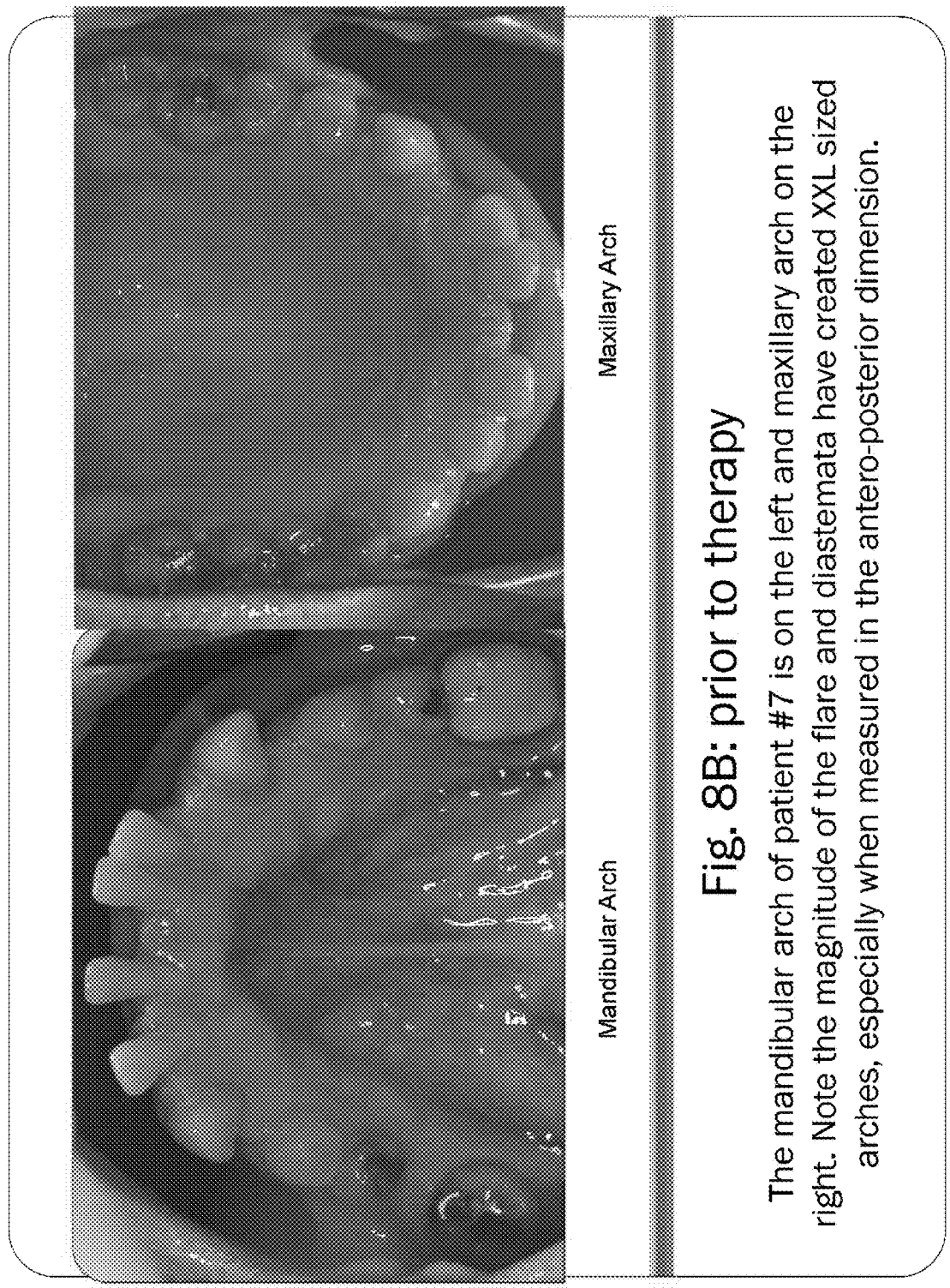
Fig. 8B: prior to therapy
The mandibular arch of patient #7 is on the left and maxillary arch on the right. Note the magnitude of the flare and diastemata have created XXL sized arches, especially when measured in the antero-posterior dimension.

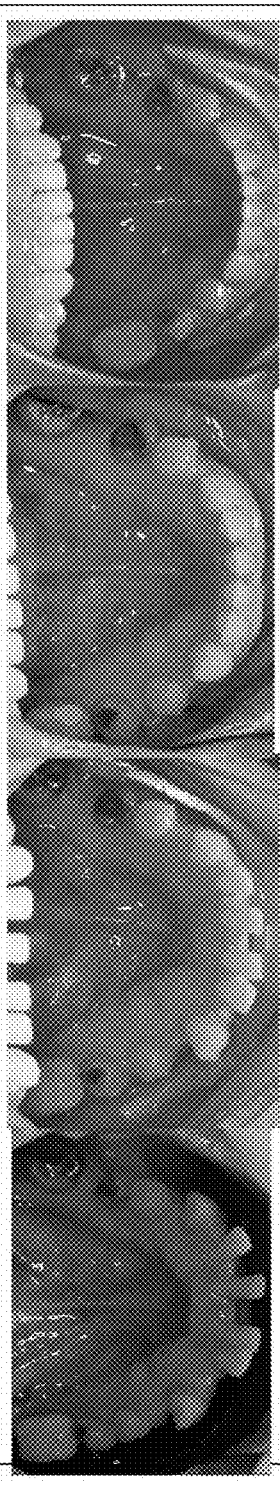
Figure 8C: Occlusal views of the mandibular arch as the BAOC reformulation process proceeds over the first 2.75 years. Note that diastemata (spaces) between the teeth and the antero-postero length of the mandibular arch have both been greatly reduced.
start / 1.25 years / 2.33 years / 2.75 years

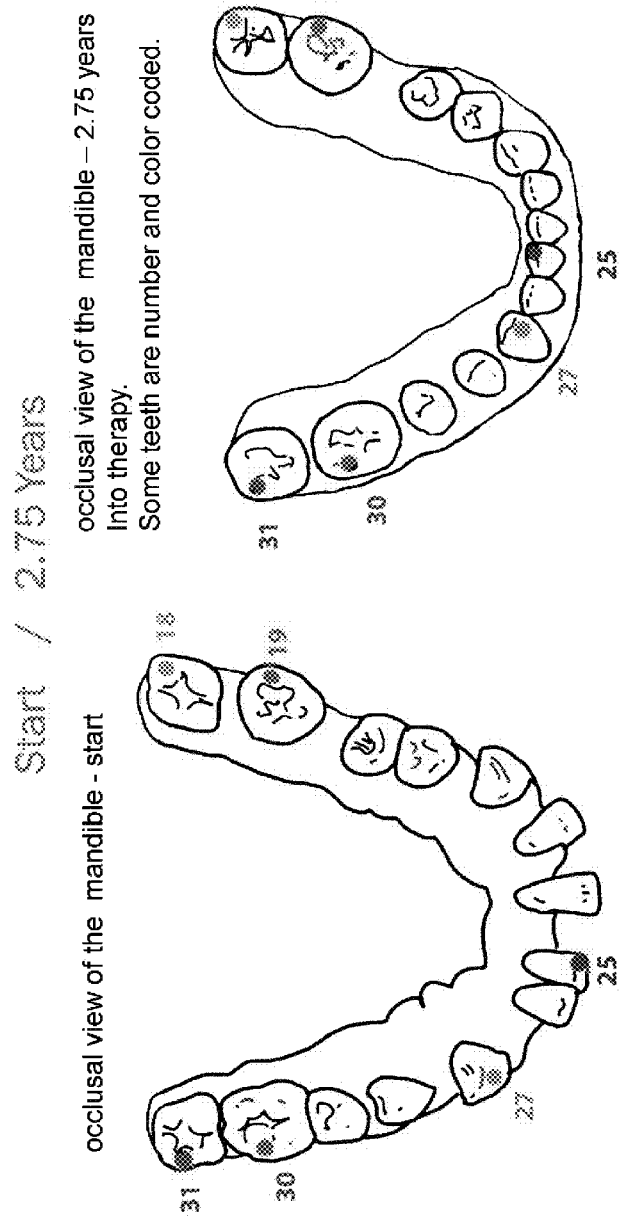
Figure 8D: Accurate depictions of the outlines of the mandibular jaw and teeth. Prior to and midway through the arch reformulation process.

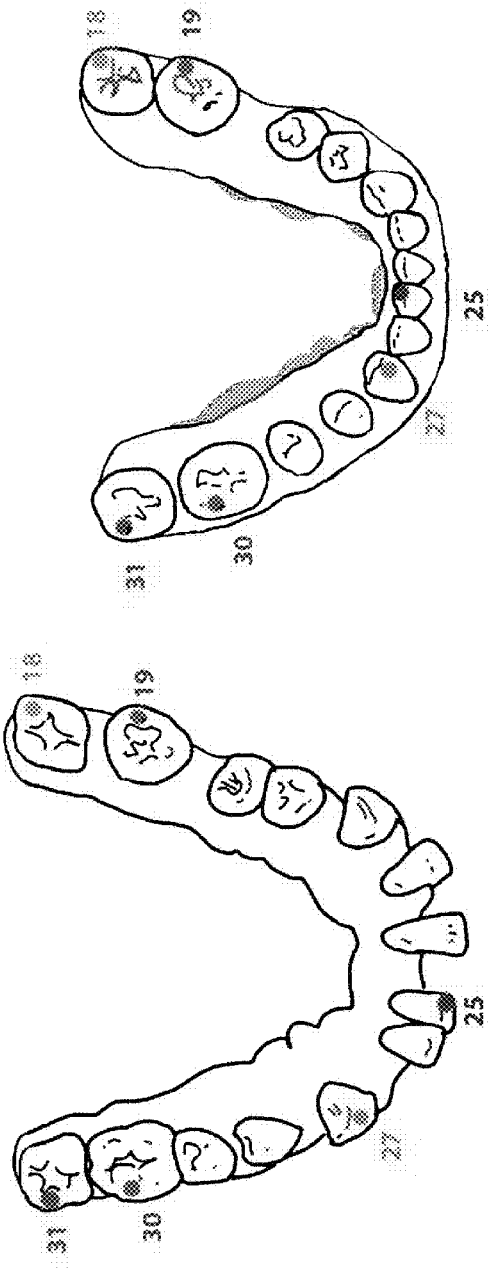
Figure 8E: Accurate depictions of the outlines of the mandibular jaw and teeth. Prior to and midway through the arch reformulation process.
light gray shading = bone was present prior to the initiation of the reformulation process
Start / 2.75 Years

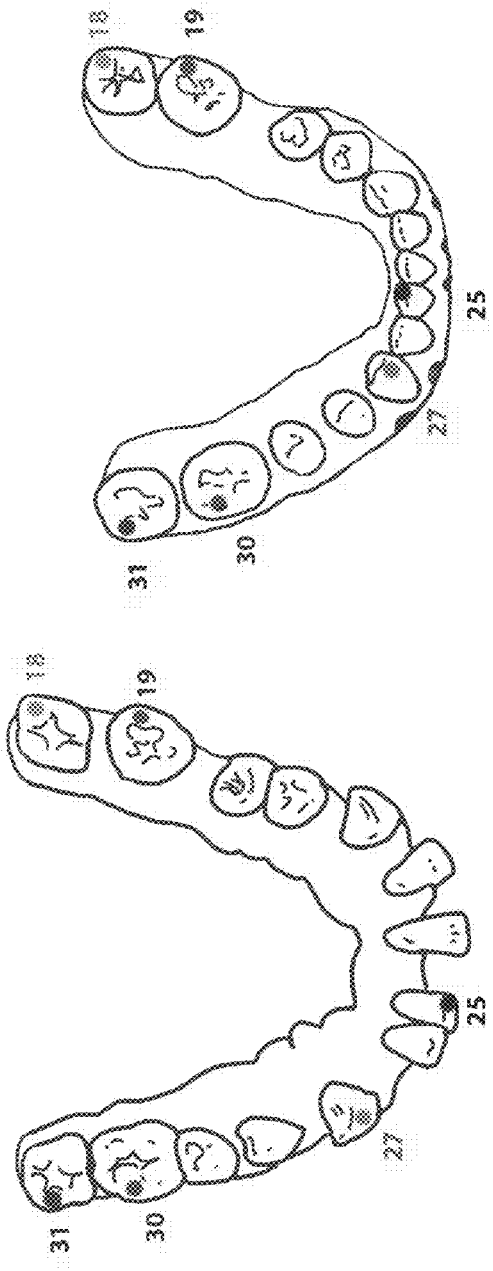
Figure 8F: Accurate depictions of the outlines of the mandibular jaw and teeth. Prior to and midway through the arch reformulation process. dark gray shading = location of new bone created during the reformulation process
Start / 2.75 Years

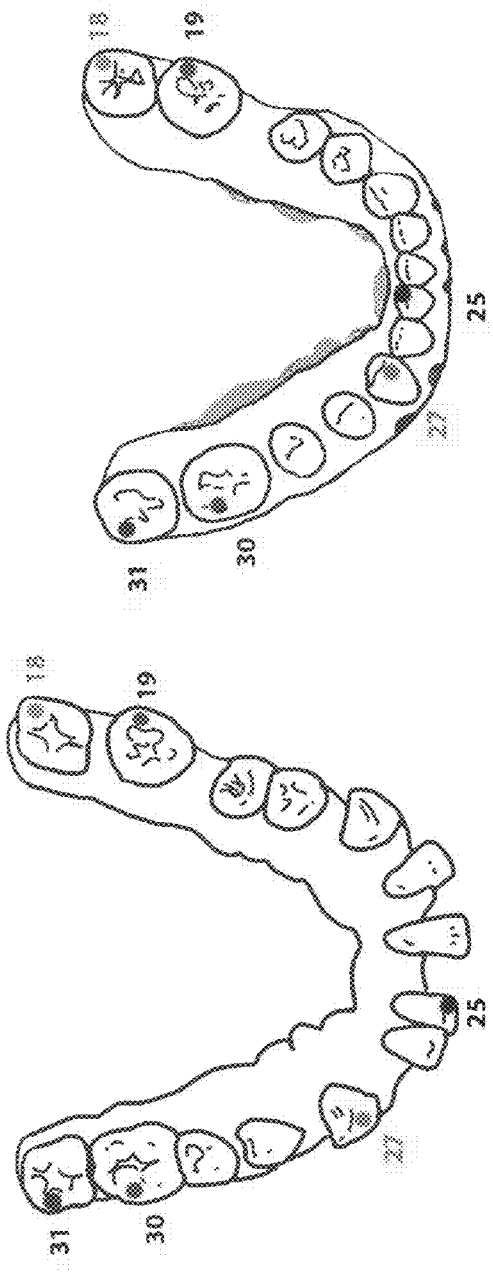

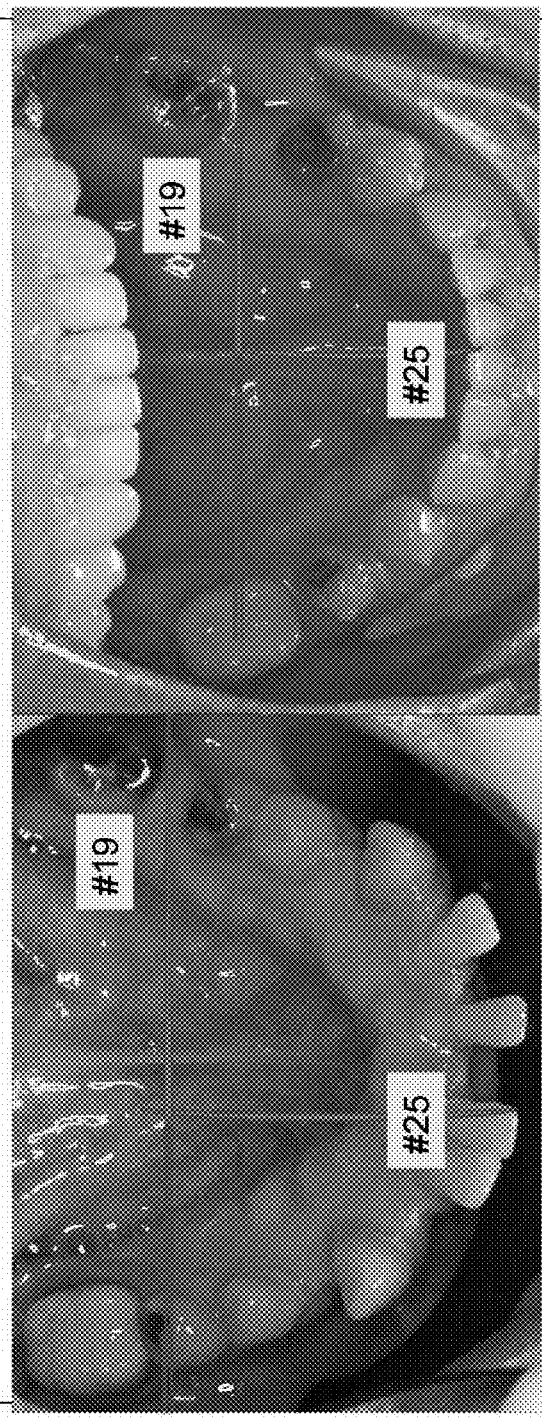
Figure 8H: one measure of the magnitude of the reformulation of the BAOC of the mandibular arch mesial occlusal tooth #19 ... mesial incisal tooth #25 arc distance reduction = 2.7cm
start = 55mm
2.75 years = 28mm

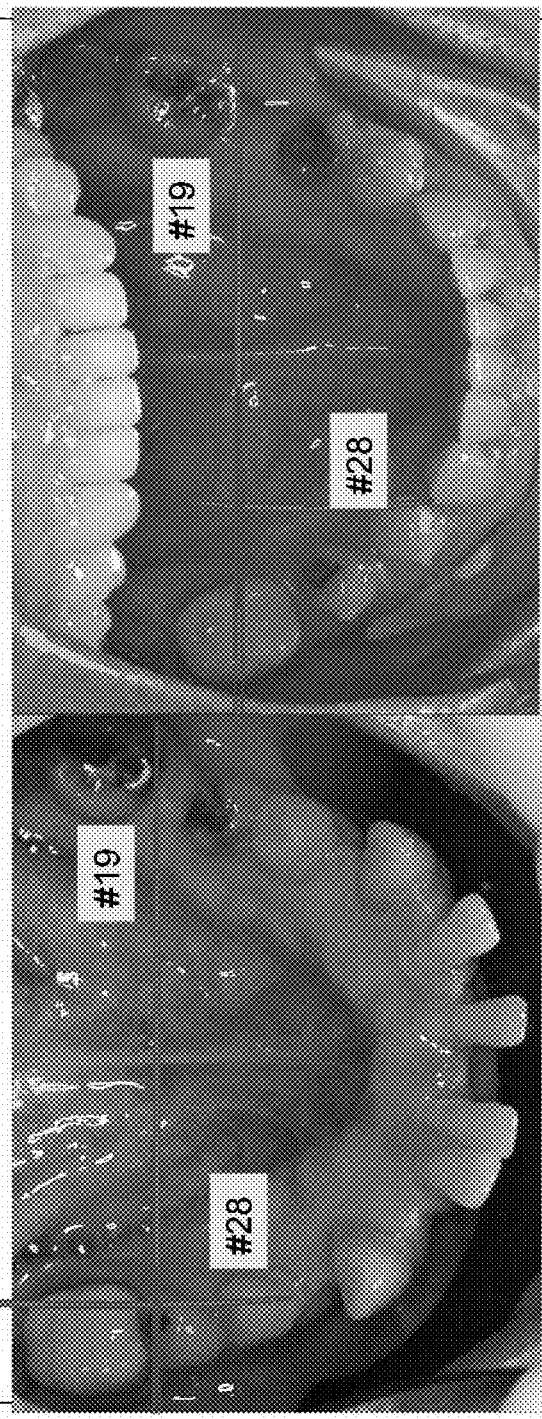
Figure 8I: another measure of the magnitude of the reformulation of the BAOC of the mandibular arch mesial occlusal tooth #19 ... mesial incisal tooth #28 arc distance reduction = 4.1cm
start = 89mm
2.75 years = 48mm

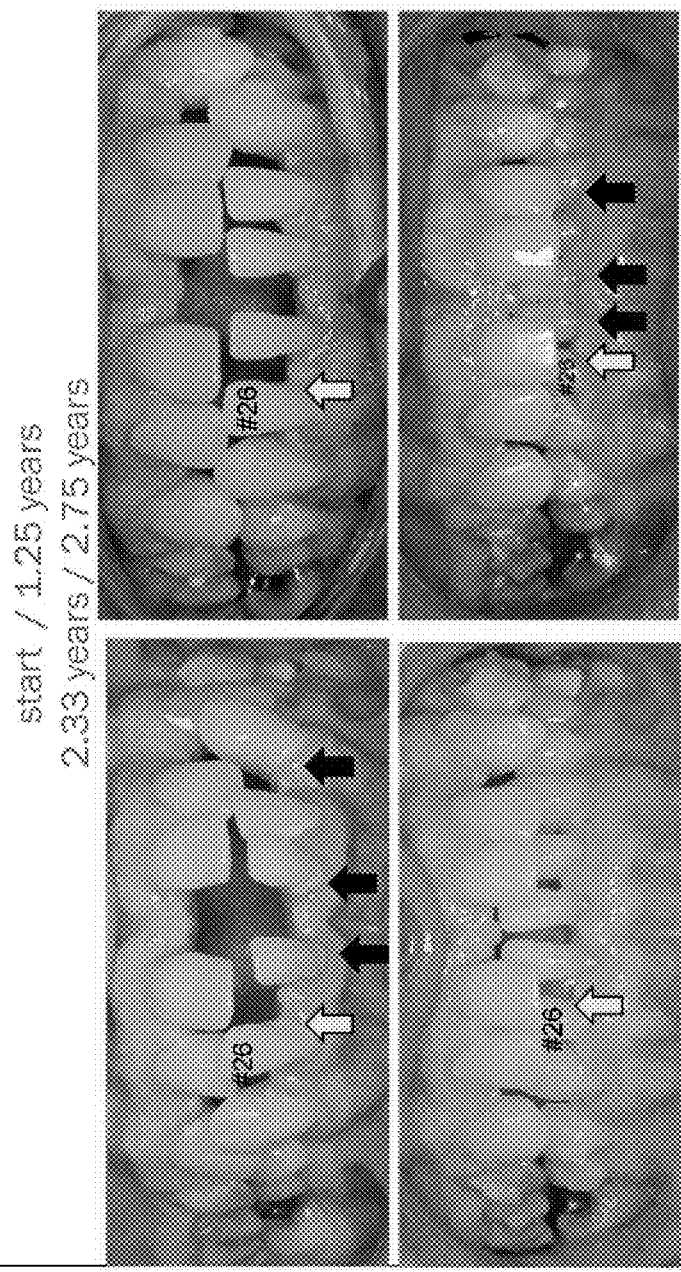
Figure 8J: Anterior views of the progression of the BAOC reformulation process over the first 2.75 years. Note the extreme flare has been greatly reduced and anterior crossbites have been corrected. Gingival recession and anterior vertical dimension have been corrected by up to 5mm. Gingival Health Level I was achieved at 2.33 years.

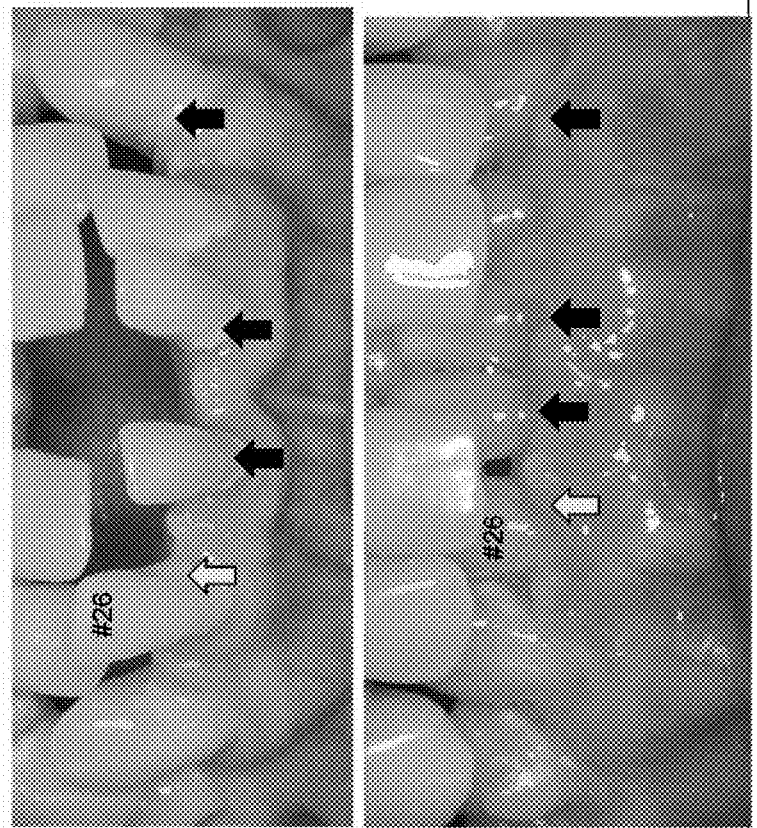
Figure 8K: Close up view of the mandibular anterior region which shows the progression of the BAOC reformulation process over the first 2.75 years. Gingival recession (up to 5mm), plaque and calculus accumulation levels have been reduced. Gingival Health Level I is being maintained at 2.75 years.

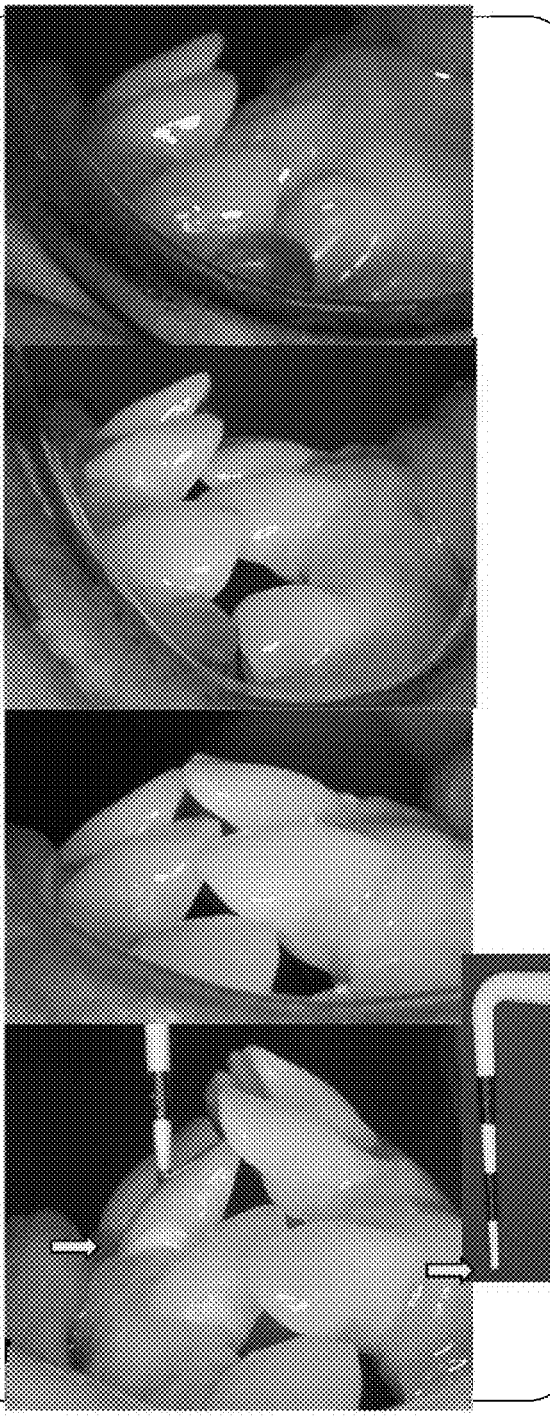

Figure 8L: Photos of the right buccal anterior view as the non-surgical correction of a Class III malocclusion proceeds. The underbite, edge-to-edge and anterior crossbite elimination stages are noted. Further progress is expected as the non-surgical BAOC reformulation proceeds. While a concern during the planning and treatment phases, the periodontal health has been maintained or improved.

start / 1 year / 2 years / 2.75 years

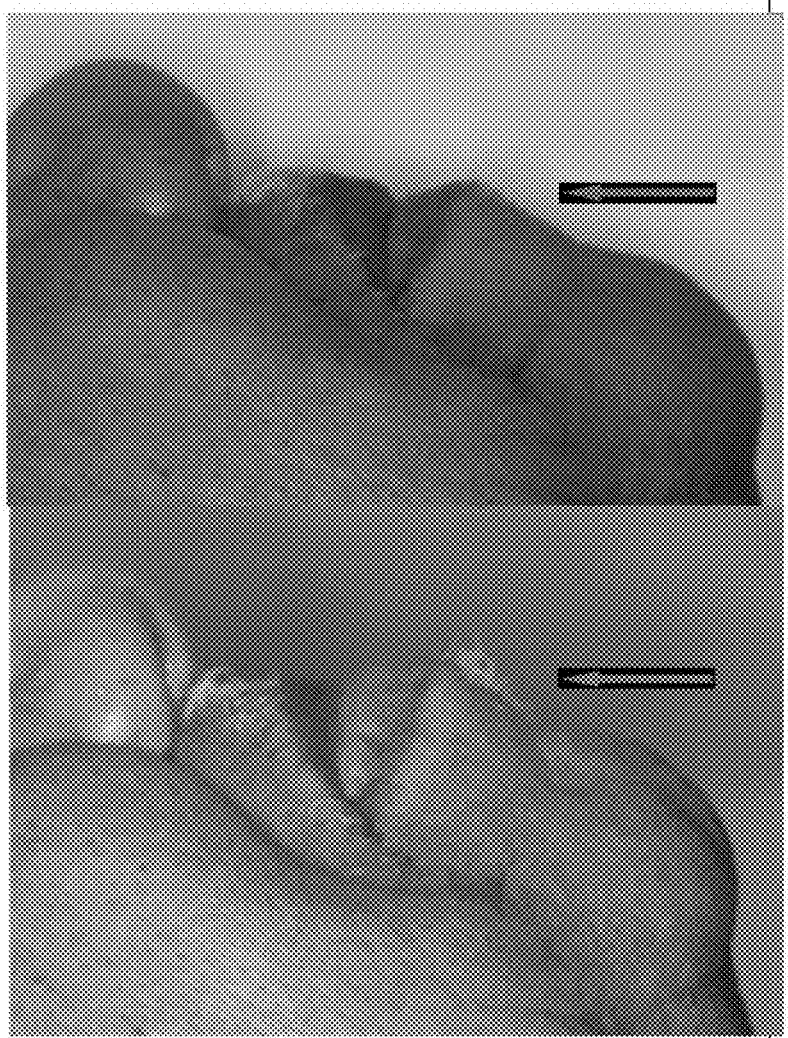
Figure 8M: Right extraoral profile photos note the progress of the non-surgical orthognathic therapy: start / 2 years

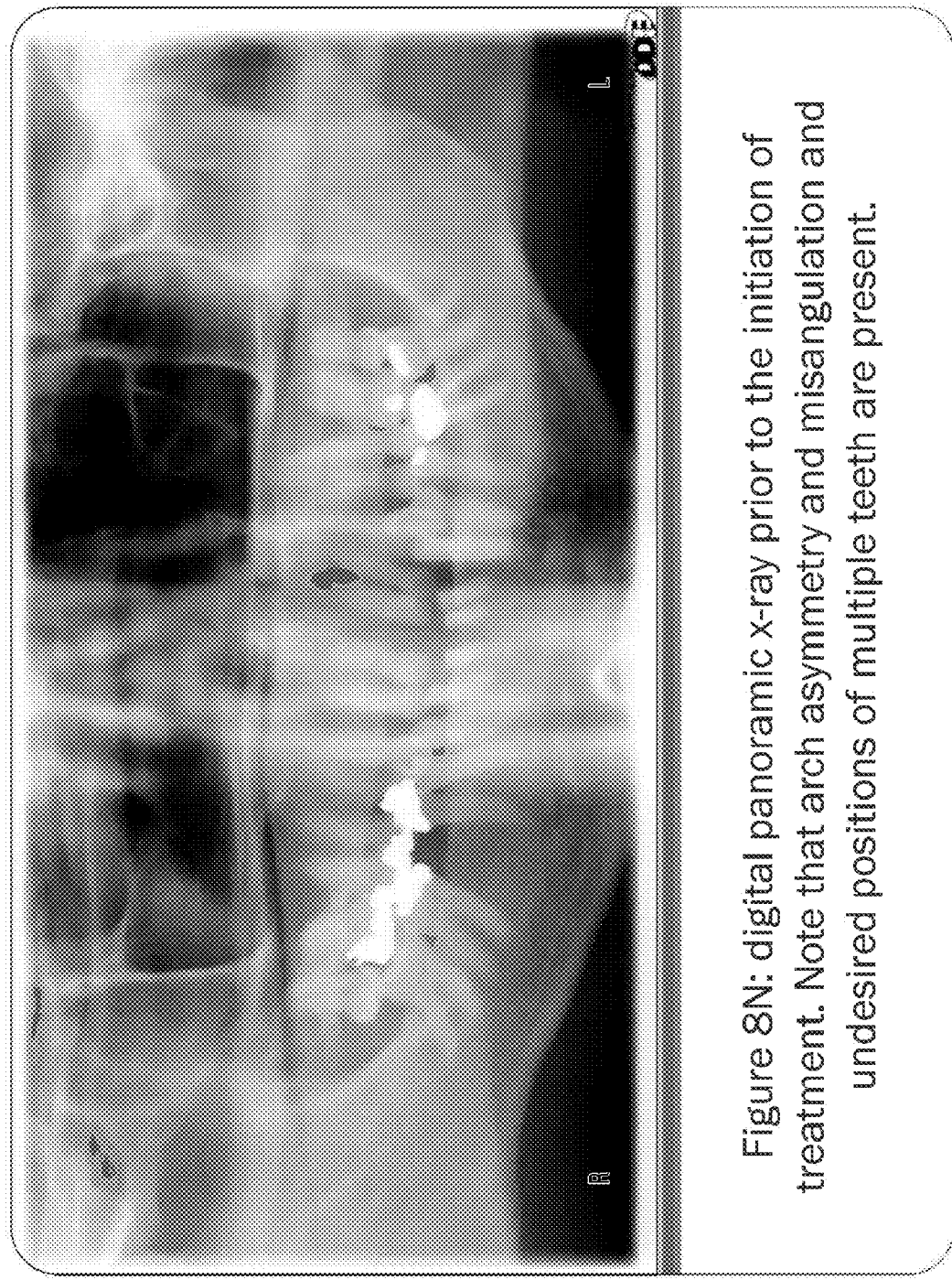
Figure 8N: digital panoramic x-ray prior to the initiation of treatment. Note that arch asymmetry and misangulation and undesired positions of multiple teeth are present.

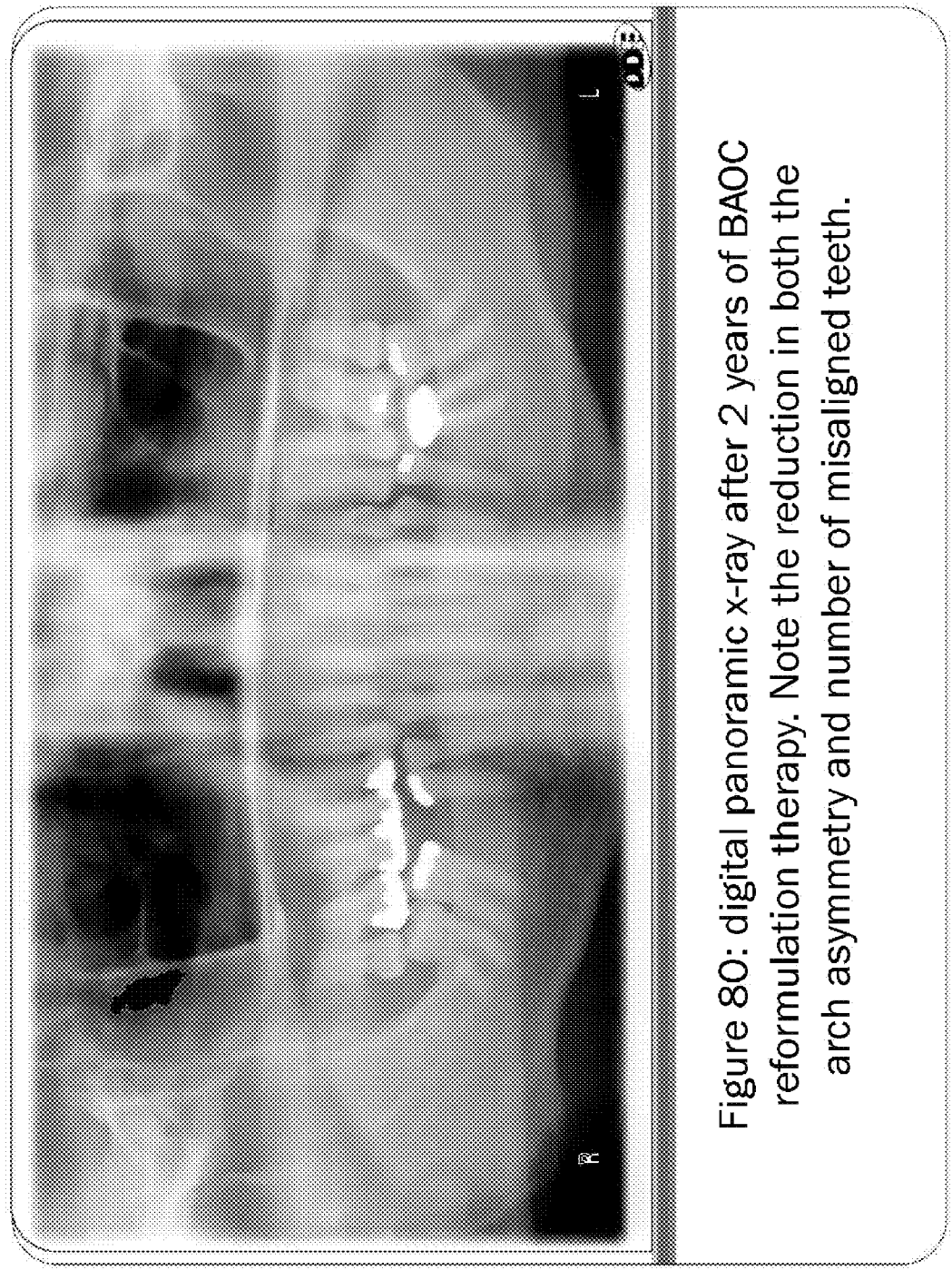
Figure 80: digital panoramic x-ray after 2 years of BAOC reformulation therapy. Note the reduction in both the arch asymmetry and number of misaligned teeth.

Fig. 8P: Levels of Gingival Health

| Month | Active Aligners Usage | Full Time Retainer Wear | Part Time Retainer Wear | Level of Gingival Health Achieved |
|---|---|---|---|---|
| 0 (Start) | | | | |
| 28 | Months 1-28 | | | Level I |
| 34 | | Months 1-34 | | Level I |

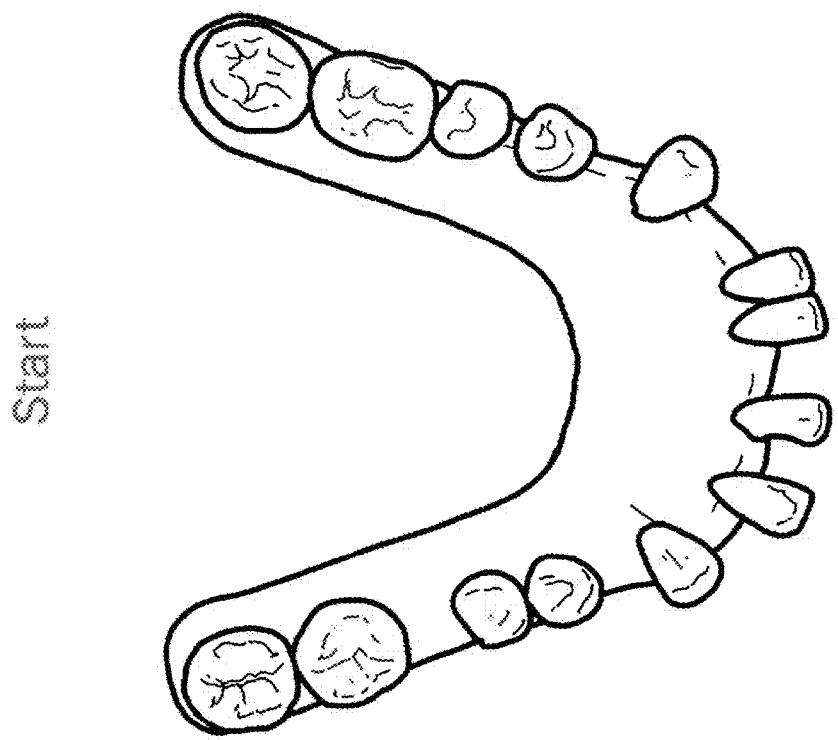
Figure 8Q: Depiction of the mandibular teeth prior to the initiation of the arch reformulation therapy.

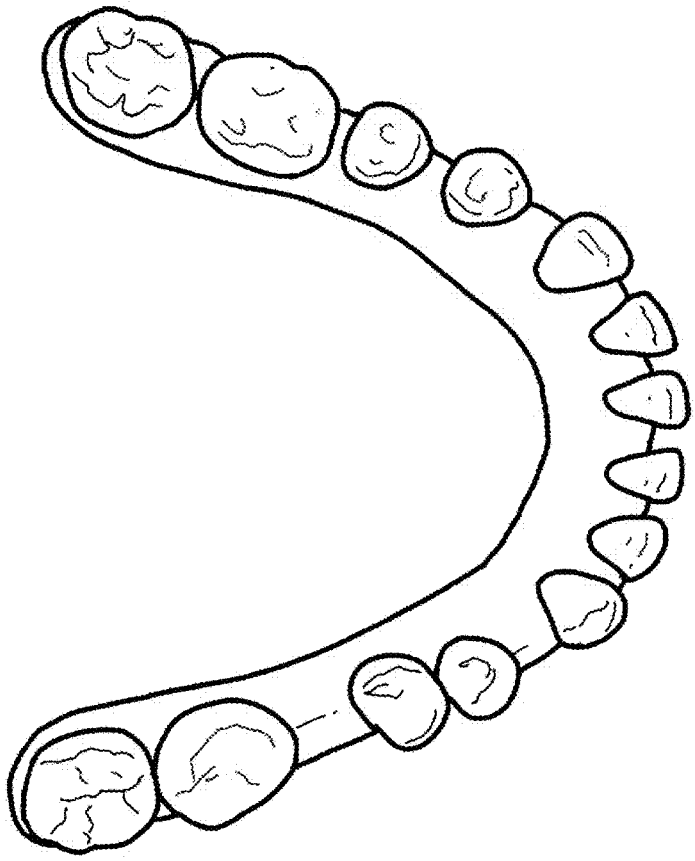
Figure 8R: Depiction of the mandibular teeth after approximately 2 years of arch reformulation therapy.

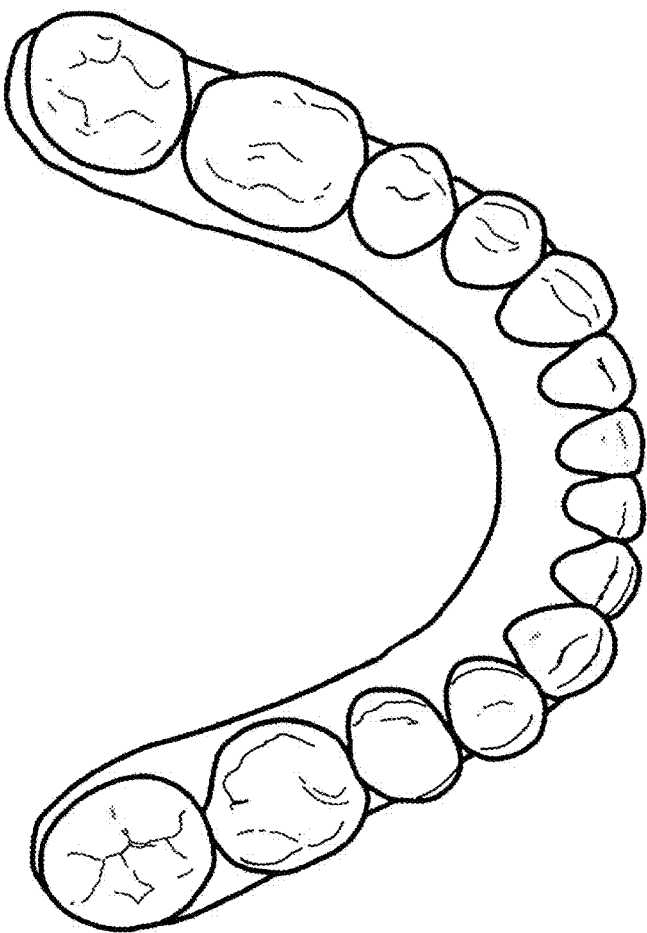
Figure 8S: Depiction of the mandibular teeth after the conclusion of arch reformulation therapy.
End of Therapy (approximately 5 years)

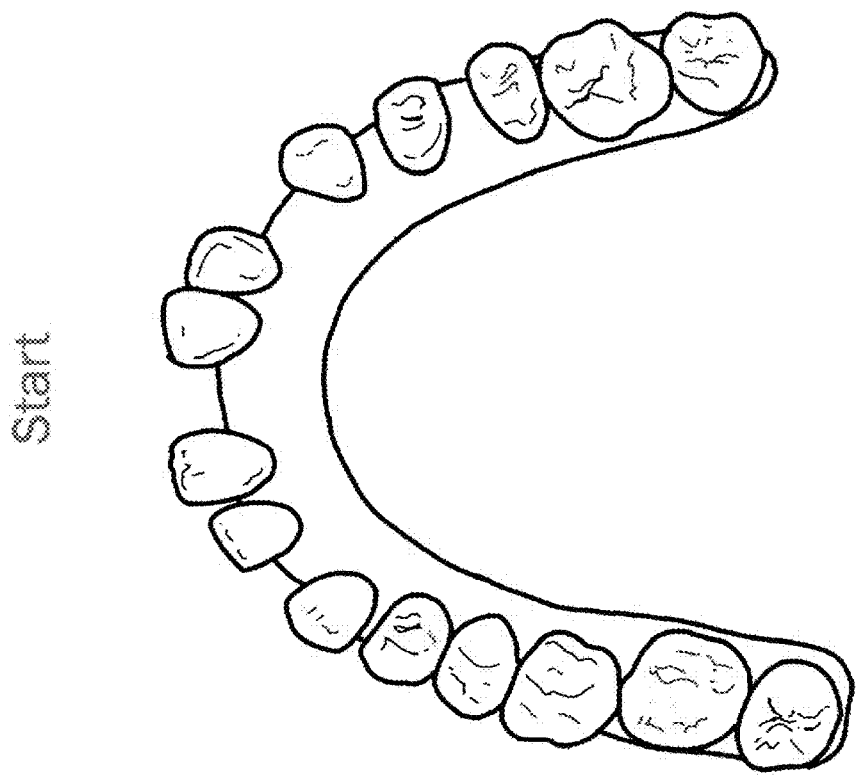
Figure 8T: Depiction of the maxillary teeth prior to the initiation of the arch reformulation therapy.

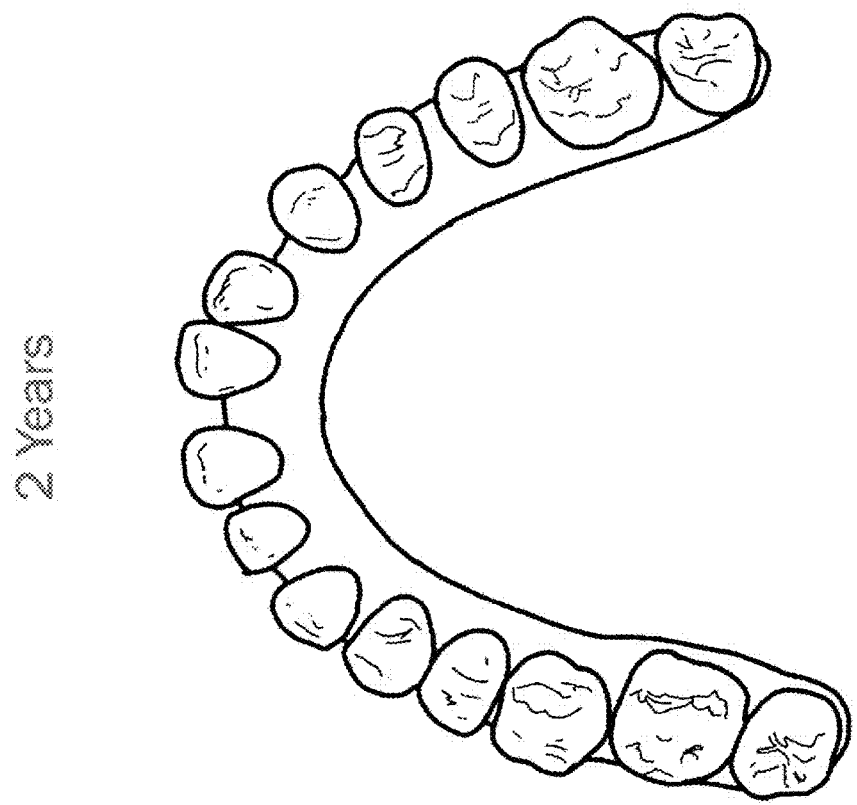
Figure 8U: Depiction of the maxillary teeth after approximately 2 years of arch reformulation therapy.

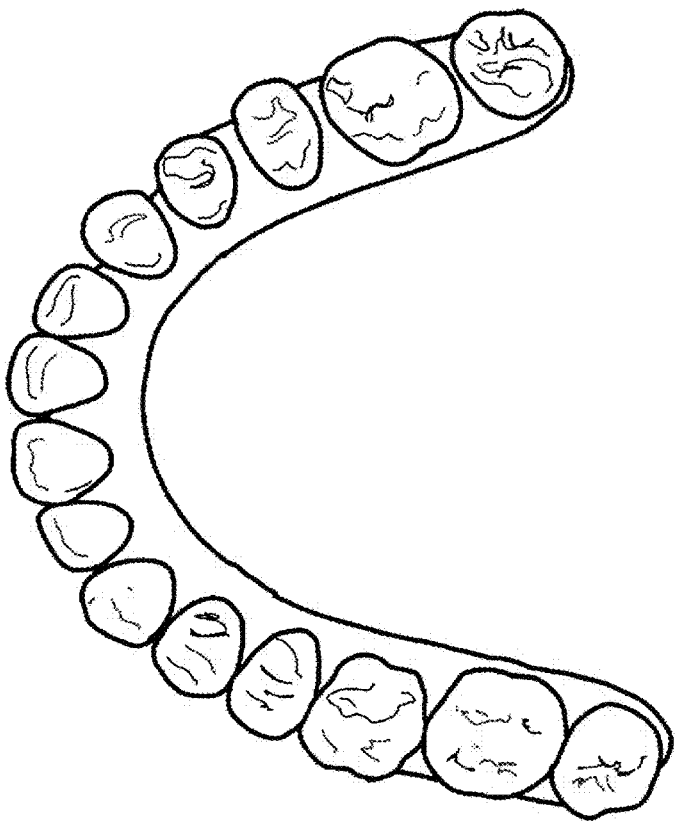
Figure 8V: Depiction of the maxillary teeth after the conclusion of arch reformulation therapy.
End of Therapy (approximately 5 years)

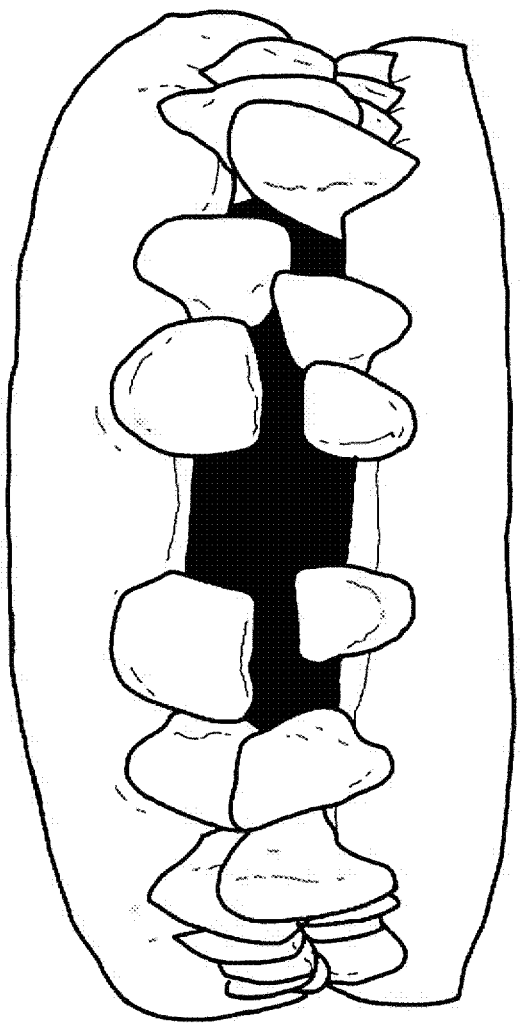
Figure 8W: Depiction of the anterior teeth prior to the initiation of the arch reformulation therapy.

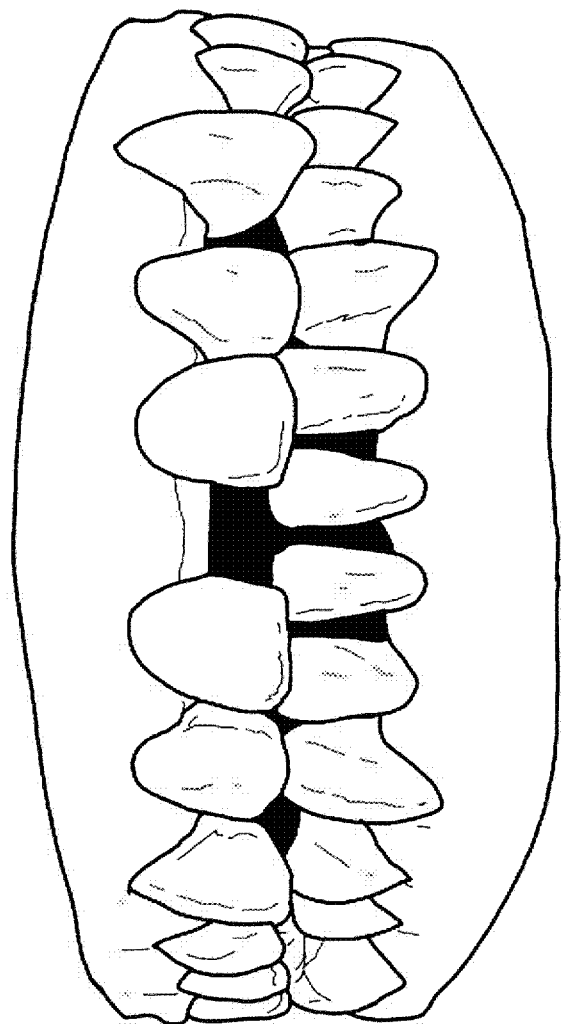
Figure 8X: Depiction of the anterior teeth after approximately 2 years of arch reformulation therapy.

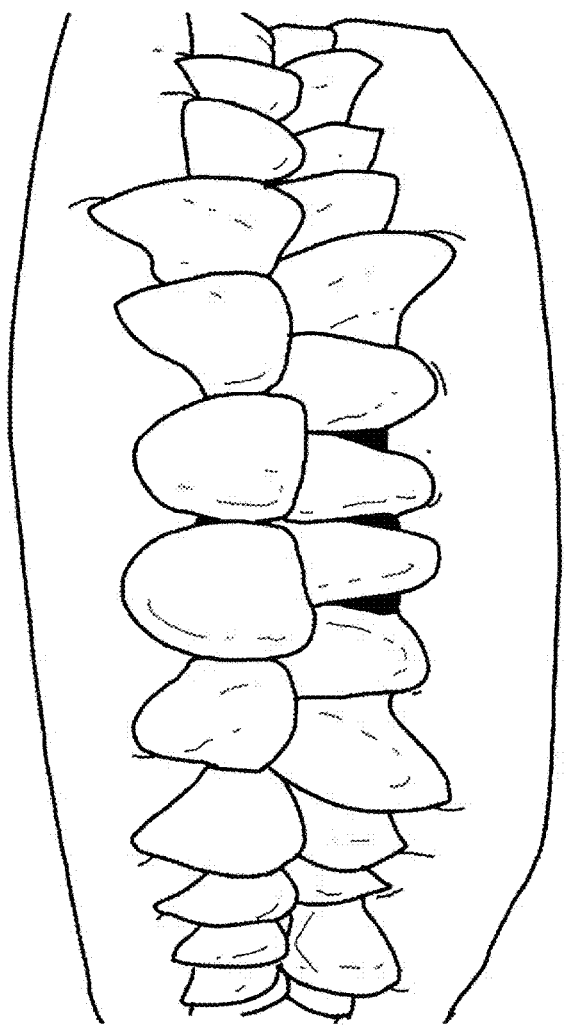
Figure 8Y: Depiction of the anterior teeth after the conclusion of arch reformulation therapy.
End of Therapy (approximately 5 years)

COMBINATION ORTHODONTIC AND PERIODONTAL; ORTHODONTIC AND IMPLANT; AND ORTHODONTIC AND TEMPEROMANDIBULAR JOINT DYSFUNCTION AND ORTHODONTIC ORTHOGNATHIC TREATMENT

CROSS REFERENCE TO RELATED APPLICATIONS

The present application claims priority to U.S. Provisional Patent Application No. 61/853,430, filed Apr. 4, 2013, the entire contents of which are incorporated in full herein by reference.

FIELD OF THE INVENTION

Disclosed is a method for the treatment of a periodontal and/or an orthognathic and/or a temperomandibular joint ("TMJ") dysfunction ("TMD") condition employing orthodontic techniques resulting in the treatment of the orthodontic condition as well as the periodontal and/or the orthognathic and/or the TMD and/or the edentulate area (e.g., tooth implant) condition.

BACKGROUND

Some braces utilize brackets that are adhered to the teeth. Other braces utilize removable devices. There are dental implements commonly referred to as aligners (removable braces) which are well known. One or more removable brace(s) are typically employed by orthodontists and dentists to gradually realign a patient's teeth along a desired path.

A well known aligner is made of a reasonably transparent medical grade customized plastic that fits onto a patient's teeth (hereafter flexible aligner). The desired alignment is achieved by configuring the aligner to induce the misaligned tooth/teeth to move and realign with the aid of the aligner. To treat a patient, several braces may be devised to induce the movement of the misaligned teeth gradually over a period of time. FIG. 1a shows a flexible aligner 100 configuration used in conventional orthodontic procedures and used in a method according to the present invention. A flexible aligner 100 which is a curved body 102 having a recess 104 that receives a patient's teeth. The curved body is flexible as illustrated in FIG. 1b. A flexible aligner is sometimes referred to as a removable aligner because it can be removed from the teeth and snapped back on by the patient.

It has been conventional thinking that not all patients are deemed responsive to treatment with flexible aligners. For example, according to the websites of major manufacturers of orthodontic flexible aligners, the guidelines for a patient who would be deemed unsuitable would have one of the following conditions:
1. Any type, method, or movement indicated as difficult.
2. Centric-relation and centric-occlusion discrepancies.
3. Teeth with short clinical crowns.
4. Arches with multiple missing teeth.
5. Patients whose second molars have not yet erupted.
6. Patients with poor oral hygiene.
7. Patients with active periodontal disease.
8. Doctor cannot confirm a patient is dentally and periodontally stable
9. Patients with dental prosthetics or implants.

While malocclusion has been associated with periodontal health conditions (pocket depth, gingivitis, alveolar bone loss, gingival recession, pocket depth), there is little evidence that malocclusion adversely affects the periodontium. Malocclusion can be treated through orthodontic treatment. It has been suggested that orthodontic treatment can be beneficial in the treatment of a periodontal condition. This suggestion, however, does not seem to have a clinical basis. Rather, it is based on the assumption that the orthodontic treatment may improve the patient's ability to clean the teeth once the teeth are properly aligned. Thus, it is not the treatment itself but it is the result of the treatment that is thought to be beneficial to the health of the patient's gums.

In a relatively recent study, a large number of studies were compared to determine whether orthodontic treatment will have a beneficial effect on a periodontal condition. In that study, it was determined that there was little clinical evidence suggesting that orthodontic treatment could be beneficial in resolving periodontal conditions. In fact, it was concluded that orthodontic treatment had a negative effect on the health of the periodontium. See Ann-Marie Bollen et al., The Effects of Orthodontic Therapy on Periodontal Health: A Systematic Review of Controlled Evidence, DADA, Vol. 139, April 2008.

Moreover, many clinicians are fearful that teeth classified as periodontally compromised are poor candidates for orthodontic treatment. They refuse to render teeth repositioning therapy to those patients because presently it is thought that the presence of an adverse periodontal condition indicates the likelihood of an unhealthy tooth that is less stable and suitable for orthodontic treatment. Indeed, removable flexible aligners are not recommended for patients with a periodontal condition.

According to accepted practice, to treat malocclusions, clinicians shrink the size of existing teeth (e.g. by shaving the teeth) to minimize the amount of movement, or omit certain malpositioned teeth from treatment. In addition, while it is known that the maxillary arch may be expanded, the recommended maximum expansion of the maxillary arch is 2 mm. Some reasons for these clinical choices are:
a) With prior materials and techniques, overlapped teeth required definitive space prior to the start of the repositioning or sometimes during the treatment.
b) Clinicians and patients prefer the duration of treatment to be as brief as possible to reduce the cost of treatment.
c) The belief that it will increase the likelihood that treatment will be completed prior to the patient becoming non-compliant or requesting cessation.
d) The less distance teeth need to move and the smaller the amount of rotation they require, the shorter the time necessary to accomplish those movements.
e) A significant increase in the length (antero-postero direction, front to back measurement) of the arches or large (>4 mm) arch expansion is considered to be unobtainable, non-feasible or unpredictable if the patient is post-pubescent (without surgery).
f) The severely maloccluded teeth are asymptomatic—they are neither painful nor present an annoyance (e.g., catch food, heavy bleeding) to the patient. Therefore, there is no desire to move those teeth.

As a consequence of these factors, the benefits of long term orthodontic treatment regimens have not been studied.

Pursuant to conventional thinking, clinicians or orthodontic training programs do not espouse the idealization of the axial inclinations of teeth to ensure the teeth stand as perfectly upright as clinically possible. According to standard practice, if the occlusal surface orientation is not worse than it was prior to therapy, or if there is some level of improvement, that is deemed acceptable. If a bite interference was created or not eliminated, then the standard practice is to shave away tooth structure to alleviate the problem. If the teeth are reasonably straight, but the incisal edges appear jagged, the standard practice is to shave down tooth structure to level the incisal edges. However, when the top, side, front or back of a tooth must be shaved down to help it fit better within an arch or to occlude better with the opposing arch, it is an indication that the proper or ideal orientation (axial inclination) of that tooth has not been realized.

A major problem with conventional orthodontic therapy is relapse. Relapse means that after the conclusion of orthodontic treatment the teeth return to their prior or another maloccluded state. The clinical reasons for relapse are not known and no retention therapy has been proposed to overcome the potential for relapse. See Simon J. Littlewood et al., Orthodontic Retention: A Systematic Review, Journal of Orthodontics, Vol. 33, 2006, pp. 205-212.

The inventor believes that relapse occurs because standard orthodontic therapy involving tooth repositioning does not properly align the teeth, which may further explain why standard orthodontic therapy has not been able promote the health of gingiva.

Moreover, it has been conventional thinking that alveolar bone height, once lost, could not be predictably and purposefully regenerated naturally by the body.

Loss of alveolar bone is sometimes accompanied by receding gums.

A conventional technique for offsetting the effects of the lost alveolar bone is gum grafting surgery. The three most common types of gingival graft surgeries are connective tissue grafts, free gingival grafts and pedicle grafts. While there are situations where each of these intraoral tissue surgeries will be the preferred procedure, none possesses the ability to induce the regrowth of the lost alveolar bone non-invasively.

There are clinical situations that require regrowth of dense bone, for example, a tooth implant procedure. When a tooth implant is being considered, it is often necessary and common to perform a bone graft surgical procedure at the time of the extraction. When the magnitude of the infection warrants, the bone graft placement may be performed at a second surgical procedure months after the tooth (or teeth) was (were) extracted. On infrequent occasions when the osseous defect is large and significant, a second bone grafting procedure may be required to augment the initial bone graft and enhance the suitability of the edentulous area to receive an implant.

The purpose of the bone graft procedure prior to the placement of a tooth implant is to have the bone become as dense as possible. The density of the alveolar bone is important. The more dense the bone, the more favorable the prognosis for the dental implant.

When a tooth is extracted, the new bone that will develop over the next few months to fill in the site once occupied by the extracted roots of the tooth (or teeth) will not be as dense as the existing or surrounding bone. If an implant were to be placed in bone that was less dense, the time required for osseointegration would be longer when compared to a site where the bone was denser and more favorable. It is possible for an area of bone to lack adequate density to withstand the placement of a dental implant altogether.

In addition, currently, the treatment options for a non-restorable maxillary first molar or an existing edentulous space in the region of the maxillary first molar are also limited. Presently, two of the more common eventual treatment options for the space after the extraction (or if already edentulous) are a dental implant (implant abutment and crown) and a 3-unit fixed bridge.

On occasion, the inferior portion of the maxillary sinus is quite close to the alveolar ridge. So little bone may be available, that the insufficient height will preclude the placement of a standard length implant, or on occasion, the placement of a reduced size or minimal length implant.

In such cases, a popular method to create an adequate amount of bone to satisfy the proper surgical and prosthetic implant requirements is to perform a sinus lift or sinus augmentation surgery.

Sinus lift surgery is accomplished by adding bone material between the sinus and the existing maxillary bone. During the surgery a membrane from the sinus is repositioned in a manner that will allow bone graft material to be placed. The goal is to have the inferior portion of the sinus repositioned so it is farther away from (creates a greater distance) the alveolar ridge. That additional space will allow for the bone graft material to harden, become utilizable and eventually enhance the quantity of bone available for an implant placement in the area.

In short, many known treatment plans require invasive and surgical procedures in order to attain dense bone.

The evidence presented herein establishes that through a regimen according to the present invention, a patient suffering from maloccluded teeth and a periodontal condition can be successfully treated.

The evidence presented herein further show that other orthodontic conditions may be treated with a regimen according to the present invention with a higher chance of avoiding relapse.

The evidence presented herein will further show that a regimen according to the present invention may be employed to grow alveolar bone without grafting or other invasive dental procedure.

SUMMARY OF THE INVENTION

An object of the present invention is the purposeful and non-invasive realignment of maloccluded teeth to assist with the reformulation of the underlying basal/alveolar osseous complexes ("BAOC"). Non-invasive as used herein means without surgery, bone grafting, and/or modification of the teeth.

Another object of the present invention is to realign maloccluded teeth and reformulate the underlying BAOC of a patient suffering from a periodontal condition in a non-invasive manner.

Another object of the present invention is to realign maloccluded teeth to reformulate the underlying BAOC to induce and attain growth of dense bone in the maxillary and mandibular arches in a non-invasive manner.

Another object of the present invention is to realign maloccluded teeth to reformulate the underlying BAOC of a patient suffering from TMD in a non-invasive manner.

Another object of the present invention is to realign maloccluded teeth to reformulate the underlying BAOC of a patient who might otherwise be treated with an orthognathic oral and maxillofacial surgery in a non-invasive manner.

A method according to the present invention employs flexible aligners to realign misaligned teeth of a patient.

A method according to the present invention includes an active phase and a retainer/retention phase. Optionally, the method may include a hybrid phase, an active/retainer phase.

During the active phase, which may be carried out in multiple sub-phases, one or more flexible aligners (see FIGS. 1a, 1b) are devised for the movement of one or more targeted teeth toward achieving an ideal arch form for the patient. The flexible aligners are prescribed to be worn by the patient on a full time basis (20-23 hours per day) during the active phase.

An active phase is concluded when ideal arch forms and occlusion are achieved (95% of the desired movements have been realized), near ideal arch forms and occlusion are achieved (90% of the desired movements have been realized), or, if the near ideal arch forms and occlusion have not been achieved and it is concluded that no additional movement of the targeted teeth can be expected. (FIGS. 1c, 1d)

During the retention/retainer phase, the targeted teeth are no longer induced to move. Rather, a flexible retainer is devised to keep the targeted teeth in place. A retainer would have the same configuration as the flexible aligners but would be less deformable and slightly thicker. The retainer/retention phase is carried out in two sub-phases, namely a full-time (FT) sub-phase (20-23 hours per day) and a part-time (PT) sub-phase (7-12 hours per day). The retainer phase may include the application of more than one flexible retainer.

Optionally, a hybrid phase may be employed before the retainer phase and after the active phase. During the hybrid phase, a flexible retainer is devised to keep some of the targeted teeth in place while other targeted teeth are simultaneously induced to move. The hybrid phase may include the utilization of more than one flexible retainer.

In each one of these phases, the flexible aligners or retainers are devised/prescribed via prescription information sent to and received by a manufacturer of flexible aligners/retainers. The flexible aligners/retainers are fabricated according to the prescription by the doctor.

The efficacy of a method according to the present invention may be judged by evaluating the health of the patient's gingiva during each phase. The following summarizes a qualitative scale for evaluating the health of a patient's gingiva who is receiving treatment according to the present invention.

Level I of Gingival Health has been achieved when, compared to a state prior to the initiation of the treatment:
1) the overall appearance of the gingiva is improved;
2) the gingiva is less inflamed;
3) the gingiva is less red.
Level II of Gingival Health has been Achieved when, Compared to Level I:
1) the overall appearance of the gingiva has improved;
2) the gingiva is less inflamed;
3) the gingiva is less red;
4) the gingiva has started to mature (is more robust and has become thicker).
Level III of Gingival Health has been Achieved when, Compared to Level II:
1) the overall appearance of the gingiva has improved;
2) the gingiva is less inflamed;
3) the gingiva is less red;
4) the gingiva has stopped receding or has started to have evidence of growth;
5) the gingiva has maintained a prior level of robustness, of maturation, or has further matured.

Further levels are characterized by further improvement in the health of the patient's gingiva, which can be determined based on the appearance of the gingiva. Preferably, photographic records of the gingiva are obtained throughout the process to help the clinician determine whether a phase in the regimen is concluded.

Presently, the health of the gingiva is not considered a primary indication of the need to initiate orthodontic therapy. Presently the health of the gingiva is not a criteria used to determine whether standard orthodontic therapy was successful at the conclusion of treatment. Additionally, the health of the gingiva is presently not a criteria used to determine whether orthodontic relapse has occurred.

Presently, if a patient presents with active periodontal disease and/or pronounced gingival recession, proceeding with orthodontic therapy is contraindicated. Only after a periodontist or general dentist certifies that the periodontal health of the patient is sufficiently stable to withstand orthodontic therapy will treatment be initiated. According to one aspect of the present invention, active periodontal disease is an indication, not a contraindication, to the initiation of therapy.

As will be understood by a skilled person upon review of the disclosure, the health of the gingival tissue is a significant indicator of malocclusion, especially chronic malocclusion that will require intervention and correction by an orthodontist, general dentist, periodontist or other dental specialist.

A method according to the present invention may be employed to treat patients diagnosed with temperomandibular joint ("TMJ") dysfunction ("TMD"), and/or non-carious teeth sensitivity, and/or periodontal manifestations or periodontal disease, and/or one or more edentulous spaces and/or chronic malocclusion, including conditions which may merit treatment with an orthognathic surgery alone or in conjunction with orthodontic therapy.

A method according to the present invention can be employed to treat, for example, gingival recession, alveolar bone loss and/or other manifestations of periodontal disease, TMD, edentulous spaces with a non-surgical non-invasive alternative to implant surgery and restoration, non-carious tooth sensitivity, malocclusion, including elective non-surgical correction of Class III malocclusions and a non-surgical non-invasive alternative to a pre-implant sinus lift grafting surgery.

A method according to the present invention employs multiple progressive removable flexible orthodontic aligners to treat patients with gingival recession, alveolar bone loss and other manifestations of periodontal disease, edentulous (or soon to be edentulous) areas, TMD, non-carious teeth sensitivity and/or other gum diseases and/or malocclusion, including a non-surgical alternative for elective orthognathic surgery. It is based on belief and anecdotal reporting from patients that TMD symptoms are relieved by this method.

For example, a 44 year old patient who had been unable to open up her mouth sufficiently wide to eat an apple reports that she can now bite an apple without having to first cut it into sections. Additionally, this patient reports that she is now able to bite into certain sandwiches and rolls without first cutting them into smaller portions. The patient has been able to open up her mouth wider than she has been able to for more than two decades. As of this submission, she has been devoid of TMJ pain for almost a year. While her TMD symptoms diminished within weeks after the initiation of therapy, it took approximately 0.5 years for the pain and discomfort to completely resolve. It took approximately 1.5 years into the 3.5-4.5 years projected therapy to allow her oral functionality (maximum opening) to improve to the point that she no longer has any physical restrictions on what she can and cannot eat. A method according to the present invention may be employed to treat patients who have had the following common dental care options recommended: dental implant placement with (or without) an accompanying bone graft surgery, maxillary sinus lift bone graft surgery, elective orthognathic surgery, non-surgical treatment for TMD, and/or periodontal manifestations or periodontal disease, and/or chronic malocclusion.

In a first embodiment, and contrary to conventional practice, a method according to the present invention may be employed to treat maloccluded teeth of a patient suffering from a periodontal condition.

Thus, a method according to the first embodiment may be an exclusively non-invasive and non-surgical orthodontic method of re-alignment of maloccluded teeth of a patient with an active periodontal condition, without modification of the patient's teeth, the re-alignment beginning at an initial state of alignment of the teeth and ending at a final state of alignment of the teeth, the final state of alignment of the teeth being closer to an ideal arch than the initial state of alignment, the method comprising an orthodontic treatment regimen, the treatment regimen including configuring a plurality of flexible aligners for the patient, the flexible aligners being configured to re-orient the patient's maloccluded teeth progressively from the initial state of alignment to the final state of alignment based on improvements in the health of the patient's gingiva. The periodontal condition may be indicated by an adverse condition of the patient's gingiva and/or the underlying osseous structure. The adverse condition of the patient's gingiva may be indicated by one of recessed gum line, bleeding, and abnormal periodontal pocket. The adverse condition of the underlying osseous structure may be radiographically diagnosed.

It has been observed that a method according to the present invention can result in natural growth of bone without bone grafting. To be more specific in a method according to the second embodiment of the present invention, natural bone growth is induced which can be an alternative to bone grafting prior to, for example, implanting a dental implant.

A method according to the second embodiment of the present invention is an exclusively non-invasive and non-surgical orthodontic method of repositioning a patient's teeth, without modification of the patient's teeth, the repositioning beginning at an initial state and ending at a final state, the method comprising an orthodontic treatment regimen, the treatment regimen including configuring a plurality of flexible aligners for the patient, the flexible aligners being configured to reposition a patient's tooth progressively from the initial state to the final state, wherein the regimen is devised to induce bone reformulation at a site which will improve the surgical suitability of the site for a dental implant placement. The site may be in the anterior or posterior of the mandibular or maxillary arch.

Thus, unlike a conventional method that employs grafting to enhance the density of bone prior to implantation, a method according to the present invention takes advantage of the diminished and less desirable density of the bone. The lower the density of the bone, the poorer the quality of the bone, the better the prognosis for application of a method according to the present invention.

In each embodiment, the treatment regimen may include an active phase during which the maloccluded teeth are reoriented and a retainer phase during which the teeth are maintained in position. The treatment regimen may further include a hybrid phase during which only some of the patient's teeth are reoriented. Each phase may include the configuring of a plurality of flexible aligners. Each phase may span more than one month, and in each phase, the flexible aligners may be prescribed for a period of time spanning less than 24 hours per day. During the active phase the flexible aligners may be prescribed for less than twenty four hours per day, and the flexible aligners may be configured to induce movement of the patient's maloccluded teeth. During the retainer phase retainers may be prescribed for less than twenty four hours per day and are configured to maintain the patient's teeth in position after completion of the active phase. The retainer phase may include a full-time phase during which flexible retainers are prescribed for more than 12 hours per day as well as a part-time phase during which flexible retainers are prescribed for less than 12 hours per day. During the hybrid phase the retainers may be prescribed for more than 12 hours per day to maintain the position of less than all of the patient's teeth, the hybrid phase following the active phase and preceding the retainer phase.

According to an aspect of the present invention, the active phase is deemed concluded when at least a near ideal arch is attained.

A method according to the present invention may be carried out in conjunction with teeth whitening. The teeth whitening may comprise the application of 10% carbamide peroxide (or a greater or lesser strength of solution).

A method according to an embodiment of the present invention may include the mesialization of the mandibular second molar to occupy the spot previously occupied by the mandibular first molar. On occasion and when appropriate for the proper development of the arch form, decongestion of the anterior region and the occlusion, the mandibular second premolar may be repositioned mesially, distally, intruded, extruded and/or uprighted by application of a method according to the present invention.

Presently, when dental implants are present or planned to be placed in an arch, the adjacent and/or surrounding teeth are not repositioned via orthodontic therapy prior to or after implant placement with flexible aligners. Furthermore, it is rare to use non-removable braces to reposition teeth prior to or after implant placement because it is thought that such procedure will not produce desirable results predictably. While not unintuitive, there are a number of reasons why orthodontic treatment before or after implant placement is rarely performed. For example, prior iterations and attempts with less robust methods have yielded underwhelming or unsatisfactory results; clinicians and patients prefer quick fixes, therapies with durations measured in months, not years; implant surgeries, pre-implant surgeries, provisional and transitional restorations have established and accepted protocols. All these factors direct clinicians away from using flexible aligners, which are thought to take longer than, for example, non-removable braces.

With the present invention described herein, many patients will benefit from this pre-implant orthodontic/periodontal therapy by requiring a reduced number of dental implants or possibly not needing any dental implants to properly address their edentulous areas and/or chronic malocclusion. When present and appropriate, the translational movement via the mesialization of the second or third molar, as well as the prudent repositioning of all other maxillary and mandibular teeth to idealize the arch forms, may be accomplished as well. The purpose of these sophisticated and significant (e.g., translational) movements is to have the posterior and anterior teeth mesh as well as possible, have the periodontal ligaments be aligned and idealized, which will facilitate the positive reformulation of the BAOC, which will improve the health of the periodontium. The increased stability at the conclusion of therapy will minimize the likelihood of the canting and non-ideal axial inclinations of teeth which are presently not uncommon results at the conclusion of orthodontic therapy, or which start to occur shortly thereafter, during the relapse phase.

Presently, the positive potential that could be garnered from the presence of wisdom teeth is often disregarded in treatment planning. Wisdom teeth in proper function will aid the occlusion to become as ideal as clinically practicable, as well as aid the mouth to become as resistant as possible to the forces of relapse.

Whereas implant considerations and treatments are hamstrung by limited amounts and levels of bone, a method according to the present invention can take advantage of the reduced amount of available alveolar bone between the ridge and maxillary sinus. While bone which is less dense may pose a hindrance for dental implant surgery, it would be an asset with BAOC reformulation accomplished by the present invention.

A method according to the present invention can result in the mesialization of the maxillary second molar to occupy the spot previously occupied by the maxillary first molar, the possible repositioning (i.e., distalization, mesialization, extrusion, intrusion, uprighting) of the maxillary second premolar and the mesialization of the mandibular third molar, if present, as well as the prudent repositioning of all other maxillary and mandibular teeth to idealize the arch forms, have the posterior and anterior teeth mesh as well as possible, and to positively reformulate the BAOC.

A method in its preferred form employs flexible aligners currently fabricated for orthodontic applications. The flexible aligner may be transparent for cosmetic purposes although other materials may be used without deviating from the present invention. The flexible aligners may be fabricated by a variety of methods (e.g., dental laboratory, orthodontic laboratory or a three dimensional printer).

Flexible aligners used in a method as disclosed herein comprise sequential progressive, relatively clear plastic, plastic-type (e.g., medical grade polyurethane aligners) and/or plastic-metal (e.g., medical grade polyurethane containing nickel titanium, or another metal/ceramic/composite) and/or other synthetic-reinforced devices.

As disclosed herein a flexible aligner, which is currently used only for treatment of orthodontic conditions, can be used to treat other forms of dental disease, including, but not limited to periodontal disease (e.g., gingivitis, periodontitis, gingival recession), TMD, cold sensitivity and other non-carious sensitive teeth, edentulous spaces with a non-surgical non-invasive alternative to implant surgery and restoration, malocclusion, including elective non-surgical correction of Class III malocclusions and a non-surgical non-invasive alternative to a pre-implant sinus lift grafting surgery.

According to an aspect of the present invention a flexible aligner is used to create near ideal (as ideal as clinically practicable) maxillary and mandibular arch forms, as well as near ideal (as ideal as clinically practicable) occlusal relationships, allowing the teeth to realign along an ideal (as ideal as clinically practicable) arch path.

It is believed that when the teeth are placed in as close to the ideal realignment as clinically practicable, the newly repositioned teeth will create as close to an ideal arch form as clinically practicable. This will facilitate the creation of an occlusion that will be as close to the ideal as clinically practicable. As the positive changes to the arch form and the occlusion are occurring, the BAOC that comprise the mandible and maxilla will be positively reformulated to be as ideal as clinically practicable.

According to the invention described herein, the positive reorganization of the osseous architecture that correlates to the new position of the teeth will have the effect of creating bone in more desirable and beneficial locations when compared to their pre-therapy positions. This will lead to an improved periodontal condition which will leave the mouth more healthful, easier to maintain (more resistant to plaque, stain and calculus accumulation) and with improved functionality.

The overall improvement in the health of the gingiva can be both quantified (i.e., reduced periodontal pockets) and qualified (i.e., clearly healthier visual appearance—less inflammation, reduced redness).

Part of the process of the idealization of the arch forms and the occlusion is to have the teeth be as upright as possible, be as derotated as possible and be as properly angulated as possible so that the occlusal forces are distributed as prudently as practicable to the periodontium and throughout the mouth to aid the purposeful and positive reformulation of the osseous composition of the maxillary and mandibular arches. The reformulated and improved BAOC will be better able to distribute the occlusal and masticatory forces, as well as be as resistant as possible to the constant and chronic forces encouraging orthodontic relapse.

It is noteworthy that simpler orthodontic repositioning solutions, which only include the movement of anterior teeth, and do not incorporate the movement of molar or premolar teeth into their design, are not sufficiently robust for use with a method according to the present invention.

A method according to the present invention preferably includes an initial diagnostic acquisition of information, initial and subsequent designs, and the active and retention therapy phases.

There are certain potential teeth movements which might be avoided or not considered when rendering traditional orthodontic care. For example, the corrections of a posterior crossbite and/or a severely rotated tooth (greater than forty five degrees) are often not attempted with orthodontic treatment. Some graduate orthodontic training programs advocate against the correction of a posterior crossbite or a patient with one or more teeth with severe rotation in a patient that has not expressed a complaint with their bite, appears to possess an asymptomatic malocclusion, or presents with complaints and/or symptoms of TMJ/TMD. However, as will be understood by a skilled person upon review of this disclosure, performing all of the prudent repositioning will be quite helpful and possibly essential to achieve the desired enhanced periodontal and/or TMJ/TMD and/or orthognathic, as well as orthodontic results.

The American Board of Orthodontics (ABO) has a quantitative grading mechanism, the Model Grading System (MGS) for scoring dental casts and panoramic radiographs which contains eight criteria. These eight criteria are: alignment, marginal ridges, buccolingual inclination, occlusal relationships, occlusal contacts, overjet, interproximal contacts, and root angulation.

A method according to the present invention may rely on two criteria to determine the efficacy of care: health of the gingiva and retention of the existing occlusion and dentition. Neither of these criteria is a consideration used to assess the success of orthodontic therapy by the ABO MGS.

Therefore, many treatments deemed to be an orthodontic success by the traditional ABO MGS would be classified as yielding an unsuccessful and unacceptable outcome by the criteria for success established by the method described herein.

The existing retention protocols for the aftercare of a patient who has undergone orthodontic therapy rarely possess strictly defined phases or periods. The inventor is not aware of any prior orthodontic technique that uses the health and the status of the gingiva as an indicator for the progression from one phase of treatment to another phase of treatment.

Presently, the orthodontic community is not in agreement—they are almost evenly divided—as to whether to affix retainers on the lingual surfaces of the mandibular anterior teeth or utilize removable retainers upon the conclusion of active orthodontic therapy. Those facts confirm that neither retention method yields results sufficiently successful that it would induce those who are non-users to convert from their present choice.

Existing post-orthodontic therapy retention protocols lack adequate guidance or provide insufficient criteria to help determine whether and when they should be continued/discontinued.

Some existing retention methods incorporate the placement of a fixed lingual retainer, usually a solid or braided metal, which is adhered via composite resin or other cement to the teeth to maintain them in their present positions.

It is not an uncommon practice for the application of a fixed lingual retainer to secure teeth into sub-ideal positions.

It is not uncommon for a patient to not be advised by a treating clinician when the fixed lingual retainer should be evaluated or removed.

In a conventional treatment regimen, active therapy is considered to be concluded when movements of the teeth are no longer encouraged by orthodontic intervention. Presently, when fixed retainers are utilized, they are commonly placed at the time active therapy has concluded. The end of active therapy in a conventional treatment regimen can be further defined as when fixed brackets are debonded or the duration of wear for the final stage aligner has been concluded.

Unfortunately, affixing lingual retention immediately after the conclusion of active therapy is almost always premature. As will be understood by a skilled person upon review of the disclosure, rigid fixed retainers will inhibit the potential efficacy that will be gained by the use of a removable retainer designed from the desired (usually the last) aligner simulation stage during the retention phases of therapy.

By not being able to reposition certain teeth (those adhered to the splint), other teeth in the arch and the opposing arch will have their ability to be moved into more desirable locations impeded or truncated. In addition to the teeth not being able to be placed in their ideal position, the supporting periodontium and the osseous reformulation will be hindered from achieving full potential due to compromised positioning.

Here is one way to quantitatively assess the efficacy of the results of a conventional orthodontic treatment. Orthodontic therapy which achieves 82% of the desired ideal results will already possess 18% relapse from that desired ideal. Therefore, orthodontic therapy is often deemed complete and active therapy is concluded, yet due to inadequate results, the detrimental relapse process is already active.

All occlusal forces (desirable or undesirable) are transferred from the tooth to the periodontium. That is why it is not just moderate and severe malocclusion, but even mild malocclusion, which will impact the periodontal health and contribute to and exacerbate unfavorable periodontal conditions (e.g., gingival recession).

Existing orthodontic treatment regimens do not incorporate sufficiently sophisticated and flexible retention protocols as an integral aspect of the overall treatment as the invention presented here espouses. Periodic Retainer Evaluation Visits ("PREV") are prescribed sessions whose purpose is to monitor and evaluate the health of the gingiva (periodontal exam which includes pocket probing), arch form, occlusion and position of the teeth. The health of the gingiva is not now and has never been a criteria for tooth and bone repositioning success (e.g., orthodontic therapy). In a method according to the present invention, PREV are used to evaluate and ensure the gingival health, arch forms, teeth positions and occlusion are improved or maintained during both the full time wear phase (20-23 hours) and part time wear phase (7-12 hours each day).

As will be described in greater detail, PREV occur near or at the conclusion of the active phase of aligner therapy, periodically during the full time and less frequently during the part time retention phases, according to the present invention.

Present prevailing protocols for all forms of braces and aligner therapy recommend evaluation of the occlusion and when necessary, modification of the occlusion prior to the initiation of therapy, during therapy (to relieve occlusal interferences), shortly after the completion of bracket debonding, or sometime after the conclusion of active therapy.

The process to modify or equilibrate the occlusion of the dentition requires that portions of the teeth be permanently removed (drilled away). As will be understood by a skilled person upon review of the disclosure, even the modest removal of healthy tooth structure at those junctures is contraindicated for the method described herein.

As will be understood by a skilled person upon review of the disclosure, occlusal adjustment performed at any of the above stages is premature, and should be avoided.

The modification of the occlusal surface can inhibit the level of idealness achieved by the eventual final occlusion, which can inhibit the development of the ideal arch form, which can inhibit the periodontium from reaching its as ideal state, which can inhibit the BAOC from achieving its ideal reformulation, or as close to ideal as clinically practicable.

Relapse presently plagues and drags down the success of the majority of orthodontic therapies, as reported by orthodontists. It is believed that a reason for relapse is the sub-ideal position and orientation of the teeth after conclusion of the active therapy, which creates forces that cause the relapse. Thus, a method according to the present invention is directed at achieving as ideal of position and as ideal of orientation for the teeth in order to prevent relapse. Thus, as will be understood by a skilled person upon review of the disclosure, establishing arch forms, an occlusion and BAOC that are as resistant to relapse as possible is an objective of a method according to the present invention.

The consequences of orthodontic relapse can range from mild to severe and asymptomatic to symptomatic. When mild and asymptomatic, no additional therapy may be indicated but may be performed (e.g., to satisfy esthetic concerns).

When severe and/or symptomatic, treatment with a method according to the present invention is indicated.

On other occasions, retreatment as described herein, as well as non-orthodontic dental care, such as periodontal therapy, may be indicated.

In short, a method according to the present invention employs flexible aligners to realign maloccluded teeth along an ideal or near ideal arch positions, which has been observed as a factor in avoiding relapse.

Other features and advantages of the present invention will become apparent from the following description of the invention, which refers to the accompanying drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A depicts an example of a flexible aligner that may be used in a treatment according to the present invention.

FIG. 1B depicts a flexible aligner in a deformed state (deformed between fingers of a person) by application of force.

FIG. 1C illustrates an example of a misaligned maxillary arch.

FIG. 1D illustrates an example of an ideally shaped maxillary arch.

FIG. 2A depicts an intraoral photograph of the $1^{st}$ patient's anterior view prior to the initiation of treatment according to the present invention.

FIG. 2B shows an intraoral photograph of the $1^{st}$ patient's anterior view after the successful conclusion of the active phase of therapy according to the present invention.

FIG. 2C shows an intraoral photograph of the $1^{st}$ patient's anterior view after the successful conclusion of the full time (FT) phase of retention therapy.

FIG. 2D shows an intraoral photograph of the $1^{st}$ patient's anterior region after 6 months of part time (PT) retention therapy.

FIG. 2E shows the $1^{st}$ patient 44 months after the start of therapy, 37 months after the conclusion of active therapy and after 31 months of PT retention therapy.

FIG. 2F is a chart which summarizes the Levels of Gingival Health achieved and maintained at various stages for the $1^{st}$ patient.

FIG. 2G shows the pre-treatment digital panoramic x-ray for patient #1.

FIGS. 2H and 2I are the smiles of patient #1 prior to the initiation of care and after the end of the active phase of therapy (7 months).

FIG. 2J is a side-by-side before/after comparison which illustrates a common response to whitening therapy with carbamide peroxide.

FIG. 2K is a side-by-side comparison of FIGS. 2A and 2E.

FIG. 3A depicts a view of the mandibular arch of the second patient before the start of a treatment according to the present invention.

FIG. 3B depicts a view of the mandibular arch of the $2^{nd}$ patient part-way through the active aligner phase of periodontally purposed orthodontic therapy according to the present invention.

FIG. 3C depicts a view of the expected location of the teeth and the new shape and increased size of the mandibular arch of the $2^{nd}$ patient after the therapy is concluded.

FIG. 3D is a photograph of the $2^{nd}$ patient's mandibular arch prior to the initiation of therapy according to the present invention.

FIG. 3E is a photograph of the second patient's mandibular arch midway through the active aligner phase of the therapy according to the present invention.

FIG. 3F depicts the $2^{nd}$ patient's maxillary arch prior to the start of the periodontally purposed therapy according to the present invention.

FIG. 3G depicts the second patient's maxillary arch midway through the active phase of therapy according to the present invention.

FIG. 3H is a photograph of the $2^{nd}$ patient's maxillary arch prior to the start of therapy according to the present invention.

FIG. 3I is a photograph of the $2^{nd}$ patient's maxillary arch midway through the active phase of therapy according to the present invention.

FIG. 3J is a photograph of the $2^{nd}$ patient's smile prior to the start of periodontally purposed therapy according to the present invention.

FIG. 3K is a photograph of the $2^{nd}$ patient's smile midway through the active phase of treatment according to the present invention.

FIG. 3L depicts the $2^{nd}$ patient's anterior view prior to the start of therapy according to the present invention.

FIG. 3M depicts the second patient's anterior view partway through the active therapy according to the present invention.

FIG. 3N is a photograph of the $2^{nd}$ patient's anterior region prior to the start of therapy according to the present invention.

FIG. 3O is a photograph of the $2^{nd}$ patient's anterior region partway (12 months) through the active phase of treatment according to the present invention.

FIG. 3P is a chart which notes that the First Level of Gingival Health has been achieved and maintained.

FIG. 4A is a photograph showing the anterior view of the third patient's teeth during the initial consultation.

FIG. 4B is a photograph showing the anterior view of the $3^{rd}$ patient's teeth 13 months after the initial consultation (FIG. 4A) and just prior to the start of periodontally purposed orthodontic therapy.

FIG. 4C is a photograph showing the anterior view of the $3^{rd}$ patient's teeth which quantifies the magnitude of the bone and gum loss in the mandibular anterior region.

FIG. 4D is a photograph of the $3^{rd}$ patient's anterior view 3 months after the initiation of therapy.

FIG. 4E is a photograph of the $3^{rd}$ patient's teeth 10 months after the initiation of periodontally purposed orthodontic treatment according to the present invention.

FIG. 4F is a photograph of the $3^{rd}$ patient's teeth 20 months after the initiation of periodontally purposed orthodontic treatment according to the present invention indicating that the gingival health improvement has been maintained while the occlusion has improved during the first 10 months of the (FT and PT) retainer phases.

FIG. 4G is a photograph of the $3^{rd}$ patient's lingual view of the mandibular anterior region prior to the initiation of therapy according to the present invention.

FIG. 4H is a photograph of the $3^{rd}$ patient's lingual view of the mandibular anterior region after 7 months of active therapy according to the present invention.

FIG. 4I is a photograph focused on the mandibular anterior buccal region of the $3^{rd}$ patient at the initial consultation visit, 15 months prior to the start of therapy. The inflamed gingiva provides hints that the health of the area may continue to decline if interventional therapy is not rendered.

FIG. 4J is a photograph focused on the mandibular anterior buccal region of the $3^{rd}$ patient 13 months after his initial consultation and 6 weeks prior to the initiation of treatment according to the present invention.

FIG. 4K is a photograph focused on the mandibular anterior buccal region of the $3^{rd}$ patient 3 months after the initiation of therapy according to the present invention.

FIG. 4L is a photograph focused on the mandibular anterior buccal region of the $3^{rd}$ patient midway (5 months) through active therapy according to the present invention.

FIG. 4M is a photograph focused on the mandibular anterior buccal gingiva of the $3^{rd}$ patient at the conclusion of active therapy (10 months) according to the present invention.

FIG. 4N is a photograph focused on the mandibular anterior buccal gingiva of the $3^{rd}$ patient after 1 month PT and 9 months FT retainer wear (20 months since the start of therapy).

FIG. 4O is a chart which notes when the $1^{st}$ and $2^{nd}$ Levels of Gingival Health were achieved and maintained.

FIG. 5A depicts a view of the mandibular arch of the $4^{th}$ patient before the start of the periodontally purposed flexible aligner orthodontic treatment according to the present invention.

FIG. 5B depicts a view of the mandibular arch of the $4^{th}$ patient at the projected conclusion of active therapy according to the present invention.

FIG. 5C is a photograph of the mandibular arch of the $4^{th}$ patient prior to the initiation of treatment.

FIG. 5D is a photograph of the $4^{th}$ patient's mandibular arch after 5 months, partway through the active phase of therapy, according to the present invention.

FIG. 5E is a photograph of the $4^{th}$ patient's mandibular arch at the conclusion (9 months) of active therapy.

FIG. 5F depicts the $4^{th}$ patient's 27 months after the initiation of therapy, 18 months after the conclusion of active therapy and 12 months PT (following the 6 months FT) retention usage according to the present invention.

FIG. 5G is a photograph of the $4^{th}$ patient's smile prior to the initiation of treatment.

FIG. 5H is a photograph of the $4^{th}$ patient's smile after the conclusion of active therapy (9 months).

FIG. 5I depicts the anterior view of the $4^{th}$ patient prior to the initiation of therapy, according to the present invention.

FIG. 5J depicts the projected finish of the anterior view of the $4^{th}$ patient after the conclusion of active therapy according to the present invention.

FIG. 5K is a photograph of the anterior view of the $4^{th}$ patient prior to the initiation of therapy.

FIG. 5L is a photograph of the anterior view of the 4th patient (9 months) at the conclusion of active therapy, according to the present invention.

FIG. 5M is a photograph of the anterior view of the $4^{th}$ patient's anterior region during a 24 month PREV (33 months after the initiation of therapy, after 6 months FT, 18 months PT retainer usage).

FIG. 5N is a photograph of the anterior open view of the $4^{th}$ patient prior to the initiation of therapy.

FIG. 5O is a photograph of the anterior open view of the $4^{th}$ patient (9 months) at the conclusion of active therapy.

FIG. 5P is a photograph of the anterior open view at the 24 month PREV, 33 months after the initiation of therapy with the $4^{th}$ patient.

FIG. 5Q is a chart which notes that the First Level of Gingival Health has been achieved and been maintained for the $4^{th}$ patient.

FIG. 6A is a photograph of the anterior view of the fifth patient prior to the initiation of therapy.

FIG. 6B is a depiction of anterior view of the $5^{th}$ patient, prior to the initiation of therapy.

FIG. 6C is a photograph of the anterior view of the 5th patient taken 11 months into active therapy. Asymptomatic transient malocclusion is present.

FIG. 6D is a photograph of the anterior view of the 5th patient taken 12 months into active therapy. The magnitude of the asymptomatic transient malocclusion has been reduced.

FIG. 6E is a depiction of the anterior view of the 5th patient after 12 months into active therapy.

FIG. 6F is a photograph of the $5^{th}$ patient after 16 months of active therapy indicating that Gingival Health Level 1 has been achieved.

FIG. 6G is a depiction which projects the conclusion of the $2^{nd}$ Phase of active therapy.

FIG. 6H is a photograph of the anterior view of the 5th patient after 24 months of active therapy indicating that Gingival Health Level II has been achieved.

FIG. 6I is a photograph of the anterior view of the 5th patient 31 months into active therapy.

FIG. 6J is a depiction of the projected result after the end of active therapy for the $5^{th}$ patient.

FIG. 6K is a photograph of the occlusal view of the mandibular arch of the $5^{th}$ patient prior to the initiation of therapy.

FIG. 6L is a depiction of the mandibular arch of the $5^{th}$ patient prior to the initiation of therapy.

FIG. 6M is a photograph of the occlusal view of the mandibular arch of the $5^{th}$ patient after 12 months of active therapy.

FIG. 6N is a depiction of the mandibular arch of the fifth patient after 12 months of active therapy.

FIG. 6O is a photograph of the occlusal view of the mandibular arch of the $5^{th}$ patient after 18 months of active therapy indicating that Gingival Health Level I is being maintained.

FIG. 6P is a depiction of the mandibular arch of the $5^{th}$ patient after 18 months of therapy.

FIG. 6Q is a chart which tracks the improvement in the Level of Gingival Health for the $5^{th}$ patient.

FIG. 7A is a photograph of the right buccal view of the sixth patient prior to the initiation of therapy.

FIG. 7B is a depiction of right canine view of the 6th patient prior to the initiation of therapy.

FIG. 7C is a depiction of the right canine view of the $6^{th}$ patient prior to the initiation of therapy.

FIG. 7D is a photograph of the right canine view of the $6^{th}$ patient immediately after the completion of Phase I (12 months) of her flexible removable sequential orthodontic therapy.

FIG. 7E is a photograph of the right buccal view of the $6^{th}$ patient after 12 months of active therapy.

FIG. 7F is a depiction of the right buccal view of the $6^{th}$ patient just prior to the initiation of the $2^{nd}$ phase of active therapy.

FIG. 7G is a depiction of the right canine view of the $6^{th}$ patient just prior to the initiation of the $2^{nd}$ phase of active therapy.

FIG. 7H is a depiction of the projected right buccal view of the $6^{th}$ patient after 20 months of active therapy.

FIG. 7I is a depiction of the right canine view of the $6^{th}$ patient 20 months into therapy.

FIG. 7J is a depiction of the right buccal view of the $6^{th}$ patient 28 months into therapy.

FIG. 7K is a depiction of the right buccal view of the $6^{th}$ patient at the conclusion of the therapy.

FIG. 7L has two depictions of the care for the $6^{th}$ patient, one after the initial phase and the other at the completion of therapy.

FIG. 8A has photographs of the anterior and right buccal anterior views of the seventh patient prior to the initiation of therapy, as well as a photo of a calibrated periodontal probe with 3 mm intervals.

FIG. 8B has two photographs of the 7th patient prior to the initiation of therapy (the mandibular arch is on the left and maxillary arch is on the right).

FIG. 8C has 4 photographs of the 7th patient which represent the occlusal (birds eye) view of the mandibular arch prior to the initiation of, and after 1.25, 2.33 and 2.75 years of BAOC arch reformulation therapy.

FIG. 8D has depictions of the outlines of the mandibular arch and the teeth prior to the initiation of care of the 7th patient and after approximately 2.75 years (~50%) of the projected therapy.

FIG. 8E has depictions of the outlines of the mandibular arch and teeth prior to and after approximately 2.75 years of therapy. The light gray areas represent where bone is no longer present, a modification of the BAOC.

FIG. 8F has depictions of the outlines of the mandibular arch and teeth prior to and after approximately 2.75 years of therapy. The dark gray shading highlights where there has been an increase in bone, a modification of the BAOC.

FIG. 8G is similar to FIGS. 8D, 8E, 8F; the light gray area highlights where bone was once present and the dark gray area highlights where new bone is now present.

FIG. 8H are photos of the mandibular arch of the 7th patient prior to the initiation and after 2.75 years of therapy.

FIG. 8I has the same photos found in FIG. 8H.

FIG. 8J has 4 photographs which represent the anterior view of the 7th patient during maximum closure prior to the initiation of, and after 1.25, 2.33 and 2.75 years of BAOC arch reformulation therapy (the yellow and black arrows point to teeth which achieved significant root coverage during the treatment).

FIG. 8K has close up views of two photographs of the 7th patient.

FIG. 8L has 4 photographs which represent the right buccal anterior view of the 7th patient during maximum closure prior to the initiation of, and after 1.25, 2.33 and 2.75 years of BAOC arch reformulation therapy.

FIG. 8M are extraoral photos of the right profile of the 7th patient prior to and after 2 years of BAOC reformulation therapy.

FIG. 8N is a digital panoramic x-ray taken prior to the initiation of therapy of the 7th patient.

FIG. 8O is a digital panoramic x-ray taken after 2 years of BAOC reformulation therapy of the 7th patient.

FIG. 8P is a chart of the Levels of Gingival Health.

FIG. 8Q is a depiction of the mandibular arch of the 7th patient prior to the initiation of therapy.

FIG. 8R is a projected depiction of the mandibular arch of the 7th patient after 2 years of BAOC reformulation therapy.

FIG. 8S is a projected depiction of the mandibular arch of the 7th patient after the conclusion of BAOC reformulation therapy.

FIG. 8T is a depiction of the maxillary arch of the 7th patient prior to the initiation of therapy.

FIG. 8U is a projected depiction of the maxillary arch of the 7th patient after 2 years of BAOC reformulation therapy.

FIG. 8V is a projected depiction of the maxillary arch of the 7th patient after the conclusion of BAOC reformulation therapy.

FIG. 8W is a depiction of the anterior view of the 7th patient prior to the initiation of therapy.

FIG. 8X is a projected depiction of the anterior view of the 7th patient after 2 years of BAOC reformulation therapy.

FIG. 8Y is a projected depiction of the anterior view of the 7th patient after the conclusion of BAOC reformulation therapy.

DETAILED DESCRIPTION

A method according to the present invention is directed at a dental procedure for the combined treatment of an orthodontic and a periodontal condition in a patient.

A method according to the present invention is further directed at a sinus lift procedure without grafting or surgery.

A method according to the present invention is further directed at inducing bone growth in the jaw bone of a post-pubescent patient through a non-invasive orthodontic method.

A method according to the present invention is particularly effective in the treatment of a patient previously considered to be an unsuitable candidate (e.g. a patient with an active periodontal condition) for orthodontic treatment with flexible aligners (e.g. transparent plastic aligners), as well as traditional orthodontic therapy (brackets, elastics and wires).

It is conventional thinking that once alveolar bone is lost, it cannot regrow naturally without the aid of a growth inducing material. This conventional thinking has driven many practitioners to recommend gum surgery in combination with the application of a bone regrowth material in order to induce the regrowth of lost alveolar bone. The methods are generally considered invasive.

It has been discovered by the inventor that candidates suffering from loss of alveolar bone if orthodontically treated with flexible aligners can experience a positive reorganization of the alveolar bone, which will have the effect of "regrowing" bone where it will be more advantageous to the overall health of the patient. This occurs organically, without the aid of a bone regrowth inducer. Furthermore, the lost gum tissue can be naturally recovered through a treatment according to a method as disclosed herein.

As will become clear from the disclosed method and examples, treating the primary diagnosis, malocclusion, as opposed to treating the periodontal symptom which is a direct consequence of the untreated malocclusion, will yield superior and more predictable long term results that will benefit the overall health of the patient.

The present state of the art is that periodontists and general dentists diagnose, address and treat periodontal manifestations and that orthodontists and general dentists diagnose, address and treat orthodontic manifestations.

Presently, it is rare for the periodontists to perform orthodontic corrective treatment beyond limited (one or a few teeth) occlusal adjustments or splint therapy. With the technique described herein, periodontists and other specialist and general practitioners can provide a wider array of periodontally purposed enhanced orthodontic therapy.

Presently, it is rare for orthodontists to perform periodontal therapy beyond a hygiene level prophylaxis. With the technique described herein, orthodontists and other specialist and general practitioners and other dental specialists may provide a wider array of periodontally purposed enhanced orthodontic therapy.

It is commonly accepted that when a tooth is tilted mesially toward the anterior (e.g., forming a 60 degree angle), there is an excess amount of bone distal and a less than desired amount of bone mesial to the tooth. If it were possible to orthodontically upright the tooth and have it repositioned to be straight at a 90 degree angle, the amount of bone surrounding the tooth would become more symmetric, harmonious and closer to the desired ideal. Thus, according to one aspect of the present invention, the treatment may be devised to re-orient the teeth to become orthodontically upright. It is believed that doing so lessens the likelihood of relapse, which is a great drawback of conventional orthodontic methods.

It is commonly assumed that volumetric quantity of bone surrounding a tooth remains relatively unchanged. In the example described, the new bone eventually formed to accommodate the new and more desirable position of the tooth within the basal/alveolar complex would approximate the amount of bone loss when the compared to the tooth in its pre-treatment position.

It is commonly assumed that when the tooth is placed as ideally as clinically practicable, one would expect the periodontium to be at a high level of health.

The positive repositioning of the teeth leads to a positive redistribution of the basal/alveolar bone which leads to an improved periodontium which leads to the gingiva being more robust and possessing a more healthful appearance. According to one aspect of the present invention, the healthful appearance of the gingiva is used as an indicator of successful bone growth resulting from the application of a method according to the present invention. This aspect of the present invention deviates from the present state of the art which solely relies on the position of the teeth to determine the overall success of therapy.

A method according to the present invention includes four phases: a diagnosis phase, an active treatment phase, a full time retention phase and a part time retention phase.

The diagnosis or pre-treatment phase identifies and qualifies the candidate as a suitable patient for receiving therapy.

The treatment phase in a method according to the present invention possesses an active therapy component and two passive or retention therapy components.

During the active therapy phase a number of flexible aligners (from one to more than a hundred) are deployed in the patient's mouth for more than 20 hours per day (22-23 hours per day is the preferred duration) over a period of time spanning months to years.

Each set of flexible aligners is usually worn for two to three weeks, but may be worn for shorter or significantly longer periods, based on the movements intended and the judgment of the skilled clinician.

During the Active Therapy Phase, minor, moderate, advanced, and complex tooth movements and repositioning are achieved. Both independent and dependent movements occur simultaneously.

On the occasions when the movements in one arch are completed prior to the movements in the other arch being completed, that arch will be placed in a stabilization or pre-retention phase. This holding pattern or pre-retention phase will include non-active or passive aligners in lieu of retainers to maintain the location of the teeth where desired to allow the basal/alveolar complex to proceed along the desired maturation process.

While achieving the same goal and sharing a similar appearance, there are some differences between aligners and retainers. Aligners are intended to be worn for weeks while retainers are intended for many months or years. There are differences in rigidity, thickness and composition, too.

The method chosen for this technique, to use non-active or passive aligners as opposed to retainers at this time is predicated on the desire to have a simpler regimen which will maximize the likelihood of compliance throughout the entire regimen.

During the Retention Phases of Therapy, the primary purpose is to keep the teeth in their newly acquired positions while the gingiva and periodontium mature.

During the Full Time Retention Phase of Therapy, there will be an occasional need for a hybrid phase. During this hybrid phase, some minor or limited tooth movements will be accomplished for a few teeth while the majority of the teeth will be concurrently proceeding with their stabilization phase. In contrast to the non-active aligner phase, the removable devices will be of retainer grade material, not aligner grade material.

Should a patient experience or demonstrate a minor relapse during the Part Time Retention Phase, the patient should be instructed to convert back to the Full Time Retainer regimen (20-23 hours/day) as long as the patient has suitable removable retainers, ones with full potency. Full potency as used herein is defined as a retainer that can move teeth up to several tenths of a millimeter. A clinician needs to ensure that the retainers have not been "stretched out" and become compromised due to improper or excessive use, or that their efficacy has not expired beyond the intended and the expected duration.

If the patient does not have suitably robust retainers which can adequately carry out the requirements and demands of the full time retention process, suitable retainers should be fabricated and provided as soon as feasible.

During the Part Time Retention Therapy Phase, the retainers need to be worn 7-12 hours each day.

During the first stage of the retention therapy phase, which immediately follows the active therapy phase, a flexible retainer is deployed in a similar manner in the patient's mouth for 20-23 hours a day.

The first stage (full time) of the retention therapy phase will usually last for about nine months. When there is a hybrid component (active therapy/retention process) the process may extend for two (or more) years.

While it will happen on some occasions that a patient will only require one phase of active therapy, the majority of patients may require two to three active phases of therapy (and on occasion a fourth or fifth).

Prior to initiation of an active phase a set of orthodontic and periodontal records should be obtained. A conventional orthodontic therapy, unlike a method according to the present invention, does not include a comprehensive periodontal exam as part of the therapy.

For a method according to the present invention, a comprehensive set of orthodontic records may include photographic, digital or analog impressions, periodontal charting and radiographs (e.g., full mouth series, panoramic and/or cephalometric), which may be used to evaluate the periodontal health and to produce a set of aligners (usually ten to thirty, although the numbers may be smaller or greater).

When progressing from a first to a second (or a second or a third, etc.) active phase of aligner therapy, comprehensive photographs along with digital or analog impressions should be acquired. Depending upon the severity of the malocclusion, periodontal condition or status of the implant treatment plan, radiographic documentation at these intermediate stages may be helpful. If more than six months have progressed, periodontal charting may be appropriate as well.

During most treatments, it is recommended that existing orthodontically and periodontally purposed attachments on the teeth be removed prior to taking analog or digital impressions of the maxillary and mandibular arches.

On some occasions, (e.g., when there were specific tracking issues that curtailed a phase from being completed) when the removal would not assist with the progress of the therapy, the orthodontically and periodontally purposed attachments can stay in place and be included in the digital or analog impressions of the maxillary and mandibular arches.

While it is common for 70-90% of the desired movements to be achieved with each phase of therapy, on occasion the desired amounts of movements may be greater or less.

Certain movements (e.g., molar intrusion, canine extrusion) may be more difficult and less predictable than other movements (e.g., incisor proclination) with flexible aligners. The time required to accomplish those desired yet difficult movements may have a tendency to have a greater variance and may take longer than the projected simulations from the orthodontic laboratory's estimate.

It is presently common practice that when programmed teeth movements fail to occur, the subsequent simulation will attempt other ways to achieve those desired movements.

In a method according to the present invention the most reliable and predictable movements should be repeated, even if they were not initially successful.

The difference in theory is based upon the fact that the reformulation of the BAOC (basal/alveolar esseous complex) proceeds at widely varying rates. So, knowing that the movements will eventually be successful, it is prudent to rely on the laboratory's most likely to be successful intermediate movements to accomplish the new re-positioning, even if that means repeating previously "unsuccessful" actions and teeth movement patterns.

The fact that some significant movements may take longer than expected should not dissuade one to change course and divert from reliable movements to those that may be less predictable and less proven to succeed. Increasing the duration of each stage of aligners beyond the manufacturer's recommendation may prove helpful, too.

In some cases commonly classified as advanced or complex, one may not be able to have a definitive desired outcome provided within a single simulation design. That is because the ultimate goal of the treatment might not yet be able to be determined or comprehended, or the desired results might be beyond the capability and scope of the planning and projection software at the initiation of care (start stage).

This is especially common when the desire is to mesialize the second and/or third molars in an attempt to avoid the one or more implant surgical procedures. Implant surgeries with or without bone grafts and/or sinus lifts are the present state of the art.

A method according to the present invention deviates from the prior art by providing a non-invasive, non-surgical and more comprehensive solution to the single tooth edentulism dilemma.

A method according to the present invention capitalizes on poor bone quality which can be an asset, not a detriment, to one's overall treatment.

Contrary to the conventional methods, density enhancements of the osseous complex with supplemental grafting materials and membranes are contraindicated when the mesialization or distalization of molars are a viable option. On those occasions, one simply has to follow the basic principles on which this invention is predicated: idealize the arch forms, occlusion, reformulation of the BAOC and position of the teeth in order to obtain the desired optimal results.

On those occasions, once one has programmed for the idealization of the arch forms, occlusion, reformulation of the BAOC and new positions of the teeth, it is likely that the second (or on occasion the third, etc.) round of therapy will allow for a design that will yield a plan for the optimal results at the end of that round of therapy with this invention.

To implement the active therapy phase, one or more flexible aligners are devised to induce the realignment of the patient's misaligned teeth. Each flexible aligner is configured to induce the realignment of each misaligned on non-ideally positioned tooth so that the patient's teeth realign to establish ideal maxillary and mandibular arch forms. Ideal as used herein means a symmetric arch with no more than a ten percent deviation from the ideal, or as close to that as can be achieved with clinical practicability.

Certain limitations (e.g., a skeletal Class III malocclusion), could preclude the 100% ideal from being achieved. However, a method according to the present invention can reach close to an ideal set of arches with good resistance to relapse.

A flexible aligner is a suitable implement for inducement of the realignment of misaligned teeth because one can configure a flexible aligner to expand or contract the patient's maxillary or mandibular arch due to the spring-like characteristic of a flexible aligner. As the teeth are repositioned, the positive reformulation of the BAOC occurs concurrently or shortly thereafter.

As illustrated below, a method according to the present invention realigns the teeth along an ideal arch and unexpectedly promotes the regrowth of alveolar bone, which leads to the regrowth of the lost gum tissue. This positive reformulation of the BAOC is accomplished to such a significant extent that the teeth and periodontium will have their ability to withstand and resist the orthodontic relapse increased.

According to conventional thinking the following conditions present in a patient should preclude their being treated with flexible aligners:
  1. Any type, method, or movement indicated as difficult.
  2. Centric-relation and centric-occlusion discrepancies.
  3. Teeth with short clinical crowns.
  4. Arches with multiple missing teeth.
  5. Patients whose second molars have not yet erupted.
  6. Patients with poor oral hygiene.
  7. Patients with active periodontal disease.
  8. Doctor cannot confirm a patient is dentally and periodontally stable
  9. Patients with dental prosthetics or implants.

It has been found that all patients except those meeting condition (#5) can be treated with a method according to the present invention. In contrast to the present state of the art, these conditions are indications to initiate osseous reformulation therapy, as opposed to being contraindications to avoid orthodontic therapy according to the present invention.

The Diagnostic and Record Acquisition Phase should include and have the diagnosis be based upon a comprehensive initial exam which includes the following:
a. Complete assessment of the patient's medical and dental history preferably with thorough orthodontic, periodontal and/or pain/discomfort questionnaires when relevant and germane.
b. Radiographic examination should be conducted. For extensive rehabilitations, both panoramic and full mouth series of x-rays should be taken. Lateral cephalometric x-rays are optional and may be taken at the discretion of the skilled clinician. On rare occasions (e.g., pathology is a concern), a cone beam 3D scan may be indicated.
c. Comprehensive periodontal examination should be carried out. Documentation should include pocket depths, bleeding upon probing, plaque presence, calculus presence, suppuration, furcation, fremitus, recession, missing teeth and mobility.

d. Comprehensive TMJ examination (extraoral and intraoral) should be carried out. While a positive result is frequently an indication to initiate therapy according to the present invention, it is almost always a contraindication to initiate traditional orthodontic therapy.

e. Patient should be prepared for the procedure. Ensure that the patient is:
 i. willing to commit to being an excellent and dedicated patient/candidate;
 ii. aware of the specific structure of the active and the passive (retention) therapy components;
 iii. provided with prudent informed consent which will include the type (removable) and duration (2-5 years) of the retainer system.
 iv. informed that contrary to presently accepted orthodontic protocols, or prior personal experience, or their personal request, fixed lingual retainers are not an option for retention at the end of therapy and will not be utilized. The rationale for avoiding the use of fixed lingual retention as an option is that they almost always truncate the ability of the BAOC to reformulate in a proper, full and ideal manner.

f. A comprehensive Malocclusion Exam should be performed. If the patient is symptomatic or possesses at least one of the following conditions, signs or symptoms, it should be considered an indication to initiate therapy:
 i. Abfractions
 ii. Absence of canine guidance
 iii. Active periodontal disease
 iv. Anesthesia required for maintenance/prophylaxis sessions
 v. Arch asymmetry
 vi. Chipped cementum/enamel/porcelain/composite
 vii. Cracked tooth or teeth
 viii. Crowns—multiple
 ix. Dental age exceeds chronologic age
 x. Endodontic therapy on multiple teeth
 xi. Exposed cementum
 xii. Fractured tooth or teeth
 xiii. Gingivitis
 xiv. "Golf ball dimpled" molars
 xv. Incisal wear
 xvi. Irregular Curve of Spee
 xvii. Irregular Curve of Wilson
 xviii. Lingual splint: fixed, from a prior orthodontic or periodontal therapy
 xix. Marginal ridge craze or fracture lines
 xx. Midline discrepancy
 xxi. Midline shift—Accommodation upon opening
 xxii. Multilevel incisal edges
 xxiii. Periodontal grafting recommended
 xxiv. "Toothbrush abrasion"—isolated gingival locations
 xxv. Plunging cusp(s)
 xxvi. Sensitivity to cold, with certain foods, etc.
 xxvii. TMD [active or prior history of]

g. Photographic image documentation should be collected:
 1. The universally accepted photographic series for the orthodontic patient incorporates the following eight photographs—extraoral: Frontal Repose and Smiling and Right Profile Repose; and intraoral photographs: Anterior, Right and Left Buccal, Mandibular and Maxillary Arch views.
 2. A method according to the present invention may require the collection of a minimum of fifteen photographs, six extraoral and nine intraoral. The additional extraoral photographs are: Smiling and Lips at Rest, Right Profile Smiling, and when significant the Left Profile Repose and Smiling views. The additional intraoral photographs are: Maxillary and Mandibular Arch views with multi-colored (e.g., blue/red) articulating paper generated marks evident to document the occlusion, Anterior Overjet view, Maxillary and Mandibular Anterior Lingual Anterior and Canine views, and the Anterior Open view.
  a. Depending on the complexity of the patient's oral condition and occlusion the following optional photographs may be taken:
   i. Photograph(s) which focus on the edentulous spaces, assist with the accurate depiction of the occlusal relationship and show all of the teeth in each of the four quadrants or six sextants (e.g., buccal/canine, anterior/canine view).
   ii. If the patient possesses fremitus, multiple photos are to be taken; one while the teeth are in atraumatic contact and another while in traumatic contact.
 h. The position of the teeth and the edentulous spaces via (i) or (ii) should be recorded:
 3. Complete sets of photographic and periodontal documentation should be taken:
  (i) prior to the initial and any subsequent phases of Active Therapy
  (ii) prior to the initiation of the Full Time (FT) Retention Phase
  (iii) prior to the initiation of the Part Time (PT) Retention Phase
  (iv) at each (of the six months to two years) PREV i. Digital Record Acquisition:
 1. A digital scanning device which will produce a universally acceptable file format (e.g., STL file) may be used to acquire digital images to produce three dimensional records of the teeth and edentulous areas in the maxillary and mandibular arches which can be submitted to an orthodontic laboratory, dental laboratory or a 3-D printer which produces a series of aligners.

ii. Analog Record Acquisition:
 1. Use an accurate synthetic dental impression material (i.e., vinyl polysiloxane ("VPS" or polyvinylsiloxane "PVS") and/or polyether recommended by the company or laboratory to obtain accurate impressions of the mandibular and maxillary arches than can be digitized and further processed.
 2. If one or more teeth have mobility greater than Class II, splint the teeth together with the minimal amount (approximately 1-3 mm) of flowable (high viscosity) composite resin necessary to stabilize them. Place a very small amount of phosphoric acid etch to the teeth prior to adding the flowable composite. Physically test the stability of the teeth to ensure that they will be able to withstand the impression process and not be inadvertently dislodged or extracted. Request that your technician or the laboratory virtually remove the composite resin prior to the initiation of the simulation for that patient. A second option is to use sufficient extraoral interproximal splinting material to keep the teeth securely splinted together throughout a portion of or the entire therapy.

iii. Occlusal Relationship Acquisition
 1. A digital scanner can be used to optically or otherwise record the precise relationship of the teeth in the maxillary and mandibular arches.
 2. Synthetic accurate dental impression material (e.g., VPS, polyether) can be utilized to obtain impressions that can be sent to the dental laboratory for digitization. That will assist with the virtual mounting and enhance the likelihood that the relationship of the mandibular and maxillary arches will be recorded precisely.

3. As discussed, supplemental photographs can be a valuable aid for conferring information about the occlusal and spatial relationships and should be furnished to your technician or the preferred dental or orthodontic laboratory.

i. Submit the patient's records with all required and supplemental information to an orthodontic laboratory which will or to a technician who will manufacture the enhanced sequential flexible aligners.

ii. When submitting the prescription for a series of removable orthodontic aligners, request that no teeth which have the potential to be restored be removed, that no interproximal reduction ("IPR") be performed; allow the arches to be expanded (or contracted) without limitations; allow all changes in the antero-postero ("A-P") dimension without restriction, allow intrusion and extrusion of both anterior and posterior teeth without restriction and rotate all teeth without restrictions.

iii. These are significant deviations from the standard recommended guidelines, existing state of the art and present overwhelming (>99%) choices by clinicians. While these instructions "violate" some of the "non-permissible" or "non-recommended" movements, they are essential for the proper execution of the presently described method.

Once the required custom attachments are placed on the teeth via the accompanying template, provide the flexible aligners and the usage instructions.

The goal of the active phase in a method according to the present invention is to attain at least 90 percent of the desired new locations for the teeth and a clearly noticeable visible improvement in the appearance (i.e., health) of the gingiva prior to proceeding to the retentive phases of therapy.

The improvement in the health of the gingiva should include several, but not less than one of the following: less bleeding, reduced redness, less inflamed tissue, less root structure visible (additional quantity of gingiva), and the like.

If after the application of the first set of aligners 90 percent or more of the desired results are not attained, then a second set of orthodontic and periodontal records as previously described should be obtained. Additional flexible aligners should be created and utilized until the active phase is completed, or a hybrid active-retentive phase may be entered where the final desired movements are achieved during an extended full time retention phase of therapy. Once the active therapy phase is deemed complete, the full time retention therapy phase should be initiated as soon as possible.

The following is a preferred regimen for the full time retainer and part time retainer phases of therapy:

i. Full Time

1. At the removal of final set of attachments session or initial Periodic Retention Evaluation Visit ("PREV"), a complete set of photographs should be taken and the patient should be periodontally charted.

Full Time Retainer Phase:

Typical Total Time=9 months with a range of 6-14 months, 20-23 hours each day.

Typical Number of Retainers required=3 with a range of 2-6.

2. If the retainer has a recommended FT wear of 3-4 months, the patient should wear the first retainer for 20-23 hours/day for the duration of its projected efficacy (i.e., 3-4 months).

3. A PREV should be scheduled after three months, and repeated every three months.

4. If all is proceeding well at the 3, 6 & 9 month PREV, the patient should be provided with the next retainer.

5. If all is not proceeding well, the next PREV should be had in two weeks and the patient re-evaluated.

a. At the two week PREV:

If the patient is not back on track (some signs of relapse—e.g., spaces between teeth edges and aligners), active therapy should be re-initiated.

If the patient has made some progress, another PREV should be had in two weeks to confirm/ensure the patient is back on track. This step should be repeated as necessary.

6. If all is proceeding well at the month 9 PREV, the patient should have a complete set of photos taken, be periodontally charted and provided with a new set of retainers. The patient is then shifted to the PT retainer wear regimen.

The patient should wear the flexible retainer:

i. 7-12 hours/day, preferably at night ii. While working out or in a sports competition where clenching is common and a stronger and more secure mouthguard is neither indicated nor recommended.

iii. A PREV should be had every 6-12 months iv. Photo documentation should be obtained.

v. Periodontally chart at each or every other PREV, at least once every two years.

7. If all is proceeding reasonably well at month 9 but the health of the gingiva or a tooth position can still be improved with additional full time wear, a new retainer should be provided with full functionality and the patient instructed to wear it full time (20-23 hours/day).

a. A PREV should be had in 3 months.

b. The above steps should be repeated, as necessary, until the patient is placed on the PT wear regimen and PREV listed above.

8. PREV should be had annually and eventually biennially. Continue to photo document and periodontally chart as appropriate.

10% Carbamide Peroxide Application Instructions

A method according to the present invention can benefit from a proper teeth whitening.

A 10% carbamide peroxide ("CP") solution which contains an enamel remineralization component ACP (amorphous calcium phosphate) and an ingredient intended as a desensitizing agent is an ideal adjunct to facilitate the teeth whitening.

10% CP is commonly referred to as teeth whitening or teeth bleaching solution.

When utilized in the aligner devices as prescribed in this unique regimen, patients will experience positive benefits that will maintain or improve their gingival health and their dental hygiene.

A key determinant that helps ensure a successful 10% CP result is to minimize the likelihood that the user will experience sensitivity in their teeth or gums. This regimen is intentionally designed to greatly reduce the likelihood of sensitivity, which would impede the progress of the gum conditioning and caries reduction essential to the smooth progression of a treatment according to the present invention.

A patient who is receiving a treatment according to the present invention should refrain from utilizing the application of the 10% CP solution during the first seven days during a ten to fourteen day aligner wear cycle, and to refrain for ten to fourteen days during a twenty one day aligner wear cycle.

The patient should be directed to apply a small amount of 10% CP in each of the front ten teeth in each arch, except with those teeth that possess a full crown.

The user should place a sufficiently small amount of 10% CP solution at the incisal edge of the tooth so that when the aligner is placed in the mouth, no less than 25% and no more than 50% of the tooth is covered with the solution. To ensure that the gingiva is kept in as healthful a state as possible, this should be done every two or three nights after the waiting periods and repeated throughout the active aligner phase of therapy and less frequently during the retention phases, according to the present invention.

In a significant departure from the accepted and prevailing whitening standards where porcelain veneers are never whitened, it is desirable to whiten the teeth which possess them, although there is an important caveat. Porcelain veneered teeth should be whitened only if they are not lighter than the adjacent and opposing teeth. That is because increasing the value of the already lighter appearing veneered teeth will continue to keep them distinguished (not a desired outcome) as opposed to having them blend in with the other (non-veneered) teeth, which is the desired outcome. This is noteworthy because the successful completion of this step will likely lead to a significantly less invasive result.

Commonly, during the preparation for a replacement porcelain veneer, the existing porcelain veneer is removed, residual resin cement is removed, and portions of the tooth structure, albeit as nominal as possible, are also removed. Each time this process occurs, the possibility that the tooth becomes sensitive and requires additional attention and corrective therapy, such as endodontic therapy, increases.

The only way to avoid increasing the likelihood that a tooth with a veneer will require additional therapy is to take all steps possible to avoid the need to replace that veneer.

The two main ways to avoid veneer replacement are visual alteration (improvement) of the tooth's appearance and the physical relocation of the tooth within the arch form. Prudent tooth repositioning, which may include intrusion to hide exposed and at one time non-visible tooth structure (i.e., exposed cementum, dentin or root), should be incorporated into the initial design plans of the projected simulation.

The presently accepted standard of treatment when a patient possessing porcelain veneers undergoes orthodontic therapy is to plan to remove the existing porcelain veneers and create new veneers prior to, during, or after orthodontic therapy has concluded. While the procedure previously described is a deviation from the presently accepted orthodontic/restorative protocols, the potential utilization of the existing porcelain veneers, and not mandating their replacement, will be significantly less invasive and potentially yield comparable, if not superior aesthetic results.

If the tooth with a veneer is significantly darker than the neighboring teeth, or the tooth has already had root canal therapy, the teeth whitening described herein should be incorporated into the treatment protocol.

The purpose of the Teeth Whitening method is to convert unsightly teeth which are darker than desirable into teeth that are indistinguishable from their adjacent teeth and those near it in the opposite arch.

With the Teeth Whitening described herein, the darker teeth (or tooth) are the only ones (one) whitened in the mouth. For example, if the two front teeth are much darker, they are the only two teeth in the mouth which will receive CP solution. It is recommended that a stronger solution that the 10% CP (up to 38% CP) be utilized, especially if the tooth is non-vital and sensitivity is not a concern. This process will continue for several months, until the darker teeth become the lighter teeth. Once the once-dark teeth are lighter than the adjacent teeth, initiate the application of 10% CP solution to all the teeth.

EXAMPLES

The following are typical examples of patients who have received treatment according to the present invention. For illustration purposes, FIG. 1C shows a set of misaligned teeth. FIG. 1D shows a set of teeth that are properly aligned along an ideal arch.

First Patient
Age: 26 Sex: Female
Medical History: Non-contributory
Oral Hygiene:
  Brushing: 2 times each day
  Flossing: sporadic
Dental Caries: none
Dental History: see below
Orthodontic Treatment History:
Therapy initiated—age 12
Duration—4 years
  Palate expander (~2 years)
  Headgear (~6 months)
  Traditional orthodontic (brackets/wires/elastics) therapy (~1 year)
  Retainers: none provided by the orthodontist
  Relapse became evident: 1-2 years after bracket debonding. Became progressively worse over subsequent decade.
Periodontal Treatment History:
  Gingival grafting (epithelial and connective tissue) surgery at age 23 in the mandibular anterior region
  Transient sensitivity, especially present during professional cleanings, was significantly reduced but not eliminated after the grafting surgery was performed
  Under the active care of a periodontist, who provides cleanings and checkups every three months
Patient's chief concerns, wish list and goals:
  would like my teeth to be straighter
  would like to not have any teeth that seem darker than the others
  would prefer to not have crooked teeth
  if possible, would like to reduce the amount of buildup on the backs of my lower front teeth
  would like to have no sensitivity while having my teeth cleaned
  would like to have my smile be even
Initial Diagnosis:
  Generalized gingival recession ranges from 1-4 mm
  Congested teeth
  Malposed teeth
  One buccally flared and one palatally inclined maxillary lateral incisor
  History of sensitive teeth during prophylaxes
  Lip is asymmetric=has both a slight protrusion and a slight deficiency
  Arch asymmetry=maxillary and mandibular
Initial Visit Therapy:
  Digital panoramic x-ray
  VPS impressions of the maxillary and mandibular arches
  Extraoral and intraoral exam Comprehensive extraoral and intraoral photographs
Periodontal exam and charting
Treatments Options Considered:
  Porcelain veneers
  Removable clear flexible aligner orthodontic therapy
  Teeth whitening
  Gingival graft surgeries
  No treatment
Treatment proposed:
  Removable clear flexible sequential aligner orthodontic therapy
  Teeth whitening: 10% carbamide peroxide (CP) therapy with ACP (amorphous calcium phosphate); At-Home teeth whitening concurrent with the flexible aligner therapy.
Active Aligner Therapy Phase:
  14 Maxillary Aligners
  12 Mandibular Aligners
Interproximal Reduction (IPR):
  Teeth #20/21=0.4 mm
  Teeth #21/22=0.4 mm
  Teeth #22/23=0.4 mm
  Teeth #23/24=0.3 mm
  Teeth #24/25=0.3 mm
    Total IPR=1.8 mm
*Note: If this treatment were to be rendered today (active therapy was concluded in 2010), no IPR would be utilized. While IPR was done on this patient and the results exceeded expectations and surpassed gingival healing as noted in the orthodontic and periodontal literature, the treatment protocol has continued to evolve. The long term results and resistance to relapse would likely have been superior without IPR. That's why this technique advocates IPR and occlusal adjustments are no longer necessary to achieve outstanding and long lasting results. Removal of any non-diseased tooth structure is contraindicated as it can inhibit the reformulation of the basal alveolar osseous complex ("BAOC") from achieving the desired ideal. Since one wants to foster the idealization to achieve the maximum benefit of the reformulation process, any action that could possibly inhibit the reformulation process from reaching its potential should be avoided. The long term results as measured by the health of the gingiva and resistance to relapse will be superior without any irreversible modification or extraction of teeth. This deviates from the state of the art where the removal of proximal and occlusal enamel surfaces predominates (as it helps reduce the duration of treatment).

The only downside to the additional increase in the size of the arches and prudent reformulation is that the duration of treatment is often increased. However, the added stability which is created by the additional expansion of the BAOC and improved occlusion would seem to more than offset a modest increase in the duration of treatment.

10% Carbamide Peroxide ("CP") with ACP ("Solution Application:
Approximate number of 10% CP+ACP ("amorphous calcium phosphate")=for enamel remineralization applications:
  ~50: 2-5/month over a period of 1.5 years
Treatment Results:
  Gingival response=excellent
  Pocket depths=stayed the same or improved
  Gingival recession=stayed the same or improved
  Lip=smile is now symmetric. No protrusion or deficit present.
  Grafting Surgery—Update:
    The periodontist who recommended that she have four more surgeries has re-evaluated her condition and has revised those recommendations. The periodontist no longer believes she is in need of any additional grafting surgeries.
    That same periodontist has also recommended that she come for an exam and cleaning only once a year, a reduction from the four times each year prior to the periodontally purposed orthodontic treatment she received and has been described herein.
    Her general dentist also examines and cleans her teeth once each year, alternating every six months with the periodontist. Her PREV interval was once a year. She now wears the PT retainer on alternate nights, not every night. Based on her excellent progress and maintenance, her PREV interval is now set for every two years.
Cost of therapy: The total fees for her periodontally purposed orthodontic therapy were significantly less than the proposed fees for the porcelain veneers and gingival grafting surgeries.
Projected longevity of therapy:
  Due to its proclivity to be resistant to relapse, the projected longevity of the periodontally purposed orthodontic therapy is excellent. Periodontists, orthodontists and general dentists who reviewed her results were unable to recall another instance where the occlusion and periodontal health continued to improve months and years after the conclusion of orthodontic therapy.
  The projected longevity of porcelain veneers is defined in two ways. The functional longevity of veneers is approximately twelve to fifteen years while their esthetic longevity of veneers is estimated at five to eight years.
Projected future costs associated with the therapy:
  Periodontally purposed orthodontic therapy—negligible (approximately $150/year for retainers and evaluation)
  Porcelain veneers therapy—based on their projected need for periodic replacement of approximately once every 10-15 years, the costs would average out to more than $1,000/year, depending on where the treatment is rendered.
Invasive/Non-invasive "rating" of therapy: The method described herein is a non-invasive non-surgical therapy. The classifications of the presently available alternative methods and the actual method rendered are detailed below:
Mildly Invasive Therapy:
  The therapy rendered subjected the patient to a cumulative reduction of 1.8 mm of tooth structure. The IPR process removed between 0.1 mm and 0.2 mm from the interproximal enamel surfaces of six teeth. This therapy would be performed today without the removal of any tooth structure and be classified as a non-invasive procedure.
Invasive Therapy:
  The proposed periodontal gum grafting surgeries.
    Because chronic malocclusion, the primary diagnosis, is not being corrected, it is likely that the patient's sensitivity will recur at some point in the future. Periodontal disease is a symptom of the primary diagnosis, chronic malocclusion. Because only grafted gingival tissue would be added, and no (natural or synthetic) osseous bone would be added and no new bone growth would be generated or stimulated, there would be no reformulation of the BAOC, the projected longevity of the gingival graft maintaining its height, without additional occlusal adjustment, would be diminished.

Porcelain veneer therapy requires the removal of 0-2 mm of enamel tooth structure from four to twenty teeth (, depending on how many teeth were to receive veneers). The projected esthetic longevity of porcelain veneers is less than five to eight years. This means that a twenty something year old patient, as she was, could expect to have this therapy repeated multiple times throughout her lifetime. Each time this procedure is repeated, the existing veneer would require removal to allow it to receive the new veneer. It is inevitable that some additional tooth structure will be removed during this aspect of therapy. Additionally, it is accepted that a tooth which possesses a cast restoration (i.e., veneer) will be more likely to require endodontic ("root canal") therapy than a tooth which does not possess a cast restoration and is in proper occlusion. Because the malocclusion is not being definitively corrected, the likelihood that the patient would subsequently experience sensitivity in the teeth and/or gums as the occlusion remained non-ideal would be increased.

Treatment Timeline:
Active Aligner Phase of Therapy: Months 1-7
Full Time Retainer Phase of Therapy: Months 8-13
Part Time Retainer Phase of Therapy: Months 14, 17, 20, 23
PREV: Annual—month 29, 44
Gingival Health Timeline:
Month 7: Level I Achieved
Month 13: Level II Achieved
Month 19: Level III Achieved
Month 29: Level III Maintained
Month 44: Level III Maintained FIG. 2A depicts an intraoral photograph of the 1$^{st}$ patient's anterior view prior to the initiation of the periodontally purposed flexible aligner sequential orthodontic therapy ("periodontally purposed orthodontic therapy" or "therapy"). Many signs of her chronic malocclusion are in evidence.

Patient #1 had been receiving active maintenance therapy which included periodontal cleanings and evaluations every 3 months with her periodontist for more than 3 years. Approximately 3.5 years prior to initiating this therapy to correct her malocclusion and generalized prominent gingival recession, she underwent a full thickness palatal donor (epithelial and connective tissue) grafting procedure in the mandibular anterior buccal region.

Patient #1 had no pocket depths greater than 3 mm, double digit teeth with gingival recession ranging from 1-4 mm, multiple posterior teeth which were sensitive upon periodontal probing.

Patient number one was apprised by her periodontist that she would likely need 4 additional periodontal grafting surgeries, one in each quadrant's posterior region.

FIG. 2B shows an intraoral photograph of the 1$^{st}$ patient's anterior view after the successful conclusion of the active phase of therapy according to the present invention. 14 sets of aligners for the maxillary arch and 12 sets for the mandibular arch were utilized over a 7 month period. Note that the demarcations between the teeth and the gingiva, especially in the maxillary anterior region, are now easier to discern. Note that the gingiva surrounding all of the teeth, especially #11, 12, are less inflamed and/or less red, signifying a decrease in the amount of buccal tissue inflammation. No teeth displayed sensitivity during periodontal probing to gauge pocket depth. All teeth are in improved positions within their respective arch. There are improved occlusal contacts with the opposing arch and a significant reduction in the magnitude of the chronic malocclusion. These factors combine to connote that Gingival Health Level I has been achieved, according to the present invention. Note that the occlusion in the left canine region, teeth #11, 21, 22, is not yet in ideal contact.

FIG. 2C shows an intraoral photograph of the 1$^{st}$ patient's anterior view after the successful conclusion of the FT phase of retention therapy, which lasted 6 months. (Note: if this treatment were to be rendered today, the duration of the FT retention phase has evolved and been refined to where it typically lasts 9 months.) Including the active therapy phase, treatment has been ongoing for a total of 13 months. Note that the maxillary anterior buccal gingival tissue is now even more tightly adhered to the teeth, as evidenced by the increase in size of the dark space between the central incisors and the pocket depths which probe 1 mm, 1.5 mm or 2 mm. These factors contribute to confirm that Gingival Health Level II has been achieved. Note that the status of the occlusion in the left canine region, by teeth #11, 21, 22, has barely changed.

FIG. 2D shows an intraoral photograph of the 1$^{st}$ patient's anterior region after 6 months PT retention therapy. Including the active and FT retention phases, treatment has been ongoing for 19 months. Note that the gingiva throughout the maxillary and mandibular arches is more robust and thicker, signifying its maturation. There are no pocket depths greater than 2 mm. There has been no sensitivity when probing or during periodontal prophylaxes for more than 12 months. The amount of gingival recession has been stable or been reduced by up to 1 mm throughout the mouth. Gingival Health Level III has been achieved. Note that the occlusion in the left canine region, by teeth #11, 21, 22 has improved significantly. No removal of tooth structure (e.g., occlusal adjustment) was necessary to achieve the improved occlusion.

FIG. 2E shows the 1$^{st}$ patient 44 months after the start of therapy, 37 months after the conclusion of active therapy and after 31 months of PT retention therapy. The periodontist, her general dentist and the inventor who rendered the periodontally purposed orthodontic therapy are all in agreement—her gingival health is excellent and has exceeded all pre-therapy expectations. She has not experienced any oral sensitivity for more than 3 years. All pocket depths are 1 mm-2 mm, which is excellent. The amount of exposed root surface has either stayed the same or been reduced by up to 2 mm. Note that the occlusion in the left canine region, by teeth #11, 21, 22 is now in ideal contact. Once again, no removal of tooth structure (e.g., occlusal adjustment) was used to achieve this occlusion. The (orthodontic and periodontal) literature is devoid of articles that chronicle comparable improvement of a patient's gingival health during the positive reformulation of their BAOC. There are no dental, periodontal or orthodontic therapies known to the inventor that can predictably yield comparable results.

Dental literature warns that gingival recession is a common occurrence at the conclusion of orthodontic therapy (non-periodontally purposed).

Dental literature suggests that prior to the initiation of an orthodontic procedure, the orthodontist and/or periodontist should determine whether it is prudent and in the best interests of the at risk patient to receive periodontal grafting surgery prior to or after the conclusion of orthodontic care.

Dental literature cautions that gingival recession can occur while a patient is undergoing 10% carbamide peroxide (CP) therapy. That is understandable because CP solution's main ingredient (CP or hydrogen peroxide) has been known for more than a century to be an oral antiseptic. It reduces the level of bacteria in the oral cavity. As the presence of undesirable bacteria is reduced, the magnitude of the inflamed gingival tissue will be reduced. Concomitantly the amount of root exposed will be increased, which will correlate to a decrease in the gingival height.

As previously noted, the inventor has noticed that non-ideal axial inclinations of teeth can contribute to and/or exacerbate chronic malocclusion. Chronic inflammation of the surrounding gingiva is not an uncommon manifestation of teeth possessing non-ideal axial inclinations. No matter how often the inflamed gingiva is professionally treated (e.g., periodontal scaling, oral prophylaxis, removal of enamel), the inflammation and accompanying bleeding will return quickly, until the offending malocclusion is alleviated (e.g., removal of enamel, reformulation therapy).

Therefore, based on the dental literature, one would expect the positive reformulation of the BAOC through the prudent repositioning of the teeth in conjunction with the CP application to greatly reduce the gingival heights and expose more root structure.

The results, when analyzed by a trained dental professional who has reviewed the photos in FIGS. 2A and 2E, will lead to the conclusion that the health of the gingiva has improved, the amount of gingiva present has stayed the same or increased, and the amount of exposed root structure has stayed the same or been diminished.

FIG. 2F is a chart which summarizes the Levels of Gingival Health achieved and maintained at various stages for the $1^{st}$ patient.

The results (FIGS. 2A, 2E) refute and positively contradict the common expectations, the present state of the art for periodontal care and orthodontic therapy.

Her independent periodontist confirmed the overall findings which include Gingival Health Level III was successfully achieved and maintained.

It would not be unreasonable for a professional to conclude that the $1^{st}$ patient's Level of Gingival Health is superior three years after the conclusion of the active therapy portion (FIG. 2E) when scrutinized against the results present at the conclusion of her active therapy (FIG. 2B). The inventor found the dental literature devoid of similar results or findings.

Contrast photographs in FIGS. 2A and 2B, at the start and 7 months later, after the active phase of the therapy was successfully concluded for the $1^{st}$ patient. The lines highlight where the most dramatic improvement in gingival health has occurred. Also highlighted are patient #1's left canines, where the potential future need for an occlusal adjustment in that region is duly noted.

Contrast the photographs in FIGS. 2B and 2C, after 7 months (conclusion of active) and 13 months (conclusion of FT retention phase) of therapy. The lines highlight the maxillary and mandibular gingiva where it is now more tightly adhered to and in a more healthful relationship to the teeth. Also highlighted is the occlusal relationship of left canines, where the interocclusal gap is unchanged. In contrast to what would be considered standard protocol, no occlusal adjustment, occlusal equilibration, or other permanent or irreversible alteration to tooth structure was performed.

Contrast the photographs in FIGS. 2C and 2D, after 13 months (conclusion of FT retention) and 19 months (6 months PT retention) of therapy. The arrows highlight the reduction of the intercanine space and improved occlusion with teeth #10, 11, 12, 20, 21, 22, (the maxillary and mandibular left lateral incisors, canines and first premolars). Prior concerns that some occlusal equilibration or adjustment might be required are starting to be allayed. The canines are progressing towards a healthy and fully functional relationship without any apparent need for enamel removal. This contrasts significantly with the existing state of the art—where the orthodontist and/or general dentist nearly always permanently and irreversibly removes enamel from one or more teeth.

Contrast the photographs in FIGS. 2A (start) and 2D (19 months) which show the significant improvement in the gingival health in both the maxillary and mandibular arches. The periodontist who rendered her treatment for nearly a decade and performed the grafting surgery in the mandibular anterior area region several years prior to the initiation of this therapy (FIG. 2A) confirmed that the gingival health throughout patient #1's oral cavity is now at a superior level. The periodontist who is independent and unaffiliated with the inventor, now believes there is no longer an indication for any additional gum grafting surgical procedures.

Contrast the photographs in FIGS. 2D (19 months) and 2E (31 months). A professional or even a lay person can easily argue the interocclusal relationships between teeth #10, 11, 21, 22 and the health of the gingiva have continued to improve. The periodontist has changed the recommended frequency of her checkups and periodontal cleanings from 4 times to 1 time each year.

FIG. 2G shows the pre-treatment digital panoramic x-ray for patient number one.

FIGS. 2H/2I depict patient number one's smiles prior to (#2H) and after (#2I) the active phase of treatment.

FIG. 2J shows two photographs which are not of patient number one. The photo on the top left depicts an intraoral anterior view of another patient prior to CP therapy. The photo on the bottom right depicts an intraoral anterior view of that same patient after the successful completion of CP therapy. The natural teeth (black arrows), those without crowns, have become lighter and less yellow. The after photo depicts gingiva which although healthier, has been reduced in overall size, exposing more of the roots of the teeth. Her teeth with existing crowns (yellow arrows) in the posterior region note where the reduction of the puffiness of the gingiva has exposed some of the root structure previously hidden by the previously enflamed and less healthy gums. The relationship of the lips to the gum line when one smiles would determine whether an esthetic concern exists, which could require attention.

Refer to FIG. 2K (photos #2A/#2E). As has been noted in scientific articles, the application of 10% CP improves the overall health of the gingiva. One characteristic of this improvement is that the gingiva becomes less inflamed, or appears to shrink. The affiliated consequence of the height of the gum diminishing is that the amount of root surface increases and becomes more visible. A trained dental professional can ponder whether the eventual gingival root coverage for Patient #1 would have been greater with the reformulation therapy alone, had CP treatment had not been incorporated.

Second Patient
Age: 52 Sex: Male
Medical History:
Non-contributory
Dental History 2011:
Oral Hygiene:
 Fair/Good
 Bleeding: moderate
 Calculus: mild/moderate
 Plaque: moderate/heavy
 Brushing: 2-3 times each day
 Flossing: 1-2 times each day
Recent Dental Findings:
 Gingival recession=generalized 1-4 mm
 Sensitivity to cold=mandibular molars
 Congested mandibular and maxillary anterior teeth
 Collapsed/lingually rotated mandibular premolars
 Rotated teeth=multiple
 Periodontal pocket depths=all less than or equal to 3 mm
Orthodontic Treatment History:
 Traditional orthodontic care started at 13 and lasted for 3 years:
  Brackets
  Wires
  Elastics
  Retainers:
   Maxillary arch—Hawley type removable retainer
   Mandibular arch—none
 Relapse became evident shortly after bracket debonding:
  Maxillary arch—clearly evident after approximately one year
  Mandibular arch—clearly evident after approximately two months
Patient's chief concerns, wish list and goals:
 would like my teeth to be straighter
 would prefer to not have crooked teeth
 would like to reduce the amount of buildup on the backs of my lower front teeth
 would prefer to never bite my tongue while chewing or talking
Initial Diagnosis:
 Gingival recession, generalized (0-4 mm)
 Congested teeth
 Poor axial inclination—multiple teeth
 Malposed teeth
 Sensitive teeth
 Irregular curves of Spee, Wilson
 Omega shaped arch
 Arch asymmetry
 Canted teeth
 Chipped incisal, occlusal surfaces
Initial Visits Prior to Initiation of Therapy:
 Digital panoramic x-ray
 VPS impressions of the maxillary and mandibular arches
 Extraoral and intraoral examinations and comprehensive photographs
Treatments Options Considered:
 Clear flexible removable aligner orthodontic therapy
 Teeth whitening with ACP
 Gingival graft surgery
 No treatment
Treatment proposed:
 Clear flexible removable aligner orthodontic therapy
 10% CP+ACP therapy (At-Home teeth whitening concurrent with clear flexible removable aligner orthodontic therapy)
Active aligner therapy Phase I: 13 months (14 days per set of aligners)
 20 maxillary aligners (20 active aligners+6 passive aligners)
 26 mandibular aligners (26 active aligners)
Active aligner therapy Phase II: 13 months [12 days per set of aligners #1-3, 16 days per set of aligners #4-24]
 13 Maxillary Aligners (13 active aligners+13 passive aligners+3 over-correction aligners)
 26 Mandibular Aligners (26 active aligners)
Active aligner therapy Phase III: (16 days/aligner):
 21 Maxillary Aligners (21 active aligners)
 21 Mandibular Aligners (14 active+7 passive aligners)
Total number of active aligners during the Active Phase of Therapy:
 54 Maxillary Aligners (additional may be necessary—to be determined—active therapy ongoing)
 73 Mandibular Aligners (additional may be necessary—to be determined—active therapy ongoing)
Active therapy is proceeding well and still ongoing
Interproximal Reduction (IPR):
 Teeth #19/20=0.4 mm
 Teeth #20/21=0.4 mm
 Teeth #21/22=0.3 mm
 Teeth #29/30=1.0 mm
 Teeth #30/31=0.5 mm
 Total IPR=2.6 mm
*Note: If this treatment were to be rendered today, no IPR would be utilized. As previously discussed, reduction of the occlusal and interproximal portions of the teeth is contraindicated with this method. That is because those actions preclude the BAOC from achieving its peak reformulation. This will subsequently preclude the periodontium, the substructure, from being as resistant to the forces of orthodontic relapse as possible.
10% CP/ACP Solution Application:
Approximate number of 10% CP+ACP applications—25: 2-5/month over a period of 3 years
Treatment Results: Mid-Therapy:
 Gingival response to therapy has been excellent
 Color of gingiva=less red and less inflamed
 Pocket depths=have stayed the same or improved
 Gingival recession=has stayed the same or improved
 Lip=smile is now symmetric
 Smile=much fuller=more teeth are visible
 Tongue=has not bit his tongue while talking or eating in more than a year
Treatment Timeline:
Active Aligner Phase of Therapy: Months=28+(ongoing)
Full Time Retainer Phase of Therapy: n/a
Part Time Retainer Phase of Therapy: n/a
Gingival Health Timeline:
Month 12: Level I achieved
Month 24: Level I maintained FIG. 3A depicts a view of the mandibular arch of patient #2 before the start of a treatment according to the present invention.

FIG. 3B depicts a view of the mandibular arch of the 2$^{nd}$ patient part-way through the active aligner phase of periodontally purposed orthodontic therapy according to the present invention. The increase in the overall size of the mandibular arch is obvious. A portion of that increase is due to the uprighting of the teeth. A larger portion of the increased size of the mandible is due to the translational repositioning of multiple teeth. Those translational movements that accompanied the diminution of the congestion in the anterior region led to the deposition of new basal/alveolar bone.

According to the dental literature, significant increases in the size of the maxillary and/or mandibular jaws should be accomplished prior to puberty or via orthognathic surgical procedures in adults.

FIG. 3C depicts a view of the expected location of the teeth and the new shape of the mandibular arch of the 2nd patient after the therapy is concluded, according to the invention.

Prevailing science emanating from post-graduate orthodontic specialty training programs state that once an adult has matured and their bones have stopped growing, those bones are too mature to predictably expand beyond a modest amount.

Presently, it is believed and advocated that the most predictable way to change the size of the mandible or maxilla in an adult is via a maxillofacial ("orthognathic") surgery, which is an invasive procedure.

Presently, it is believed and recommended that arch expansion procedures be conducted on pre-pubescent children whose bones are still growing.

FIG. 3D is a photograph of the $2^{nd}$ patient's mandibular arch prior to the initiation of therapy according to the present invention.

FIG. 3E which is a photograph of the second patient's mandibular arch midway through the active aligner phase of the therapy according to the present invention. The improvement of the configuration and composition of the BAOC which has manifested in an improved mandibular arch shape, along with an increase in its overall size, are obvious to a trained dental professional. Note that the length and width of the black arrows in FIGS. 3D and 3E are equal.

FIG. 3F depicts the $2^{nd}$ patient's maxillary arch prior to the start of the periodontally purposed therapy according to the present invention.

FIG. 3G depicts the second patient's maxillary arch midway through the active phase of therapy according to the present invention.

FIG. 3H is a photograph of the $2^{nd}$ patient's maxillary arch prior to the start of therapy according to the present invention.

FIG. 3I is a photograph of the $2^{nd}$ patient's maxillary arch midway through the active phase of therapy according to the present invention. Significant expansion of the maxillary arch is evident.

FIG. 3J is a photograph of the $2^{nd}$ patient's smile prior to the start of periodontally purposed therapy according to the present invention. Notice how few teeth are visible in their entirety in the maxillary and mandibular arches. Prominent dark spaces are visible in the buccal vestibules bilaterally. Congestion in both the mandibular and maxillary anterior regions is clearly visible to both dental professionals as well as lay people.

FIG. 3K is a photograph of the $2^{nd}$ patient's smile midway through the active phase of treatment according to the present invention. Notice how many of the top teeth are presently visible in their entirety due to the increased size of the maxillary arch which is being accomplished via the reformulation of the BAOC. Notice that the congestion previously present in both the maxillary and mandibular anterior regions is greatly reduced which allows healthful, not inflamed gingiva, to predominate.

FIG. 3L depicts the $2^{nd}$ patient's anterior view prior to the start of therapy according to the present invention.

FIG. 3M depicts the second patient's anterior view partway through the active therapy according to the present invention.

FIG. 3N is a photograph of the anterior view of the $2^{nd}$ patient prior to the start of therapy according to the present invention. Numerous signs of malocclusion and chronic gingival inflammation are rampant throughout his mouth.

FIG. 3O is a photograph of the $2^{nd}$ patient's anterior view partway (24 months) through the active phase of treatment according to the present invention. The magnitude of the reduction in both the malocclusion and gingival inflammation and irritation provide evidence of the significant generalized improvement in the health of the gingiva as well as the interarch occlusal relationships. Gingival Health Level I is being maintained.

FIG. 3P is a chart which notes that the First Level of Gingival Health has been achieved and maintained. The periodontally purposed flexible aligner orthodontic treatment is active and ongoing in a positive manner, according to the present invention.

Third Patient
Age: 28 Sex: Male
Medical History:
Non-contributory
Dental History 2011:
Oral Hygiene:
  Fair
  Bleeding: moderate
  Calculus: mild/moderate
  Plaque: moderate/heavy
  Brushing: 1 time/day
  Flossing: infrequent
Recent Dental Findings:
  Gingival recession=generalized 1-4 mm
  Gingiva=bleeds when brushing, flossing, eating
  Periodontal pocket depths=all less than or equal to 3 mm
  Teeth #26, 27=Remnants of a fixed mandibular splint, anterior lingual orthodontic retainer (teeth #22-27)
Orthodontic Treatment History:
  Traditional orthodontic care for 3-4 years:
    Brackets
    Wires
    Elastics
  Retainer therapy:
    Mandibular
      anterior lingual fixed retainer
    Maxillary
      Hawley type (removable)
  Relapse became evident 0.5-1 year after bracket debonding, in high school. The patient states that his compliance with the maxillary removable retainer was poor. The relapse continued to get progressively worse over the next decade.
Patient's chief concerns, wish list and goals:
  Want my smile to be whiter
  Want to make sure that the spaces that used to be between my teeth are not returning
Initial Diagnosis:
  moderate gingivitis
  mild/moderate malocclusion Initial Visits Therapy:
  digital panoramic x-ray
  VPS impressions of the maxillary and mandibular arches
  extraoral and intraoral examination and comprehensive photographs
  splint removal and debridement
  Oral prophylaxis
Treatments Options Considered:
  Free gingival graft periodontal surgery—mandibular anterior
  Clear flexible removable aligner periodontally purposed orthodontic therapy
  Teeth whitening
    Instant In-Office
    Custom At-Home
  Periodontal scaling and root planing
  No treatment
Treatment Proposed:
  Clear flexible removable aligner periodontally purposed orthodontic therapy
  10% CP with ACP (at-home teeth whitening concurrent with clear flexible removable aligner periodontally purposed orthodontic therapy)
  Oral prophylaxes every 12 weeks
Active Aligner Therapy Phase I:
  Duration: 5 months (14 days/aligner)
  10 maxillary aligners
  10 mandibular aligners
Active Aligner Therapy Phase II:
  Duration: 4.5 months (14 days/aligner)
  9 maxillary aligners
  9 mandibular aligners
Total Number of Aligners in the Active Phases I-II of Therapy:
  19 Maxillary
  19 Mandibular
Interproximal Reduction (IPR) Performed: None
10% CP with ACP solution application:
Approximate number of 10% CP+ACP applications~15:
1-2/month over a period of 10 months
Treatment Results (Progress—PT Retention Therapy):
  Gingival response=excellent
  Pocket depths=stayed the same or have improved
  Gingival recession=stayed the same or improved
  Tooth #25=gingival height improvement (regeneration of the periodontium complex) has been highly significant (>3 mm)
Treatment Timeline:
Active aligner Phase of therapy: months=9.5
FT retainer Phase of therapy: 9 months
PT retainer Phase of therapy: month 2 (ongoing)
Gingival Health Timeline:
Month 3: Level I achieved
Month 10: Level II achieved
Month 19: Level II maintained FIG. 4A is a photograph showing the anterior view of the 3$^{rd}$ patient's teeth during the initial consultation. All periodontal pocket depths are less than 4 mm. There is generalized mild to moderate bleeding while probing throughout the mouth. In the mandibular anterior region, the patient experiences sensitivity. Heavy bleeding occurred during probing of the mandibular anterior region.

FIG. 4B is a photograph showing the anterior view of the 3$^{rd}$ patient's teeth 13 months after the initial consultation (FIG. 4A) and just prior to the start of periodontally purposed orthodontic therapy. No dental treatment was rendered during the intervening 13 months. As is visually evident, especially in the areas noted by the arrows, his dental condition has worsened.

FIG. 4C is a photograph showing the anterior view of the 3$^{rd}$ patient's teeth which helps quantify the magnitude of the bone and gum loss in the mandibular anterior region. The gingival levels at the inferior portion of the mandibular incisors should be relatively even (within 1 mm). Those gingival levels now differ by 3-4 mm. A common recommended treatment commonly performed by periodontists to correct this condition would be the free gingival graft surgery, an invasive procedure.

FIG. 4D is a photograph of the 3$^{rd}$ patient's anterior view 3 months after the initiation of therapy. A subtle improvement in the occlusion in conjunction with improved axial inclinations of multiple teeth accompanies an extraordinary and visually dramatic improvement in the health of the gingiva (black arrows). Gingival Health Level I has been achieved.

The results achieved directly conflict with what one would expect based on the findings and conclusions espoused in the dental literature. To accent this point, the consensus of the dental literature recommends that an orthodontist and/or periodontist and/or general dentist determine whether the invasive surgical grafting procedure be performed prior to or after orthodontic therapy. The literature is silent on the recommendation that clinicians not consider periodontal surgical graft intervention as an option.

FIG. 4E is a photograph of the 3$^{rd}$ patient's teeth 10 months after the initiation of periodontally purposed flexible aligner orthodontic treatment according to the present invention. Notice the maturation of the gingiva throughout the mouth at the conclusion of the active phase of therapy. There is no bleeding while probing pocket depths which are all now 3 mm or less. The occlusion, especially the interocclusal space in the canine regions bilaterally, is being actively monitored (black arrows). The occlusion in the canine regions bilaterally is still non-ideal. Contrary to the standard orthodontic guidelines, no adjustments were made to enhance the occlusion (irreversibly remove tooth structure from multiple teeth). The decision was made to proceed with the retention phase of therapy and re-evaluate at the subsequent PREV. While the patient's dedication to oral hygiene compliance remains an ongoing challenge, the enhanced firmness and fullness of the gingiva (black lines) provides a measure of optimism and confirms that Gingival Health Level II has been achieved.

FIG. 4F is a photograph of the anterior view of the 3$^{rd}$ patient which shows the oral condition 20 months after the initiation of therapy. The maintenance of the BAOC and generalized health of the gingiva in the mandibular anterior, particularly tooth #25, is noted. The improvement of the occlusion, most noticeable in the canine regions bilaterally (#6/27,28); #11/21,22), is noted. Compare the areas above the black arrows in FIGS. 4E & 4F. This improved occlusion allays concerns that the irreversible procedure of the removal of the occlusal, lingual and incisal tooth structure will not be necessary. This is in spite of the fact that his oral hygiene is still an issue (as evidenced by the plaque at the gingival margins of teeth #6, 11).

FIG. 4F shows positive clinical results that were unexpected, the regrowth and sustained health of the facial gingival surface of tooth #25, where 3-4 mm gingiva and bone loss was once present. Those results, achieved without periodontal gingival graft surgery (which is 2 surgeries—the donor and recipient sites), without the permanent removal of tooth enamel (occlusal adjustment of the lingual surfaces #8, 9; facial surface #25), without any augmentation from a bone regeneration material, are highly significant.

FIG. 4G is a photograph of the 3$^{rd}$ patient's teeth—the lingual view of the mandibular anterior region prior to the initiation of therapy according to the present invention. Note the remnants of the fixed lingual splint adhered to the lingual surfaces of teeth #26, 27 immediately after the conclusion of his initial orthodontic therapy. It is highly likely that at one point the splint adhered to and connected six teeth, #22-27.

FIG. 4H is a photograph of the 3$^{rd}$ patient's teeth—the lingual view of the mandibular anterior region after 7 months of active therapy according to the present invention. 4.5 months have passed since his most recent dental cleaning.

FIGS. 4G and 4H are photographs which depict the views of the lingual surfaces of the mandibular front teeth prior to the initiation of and 7 months into active aligner therapy of the 3$^{rd}$ patient. The amount of accumulated stain and plaque is greatly reduced, and the redness of the gingiva has been reduced, albeit after a shorter time period, (12 months vs. 4.5 months) since the prior professional prophylaxes.

This result helps confirm that subtle, not just glaring improvements, can have a positive impact on the self-cleansing aspects of, or resistance to plaque/stain accumulation, in one's oral cavity according to the present invention. This was result was also unexpected based on the fact that the patient still lacks a prudent oral hygiene regimen.

FIG. 4I is a photograph focused on the mandibular anterior buccal region of the 3$^{rd}$ patient at his initial consultation visit, 15 months prior to the start of therapy.

FIG. 4J is a photograph focused on the mandibular anterior buccal region of the 3$^{rd}$ patient 13 months after his initial consultation and 2 months prior to the initiation of treatment according to the present invention. The arrows point to the areas of chief concern, an acute periodontal flare up. This is a potential consequence when one possesses a chronic malocclusion.

FIG. 4K is a photograph focused on the mandibular anterior buccal region of the 3$^{rd}$ patient 3 months after the initiation of therapy according to the present invention. The increased breadth and height of the gingiva along with the reduced inflammation help confirm that Gingival Health Level I has been successfully achieved FIG. 4L is a photograph focused on the mandibular anterior buccal region of the 3$^{rd}$ patient midway through (5 months) active therapy according to the present invention. As discussed, patient #3 is maintaining Gingival Health Level I.

FIG. 4M is a photograph focused on the mandibular anterior buccal gingiva of the 3$^{rd}$ patient at the conclusion (10 months) of active therapy according to the present invention. As noted, while mild amounts of stain and plaque are present, the improved thickness and firmness of the gingiva confirm that Gingival Health Level II has been achieved.

FIG. 4N is a photograph focused on the mandibular anterior buccal gingiva of the 3$^{rd}$ patient after 20 months of therapy (1 month PT+9 months FT retainer wear). While oral hygiene remains an issue, Gingival Health Level II is being maintained.

FIG. 4O is a chart which notes that the 1$^{st}$ two Levels of Gingival Health have been achieved and maintained. Due to the concerns with his oral hygiene, the intervals between PREV will be shorter than what would be typically recommended with a patient who was maintaining a standard or superior level of oral hygiene.

Fourth Patient
Age: 55 Sex: Female
Medical History:
A severe automobile accident in 1994 resulted in a fractured portion of the anterior maxilla and the dislodging of five anterior teeth which required their extraction. A bone graft, three osseointegrated implants and a bridge were placed.
Dental History 2011:
Oral Hygiene:
  Fair
  Bleeding: moderate
  Calculus: moderate/heavy
  Plaque: moderate/heavy
  Brushing: 4 times/day
  Flossing: 2 times/day
Recent Dental Findings:
  Gingival recession: generalized 1-2 mm
  Gingiva bleeds: when brushing, flossing, eating
  Periodontal pocket depths: ranges from 2-6 mm
  Teeth #25/26: two acute periodontal abscesses in the past half decade
  Teeth #23, 26: accumulate heavy stains
Orthodontic Treatment History:
  None
Patient's Chief Concerns, Wish List and Goals:
  Don't want to ever have another abscess
  Would like my teeth to look less dirty
  Would like my teeth to look less uneven when I talk and smile
Initial Diagnosis:
  Mild generalized gingivitis: recession/exposed roots
  Mild/moderate chronic malocclusion
  Mild periodontitis
  Calculus accumulation—mandibular anterior lingual surfaces: heavy
Initial Visits Therapy:
  Digital panoramic x-ray
  VPS impressions of the maxillary and mandibular arches
  Extraoral and intraoral examination, extraoral and intraoral comprehensive photographs
Treatments Options Considered:
  Periodontally purposed orthodontic therapy
  Teeth whitening
  Enamel microabrasion therapy
  No treatment
Treatment proposed:
  Periodontally purposed orthodontic therapy (single arch)
  10% CP+ACP
[at-home teeth whitening concurrent with the removable orthodontic therapy]
Active Therapy Phase I:
  Duration: 5 months (14 days/aligner)
  10 mandibular aligners
Active Therapy Phase II:
  Duration: 4 months (14 days/aligner)
  8 mandibular aligners
Full Time Retainer Therapy:
  Duration: 6 months
  2 retainers, each for 3 months
Part Time Retainer Therapy
  2 retainer, 1$^{st}$ for 12 months, 2$^{nd}$ for 8 months (ongoing)
Note: due to the existing implant and teeth-borne fixed bridgework, periodontally purposed orthodontic treatment was not a consideration for the maxillary arch.
IPR: none
10% CP+ACP=application regimen:
  Approximate number of 10% CP/ACP nighttime applications:

About 50 [2-5/month over a period of 2 years]
Treatment Results (Therapy Still Ongoing):
  Gingival response to therapy: has been excellent.
  Pocket depths=have stayed the same or improved
  Gingival recession=has stayed the same or improved
  Teeth #23, 26=stain accumulation greatly reduced
  Oral hygiene improved
  Less oral hygiene effort required=mouth is more self-cleansing
    Flossing 1x/day, brushing 2x/day
Treatment Timeline:
Active Aligner Phase of Therapy: 9 Months
Full time retainer phase of therapy:
Months 10-15
Part Time Retainer Phase of Therapy:
Months 16-30 (ongoing)
Gingival Health Timeline:
Month 9: Gingival Health Level I Achieved
Month 15: Gingival Health Level I Maintained
Month 30: Gingival Health Level I Maintained FIG. 5A depicts a view of the mandibular arch of the 4$^{th}$ patient before the start of the periodontally purposed flexible aligner orthodontic treatment according to the present invention. This patient has one implant and two teeth-borne bridges in the maxillary arch. Therefore, repositioning and osseous reformulation therapy can and will only be conducted within the mandibular arch.

FIG. 5B depicts a view of the mandibular arch of the 4$^{th}$ patient at the projected conclusion of active therapy according to the present invention. Please note, the edentulate area by tooth #19 is depicted with a half tooth. It is expected that an implant, abutment and crown will one day be placed in that area (tooth #19).

FIG. 5C is a photograph of the mandibular arch of the 4$^{th}$ patient prior to the initiation of treatment. The amount of calculus that builds up swiftly after professional prophylaxes is moderate to heavy. On more than one prior occasion, the patient suffered an acute periodontal abscess at the gingival interface between teeth #25, 26 necessitating periodontal treatment.

FIG. 5D is a photograph of the 4$^{th}$ patient's mandibular arch after 5 months, partway through the active phase of therapy, according to the present invention. Note the size of the arch has been increased, the shape of the arch form has improved, there is a reduction in the accumulation of plaque, stain and calculus and the edentulate space (tooth #19) has been improved, when compared to FIG. 5C.

FIG. 5E is a photograph of the 4$^{th}$ patient's mandibular arch at the conclusion of active therapy (9 months). The improvement in the health of the gingiva is supported by the reduced amount of calculus, congestion, redness and asymmetry along with its increased firmness.

FIG. 5F depicts the 4$^{th}$ patient's 27 months after the initiation of therapy, 18 months after the conclusion of active therapy and 12 months PT retention usage according to the present invention. The patient has not experienced an acute periodontal episode since the initiation of therapy.

FIG. 5G depicts the 4$^{th}$ patient's smile prior to the initiation of treatment. Note that two mandibular teeth stick out because they are significantly darker than their neighbors. Their darkness is due to a combination of their being lingually displaced as well as their proclivity to accumulate stain, plaque and calculus.

FIG. 5H is a photograph of the 4$^{th}$ patient's smile after the conclusion of active therapy (9 months). Note those two previous dark teeth (#23, 26) now blend in much more harmoniously with their adjacent teeth and no longer stick out. Also important, the improvement of the location of the teeth within the arch and the idealized axial inclinations have led to those teeth accumulating significantly diminished amounts of plaque, stain and calculus when compared to the pre-treatment rate.

FIG. 5I depicts the anterior view of the 4$^{th}$ patient prior to the initiation of therapy, according to the present invention.

FIG. 5J depicts the projected finish of the anterior view of the 4$^{th}$ patient after the conclusion of active therapy according to the present invention.

FIG. 5K is a photograph of the anterior view of the 4th patient prior to the initiation of therapy. A main concern is gingival interproximal area between her mandibular right central and lateral incisors, teeth #25 & 26, which was the location of two prior acute periodontal abscesses. As is presently evident, calculus is still visible albeit in a smaller quantity when compared with prior pre-therapy levels. This will be one of the factors used by a trained professional to determine when to modify the intervals between PREV.

FIG. 5L is a photograph of the anterior view of the 4th patient at the conclusion of active therapy (9 months), according to the present invention. While this photo may not give it its full due (the patient wore her present flexible aligner for a longer than expected duration), the gingiva and teeth are accumulating significantly reduced amounts of plaque, stain and calculus. There is a reduced amount of redness, an increased firmness to the gingiva and an increased amount of adherence of the gingiva to the teeth. The patient reports and the clinical exam confirmed that the gingival area between teeth #25 & 26 is now easier to clean and accumulates less food residue and plaque. Some of the calculus present may be due to the infrequent, yet ongoing CP therapy, which as was previously discussed, is a known and literature documented consequence. The arch form is larger, more harmonious and has a decreased amount of asymmetry. The number of mandibular teeth in function and properly occluding with the maxillary teeth has increased. The magnitude of her chronic malocclusion has been significantly reduced. This is confirmation that Gingival Health Level I has been achieved.

FIG. 5M is a photograph of the anterior view of the 4th patient's anterior region during a 24 month PREV (, 33 months after initiation of therapy, 18 months of PT retainer usage). Note the reduction in the amount of gingival inflammation and calculus accumulation. The arch symmetry and occlusion has remained stable. There are no subtle or overt signs of relapse. There is sufficient evidence of generalized improvement of the gingiva throughout the mandibular anterior region to confirm that Gingival Health Level I has been successfully maintained.

FIG. 5N is a photograph of the anterior open view of the 4$^{th}$ patient prior to the initiation of therapy.

FIG. 5O is a photograph of the anterior open view of the 4$^{th}$ patient at the conclusion of active therapy (9 months). Note that there is a significant reduction in the amount of asymmetry in the mandibular arch form and an improved level of periodontal health. While significant progress was made, an ideal reformulation of the mandibular arch form was precluded by the fact that the maxillary arch could not be reformulated. As previously noted, Gingival Health Level I has been achieved.

FIG. 5P is a photograph of the 24 month PREV [6 months FT, 18 months PT], 30 months after the initiation of therapy with the 4$^{th}$ patient. The patient states that her mouth feels stronger and less fragile. While her oral hygiene required encouragement, the photo confirms that Gingival Health Level I has been maintained.

FIG. 5Q is a chart which notes that the First Level of Gingival Health has been achieved and been maintained for the 4th patient. Although only one arch was able to be treated, significant improvement was achieved and the positive reformulation of the BAOC has been maintained.

Fifth Patient
Age: 52 Sex: Female Date of Initial Visit: Dec. 4, 2010
Medical History:
Patient is deaf/mute.
Dental History 2011:
Oral Hygiene:
    Fair
    Bleeding: moderate
    Calculus: moderate/heavy
    Plaque: moderate/heavy
    Brushing: 1×/day
    Flosses: no
Recent Dental Findings:
    Gingival recession: 0-4 mm
    Gingiva bleeds: when brushing and flossing
    Periodontal pocket depths: ranges from 2-4 mm
Orthodontic Treatment History:
    None
Patient's Chief Concerns, Wish List and Goals:
    Want straight teeth
    Would like my teeth to look less dirty (photos were taken after the successful completion of periodontal debridement treatments to remove heavy calculus and stain)
    Would like my teeth to fit in my mouth
Initial Diagnosis:
    Mild generalized gingival recession/exposed roots
    Moderate chronic malocclusion
    Calculus accumulation: lingual mandibular anterior—heavy
Initial Visits Therapy:
    Consultation
    Panoramic x-ray
    VPS impressions of the maxillary and mandibular arches
    Extraoral and intraoral examination, extraoral and intraoral comprehensive photographs
Treatments Options Considered:
    Periodontally purposed flexible aligner therapy
    Teeth whitening
    No treatment
Treatment Proposed:
    Periodontally purposed flexible removable aligner orthodontic therapy
    10% CP+ACP (At-Home teeth whitening concurrent with the removable orthodontic therapy)
Active Therapy Phase I:
    Duration: 12 months (14 days/aligner)
    24 Mandibular aligners
    19 Maxillary aligners
Active Therapy Phase II:
    Duration: 6 months (14 days/aligner)
    12 Mandibular aligners
    12 Maxillary aligners
Active Therapy Phase III:
    Duration: 6 months (14 days/aligner)
    12 Mandibular aligners
    9 Maxillary aligners
Active Therapy Phase IV:
    Duration: 11 months (21 days/aligner—ongoing)
    13 mandibular aligners
    15 maxillary aligners
Interproximal Reduction (IPR) Performed:
    Teeth #19/20=0.5 mm
    Teeth #20/21=0.5 mm
    Teeth #21/22=0.5 mm
    Teeth #22/23=0.2 mm
    Teeth #27/28=0.5 mm
    Teeth #28/29=0.5 mm
    Teeth #29/30=0.5 mm
Total IPR=3.2 mm
* Note: If this patient were treated today, no IPR would be utilized.
10% (CP)+(ACP) Solution=Application Regimen:
    Approximate number of 10% CP/ACP nighttime applications:
    About 60 (2-5/month over a period of 2.5 years)
    Treatment Results (therapy still ongoing):
    Gingival response to therapy: excellent
    Pocket depths=all have stayed the same or improved
    Gingival recession=all have stayed the same or improved
    Oral hygiene improved (very good/excellent)
Treatment Timeline:
Active Aligner Phase of Therapy: 31 Months (ongoing)
Full Time Retainer Phase of Therapy: n/a
Part Time Retainer Phase of Therapy: n/a
Gingival Health Timeline:
Month 18: Level I achieved
Month 24: Level II achieved
Month 30: Level II maintained FIG. 6A is a photograph of the anterior view of patient #5 prior to the initiation of therapy. Teeth #21, 22, 25 and 28 are some of the more maloccluded teeth.

FIG. 6B is a depiction of anterior view of patient #5 prior to the initiation of therapy.

FIG. 6C is a photograph of the anterior view of the 5th patient taken during a scheduled periodic orthodontic visit (POV) to evaluate the 22nd set of aligners, 11 months into active therapy. Since the patient presented with a transient malocclusion (arrows note the teeth in contact), albeit an asymptomatic one, the status was photo documented. It is recommended that each sign of transient malocclusion be documented, according to the present invention. Note that no more than 8 teeth are in contact, 4 in each of the maxillary and mandibular arches.

There are multiple explanations why a patient will be asymptomatic when so few teeth are in minimal occlusal function during maximum closure or centric relation (FIG. 6C). When teeth are being repositioned, with their primary purpose being the reformulation of the BAOC and the creation of ideal arch forms, or as ideal as clinically practicable, transient malocclusions will be common and should be expected. If the teeth are tracking reasonably well within the periodontally purposed orthodontic aligners, these transient malocclusions should be monitored only—no tooth structure should be irreversibly removed. No occlusal, incisal or lingual reduction, which diminishes the size of the teeth, should be performed. If need be, reduce the interval between POV to 2 or 3 weeks and re-evaluate the occlusion, any active interferences and/or mobility of the involved teeth. This is a significant deviation from present orthodontic protocols. The standard remedy for teeth experiencing transient malocclusion is to remove the offending portions of tooth structure in an effort to minimize the likelihood of further occlusal interferences, minimize the likelihood of teeth becoming mobile and to remove an impediment to care. This protocol or any other which advocates the permanent removal of tooth structure must be resisted according to the present invention. As stated previously, the ingrained instinct to irreversibly remove tooth structure must be avoided to ensure a result that is as periodontally satisfactory as clinically practicable, possesses an occlusion as ideal as clinically practicable, which will help achieve a final result that will be as resistant to clinical relapse as possible.

The existing state of the art conflicts 180° with this concept. The overwhelming preponderance of scientific literature advocates that all occlusal interferences be eliminated prior to the initiation of, during, and at the conclusion of therapy.

Prior art advocates that occlusal interferences inhibit tooth movement, or can compromise the stability of the involved teeth. That's why the "problem" needs to be immediately corrected through the permanent elimination of the interference. Prior art advocates that the failure to eliminate occlusal interferences can lead to a compromised outcome.

According to the present invention, the immediate elimination of an occlusal interference via the permanent reduction of tooth structure will not aid, and will almost always inhibit the BAOC from reaching its ideal magnitude of reformulation, which will lead to a compromised outcome or decrease the likelihood that the "ideal as clinically practicable" goal will be achieved.

This invention stresses that the need to ideally reformulate the BAOC must take precedence over any desire to permanently and irreversibly alter the shape of even one tooth. Therefore, anything that might limit the mandibular and/or maxillary arches from achieving their idealized reformulated states, such as the permanent irreversible removal of tooth structure or the removal of a non-infected tooth or a tooth eligible to be restored, must be avoided. An irreversible occlusal adjustment will diminish the magnitude of the desired improvement and therefore should be avoided.

This is a novel concept. The dental literature is silent on this topic. The inventor is not aware of a study contrasting therapy with and without permanent tooth enamel elimination.

A trained clinician should consider and treat the transient malocclusion state as a positive progression within the therapy and treat it accordingly. Therefore, no action should be taken by a clinician when a patient has asymptomatic transient malocclusion. Each mention in the scientific literature on the topic stresses the complete opposite approach.

To date, the inventor has not observed any patient while receiving periodontal, orthognathic and/or TMD purposed aligner therapy, experience symptomatic transient malocclusion. Every patient who experienced transient malocclusion has been asymptomatic.

FIG. 6D is the anterior view of the 5$^{th}$ patient taken after 12 months of active therapy. Notice that in just one month, how the transient malocclusion is less severe, but still present, and still asymptomatic. Notice also that the health and appearance of the gingiva shows multiple signs of improvement. Based on the existing scientific literature, none of these results would have been expected four weeks ago, especially because of the "failure" to permanently remove those "harmful" occlusal interferences.

When the goals of BAOC reformulation and ideal arch form development include the correction of teeth which are rotated; lingually, buccally or palatally displaced; misangulated and/or in need of uprighting; or in posterior or anterior crossbite, transient malocclusions will be common. According to the major orthodontic laboratories and scientific literature, scant few clinicians choose to correct posterior crossbites, upright malposed posterior teeth, etc., with removable flexible sequential orthodontic aligners.

However, unless those corrections are addressed (e.g., posterior crossbite, arch form asymmetry, proximal alignment, anterior/posterior relationships), occlusion and periodontal health will not reach their full potential or possibly even a level deemed desirable. Contrary to the prevailing state of the art, each of these shortcomings and discrepancies merit attention and warrant thorough and diligent correction.

The prevailing failure to address these issues may be due to the definition of success set by the American Board of Orthodontics Grading Systems. These Grading Systems omit two factors essential to successful patient therapy; the health of the gingiva and the ability of the patient to maintain the results without suffering relapse.

On occasion, the consequences of not obtaining or not maintaining a satisfactory orthodontic result may be inconsequential. The majority of the time, the consequences of neither obtaining the desired orthodontic results nor maintaining those results will require intervention and correction by an orthodontist, periodontist, general dentist, oral surgeon, endodontist, etc. The oral health and dental consequences due to the existing state of the art are real, widespread and quite common.

Based upon patients who have successfully completed the active and full time retainer regimens, who have experienced dramatically improved arch forms, elimination of crossbites, uprighted and aligned teeth; and are utilizing PT retainers, an experienced clinician would have no choice but to unequivocally conclude that the typical concerns surrounding orthodontic relapse have been significantly diminished, if not eliminated.

FIG. 6E is a depiction of the anterior view of the 5th patient after 12 months of active therapy.

FIG. 6F is a photograph of the 5$^{th}$ patient after 16 months of active therapy. Notice the overall health of the gingiva in both arches is continuing to improve to the point that Gingival Health Level I has been achieved.

FIG. 6G is a depiction which projects the state of the mouth after 18 months of therapy.

FIG. 6H is a photograph of the anterior view of the 5$^{th}$ patient after 24 months of active therapy. The arrows point to bilateral posterior transient disclusion which is a common occurrence when arches are being increased in size. Note the amount of recession and exposed root surface has stayed the same or decreased by up to 1 mm (teeth #21, 28). According to the dental literature, these results are rarely achieved.

To the contrary, existing orthodontic and periodontal articles and case studies warn clinicians that gingival recession and diminished gingival health are common and expected results from traditional (non-periodontally purposed) orthodontic therapy, especially those which incorporate CP solution into the regimen.

FIG. 6I is a photograph of the anterior view of the 5th patient after 31 months of active therapy. The overall health of the gingival has stayed the same or improved. Transient malocclusion, as expected with the expansion of one or both of the arches, is evident and asymptomatic. The amount of recession and exposed root surface has stayed the same or showed some subtle improvement. All pocket depths are less than or equal to 3 mm. Gingival Health Level II has been achieved.

It is highly significant to note in FIG. 6I that the reformulation of the BAOC which included bilateral posterior expansion of the maxillary and mandibular arches is progressing precisely as designed and is near completion. A skilled clinician will be able to easily visualize that as therapy proceeds through the retention (FT & PT) phases, the occlusal spaces between the posterior maxillary and mandibular teeth will gradually diminish and leave the patient with ideal arch forms, ideal occlusion, ideal alignment of the periodontal ligaments, or very close to the clinically practicable ideal. This is the desired sign of confirmation to alert a skilled clinician that the positive reformulation of the BAOC is approaching its successful conclusion.

FIG. 6J is a depiction of the anterior view at the conclusion of the active therapy for the 5$^{th}$ patient.

FIG. 6K is a photograph of the occlusal view of the mandibular arch of the 5$^{th}$ patient prior to the initiation of therapy.

FIG. 6L is a depiction of the mandibular arch of the 5$^{th}$ patient prior to the initiation of therapy.

FIG. 6M is a photograph of the occlusal view of the mandibular arch of the 5$^{th}$ patient after 12 months of active therapy. Note that the color of the gingiva has more of the desirable and healthier pink hues, with less red (e.g., connotes inflammation). Note that the arch form is more harmonious and less asymmetric. That is due to an increase in the overall quantity of bone, which has created additional space for the incisors, canines and first premolars.

FIG. 6N is a projected depiction of the mandibular arch of the 5$^{th}$ patient after 12 months of active aligner therapy.

FIG. 6O is a photograph of the occlusal view of the mandibular arch of the 5$^{th}$ patient after 18 months of active therapy. Her dental hygienist, who spent extensive visits removing heavy deposits of calculus, plaque and stain throughout her mouth prior to her initial photographs, reports that she has significantly improved level of oral hygiene. The mandibular arch is now 4 mm longer in an antero/postero dimension, as well as being wider by more than 1.5 mm, than it was prior to the initiation of therapy. The reformulated BAOC, specifically the increased width and length of the mandible, increases the stability of the arches and makes them significantly more resistant to the potent forces of orthodontic and occlusal relapse.

The dental literature strongly advocates that when necessary, the skilled clinician should take steps to increase the size of the maxillary and mandibular arches in pre-pubescent children (e.g., palate expander). The dental literature does not advocate the same magnitude of arch size increases in the adult population. The literature advocates that insufficient arch sizes be addressed by the elimination of teeth, the reduction in the size of teeth, or when appropriate, permanent modification of the jaw with an orthognathic surgery.

The prevailing belief is that post-pubescent patients are unable to have their arches sufficiently expanded or they cannot be expanded with adequate reliability. This patient supports the contention that not only is the expansion of the arch forms possible in both the mandible and the maxilla, it is a more desirable option. This is especially true when compared to the present techniques utilized by the supermajority of clinicians in practice.

Here is a simple way one can quantify the increase in the overall size of patient #5's mandible over those first 18 months of treatment. A size large tray was required to capture the mandibular impression at the start of therapy. A size extra-large tray was needed for the mandibular impression a subsequent phase of therapy, 18 months later. The larger sized tray was required to accommodate each and every tooth in an arch which had been increased by 4 mm in the length and by 1.5 mm in the width.

FIG. 6P is a depiction of the mandibular arch of the 5$^{th}$ patient after 18 months of therapy.

FIG. 6Q is a chart which tracks the improvement in the health of the gingiva of the 5$^{th}$ patient. Notice that Gingival Health Level I was first achieved after 18 months of active therapy. Gingival Health level II was achieved after 31 months of active therapy and has been maintained during the subsequent POV.

Sixth Patient
Age: 39
Sex: Female
Date of Initial Visit: Apr. 2, 2012
Medical History:
Significant Personal History: a professional singer; wants to ensure that the treatment will not inhibit her ability to perform.
Dental History 2012:
Oral Hygiene:
  Good/Fair
  Bleeding: moderate—generalized
  Calculus: moderate/localized—mandibular arch
  Plaque: moderate—generalized
  Brushing: 1×/day—bleeding when brushing (occasionally)
  Flosses: none
Recent Dental Findings:
  Gingival recession: 0-4 mm
  Gingiva bleeds when brushing and flossing
  Calculus accumulation: lingual mandibular anterior—moderate
  Periodontal pocket depths: ranges from 2-4 mm
  Incisal enamel chips: 5 teeth
  Axial inclination: multiple teeth=atypical
  Canted teeth
  Chronic malocclusion: present
  Dental caries—none
  TMD—active
  Crowding: multiple areas
  Edentulous areas: teeth—#2, 5, 21, 28, 30
  Inadequate space for a dental implant—mandibular right posterior region—even though two edentulous areas are present
  Axial inclination: multiple teeth—poor
  Prior history of orthodontic therapy
  Orthodontic therapy relapse: generalized, severe, symptomatic
  Maxillary right posterior: sinus lift pre-implant surgery likely
  Teeth: multiple sensitive to cold
Orthodontic Treatment History:
  Age 11-12.5: traditional braces for approximately 1.25 years
  Teeth removed: #5, 21, 28 (along with four primary teeth)
  Retainer therapy: none
  Relapse first became evident within a few years. Increased in severity into her early 20's.
Patient's Chief Concerns, Wish List and Goals:
  Want straight teeth
  Would like my teeth to look like they did 15 years ago
  Would like to correct my odd shaped teeth or make them less obvious
  Embarrassed by the appearance of her teeth
  Orthodontists in London, England (2011) and New York (US) (2012) corroborated why she was not a candidate for removable flexible sequential orthodontic therapy
Initial Diagnosis:
  Moderate generalized gingival recession
  Chronic malocclusion
Initial Visits Therapy:
  Consultation
  Panoramic x-ray
  VPS impressions of the maxillary and mandibular arches Extraoral and intraoral examination, extraoral and intraoral comprehensive photographs Treatments Options Considered:
   Flexible removable sequential aligner periodontally purposed orthodontic therapy
   Teeth whitening
   No treatment Treatment Proposed:
   Flexible removable sequential aligner periodontally purposed orthodontic therapy
   10% CP+ACP
   (at-home teeth whitening concurrent with the flexible removable sequential orthodontic therapy)

Active Clear Flexible Aligner Therapy: Phase I
   Duration: 12 months (14 days/aligner)
   23 mandibular aligners
   23 maxillary aligners Active Clear Flexible Aligner Therapy: Phase II
   Duration: 24 months (16-18 days/aligner) [ongoing]
   30 mandibular aligners
   25 maxillary aligners 10% (CP)+(ACP) Solution—Application Regimen:
   Approximate number of 10% CP/ACP nighttime applications:
      About 40 (2-3/month over a period of 2 years)

Treatment Results (Therapy is Ongoing):
   Gingival response to therapy has been excellent.
   Pocket depths: have stayed the same or improved
   Gingival recession: has stayed the same or improved
   Oral hygiene improved
   TMD: resolved (no longer sees a physical therapist to relieve her pain)

Treatment Timeline:
active aligner phase of therapy: 48 months (projected—ongoing—presently at month 18
FT retainer phase of therapy: n/a
PT retainer phase of therapy: n/a
Gingival Health Timeline:
Month 12: Level I Achieved FIG. 7A is a photograph of the right buccal view of patient #6 prior to the initiation of therapy. The main goals of her therapy were to idealize the arch forms, idealize the posterior occlusion, diminish/resolve her TMD, diminish/resolve her teeth's sensitivity to cold stimuli, minimize eliminate the asymmetry in her arches and smile.

FIG. 7B is a depiction of right canine view of patient #6 prior to the initiation of the flexible removable sequential orthodontic therapy. The goals for patient #6 were scaled down at the onset due to a high level of anxiety by the patient. She stated that each time she underwent extensive dental therapy, she wound up with her mouth feeling worse or being in poorer dental health than it was prior to when she started. So, the initial goals were not to achieve the ideal—they were more modest (i.e., scaled down). After experiencing a successful initial round of therapy, the therapy proceeded with the robust goal of achieving the ideal.

FIG. 7C is a depiction of the right canine view of the $6^{th}$ patient prior to the initiation of therapy. Note that teeth #2, 28 and 30 are not present. Here are the consequences of no corrective dental treatment with arch reformulation therapy: In the maxillary arch, a sinus graft augmentation procedure will be required prior to the surgical implant placement. In the mandibular arch, although there are two edentulous spaces, neither is adequate for a dental implant placement. Two of the goals are to (1) obviate the need for a sinus lift surgery and (2) allow for a prudent sized implant placement in the mandibular arch.

FIG. 7D is a photograph of the right canine view of the $6^{th}$ patient immediately after the completion of Phase I of her therapy. Note that tooth #29 has been moved mesially to the point that it now occupies the ideal space where tooth #28 should be. It is now possible to place a proper sized premolar dental implant in the mandibular right posterior region mesial to tooth #30.

Note the location of tooth #3. During this phase and potentially during a subsequent phase, tooth #3 will be moved distally to re-occupy the position it should ideally be occupying. Presently it is occupying the space of tooth #4, a second premolar. Presently tooth #4, the second premolar, is occupying the space of tooth #5, a first premolar.

Presently teeth #1 and #3 surround an edentulous space which more closely resembles an undersized maxillary premolar than a maxillary molar. If one were to attempt to place an implant in that location, the limited amount of bone between the sinus and the ridge would preclude a direct placement of an implant. Also, the further back in the mouth the implant surgery, the more difficult the access for a skilled surgeon and the surgical assistant, which increases the overall difficulty of the surgery.

The present standard of care would call for a maxillary sinus lift augmentation surgery. This surgery, once successful healing has occurred, would result in an increase in the amount of available bone to allow a proper sized implant with a desired length to be placed.

The main rationale for the distalization of tooth #3 to abut the mesial surface of tooth #1 is to obviate the need for a maxillary sinus graft surgery. Additionally, moving the surgical site closer to the front of the mouth would aid the implant surgeon and the surgical assistant with the implant surgery, to be in the area of a tooth #4. Additionally, the bone in the area near the maxillary sinus may be of a poorer quality than the quality of the bone located mesial to it. So, by distalizing tooth #3 via a translational movement, a skilled clinician is potentially increasing the quality of bone that will be utilized for the eventual implant surgery in the area of tooth #4, which will both increase the likelihood of initial success as well as the projected longevity.

If tooth #3 were kept in its present location, it would perpetuate and reinforce a compromised occlusion. Typically, from the posterior to the anterior, two molars abut each other followed by two premolars abutting each other prior to the mesial premolar abutting the distal surface of the canine.

If no repositioning therapy were achieved, the clinician would need to overcome the occlusion and restorative dilemmas that would accompany having a maxillary molar, premolar, molar, premolar opposing a mandibular molar, molar, premolar, premolar.

Having the occlusion be as ideal as clinically practicable is an essential aspect of the method described herein for this present invention.

Any time a clinician can achieve results without the need of an invasive surgical procedure, especially one which will likely yield equal or superior projected results, that non-invasive alternative must be given strong consideration over the existing state of the art.

FIG. 7E is a photograph of the right buccal view of the $6^{th}$ patient at the conclusion of 12 months of active therapy. The suitability of the mandibular implant site (tooth #30) is evident and quite close to the ideal.

FIG. 7F is a depiction of the right buccal view of patient #6 after 12 months of active therapy.

FIG. 7G is a depiction of the right canine view of patient #6 after 12 months of active therapy.

FIG. 7H is a projected depiction of the right buccal view of the 6th patient after 20 months of active therapy. Note that the first molar, tooth #3, is straddling the molar/premolar region, being distalized (via a translational movement) back to the molar position. Once the process is completed, it is expected to eliminate the need for a sinus lift graft surgery or any other pre-implant placement surgery.

FIG. 7I is a projected depiction of the right canine view of the 6th patient 20 months after the initiation of active therapy. Her maxillary 2nd molar was extracted after a series of dental procedures were unsuccessful as an adult in her 20s.

FIG. 7J is a projected depiction of the right canine view of the 6th patient after 28 months of the active therapy. Note that the maxillary first molar is projected to be sufficiently distalized that it would be in close contact with wisdom tooth (#1), which will soon be occupying the space of the second molar and be in full function with tooth #31, in the mandibular arch.

FIG. 7K is a projected depiction of the right canine view of the 6th patient after the completion of the active therapy. Note that the maxillary 1st molar is projected to be sufficiently distalized that it will be in contact with the wisdom tooth (#1), which will be occupying the space of the 2nd molar (tooth #2). Also note that the edentulous space for tooth #29, a second premolar, has been idealized.

FIG. 7L has two depictions of the care for the 6th patient. On the left is month 12 and on the right is the projected completion (month 32). A main goal of Phase II is to avoid the need for a sinus graft surgical procedure prior to an implant being placed in the maxillary right posterior region, according to the current invention.

Seventh Patient
Age: 68
Sex: Male
Date of Initial Visit: November, 2010
Medical History: non-contributory
Dental History 2010:
Oral Hygiene:
  Good/very good
  Bleeding: mild/moderate—generalized
  Calculus: moderate—generalized
  Plaque: moderate—generalized
  Brushing: 2x/day—no bleeding when brushing
  Flosses: none
Recent Dental Findings:
  Gingival recession: 0-6 mm
  Gingiva bleeds when brushing and flossing
  Calculus accumulation: moderate, generalized
  Periodontal pocket depths: ranges from 2-3 mm
  Buccal flare: multiple teeth>40 degrees
  Axial inclination: multiple teeth=atypical (severe)
  Canted, rotated teeth: multiple
  Chronic malocclusion: present
  Dental caries—none
  TMD—none
  Spacing between teeth: multiple areas, 0-7 mm
  Edentulous areas: none
  Underbite: severe, anterior crossbite
  Prior history of orthodontic therapy: unsuccessful—treatment not completed
Orthodontic Treatment History:
  Age 20's: traditional braces for approximately 1.5 years
  Fixed appliances: mandibular and maxillary arches
  Retainer therapy: n/a (treatment not completed)

Patient's Chief Concerns, Wish List and Goals:
  Want my mouth to look reasonably normal. That means wearing a denture with some teeth so the spaces in my mouth are filled in
  Past treatment plan (summary): Non-surgical—recommended the removal of the lower anterior teeth and the placement of dental implants and orthodontic braces
  Past treatment plan (summary): Surgical—recommended orthodontic therapy in conjunction with an orthognathic surgery; the goal of a segmental osteotomy would have been the lingual rotation of the mandibular anterior segment so the incisal edges of the teeth would be in Class I occlusion with the maxillary anterior.
  Embarrassed by the appearance of my teeth. Even though I'm retired, I know my facial appearance and lack of a true smile held me back at work.
Initial Diagnosis:
  Class III malocclusion
Initial Visits Therapy:
  Consultation
  Panoramic x-ray
  VPS impressions of the maxillary and mandibular arches
  Extraoral and intraoral examination, extraoral and intraoral comprehensive photographs
Treatments Options Considered:
  Flexible removable sequential aligner orthognathically purposed orthodontic therapy
  Teeth whitening
  No treatment
Treatment Proposed:
  Flexible removable sequential aligner orthognathically purposed orthodontic therapy ("therapy")
  10% CP+ACP
  (At-Home teeth whitening concurrent with the orthognathically purposed orthodontic therapy)
Active therapy: Phase I
  Duration: 2 years
  47 mandibular aligners (14 days/aligner)
  22 maxillary aligners
    aligners #1-10 (42 days/aligner)
    aligners #11-22 (14 days/aligner)
Active Therapy: Phase II
  Duration: 3 years (14-16 days/aligner) [ongoing]
  70 mandibular aligners
  70 maxillary aligners
10% (CP)+(ACP) Solution—Application Regimen:
  Approximate number of 10% CP/ACP nighttime applications:
    About 50 (2-3/month over a period of 2.5 years)
Treatment Results (Therapy is Ongoing):
  Gingival response to therapy has been excellent.
  Transient mobility: reached a peak of Class III+/fremitus of multiple mandibular anterior teeth due to the severity of the correction. Present mobility/fremitus ranges from Class 0.5-11. While this is at the high range of normal, it is within limits of what a skilled clinician would anticipate during a course of orthodontic therapy of this magnitude and difficulty.
  Pocket depths: have stayed the same or improved
  Gingival recession: has stayed the same or improved
  Oral hygiene: improved
Treatment Timeline:
Active aligner phase of therapy: 5 years (approximate projected; ongoing—presently at 3 years)
FT retainer phase of therapy: n/a
PT retainer phase of therapy: n/a Gingival Health Timeline:
Month 28: Gingival Health Level I achieved
Month 34: Gingival Health Level I maintained (ongoing)

FIG. 8A has photographs of the anterior and right buccal anterior views of patient #7 prior to the initiation of therapy and a close-up view of a gradated (3 mm increments) periodontal probe. The photograph on the left shows the anterior view. Multiple large diastemata, Class III malocclusion, pronounced buccal flare, reduced interarch space, underbite, multiple anterior crossbites, canted teeth, etc., are evident.

The photograph on the bottom right in FIG. 8A shows the right buccal anterior view. The magnitude of the flare (~1.3 cm) can be quantified when the entire periodontal probe is visible (top right). Starting from the probe tip, each color, yellow/black/yellow/black represents 3 mm. The yellow arrows point to where the tip of the periodontal probe is resting on the maxillary arch, midway between the central incisors.

Prior to the present method of arch reformulation described herein, there were no satisfactory non-invasive dental treatment options available to this patient over the proceeding five decades. Even the highly invasive options; elective segmental orthognathic surgery in the mandibular (and possibly maxillary) arch(es); extraction of multiple teeth, dental implant surgeries in conjunction with prosthodontic and orthodontic therapy, etc., possessed significant consequences and risks. Over the past half century, during his many regular dental visits, he had been provided with limited and very poor options for his dental rehabilitation.

FIG. 8B has two photographs of patient #7 prior to the initiation of therapy; the mandibular arch is on the left and maxillary arch is on the right. Note that the large amount of anterior flare and the multiple diastemata have created arches which are quite large, especially when measured in the antero-posterior dimension. To amplify this point, stock XL impression trays were inadequate. Modified trays approximating an XXL size were used to capture all of the surfaces of all of the teeth present in his arches.

FIG. 8C has 4 photographs which represent the occlusal (birds eye) view of the mandibular arch prior to the initiation of, and after 1.25, 2.33 and 2.75 years of BAOC arch reformulation therapy. These snapshots show the start and intermediate progress views which represent approximately 20%, 33% and 50% of the projected reformulation activity.

FIG. 8D has accurate depictions of the outlines of the mandibular arch and the teeth prior to the initiation of care of the $7^{th}$ patient and after approximately 2.75 years (~50%) of the projected therapy. Note that the number and size of the diastemata and the buccal flare have already been greatly reduced. Note that the shape and size of the mandible have been significantly modified by the reformulation process. If one were to draw an arc from the distal buccal gingival line angle of one $2^{nd}$ molar (tooth #18) and continue along the superior portion of the buccal gingival surfaces of all the other molar, premolar and anterior teeth to the distal buccal gingival ling angle of the other $2^{nd}$ molar (tooth #31), the reduction in the buccal perimeter of the mandible would be approximately 5 cm. To put the magnitude of this reformulation in perspective, many invasive surgical orthognathic procedures yield changes to the size and shape of the mandible in the 2-3 cm range. The inventor was unable to locate any prior documentation in a scientific journal of a similar non-surgical result.

FIG. 8E has accurate depictions of the outlines of the mandibular arch and teeth prior to and after approximately 2.75 years of therapy and closely resemble the drawings in FIG. 8D. Note the light gray shading which shows where bone was once present, but as the reformulation of the BAOC proceeded, it is no longer present.

FIG. 8F is similar to FIGS. 8D, 8E. Note the dark gray shading highlights where there has appears to be an increase in bone as the BAOC was reformulated.

FIG. 8G is similar to FIGS. 8D, 8E, 8F. Note the light gray area highlights where bone was once present and the dark gray area highlights where new bone has been deposited. This helps summarize the changes in the BAOC which are expected to continue as the reformulation therapy proceeds along its expected course.

FIG. 8H are photos of the mandibular arch of the $7^{th}$ patient prior to the initiation and after 2.75 years of therapy. Another measure of the magnitude of the reformulation of the mandible: the arc distance from the mesial of the left first molar (tooth #19) to the mesial of the right lateral incisor (tooth #25) has been reduced by 2.7 cm (~1.1").

FIG. 8I has the same photos that are in FIG. 8H. Another measure of the magnitude of the reformulation of the mandible: the arc distance from the mesial of the left first molar (tooth #19) to the mesial of the right canine (tooth #28) has been reduced by 4.1 cm (1.6").

FIG. 8J has 4 photographs which represent the anterior view of the $7^{th}$ patient during maximum closure (centric relation) prior to the initiation of, and after 1.25, 2.33 and 2.75 years of BAOC arch reformulation therapy. These snapshots show the start and intermediate progress views which represent approximately 20%, 33% and 50% of the projected reformulation activity. The black and yellow arrows point to the gingival recession present on several teeth.

FIG. 8K has two photographs of the $7^{th}$ patient. These close-up views focus on the gingival recession in the mandibular anterior region. Note that the amount of recession has been reduced by up to 5 mm (tooth #26). While it has long been known that the ideal uprighting of teeth can reduce the amount of gingival recession, the magnitude of the regeneration of the gingiva and accompanying bone via the present BAOC reformulation has been unusually positive. The scientific literature is void of reports of non-surgical gingival regeneration via orthodontic methods, or any other non-surgical method, of 5 mm or greater. As treatment progresses, it is expected that additional positive results, results which have already exceeded optimistic expectations, will continue to be achieved by this patient in his eighth decade.

FIG. 8L has 4 photographs which represent the right buccal anterior view of the $7^{th}$ patient during maximum closure (centric relation) prior to the initiation of, and after 1.25, 2.33 and 2.75 years of BAOC arch reformulation therapy. These snapshots show the start and intermediate progress views which represent approximately 20%, 33% and 50% of the projected reformulation activity. The photo of the periodontal probe helps one visualize one measurement of the magnitude of the chronic malocclusion prior to the initiation of therapy. The mandibular incisal edges are flared approximately 1.2-1.4 cm buccal to where one would expect them to be in a Class I occlusion.

FIG. 8M are extraoral photos of the right profile view of the $7^{th}$ patient prior to the start and after 2 years of BAOC reformulation therapy. While no surgery was done, the results resemble or might even exceed what one would expect from a successful surgical orthognathic procedure.

FIG. 8N is a digital panoramic x-ray taken prior to the initiation of therapy of the $7^{th}$ patient. Significant arch asymmetry, misangulated and flared teeth, etc., are evident.

FIG. 8O is a digital panoramic x-ray taken after 2 years of BAOC reformulation therapy of the $7^{th}$ patient. Note the significant reduction in the arch asymmetry and number of misaligned teeth.

FIG. 8P is a chart of the Levels of Gingival Health. Gingival Health Level I was achieved after 2.33 years and has been maintained. Based on similar patients who experienced similar positive progress, it is expected that the $7^{th}$ patient will likely attain gingival Health Level II sometime during his $4^{th}$ year of therapy, once the majority of the anterior transformations and reformulation have been achieved.

FIG. 8Q is a depiction of the mandibular arch of the $7^{th}$ patient prior to the initiation of therapy.

FIG. 8R is a projected depiction of the mandibular arch of the $7^{th}$ patient after 2 years of BAOC reformulation therapy. The buccal flare and diastemata were expected to be significantly reduced and they were as was evident in the photographs (FIG. 8C).

FIG. 8S is a projected depiction of the mandibular arch of the $7^{th}$ patient at the completion of BAOC reformulation therapy. The buccal flare and diastemata are expected to be almost completely eliminated. Based on the progress made during the first three years, as is evident in the photographs in FIG. 7C, as well as subsequent observations during POV, it is expected that the patient will achieve and maintain Gingival Health Level II and achieve this projected depiction.

FIG. 8T is a depiction of the maxillary arch of the $7^{th}$ patient prior to the initiation of therapy.

FIG. 8U is a projected depiction of the maxillary arch of the $7^{th}$ patient after 2 years of BAOC reformulation therapy. The buccal flare and diastemata were expected to be significantly reduced and they were (FIG. 8J).

FIG. 8V is a projected depiction of the maxillary arch of the $7^{th}$ patient after the completion of BAOC reformulation therapy. The buccal flare and diastemata are expected to be almost completely eliminated. Based on the progress made during the first three years (FIG. 8J) as well as subsequent observations during POV, it is expected that the patient will achieve and maintain Gingival Health Level II and achieve the projected depiction.

FIG. 8W is a depiction of the anterior view of the 7th patient prior to the initiation of therapy.

FIG. 8X is a projected depiction of the anterior view of the $7^{th}$ patient after 2 years of BAOC reformulation therapy. The buccal flare and diastemata were expected to be significantly reduced and they were (FIG. 8J).

FIG. 8Y is a projected depiction of the anterior view of the $7^{th}$ patient after the completion of BAOC reformulation therapy. The buccal flare and diastemata are expected to be almost completely eliminated. Based on the progress made during the first three years (FIG. 8J) as well as subsequent observations during POV, it is expected that the patient will achieve and maintain Gingival Health Level II and achieve the projected depiction.

Eighth Patient:
Age: 42
Sex: Female
Date of Initial Visit: August, 2011
Medical History: TMJ/TMD for more than two decades
Dental History 2010:
Oral Hygiene:
  Very good
  Bleeding: slight—generalized
  Calculus: moderate—generalized
  Plaque: moderate—generalized
  Brushing: 2×/day—no bleeding when brushing
  Flosses: 1×/day—1×/week
Recent Dental Findings:
  Porcelain veneers: 7 teeth (#4, 5, 6, 7, 10, 11, 12)
  Porcelain fused to metal crowns: 2 teeth (#8, 9)
  Number of teeth not occluding during central occlusion: 6
  Gingival recession: 0-4 mm
  Periodontal pocket depths: ranges from 1-3 mm
  Buccal flare: 0-20 degrees
  Axial inclination: multiple teeth=atypical (severe)
  Canted, rotated teeth: multiple
  Chronic malocclusion: present
  Dental caries—none
  TMD: symptomatic history more than two decades. Unable to bite directly into apples, pears, hard bread sandwiches, etc.
  Maximum opening: ~1.5"
  Crowding: maxillary and mandibular anterior regions
  Edentulous areas: none (#25 extracted ~8 years prior as per request of recommendation of prior orthodontist)
  Wisdom teeth: four partially impacted
  Overbite: 2-6 mm
  Overjet: 1-5 mm
  Prior history of orthodontic therapy: unsuccessful
    Conditions present prior to orthodontic treatment in 2003 (age 34)
      Class II, Division I Subdivision left
      Excessive overjet (4-6 mm)
      Anterior deep bite: 90%
      Constricted maxillary and mandibular arches
      Maxillary arch—crowding: moderate (5-6 mm)
      Mandibular arch—crowding: severe (10-12 mm)
      Malaligned maxillary and mandibular incisors
      Retroclined maxillary incisors
      Upright mandibular incisors
      Excessive Curve of Spee
      High palatal vault
      Maxillary midline deviates to the right by 2 mm
      Endodontic therapy #8, 9
      Impacted third molars
      Suggested Orthodontic Treatment:
        "Extraction procedure of the maxillary left and right first premolars and a mandibular central incisor to gain additional arch length to place 'her' teeth in their proper positions"
    Timeline of prior orthodontic therapy
      August 2003: $2^{nd}$ (orthodontist) opinion—removal of mandibular right central incisor confirmed; a more aggressive orthodontic treatment therapy including additional extractions and a greater projected duration of treatment was recommended, but not selected.
      September 2003: mandibular right central incisor removed
      September 2003-September 2006: Adjustable removable retainer worn. Intention was to eventually have traditional braces. Brackets were placed to supplement and aid retainer with the movement of the teeth. Treatment repeated on two occasions. Each time brackets quickly debonded. Patient advised likely cause of debonding was her deep bite (being resistant to correction). Treatment was discontinued by patient due to multiple problems and changes with the therapy, lack of progress, slight exacerbation with TMD related symptoms, increased time commitment (visits increased to every other week) and general disappointment with the poor progress and frequent setbacks after three years of treatment. Sometime during the early aspects of the orthodontic therapy, audible sounds from the jaw became noticeable and were sporadically symptomatic.

September 2006-December 2009: TMD became consistently and progressively worse. Maximum oral opening decreased to 1". Patient was unable to bite into and eat a sandwich. She needed to break off bite sized pieces.

May 2008—received palliative treatment from general practitioner to relieve TMJ pain. Maximum oral opening of 1" is confirmed.

January 2010-October 2011: TMD progressed to daily episodes of lock jaw.

October 2011: During first phase of TMD purposed flexible sequential aligner orthodontic therapy ("therapy"), TMJ symptoms varied from asymptomatic to mildly symptomatic.

June 2012: TMD—lock jaw ceased

May 2013: 2$^{nd}$ Phase of therapy—continued steady improvement of TMJ.

November 2013: Mouth opening=3". No symptoms have been present for "at least a few months." Lock jaw, clicking and crackling have completely ceased. Patient no longer possesses a physical impediment to consume any food any way she would like. Patient is able to bite into an apple for the first time in approximately two decades.

Initial Visits Therapy:
  Consultation
  VPS impressions of the maxillary and mandibular arches
  Extraoral and intraoral examination, extraoral and intraoral comprehensive photographs
Treatments Options Considered:
  Flexible removable sequential aligner TMJ/TMD purposed orthodontic therapy
  No treatment
Treatment Proposed:
  Flexible removable sequential aligner orthognathically purposed orthodontic therapy ("therapy")
  10% CP+ACP
  [At-Home teeth and Manhattan Method for teeth whitening of uneven smiles concurrent with the orthognathically purposed orthodontic therapy]
Active Therapy: Phase I
  Duration: 1 years (14-17 days/aligners)
  20 mandibular aligners
  17 maxillary aligners
  Note: patient compliance was an issue due to a perceived self-consciousness when giving presentations.
Active Therapy: Phase II
  Duration: 2 years (17-21 days/aligner) [ongoing]
  19 mandibular aligners
  35 maxillary aligners
Projected Duration of Therapy: 3.5-4.5 Years
10% (CP)+(ACP) Solution—Application Regimen:
  Approximate number of 10% CP/ACP nighttime applications:
    About 20 [1-2/month over a period of 2+years]
Treatment Results (Therapy is Ongoing):
  Gingival response to therapy has been excellent.
  TMJ/TMD: responses have been excellent. Patient has been asymptomatic for many months.
  Maximum oral opening: significant improvement (1.5"→3")
  Pocket depths: have stayed the same or improved
  Gingival recession: has stayed the same or improved
  Oral hygiene: improved
Gingival Health Timeline:
  Month 12: Gingival Health Level I achieved
  Month 24: Gingival Health Level I maintained (ongoing)

Based on her dramatic and profound progress, the resolution of her TMD is expected to be maintained as treatment continues and throughout the remaining portions of the active and retention phases. The significant improvement of her Curves of Spee and Wilson as well as her alignment progressing towards a Class I occlusion, validate the theory of the invention and are all quite encouraging.

Presently, active TMD is almost always a contraindication to initiate orthodontic therapy. So much so, that it is a common warning included in standard informed consents required prior to the initiation of an orthodontic therapy. When mentioned in the same breath with orthodontic treatment, the goal is merely to ensure the severity of the TMD condition is not exacerbated. The inventor is confident that a skilled clinician who properly follows the methodology described herein will be able to offer a predictable and long term remedy to resolve those suffering with TMJ/TMD conditions.

During her initial orthodontic (non-TMD purposed) treatment, the symptoms of her TMD increased in magnitude and amplitude. A skilled clinician would appreciate that the method described herein eradicated her symptoms. A skilled clinician would also appreciate that her reformulated BAOC in addition to the idealized axial inclinations of the teeth soon to be in Class I occlusion, created such a profound improvement that the likelihood of a relapse is highly unlikely.

Based on this patient and several others (including patient #6) who have similarly experienced complete resolution of their TMD, a skilled clinician would deduce that a patient with TMD would be a strong candidate to have the TMD-purposed removable flexible sequential orthodontic therapy described herein.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of treating a dental condition of a post-pubescent patient comprising the steps of:
  implementing an exclusively non-invasive, non-surgical procedure that includes,
  re-aligning of maloccluded teeth of a post-pubescent patient without modification of the patient's teeth according to an orthodontic treatment regimen, the treatment regimen including configuring a plurality of flexible aligners for the patient, the flexible aligners being configured to re-orient the patient's maloccluded teeth progressively from an initial state of alignment to a final state of alignment, the re-aligning beginning at the initial state of alignment of the teeth and ending at the final state of alignment of the teeth, the final state of alignment of the teeth being closer to an ideal arch than the initial state of alignment; wherein the patient suffers from chronic malocclusion and an adverse periodontal condition indicative of a periodontal disease; wherein the treatment regimen includes a plurality of phases; wherein the phases include at least an active phase during which the flexible aligners are prescribed for less than twenty fours hours per day, and the flexible aligners are configured to induce movement of the patient's maloccluded teeth, and a retainer phase during which flexible retainers are prescribed for less than twenty four hours per day and are configured to maintain the patient's teeth in position after completion of the active phase; and wherein the active phase is concluded when a near ideal arch or ideal arch is attained, the near ideal arch or ideal arch being attained when 90%-95% of movements of the teeth are realized.

2. The method of claim 1, wherein the treatment regimen further includes a hybrid phase during which only some of the patient's teeth are reoriented.

3. The method of claim 1, wherein each phase includes the configuring of a plurality of flexible aligners.

4. The method of claim 3, wherein each phase spans more than one month.

5. The method of claim 4, wherein, in each phase, the flexible aligners are prescribed for a period of time spanning less than 24 hours per day.

6. The method of claim 1, wherein the retainer phase includes a full-time phase during which flexible retainers are prescribed for more than 12 hours per day as well as a part-time phase during which flexible retainers are prescribed for less than 12 hours per day.

7. The method of claim 1, further comprising a hybrid phase during which the retainers are prescribed for more than 12 hours per day to maintain the position of less than all of the patient's teeth, the hybrid phase following the active phase and preceding the retainer phase.

\* \* \* \* \*